United States Patent
Sammons et al.

(10) Patent No.: US 9,121,022 B2
(45) Date of Patent: *Sep. 1, 2015

(54) METHOD FOR CONTROLLING HERBICIDE-RESISTANT PLANTS

(75) Inventors: Robert D. Sammons, New Melle, MO (US); Sergey Ivashuta, Ballwin, MO (US); Hong Liu, St. Louis, MO (US); Dafu Wang, St. Louis, MO (US); Paul C. C. Feng, Wildwood, MO (US); Andrei Y. Kouranov, Chesterfield, MO (US); Scott E. Andersen, Manchester, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/042,856

(22) Filed: Mar. 8, 2011

(65) Prior Publication Data

US 2011/0296556 A1 Dec. 1, 2011

Related U.S. Application Data

(60) Provisional application No. 61/311,762, filed on Mar. 8, 2010, provisional application No. 61/349,807, filed on May 28, 2010, provisional application No. 61/381,556, filed on Sep. 10, 2010.

(51) Int. Cl.

| | | |
|---|---|---|
| *C12N 15/113* | (2010.01) | |
| *C12N 15/87* | (2006.01) | |
| *A01P 13/00* | (2006.01) | |
| *A01N 25/30* | (2006.01) | |
| *A01N 57/16* | (2006.01) | |
| *A01N 63/02* | (2006.01) | |
| *C12N 15/82* | (2006.01) | |

(52) U.S. Cl.
CPC ............ *C12N 15/1137* (2013.01); *A01N 57/16* (2013.01); *A01N 63/02* (2013.01); *C12N 15/8206* (2013.01); *C12N 15/8207* (2013.01); *C12N 15/8218* (2013.01)

(58) Field of Classification Search
None
See application file for complete search history.

(56) References Cited

U.S. PATENT DOCUMENTS

| | | | |
|---|---|---|---|
| 3,687,808 A | 8/1972 | Merigan et al. | |
| 3,791,932 A | 2/1974 | Schuurs et al. | |
| 3,839,153 A | 10/1974 | Schuurs et al. | |
| 3,850,578 A | 11/1974 | McConnell | |
| 3,850,752 A | 11/1974 | Schuurs et al. | |
| 3,853,987 A | 12/1974 | Dreyer | |
| 3,867,517 A | 2/1975 | Ling | |
| 3,879,262 A | 4/1975 | Schuurs et al. | |
| 3,901,654 A | 8/1975 | Gross | |
| 3,935,074 A | 1/1976 | Rubenstein et al. | |
| 3,984,533 A | 10/1976 | Uzgiris | |
| 3,996,345 A | 12/1976 | Ullman et al. | |
| 4,034,074 A | 7/1977 | Miles | |
| 4,098,876 A | 7/1978 | Piasio et al. | |
| 4,469,863 A | 9/1984 | Ts'o et al. | |
| 4,476,301 A | 10/1984 | Imbach et al. | |
| 4,535,060 A | 8/1985 | Comai | |
| 4,581,847 A | 4/1986 | Hibberd et al. | |
| 4,666,828 A | 5/1987 | Gusella | |
| 4,683,202 A | 7/1987 | Mullis | |
| 4,761,373 A | 8/1988 | Anderson et al. | |
| 4,769,061 A | 9/1988 | Comai | |
| 4,801,531 A | 1/1989 | Frossard | |
| 4,810,648 A | 3/1989 | Stalker | |
| 4,879,219 A | 11/1989 | Wands et al. | |
| 4,940,835 A | 7/1990 | Shah et al. | |
| 4,971,908 A | 11/1990 | Kishore et al. | |
| 5,004,863 A | 4/1991 | Umbeck | |
| 5,011,771 A | 4/1991 | Bellet et al. | |
| 5,013,659 A | 5/1991 | Bedbrook et al. | |
| 5,015,580 A | 5/1991 | Christou et al. | |
| 5,023,243 A | 6/1991 | Tullis | |
| 5,034,506 A | 7/1991 | Summerton et al. | |
| 5,094,945 A | 3/1992 | Comai | |
| 5,141,870 A | 8/1992 | Bedbrook et al. | |
| 5,145,783 A | 9/1992 | Kishore et al. | |
| 5,159,135 A | 10/1992 | Umbeck | |
| 5,166,315 A | 11/1992 | Summerton et al. | |
| 5,177,196 A | 1/1993 | Meyer, Jr. et al. | |
| 5,185,444 A | 2/1993 | Summerton et al. | |
| 5,188,642 A | 2/1993 | Shah et al. | |
| 5,188,897 A | 2/1993 | Suhadolnik et al. | |

(Continued)

FOREIGN PATENT DOCUMENTS

| | | |
|---|---|---|
| CN | 101279950 A | 10/2008 |
| CN | 101279951 A | 10/2008 |

(Continued)

OTHER PUBLICATIONS

Gaines et al (PNAS, 107(3), p. 1029-1034, 2010).*
Kirkwood (Pestic Sci, 38:93-102, 1993).*
Kusaba et al (The Plant Cell, 15(6), p. 1455-1467, 2003).*
GenBank accession No. AY545657.1, published 2004.*
Zhang et al (Journal of Controlled Release, 123(1), pp. 1-10, 2007).*
Tenllado et al (BMC Biotechnology 3:3, pp. 3-14, 2003); cited on IDS filed Nov. 29, 2012.*
Stock et al (Pestic. Sci., 38, pp. 165-177, 1993).*
GenEmbl FJ861243 (Published Feb. 3, 2010); see alignment appended to the Action.*
International Preliminary Report on Patentability issued on Sep. 11, 2012 for PCT/US2011/027528.

(Continued)

*Primary Examiner* — David T Fox
*Assistant Examiner* — Stephen Uyeno
(74) *Attorney, Agent, or Firm* — Amanda Carmany-Rampey; David R. Marsh; Arnold & Porter LLP

(57) ABSTRACT

This invention provides polynucleotide molecules and methods for regulating genes in plants, e.g., by providing RNA for systemic regulation of genes. Various aspects of the invention provide polynucleotide molecules and methods for regulating endogenous genes and transgenes in a plant cell and polynucleotide molecules.

30 Claims, 42 Drawing Sheets

(56) References Cited

U.S. PATENT DOCUMENTS

| | | |
|---|---|---|
| 5,192,659 A | 3/1993 | Simons |
| 5,214,134 A | 5/1993 | Weis et al. |
| 5,216,141 A | 6/1993 | Benner |
| 5,235,033 A | 8/1993 | Summerton et al. |
| 5,264,423 A | 11/1993 | Cohen et al. |
| 5,264,562 A | 11/1993 | Matteucci |
| 5,264,564 A | 11/1993 | Matteucci |
| 5,272,057 A | 12/1993 | Smulson et al. |
| 5,276,019 A | 1/1994 | Cohen et al. |
| 5,281,521 A | 1/1994 | Trojanowski et al. |
| 5,286,717 A | 2/1994 | Cohen et al. |
| 5,304,732 A | 4/1994 | Anderson et al. |
| 5,310,667 A | 5/1994 | Eichholtz et al. |
| 5,312,910 A | 5/1994 | Kishore et al. |
| 5,321,131 A | 6/1994 | Agrawal et al. |
| 5,331,107 A | 7/1994 | Anderson et al. |
| 5,339,107 A | 8/1994 | Henry et al. |
| 5,346,107 A | 9/1994 | Bouix et al. |
| 5,378,824 A | 1/1995 | Bedbrook et al. |
| 5,390,667 A | 2/1995 | Kumakura et al. |
| 5,392,910 A | 2/1995 | Bell et al. |
| 5,393,175 A | 2/1995 | Courville |
| 5,399,676 A | 3/1995 | Froehler |
| 5,405,938 A | 4/1995 | Summerton et al. |
| 5,405,939 A | 4/1995 | Suhadolnik et al. |
| 5,416,011 A | 5/1995 | Hinchee et al. |
| 5,453,496 A | 9/1995 | Caruthers et al. |
| 5,455,233 A | 10/1995 | Spielvogel et al. |
| 5,460,667 A | 10/1995 | Moriyuki et al. |
| 5,462,910 A | 10/1995 | Ito et al. |
| 5,463,174 A | 10/1995 | Moloney et al. |
| 5,463,175 A | 10/1995 | Barry et al. |
| 5,466,677 A | 11/1995 | Baxter et al. |
| 5,470,967 A | 11/1995 | Huie et al. |
| 5,476,925 A | 12/1995 | Letsinger et al. |
| 5,489,520 A | 2/1996 | Adams et al. |
| 5,489,677 A | 2/1996 | Sanghvi et al. |
| 5,491,288 A | 2/1996 | Chaubet et al. |
| 5,510,471 A | 4/1996 | Lebrun et al. |
| 5,518,908 A | 5/1996 | Corbin et al. |
| 5,519,126 A | 5/1996 | Hecht |
| 5,536,821 A | 7/1996 | Agrawal et al. |
| 5,538,880 A | 7/1996 | Lundquist et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,550,318 A | 8/1996 | Adams et al. |
| 5,550,398 A | 8/1996 | Kocian et al. |
| 5,550,468 A | 8/1996 | Haberlein et al. |
| 5,561,225 A | 10/1996 | Maddry et al. |
| 5,561,236 A | 10/1996 | Leemans et al. |
| 5,563,253 A | 10/1996 | Agrawal et al. |
| 5,569,834 A | 10/1996 | Hinchee et al. |
| 5,571,799 A | 11/1996 | Tkachuk et al. |
| 5,587,361 A | 12/1996 | Cook et al. |
| 5,591,616 A | 1/1997 | Hiei et al. |
| 5,593,874 A | 1/1997 | Brown et al. |
| 5,596,086 A | 1/1997 | Matteucci et al. |
| 5,602,240 A | 2/1997 | De Mesmaeker et al. |
| 5,605,011 A | 2/1997 | Bedbrook et al. |
| 5,608,046 A | 3/1997 | Cook et al. |
| 5,610,289 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,627,061 A | 5/1997 | Barry et al. |
| 5,633,360 A | 5/1997 | Bischofberger et al. |
| 5,633,435 A | 5/1997 | Barry et al. |
| 5,633,448 A | 5/1997 | Lebrun et al. |
| 5,639,024 A | 6/1997 | Mueller et al. |
| 5,646,024 A | 7/1997 | Leemans et al. |
| 5,648,477 A | 7/1997 | Leemans et al. |
| 5,663,312 A | 9/1997 | Chaturvedula |
| 5,677,437 A | 10/1997 | Teng et al. |
| 5,677,439 A | 10/1997 | Weis et al. |
| 5,719,046 A | 2/1998 | Guerineau et al. |
| 5,721,138 A | 2/1998 | Lawn |
| 5,731,180 A | 3/1998 | Dietrich |
| 5,739,180 A | 4/1998 | Taylor-Smith |
| 5,746,180 A | 5/1998 | Jefferson et al. |
| 5,767,361 A | 6/1998 | Dietrich |
| 5,767,373 A | 6/1998 | Ward et al. |
| 5,780,708 A | 7/1998 | Lundquist et al. |
| 5,804,425 A | 9/1998 | Barry et al. |
| 5,824,877 A | 10/1998 | Hinchee et al. |
| 5,837,848 A | 11/1998 | Ely et al. |
| 5,859,347 A | 1/1999 | Brown et al. |
| 5,866,775 A | 2/1999 | Eichholtz et al. |
| 5,874,265 A | 2/1999 | Adams et al. |
| 5,879,903 A | 3/1999 | Strauch et al. |
| 5,914,451 A | 6/1999 | Martinell et al. |
| 5,919,675 A | 7/1999 | Adams et al. |
| 5,928,937 A | 7/1999 | Kakefuda et al. |
| 5,939,602 A | 8/1999 | Volrath et al. |
| 5,969,213 A | 10/1999 | Adams et al. |
| 5,981,840 A | 11/1999 | Zhao et al. |
| 5,985,793 A | 11/1999 | Sandbrink et al. |
| RE36,449 E | 12/1999 | Lebrun et al. |
| 6,040,497 A | 3/2000 | Spencer et al. |
| 6,056,938 A * | 5/2000 | Unger et al. ................. 424/1.21 |
| 6,069,115 A | 5/2000 | Pallett et al. |
| 6,084,089 A | 7/2000 | Mine et al. |
| 6,084,155 A | 7/2000 | Volrath et al. |
| 6,118,047 A | 9/2000 | Anderson et al. |
| 6,121,513 A | 9/2000 | Zhang et al. |
| 6,130,366 A | 10/2000 | Herrera-Estrella et al. |
| 6,140,078 A | 10/2000 | Sanders et al. |
| 6,153,812 A | 11/2000 | Fry et al. |
| 6,160,208 A | 12/2000 | Lundquist et al. |
| 6,177,616 B1 | 1/2001 | Bartsch et al. |
| 6,194,636 B1 | 2/2001 | McElroy et al. |
| 6,225,105 B1 | 5/2001 | Sathasivan et al. |
| 6,225,114 B1 | 5/2001 | Eichholtz et al. |
| 6,232,526 B1 | 5/2001 | McElroy et al. |
| 6,245,968 B1 | 6/2001 | Boudec et al. |
| 6,248,876 B1 | 6/2001 | Barry et al. |
| 6,252,138 B1 | 6/2001 | Karimi et al. |
| RE37,287 E | 7/2001 | Lebrun et al. |
| 6,268,549 B1 | 7/2001 | Sailland et al. |
| 6,271,359 B1 | 8/2001 | Norris et al. |
| 6,282,837 B1 | 9/2001 | Ward et al. |
| 6,288,306 B1 | 9/2001 | Ward et al. |
| 6,288,312 B1 | 9/2001 | Christou et al. |
| 6,294,714 B1 | 9/2001 | Matsunaga et al. |
| 6,326,193 B1 | 12/2001 | Liu et al. |
| 6,329,571 B1 | 12/2001 | Hiei |
| 6,348,185 B1 | 2/2002 | Piwnica-Worms |
| 6,365,807 B1 | 4/2002 | Christou et al. |
| 6,384,301 B1 | 5/2002 | Martinell et al. |
| 6,385,902 B1 | 5/2002 | Schipper et al. |
| 6,399,861 B1 | 6/2002 | Anderson et al. |
| 6,403,865 B1 | 6/2002 | Koziel et al. |
| 6,414,222 B1 | 7/2002 | Gengenbach et al. |
| 6,421,956 B1 | 7/2002 | Boukens et al. |
| 6,426,446 B1 | 7/2002 | McElroy et al. |
| 6,433,252 B1 | 8/2002 | Kriz et al. |
| 6,437,217 B1 | 8/2002 | McElroy et al. |
| 6,453,609 B1 | 9/2002 | Soll et al. |
| 6,506,559 B1 † | 1/2003 | Fire et al. |
| 6,644,341 B1 | 11/2003 | Chemo et al. |
| 6,768,044 B1 | 7/2004 | Boudec et al. |
| 6,992,237 B1 | 1/2006 | Habben et al. |
| 7,022,896 B1 | 4/2006 | Weeks et al. |
| 7,026,528 B2 | 4/2006 | Cheng et al. |
| RE39,247 E | 8/2006 | Barry et al. |
| 7,105,724 B2 | 9/2006 | Weeks et al. |
| 7,297,541 B2 | 11/2007 | Moshiri et al. |
| 7,304,209 B2 | 12/2007 | Zink et al. |
| 7,312,379 B2 | 12/2007 | Andrews et al. |
| 7,323,310 B2 | 1/2008 | Peters et al. |
| 7,371,927 B2 | 5/2008 | Yao et al. |
| 7,392,379 B2 | 6/2008 | Le Pennec et al. |
| 7,405,347 B2 | 7/2008 | Hammer et al. |
| 7,406,981 B2 | 8/2008 | Hemo et al. |

(56) References Cited

U.S. PATENT DOCUMENTS

| | | |
|---|---|---|
| 7,462,379 B2 | 12/2008 | Fukuda et al. |
| 7,485,777 B2 | 2/2009 | Nakajima et al. |
| 7,525,013 B2 | 4/2009 | Hildebrand et al. |
| 7,550,578 B2 | 6/2009 | Budworth et al. |
| 7,622,301 B2 | 11/2009 | Ren et al. |
| 7,657,299 B2 | 2/2010 | Huizenga et al. |
| 7,671,254 B2 | 3/2010 | Tranel et al. |
| 7,714,188 B2 | 5/2010 | Castle et al. |
| 7,738,626 B2 | 6/2010 | Weese et al. |
| 7,807,791 B2 | 10/2010 | Sekar et al. |
| 7,838,263 B2 | 11/2010 | Dam et al. |
| 7,838,733 B2 | 11/2010 | Wright et al. |
| 7,842,856 B2 | 11/2010 | Tranel et al. |
| 7,884,262 B2 | 2/2011 | Clemente et al. |
| 7,910,805 B2 | 3/2011 | Duck et al. |
| 7,935,869 B2 | 5/2011 | Pallett et al. |
| 7,943,819 B2 | 5/2011 | Baum et al. |
| 7,973,218 B2 | 7/2011 | McCutchen et al. |
| 8,090,164 B2 | 1/2012 | Bullitt et al. |
| 8,143,480 B2 | 3/2012 | Axtell et al. |
| 8,548,778 B1 | 10/2013 | Hart et al. |
| 8,554,490 B2 | 10/2013 | Tang et al. |
| 2001/0042257 A1 | 11/2001 | Connor-Ward et al. |
| 2002/0114784 A1 | 8/2002 | Li et al. |
| 2003/0150017 A1 | 8/2003 | Mesa et al. |
| 2003/0154508 A1 | 8/2003 | Stevens et al. |
| 2003/0167537 A1 | 9/2003 | Jiang |
| 2003/0235916 A1 | 12/2003 | Monahan et al. |
| 2004/0053289 A1 | 3/2004 | Christian et al. |
| 2004/0055041 A1 | 3/2004 | Labate et al. |
| 2004/0072692 A1 | 4/2004 | Hoffman et al. |
| 2004/0082475 A1 | 4/2004 | Hoffman et al. |
| 2004/0123347 A1 | 6/2004 | Hinchey et al. |
| 2004/0126845 A1 | 7/2004 | Eenennaam et al. |
| 2004/0133944 A1 | 7/2004 | Hake et al. |
| 2004/0147475 A1 | 7/2004 | Li et al. |
| 2004/0177399 A1 | 9/2004 | Hammer et al. |
| 2004/0216189 A1 | 10/2004 | Houmard et al. |
| 2004/0244075 A1 | 12/2004 | Cai et al. |
| 2005/0215435 A1 | 9/2005 | Menges et al. |
| 2006/0009358 A1 | 1/2006 | Kibler et al. |
| 2006/0021087 A1 | 1/2006 | Baum et al. |
| 2006/0111241 A1 | 5/2006 | Gerwick, III et al. |
| 2006/0130172 A1 | 6/2006 | Whaley et al. |
| 2006/0135758 A1 | 6/2006 | Wu |
| 2006/0200878 A1 | 9/2006 | Lutfiyya et al. |
| 2006/0223708 A1 | 10/2006 | Hoffman et al. |
| 2006/0223709 A1 | 10/2006 | Helmke et al. |
| 2006/0247197 A1 | 11/2006 | Van De Craen et al. |
| 2006/0272049 A1 | 11/2006 | Waterhouse et al. |
| 2006/0276339 A1 | 12/2006 | Windsor et al. |
| 2007/0011775 A1 | 1/2007 | Allen et al. |
| 2007/0050863 A1 | 3/2007 | Tranel et al. |
| 2007/0124836 A1 | 5/2007 | Baum et al. |
| 2007/0199095 A1 | 8/2007 | Allen et al. |
| 2007/0250947 A1 | 10/2007 | Boukharov et al. |
| 2007/0259785 A1 | 11/2007 | Heck et al. |
| 2007/0281900 A1 | 12/2007 | Cui et al. |
| 2007/0300329 A1 | 12/2007 | Allen et al. |
| 2008/0022423 A1 | 1/2008 | Roberts et al. |
| 2008/0050342 A1 | 2/2008 | Fire et al. |
| 2008/0092256 A1 | 4/2008 | Kohn |
| 2008/0155716 A1 | 6/2008 | Sonnewald et al. |
| 2008/0214443 A1* | 9/2008 | Baum et al. .......... 514/8 |
| 2009/0011934 A1 | 1/2009 | Zawierucha et al. |
| 2009/0018016 A1 | 1/2009 | Duck et al. |
| 2009/0036311 A1 | 2/2009 | Witschel et al. |
| 2009/0054240 A1 | 2/2009 | Witschel et al. |
| 2009/0098614 A1 | 4/2009 | Zamore et al. |
| 2009/0118214 A1 | 5/2009 | Paldi et al. |
| 2009/0137395 A1 | 5/2009 | Chicoine et al. |
| 2009/0165153 A1 | 6/2009 | Wang et al. |
| 2009/0165166 A1 | 6/2009 | Feng et al. |
| 2009/0205079 A1 | 8/2009 | Kumar et al. |
| 2009/0215628 A1 | 8/2009 | Witschel et al. |
| 2009/0293148 A1 | 11/2009 | Ren et al. |
| 2009/0298787 A1* | 12/2009 | Raemaekers et al. .......... 514/44 |
| 2009/0307803 A1 | 12/2009 | Baum et al. |
| 2010/0005551 A1 | 1/2010 | Roberts et al. |
| 2010/0068172 A1 | 3/2010 | Van De Craen |
| 2010/0071088 A1 | 3/2010 | Sela et al. |
| 2010/0099561 A1 | 4/2010 | Selby et al. |
| 2010/0152443 A1 | 6/2010 | Hirai et al. |
| 2010/0154083 A1 | 6/2010 | Ross et al. |
| 2010/0247578 A1 | 9/2010 | Salama |
| 2011/0015084 A1 | 1/2011 | Christian et al. |
| 2011/0015284 A1 | 1/2011 | Dees et al. |
| 2011/0053226 A1 | 3/2011 | Rohayem |
| 2011/0098180 A1 | 4/2011 | Michel et al. |
| 2011/0105329 A1 | 5/2011 | Song et al. |
| 2011/0112570 A1 | 5/2011 | Mannava et al. |
| 2011/0126310 A1 | 5/2011 | Feng et al. |
| 2011/0126311 A1 | 5/2011 | Velcheva et al. |
| 2011/0152339 A1 | 6/2011 | Brown et al. |
| 2011/0152346 A1 | 6/2011 | Karleson et al. |
| 2011/0152353 A1 | 6/2011 | Koizumi |
| 2011/0160082 A1 | 6/2011 | Woo et al. |
| 2011/0166022 A1 | 7/2011 | Israels et al. |
| 2011/0171176 A1 | 7/2011 | Baas et al. |
| 2011/0171287 A1 | 7/2011 | Saarma et al. |
| 2011/0177949 A1 | 7/2011 | Krapp et al. |
| 2011/0185444 A1 | 7/2011 | Li et al. |
| 2011/0185445 A1 | 7/2011 | Bogner et al. |
| 2011/0191897 A1 | 8/2011 | Poree et al. |
| 2011/0201501 A1 | 8/2011 | Song et al. |
| 2011/0296555 A1 | 12/2011 | Ivashuta et al. |
| 2011/0296556 A1 | 12/2011 | Sammons et al. |
| 2012/0036594 A1 | 2/2012 | Cardoza et al. |
| 2012/0107355 A1 | 5/2012 | Harris et al. |
| 2012/0108497 A1 | 5/2012 | Paldi et al. |
| 2012/0137387 A1 | 5/2012 | Baum et al. |
| 2012/0150048 A1 | 6/2012 | Kang et al. |
| 2012/0156784 A1 | 6/2012 | Adams, Jr. et al. |
| 2012/0164205 A1 | 6/2012 | Baum et al. |
| 2012/0185967 A1 | 7/2012 | Sela et al. |
| 2012/0230565 A1 | 9/2012 | Steinberg et al. |
| 2012/0258646 A1 | 10/2012 | Sela et al. |
| 2013/0047297 A1 | 2/2013 | Sammons et al. |
| 2013/0060133 A1 | 3/2013 | Kassab et al. |
| 2013/0067618 A1 | 3/2013 | Ader et al. |
| 2013/0097726 A1 | 4/2013 | Ader et al. |
| 2013/0212739 A1* | 8/2013 | Giritch et al. ............. 800/279 |
| 2013/0226003 A1 | 8/2013 | Edic et al. |
| 2013/0247247 A1 | 9/2013 | Ader et al. |
| 2013/0254940 A1 | 9/2013 | Ader et al. |
| 2013/0254941 A1 | 9/2013 | Ader et al. |
| 2013/0288895 A1 | 10/2013 | Ader et al. |
| 2013/0318657 A1 | 11/2013 | Avniel et al. |
| 2013/0318658 A1 | 11/2013 | Ader et al. |
| 2013/0324842 A1 | 12/2013 | Mittal et al. |
| 2013/0326731 A1 | 12/2013 | Ader et al. |
| 2014/0018241 A1 | 1/2014 | Sammons et al. |
| 2014/0057789 A1 | 2/2014 | Sammons et al. |
| 2014/0109258 A1 | 4/2014 | Van De Craen et al. |
| 2014/0230090 A1 | 8/2014 | Avniel et al. |
| 2014/0274712 A1 | 9/2014 | Finnessy et al. |
| 2014/0296503 A1 | 10/2014 | Avniel et al. |

FOREIGN PATENT DOCUMENTS

| | | |
|---|---|---|
| DE | 10000600 A1 | 7/2001 |
| DE | 10116399 A1 | 10/2002 |
| DE | 10256353 A1 | 6/2003 |
| DE | 10256354 A1 | 6/2003 |
| DE | 10256367 A1 | 6/2003 |
| DE | 10204951 A1 | 8/2003 |
| DE | 10234875 A1 | 2/2004 |
| DE | 10234876 A1 | 2/2004 |
| DE | 102004054666 A1 | 5/2006 |
| DE | 102005014638 A1 | 10/2006 |
| DE | 102005014906 A1 | 10/2006 |
| DE | 102007012168 A1 | 9/2008 |
| DE | 102010042866 A1 | 5/2011 |
| EP | 1 157 991 A2 | 11/2001 |

(56) References Cited

FOREIGN PATENT DOCUMENTS

| | | |
|---|---|---|
| EP | 1 238 586 A1 | 9/2002 |
| EP | 1 416 049 A1 | 5/2004 |
| EP | 1416049 A1 | 5/2004 |
| EP | 2 147 919 A1 | 1/2010 |
| EP | 2 160 098 B1 | 11/2010 |
| EP | 2 530 159 A1 | 3/2011 |
| JP | 06343473 | 12/1994 |
| JP | 2001253874 A | 9/2001 |
| JP | 2002080454 A | 3/2002 |
| JP | 2002138075 A | 5/2002 |
| JP | 2002145707 A | 5/2002 |
| JP | 2002220389 A | 8/2002 |
| JP | 2003064059 A | 3/2003 |
| JP | 2003096059 A | 4/2003 |
| JP | 2004051628 A | 2/2004 |
| JP | 2004107228 A | 4/2004 |
| JP | 2005008583 A | 1/2005 |
| JP | 2005239675 A | 9/2005 |
| JP | 2005314407 A | 11/2005 |
| JP | 2006232824 A | 9/2006 |
| JP | 2006282552 A | 10/2006 |
| JP | 2007153847 A | 6/2007 |
| JP | 2007161701 A | 6/2007 |
| JP | 2007182404 A | 7/2007 |
| JP | 2008074840 A | 4/2008 |
| JP | 2008074841 A | 4/2008 |
| JP | 2008133207 A | 6/2008 |
| JP | 2008133218 A | 6/2008 |
| JP | 2008169121 A | 7/2008 |
| JP | 2009067739 A | 4/2009 |
| JP | 2009114128 A | 5/2009 |
| JP | 2009126792 A | 6/2009 |
| JP | 2009137851 A | 6/2009 |
| WO | WO 89/11789 | 12/1989 |
| WO | WO 89/11789 A1 | 12/1989 |
| WO | 9605721 A1 | 2/1996 |
| WO | WO 96/33270 A1 | 10/1996 |
| WO | WO 96/38567 A2 | 12/1996 |
| WO | WO 96/40964 A2 | 12/1996 |
| WO | WO 99/24585 A1 | 5/1999 |
| WO | WO 99/26467 A1 | 6/1999 |
| WO | WO 99/27116 | 6/1999 |
| WO | WO 99/27116 A2 | 6/1999 |
| WO | WO 99/32619 | 7/1999 |
| WO | WO 99/32619 A1 | 7/1999 |
| WO | WO 99/61631 | 12/1999 |
| WO | WO 00/44914 | 8/2000 |
| WO | WO 02/14472 A2 | 2/2002 |
| WO | WO 03/000679 A2 | 1/2003 |
| WO | WO 03/006422 A1 | 1/2003 |
| WO | WO 03/013247 A1 | 2/2003 |
| WO | WO 03/016308 A1 | 2/2003 |
| WO | WO 03/020704 A1 | 3/2003 |
| WO | WO 03/022051 A1 | 3/2003 |
| WO | WO 03/022831 A1 | 3/2003 |
| WO | WO 03/022843 A1 | 3/2003 |
| WO | WO 03/029243 A2 | 4/2003 |
| WO | WO 03/037085 A1 | 5/2003 |
| WO | WO 03/037878 A1 | 5/2003 |
| WO | WO 03/045878 A2 | 6/2003 |
| WO | WO 03/050087 A2 | 6/2003 |
| WO | WO 03/051823 A1 | 6/2003 |
| WO | WO 03/051824 A1 | 6/2003 |
| WO | WO 03/051846 A2 | 6/2003 |
| WO | WO 03/076409 A1 | 9/2003 |
| WO | WO 03/077648 A2 | 9/2003 |
| WO | WO 03/087067 A1 | 10/2003 |
| WO | WO 03/090539 A1 | 11/2003 |
| WO | WO 03/091217 A1 | 11/2003 |
| WO | WO 03/093269 A2 | 11/2003 |
| WO | WO 03/104206 A2 | 12/2003 |
| WO | WO 03/106636 A2 | 12/2003 |
| WO | WO 2004/002947 A1 | 1/2004 |
| WO | WO 2004/002981 A2 | 1/2004 |
| WO | WO 2004/005485 A2 | 1/2004 |
| WO | WO 2004/009761 | 1/2004 |
| WO | WO 2004/009761 A2 | 1/2004 |
| WO | WO 2004/011429 A1 | 2/2004 |
| WO | 2004022771 A2 | 3/2004 |
| WO | WO 2004/029060 A1 | 4/2004 |
| WO | WO 2004/035545 A2 | 4/2004 |
| WO | WO 2004/035563 A1 | 4/2004 |
| WO | WO 2004/035564 A1 | 4/2004 |
| WO | WO 2004/037787 A1 | 5/2004 |
| WO | WO 2004/049806 A1 | 6/2004 |
| WO | WO 2004/067518 A1 | 8/2004 |
| WO | WO 2004/067527 A1 | 8/2004 |
| WO | WO 2004/074443 | 9/2004 |
| WO | WO 2004/074443 A2 | 9/2004 |
| WO | WO 2004/077950 A1 | 9/2004 |
| WO | WO 2005/000824 A1 | 1/2005 |
| WO | WO 2005/003362 | 1/2005 |
| WO | WO 2005/003362 A2 | 1/2005 |
| WO | WO 2005/007627 A1 | 1/2005 |
| WO | WO 2005/040152 A1 | 5/2005 |
| WO | WO 2005/047233 A1 | 5/2005 |
| WO | WO 2005/047281 A1 | 5/2005 |
| WO | WO 2005/061443 A2 | 7/2005 |
| WO | WO 2005/061464 A1 | 7/2005 |
| WO | WO 2005/068434 A1 | 7/2005 |
| WO | WO 2005/070889 A1 | 8/2005 |
| WO | WO 2005/089551 A1 | 9/2005 |
| WO | WO 2005/095335 A1 | 10/2005 |
| WO | WO 2005/107437 | 11/2005 |
| WO | WO 2005/107437 A1 | 11/2005 |
| WO | WO 2005/110068 A2 | 11/2005 |
| WO | WO 2006/006569 A1 | 1/2006 |
| WO | WO 2006/024820 A1 | 3/2006 |
| WO | WO 2006/029828 A1 | 3/2006 |
| WO | WO 2006/029829 A1 | 3/2006 |
| WO | WO 2006/037945 A1 | 4/2006 |
| WO | WO 2006/050803 A1 | 5/2006 |
| WO | WO 2006/074400 A2 | 7/2006 |
| WO | WO 2006/090792 A1 | 8/2006 |
| WO | WO 2006/123088 A2 | 11/2006 |
| WO | WO 2006/125687 A1 | 11/2006 |
| WO | WO 2006/125688 A1 | 11/2006 |
| WO | WO 2006/138638 A1 | 12/2006 |
| WO | WO 2007/003294 A1 | 1/2007 |
| WO | WO 2007/007316 A1 | 1/2007 |
| WO | WO 2007/024783 | 3/2007 |
| WO | WO 2007/026834 A1 | 3/2007 |
| WO | WO 2007/035650 A2 | 3/2007 |
| WO | WO 2007/039454 | 4/2007 |
| WO | WO 2007/039454 A1 | 4/2007 |
| WO | WO 2007/071900 A1 | 6/2007 |
| WO | WO 2007070389 A2 * | 6/2007 |
| WO | WO 2007/074405 A2 | 7/2007 |
| WO | WO 2007/077201 A1 | 7/2007 |
| WO | WO 2007/077247 A1 | 7/2007 |
| WO | WO 2007/080126 A2 | 7/2007 |
| WO | WO 2007/080127 A2 | 7/2007 |
| WO | WO 2007/096576 A1 | 8/2007 |
| WO | WO 2007/119434 A1 | 10/2007 |
| WO | WO2007051462 | 10/2007 |
| WO | WO 2007/134984 A1 | 11/2007 |
| WO | WO 2008/007100 A2 | 1/2008 |
| WO | WO 2008/009908 A1 | 1/2008 |
| WO | WO 2008/029084 A1 | 3/2008 |
| WO | WO 2008/059948 A1 | 5/2008 |
| WO | WO 2008/063203 A2 | 5/2008 |
| WO | WO 2008/071918 A1 | 6/2008 |
| WO | WO 2008/074991 A1 | 6/2008 |
| WO | WO 2008/084073 A1 | 7/2008 |
| WO | WO 2008/100426 A2 | 8/2008 |
| WO | WO 2008/102908 A1 | 8/2008 |
| WO | WO 2008/148223 A1 | 12/2008 |
| WO | WO 2008/152072 A2 | 12/2008 |
| WO | WO 2008/152073 A2 | 12/2008 |
| WO | WO 2009/000757 A1 | 12/2008 |
| WO | WO 2009/005297 A2 | 1/2009 |
| WO | WO 2009/035150 A2 | 3/2009 |
| WO | WO 2009/046384 A1 | 4/2009 |
| WO | WO 2009/063180 A1 | 5/2009 |

(56) References Cited

FOREIGN PATENT DOCUMENTS

| | | |
|---|---|---|
| WO | WO 2009/068170 A2 | 6/2009 |
| WO | WO 2009/068171 A2 | 6/2009 |
| WO | WO 2009/086041 A1 | 7/2009 |
| WO | WO 2009/090401 A2 | 7/2009 |
| WO | WO 2009/090402 A2 | 7/2009 |
| WO | WO 2009/115788 A1 | 9/2009 |
| WO | WO 2009/116558 A1 | 9/2009 |
| WO | WO 2009/125401 A2 | 10/2009 |
| WO | WO 2009/152995 A1 | 12/2009 |
| WO | WO 2009/158258 A1 | 12/2009 |
| WO | WO 2010/012649 A1 | 2/2010 |
| WO | WO 2010/026989 A1 | 3/2010 |
| WO | WO 2010/034153 A1 | 4/2010 |
| WO | WO 2010/049270 A1 | 5/2010 |
| WO | WO 2010/049369 A1 | 5/2010 |
| WO | WO 2010/049405 A1 | 5/2010 |
| WO | WO 2010/049414 A1 | 5/2010 |
| WO | WO 2010/063422 A1 | 6/2010 |
| WO | WO 2010/069802 A1 | 6/2010 |
| WO | WO 2010/078906 A2 | 7/2010 |
| WO | WO 2010/078912 A1 | 7/2010 |
| WO | WO 2010/104217 A1 | 9/2010 |
| WO | WO 2010/108611 A1 | 9/2010 |
| WO | WO 2010/112826 A2 | 10/2010 |
| WO | WO 2010/116122 A2 | 10/2010 |
| WO | WO 2010/119906 A1 | 10/2010 |
| WO | WO 2010/130970 A1 | 11/2010 |
| WO | WO 2011/001434 A1 | 1/2011 |
| WO | WO 2011/003776 A2 | 1/2011 |
| WO | WO 2011/035874 A1 | 3/2011 |
| WO | WO 2011/065451 A1 | 6/2011 |
| WO | WO 2011/067745 A2 | 6/2011 |
| WO | WO 2011/080674 A2 | 7/2011 |
| WO | WO 2011/112570 | 9/2011 |
| WO | WO 2011/112570 A1 | 9/2011 |
| WO | WO 2011/132127 A1 | 10/2011 |
| WO | WO 2012/001626 A1 | 1/2012 |
| WO | WO 2012/056401 A1 | 5/2012 |
| WO | WO 2012/092580 A2 | 7/2012 |
| WO | WO 2013/010691 A1 | 1/2013 |
| WO | WO 2013/025670 A1 | 2/2013 |
| WO | WO 2013/039990 A1 | 3/2013 |
| WO | WO 2013/040005 A1 | 3/2013 |
| WO | WO 2013/040021 A1 | 3/2013 |
| WO | WO 2013/040033 A1 | 3/2013 |
| WO | WO 2013/040049 A1 | 3/2013 |
| WO | WO 2013/040057 A1 | 3/2013 |
| WO | WO 2013/040116 A9 | 3/2013 |
| WO | WO 2013/040117 A9 | 3/2013 |
| WO | WO 2013/175480 A1 | 11/2013 |
| WO | WO 2014/106837 A2 | 7/2014 |
| WO | WO 2014/106838 A2 | 7/2014 |
| WO | WO 2014/151255 A1 | 9/2014 |
| WO | WO 2014/164761 A1 | 10/2014 |
| WO | WO 2014/164797 A1 | 10/2014 |

OTHER PUBLICATIONS

Hunter et al "RNA Interference Strategy to suppress Psyllids & Leafhoppers" International Plant and Animal Genome XIX, Jan. 15-19, 2011.
International Search Report and Written Opinion for PCT/US11/27528 mailed May 10, 2011.
Gan et al "Bacterially expressed dsRNA protects maize against SCMV infection" Plant Cell Rep (2010) 11:1261-1268.
Tenllado et al "Crude extracts of bacterially expressed dsRNA can be used to protect plants against virus infection" BMC Biotechnology (2003) 3(3):1-11.
Sun et al "Antisense oligodeoxynucleotide inhibition as a potent strategy in plant biology: identification of SUSIBA2 as a transcriptional activator in plant sugar signalling" The Plant Journal (2005) 44:128-138.
Balcombe "RNA silencing and heritable epigenetic effects in tomato and *Arabidopsis*" Abstract 13th Annual Fall Symposium, Plant Genomes to Phenomes, Donald Danforth Plant Science Center, Sep. 28-30, 2011.
Himber et al "Transitivity-dependant and -independent cell-to-cell movement of RNA silencing" The EMBO Journal (2003) 22(17):4523-4533.
Ryabov et al "Cell-to-Cell, but Not Long-Distance, Spread of RNA Silencing That Is Induced in Individual Epidermal Cells" Journal of Virology (2004) 78(6):3149-3154.
CN101914540 Patent Disclosure "Introduction of RNA into plant by interference" (Aug. 9, 2010) with translation.
COST Action FA0806 progress report "Plant virus control employing RNA-based vaccines: A novel non-transgenic strategy" (2010).
European Cooperation in the field of Scientific and Technical Research—Memorandum of Understanding for COST Action FA0806 (2008).
Devgen "The mini-Monsanto" KBC Securities (2006).
Clough "Floral dip: a simplified method for *Agrobacterium*-mediated transformation of *Arabidopsis thaliana*" The Plant Journal (1998) 16(6):735-743.
Nowak et al "A new and efficient method for inhibition of RNA viruses by DNA interference" The FEBS Journal (2009) 276:4372-4380.
Klahre et al "High molecular weight RNAs and small interfering RNAs induce systemic posttranscriptional gene silencing in plants" PNAS (2002) 99(18):11981-11986.
Liu et al "Comparative study on the interaction of DNA with three different kinds of surfactants and the formation of multilayer films" Bioelectrochemistry (2007) 70:301-307.
Melnyk et al "Intercellular and systemic movement of RNA silencing signals" The EMBO Journal (2011) 30:3553-3563.
Reddy et al "Organosilicone Adjuvants Increased the Efficacy of Glyphosate for Control of Weeds in *Citrus* (*Citrus* spp.)" HortScience (1992) 27(9):1003-1005.
Zhu et al "Ingested RNA interference for managing the populations of the Colorado potato beetle, *Leptinotarsa decemlineata*" Pest Manag Sci (2010) 67:175-182.
Maas et al "Mechanism and optimized conditions for PEG mediated DNA transfection into plant protoplasts" Plant Cell Reports (1989) 8:148-151.
Wardell "Floral Activity in Solutions of Deoxyribonucleic Acid Extracted from Tobacco Stems" Plant Physiol (1976) 57:855-861.
Wardell "Floral Induction of Vegetative Plants Supplied a Purified Fraction of Deoxyribonucleic Acid from Stems of Flowering Plants" Plant Physiol (1977) 60:885-891.
Hewezi et al "Local infiltration of high- and low-molecular-weight RNA from silenced sunflower (*Helianthus annuus* L.) plants triggers post-transcriptional gene silencing in non-silenced plants" Plant Biotechnology Journal (2005) 3:81-89.
Zhao et al "*Phyllotreta striolata* (Coleoptera: Chrysomelidae):Arginine kinase cloning and RNAi-based pest control" European Journal of Entomology (2008) 105(5):815-822.
Hannon "RNA interference" Nature Publishing Group (2002) 481:244-251.
Tenllado et a "RNA interference as a new biotechnological tool for the control of virus diseases in plants" Virus Research (2004) 102:85-96.
Gong et al "Silencing of Rieske iron—sulfur protein using chemically synthesised siRNA as a potential biopesticide against *Plutella xylostella*" Pest Manag Sci (2011) 67:514-520.
Dunoyer et al "Small RNA Duplexes Function as Mobile Silencing Signals Between Plant Cells" Science (2010) 328:912-916.
Molnar et al "Small Silencing RNAs in Plants Are Mobile and Direct Epigenetic Modification in Recipient Cells" Science (2010) 328:872-875.
Sun et al "Sweet delivery—sugar translocators as ports of entry for antisense oligodeoxynucleotides in plant cells" The Plant Journal (2007) 52:1192-1198.
Vionnet et al "Systemic Spread of Sequence-Specific Transgene RNA Degradation in Plants Is Initiated by Localized Introduction of Ectopic Promoterless DNA" Cell (1998) 95:177-187.

(56) References Cited

OTHER PUBLICATIONS

An et al "Transient RNAi Induction against Endogenous Genes in *Arabidopsis* Protoplasts Using in Vitro-Prepared Double-Stranded RNA" Biosci Biotechnol Biochem (2005) 69(2):415-418.
YouTube video by General Electric Company "Silwet Surfactants," screen shot taken on Jan. 11, 2012 of video of www.youtube.com/watch?v=WBw7nXMqHk8 (uploaded Jul. 13, 2009).
Artymovich et al "Using RNA Interference" Basic Bio (2009) 5:7-12.
Li et al "The Fast Technique" Bio Med (2009) 5:6.
Zhang et al "*Agrobacterium*-Meditaed Transformation" Nature Protocols (2006) 1(2):1-6.
Paungfoot-Lonhienne et al "DNA Is Taken Up by Root Hairs and Pollen, and Stimulates Root and Pollen Tube Growth" Plant Physiology (2010) 153:799-805.
Paungfoot-Lonhienne et al "DNA uptake by *Arabidopsis* induces changes in the expression of CLE peptides which control root morphology" Plant Signaling & Behavior (2010) 5(9):1112-1114.
First Examination Report issued for New Zealand Application No. 601784 on Apr. 23, 2013.
Baerson et al., "Glyphosate-Resistant Goosegrass. Identification of Mutation in the Target Enzyme 5-Enolpyruvylshikimate-3-Phosphate Synthase" (2002) Plant Physiol., 129(3) 1265-1275.
Broderson and Voinnet, "The diversity of RNA silencing pathways in plants" (2006) Trends Genetics, 22(5):268-280.
Gaines et al., "Gene amplification confers glyphosate resistance in *Amaranthus paleri*" (2010) Proc. Natl. Acad. Sci. USA, 107(3)1029-1034.
Ge et al., "Rapid vacuolar sequestration: the horseweed glyphosate resistance mechanism" (2010) Pest Management, Sci. 66:345-348.
Hidayat et al., "Enhanced Metabolism of Fluazifop Acid in a Biotype of *Digitaria sanguinalis* Resistant to the Herbicide Fluazifop-P-Butyl" (1997) Pesticide Biochem Physiol., 57(2) 137-146.
Hirschberg et al., "Molecular Basis of Herbicide Resistance in *Amaranthus hybridus*" (1983), Science, 222:1346-1349.
Jones-Rhoades et al., "MicroRNAs and Their Regulatory Roles in Plants" (2006) Annu. Rev. Plant Biol., 57:19-53.
Kam et al., "Nanotube Molecular Transporters: Internalization of Carbon Nanotube-Protein Conjugates into Mammalian Cells" (2004) J. Am. Chem. Soc., 126(22):6850-6851.
Khodakovskaya et al., "Carbon Nanotubes Are Able to Penetrate Plant Seed Coat and Dramatically Affect Seed Germination and Plant Growth" (2009) ACS Nano 3(10):3221-3227.
Makoto Kusaba, "RNA interference in crop plants" (2004) Current Opinion in Biotechnology, 15(2) 139-143.
Liu et al., "Carbon Nanotubes as Molecular Transporters for Walled Plant Cells" (2009) Nano Lett., 9(3): 1007-1010.
Meins et al., "RNA Silencing Systems and Their Relevance to Plant Development" (2005) Annu. Rev. Cell Dev. Biol., 21:297-318.
Molnar et al., "Plant Virus-Derived Small Interfering RNAs Originate Predominantly from Highly Structured Single-Stranded Viral RNAs" (2005) Journal of Virology, 79(12) 7812-7818.
Palauqui et al., "Activation of systemic acquired silencing by localised introduction of DNA" (1999) Current Biology 9:59-66.
Paungfoot-Lonhienne et al., "DNA uptake by *Arabidopsis* induces changes in the expression of CLE peptides which control root morphology" (2010) Plant Signaling & Behavior, 5(9) 1112-1114.
Preston et al., "Multiple effects of a naturally occurring proline to threonine substitution within acetolactate synthase in two herbicide-resistant populations of *Lactuca serriola*" (2006) Pesticide Biochemistry and Physiology, 84(3) 227-235.
Chen Qiwei, "Progress in DNA interference," (2009) Progress in Veterinary Medicine, 30(1) 71-75.
Reddy et al., "Aminomethylphosphonic Acid Accumulation in Plant Species Treated with Glyphosate" (2008) J. Agric. Food Chem., 56(6) 2125-2130.
Tomari and Zamore, "Perspective: machines for RNAi" (2005) Genes & Dev., 19:517-529.
Vaucheret, "Post-transcriptional small RNA pathways in plants: mechanisms and regulations" (2006) Genes Dev., 20:759-771.

Wakelin et al., "A target-site mutation is present in a glyphosate-resistant *Lolium rigidum* population" (2006) Weed Research 46(5) 432-440.
Waterhouse et al., "Virus resistance and gene silencing in plants can be induced by simultaneous expression of sense and antisense RNA" (1998) Proc Natl Acad Sci USA, 95 13959-13964.
Australian Patent Examination report No. 1 issued Nov. 11, 2013 in Australian Application No. 2011224570.
Chinese Office Action issued Aug. 28, 2013 in Chinese Application No. 201180012795.2.
Colombian Office Action issued Aug. 2, 2013 in Application No. 12 152898.
Colombian Office Action issued Feb. 21, 2014 in Application No. 12 152898.
Eurasian Office Action issued Feb. 24, 2014 in Application No. 201201264.
European Supplemental Search Report issued Oct. 8, 2013 in Application No. 11753916.3.
Further Examination Report issued in New Zealand Patent Application No. 601784, by the Intellectual Property Office of New Zealand on May 16, 2014.
Second Chinese Office Action issued in Chinese Patent Application No. 201180012795.2, dated Jun. 10, 2014.
Mexican Office Action issued in Mexican Patent Application No. MX/a/2012/010479, dated Feb. 17, 2014.
Anonymous, "Do Monsanto have the next big thing?," Austalian Herbicide Resistance Initative (AHRI), XP007922963, retrieved on Jan. 19, 2015.
Busi et al., "Gene flow increases the initial frequency of herbicide resistance alleles in unselected *Lolium rigidum* populations," *Agriculture, Ecosystems and Environments*, 142:403-409 (2011).
Gressel et al., "A strategy to provide long-term control of weedy rice while mitigating herbicide resistance transgene flow, and its potential use for other crops with related weeds," *Pest Manag Sci*, 65:723-731 (2009).
Supplementary European Search Report issued on Jan. 21, 2015, in European Patent Application No. 12832415.9.
Supplementary European Search Report issued on Jan. 29, 2015, in European Patent Application No. 12831567.8.
Colbourne et al., "The Ecoresponsive Genome of *Daphnia pulex*," *Science*, 331:555-561 (2011).
Database EMBL CBIB *Daphnia*—XP-002732239 (2011).
Invitation to Pay Additional Fees dated Nov. 25, 2014, in International Application No. PCT/US2014/047204.
Kumar et al., "Sequencing, De Novo Assembly and Annotation of the Colorado Potato Beetle, *Leptinotarsa decemlineata*,Transcriptome," *PLoS One*, 9(1):e86012 (2014).
Kusaba, "RNA interference in crop plants," *Curr Opin Biotechnol*, 15(2):139-143 (2004).
Llave et al., "Endogenous and Silencing-Associated Small RNAs in Plants," *The Plant Cell*, 14:1605-1619 (2002).
Molnar et al., "Plant Virus-Derived Small Interfering RNAs Originate redominantly from Highly Structured Single-Stranded Viral RNAs," *Journal of Virology*, 79(12):7812-7818 (2005).
Office Action issued on Nov. 3, 2014, in Chinese Patent Application No. 201180012795.2.
Office Action issued on Nov. 19, 2014, in Eurasian Patent Application No. 201201264/28.
Office Action issued on Jan. 6, 2015, in Japanese Patent Application No. 2012-557165.
Alarcón-Reverte et al., "Resistance to ACCase-inhibiting herbicides in the weed *Lolium multiflorum*," *Comm. Appl. Biol. Sci.*, 73(4):899-902 (2008).
Amarzguioui et al., "An algorithm for selection of functional siRNA sequences," *Biochemical and Biophysical Research Communications*, 316:1050-1058 (2004).
Ambrus et al., "The Diverse Roles of RNA Helicases in RNAi," *Cell Cycle*, 8(21):3500-3505 (2009).
Anonymous, "A handbook for high-level expression and purification of 6xHis-tagged proteins," *The QIAexpressionist*, (2003).
Aoki et al., "In Vivo Transfer Efficiency of Antisense Oligonucleotides into the Myocardium Using HVJ-Liposome Method," *Biochem Biophys Res Commun*, 231:540-545 (1997).

(56) References Cited

OTHER PUBLICATIONS

Arpaia et al., "Production of transgenic eggplant (*Solanum melongena* L.) resistant to Colorado Potato Beetle (*Leptinotarsa decemlineata* Say)," (1997) *Theor. Appl. Genet.*, 95:329-334 (1997).
Artmymovich, "Using RNA interference to increase crop yield and decrease pest damage," *MMG 445 Basic Biotech.*, 5(1):7-12 (2009).
Axtell et al., "A Two-Hit Trigger for siRNA Biogenesis in Plants," *Cell*, 127:565-577 (2006).
Baerson et al., "Glyphosate-Resistant Goosegrass. Identification of a Mutation in the Target Enzyme 5-Enolpyruvylshikimate-3-Phosphate Synthase," *Plant Physiol.*, 129(3):1265-1275 (2002).
Bannerjee et al., "Efficient production of transgenic potato (*S. tuberosum* L. ssp. *Andigena*) plants via *Agrobacterium tumefaciens*-mediated transformation," *Plant Sci.*, 170:732 738 (2006).
Bayer et al., "Programmable ligand-controlled riboregulators of eukaryotic gene expression," *Nature Biotechnol.*, 23(3):337-343 (2005).
Beal, et al., "Second Structural Motif for Recognition of DNA by Oligonucleotide-Directed Triple-Helix Formation," *Science*, 251:1360-1363 (1992).
Becker et al., "Fertile transgenic wheat from microprojectile bombardment of scutellar tissue," *The Plant Journal*, 5(2):299-307 (1994).
Bhargava et al., "Long double-stranded RNA-mediated RNA interference as a tool to achieve site-specific silencing of hypothalamic neuropeptides," *Brain Research Protocols*, 13:115-125 (2004).
Boletta et al., "High Efficient Non-Viral Gene Delivery to the Rat Kidney by Novel Polycationic Vectors," *J. Am Soc. Nephrol.*, 7:1728 (1996).
Bolognesi et al., "Characterizing the Mechanism of Action of Double-Stranded RNA Activity against Western Corn Rootworm(*Diabrotica virgifera virgifera* LeConte)," PLoS ONE 7(10):e47534 (2012).
Bolter et al., "A chloroplastic inner envelope membrane protease is essential for plant development," *FEBS Letters*, 580:789-794 (2006).
Breaker et al., "A DNA enzyme with $Mg2^+$-dependent RNA phosphoesterase activity," *Chemistry and Biology*, 2:655-660 (1995).
Brodersen et al., "The diversity of RNA silencing pathways in plants," *Trends in Genetics*, 22(5):268-280 (2006).
Butler et al., "Priming and re-drying improve the survival of mature seeds of *Digitalis purpurea* during storage," *Annals of Botany*, 103:1261-1270 (2009).
Bytebier et al., "T-DNA organization in tumor cultures and transgenic plants of the monocotyledon *Asparagus officinalis*," *Proc. Natl. Acad. Sci. U.S.A.*, 84:5345-5349 (1987).
Chabbouh et al., "Cucumber mosaic virus in artichoke," *FAO Plant Protection Bulletin*, 38:52-53 (1990).
Chakravarty et al., "Genetic Transformation in Potato: Approaches and Strategies," *Amer J Potato Res*, 84:301 311 (2007).
Chee et al., "Transformation of Soybean (*Glycine max*) by Infecting Germinating Seeds with *Agrobacterium tumefaciens*," *Plant Physiol.*, 91:1212-1218 (1989).
Chen et al., "In Vivo Analysis of the Role of atTic20 in Protein Import into Chloroplasts," *The Plant Cell*, 14:641-654 (2002).
Cheng et al., "Production of fertile transgenic peanut (*Arachis hypogaea* L.) plants using *Agrobacterium tumefaciens*," *Plant Cell Reports*, 15:653-657 (1996).
Chi et al., "The Function of RH22, a DEAD RNA Helicase, in the Biogenesis of the 505 Ribosomal Subunits of *Arabidopsis* Chloroplasts," *Plant Physiology*, 158:693-707 (2012).
Cooney et al., "Site-Specific Oligonucleotide Binding Represses Transcription of the Human c-myc Gene in Vitro," *Science*, 241:456-459 (1988).
Dalmay et al., "An RNA-Depenedent RNA Polymerase Gene in *Arabidopsis* Is Required for Posttranscriptional Gene Silencing Mediated by a Transgene but Not by a Virus," *Cell*, 101:543-553 (2000).
Davidson et al., "Engineering regulatory RNAs," *TRENDS in Biotechnology*, 23(3):109-112 (2005).

De Block, et al. "Engineering herbicide resistance in plants by expression of a detoxifying enzyme," *EMBO J.* 6(9):2513-2519 (1987).
De Framond, "MINI-Ti: A New Vector Strategy for Plant Genetic Engineering," *Nature Biotechnology*, 1:262-269 (1983).
della-Cioppa et al., "Import of a precursor protein into chloroplasts is inhibited by the herbicide glyphosate," *The EMBO Journal*, 7(5):1299-1305 (1988).
Diallo et al., "Long Endogenous dsRNAs Can Induce Complete Gene Silencing in Mammalian Cells and Primary Cultures," *Oligonucleotides*, 13:381-392 (2003).
Du et al., "A systematic analysis of the silencing effects of an active siRNA at all single-nucleotide mismatched target sites," *Nucleic Acids Research*, 33(5):1671-1677 (2005).
Ellington et al., "In vitro selection of RNA molecules that bind specific ligands," *Nature*, 346:818-822 (1990).
Farooq et al., "Rice seed priming," *IPRN*, 30(2):45-48 (2005).
Fire et al., "Potent and specific genetic interference by double-stranded RNA in *Caenorhabditis elegans*," *Nature*, 391:806-811 (1998).
First Examination Report issued on Jul. 28, 2014, in New Zealand Patent Application No. 627060.
Fukuhara et al., "Enigmatic Double-Stranded RNA in Japonica Rice," *Plant Molecular Biology*, 21:1121-1130 (1993).
Fukuhara et al., "The Unusual Structure of a Novel RNA Replicon in Rice," *The Journal of Biological Chemistry*, 270(30):18147-18149 (1995).
Fukuhara et al., "The wide distribution of endornaviruses, large double-stranded RNA replicons with plasmid-like properties," *Archives of Virology*, 151:995-1002 (2006).
Gaines et al., "Gene amplification confers glyphosate resistance in *Amaranthus palmeri*," *Proc. Natl. Acad. Sci. USA*, 107(3):1029-1034 (2010).
Gallie et al., "Identification of the motifs within the tobacco mosaic virus 5'-leader responsible for enhancing translation," *Nucleic Acids Res.*, 20(17):4631-4638 (1992).
Ge et al., "Rapid vacuolar sequestration: the horseweed glyphosate resistance mechanism," *Pest Management Sci.*, 66:345-348 (2010).
GenBank Accession No. DY640489, PU2_plate27_F03 PU2 *Prunus persica* cDNA similar to expressed mRNA inferred from *Prunus persica* hypothetical domain/motif containing IPR011005:Dihydropteroate synthase-like, MRNA sequence (2006) [Retrieved on Feb. 4, 2013]. Retrieved from the internet <URL: http://www.ncbi.nlm.nih.gov/nucest/DY640489>.
GenBank Accession No. EU24568—"*Amaranthus hypochondriacus* acetolactate synthase (ALS) gene," (2007).
GenBank Accession No. FJ972198, *Solanum lycopersicum* cultivar Ailsa Craig dihydropterin pyrophosphokinase-dihydropteroate synthase (HPPK-DHPS) gene, complete cds (2010) [Retrieved on Nov. 26, 2012]. Retrieved from the internet ,URL: http://www.ncbi.nlm.nih.gov/nuccore/FJ972198>.
Gutensohn et al., "Functional analysis of the two *Arabidopsis* homologues of Toc34, a component of the chloroplast protein import apparatus," *The Plant Journal*, 23(6):771-783 (2000).
Haigh, "The Priming of Seeds: Investigation into a method of priming large quantities of seeds using salt solutions," Thesis submitted to Macquarie University (1983).
Hamilton et al., "Guidelines for the Identification and Characterization of Plant Viruses," *J. gen. Virol.*, 54:223-241 (1981).
Hamilton et al., "Two classes of short interfering RNA in RNA silencing," *EMBO J.*, 21(17):4671-4679 (2002).
Han et al., "Molecular Basis for the Recognition of Primary microRNAs by the Drosha-DGCR8 Complex," *Cell*, 125(5):887-901 (2006).
Hardegree, "Drying and storage effects on germination of primed grass seeds," *Journal of Range Management*, 47(3):196-199 (1994).
Herman et al., "A three-component dicamba O-demethylase from *Pseudomonas maltophilia*, strain DI-6: gene isolation, characterization, and heterologous expression," *J. Biol. Chem.*, 280: 24759-24767 (2005).
Hidayat et al., "Enhanced Metabolism of Fluazifop Acid in a Biotype of *Digitaria sanguinalis* Resistant to the Herbicide Fluazifop-P-Butyl," *Pesticide Biochem. Physiol.*, 57:137-146 (1997).

(56) References Cited

OTHER PUBLICATIONS

Hirschberg et al., "Molecular Basis of Herbicide Resistance in *Amaranthus hybridus,*" *Science,* 222:1346-1349 (1983).
Hoekema et al., "A binary plant vector strategy based on separation of *vir-* and T-region of the *Agrobacterium tumefaciens* Ti-plasmid," *Nature,* 303:179-180 (1983).
Hofgen et al., "Repression of Acetolactate Synthase Activity through Antisense Inhibition: Molecular and Biochemical Analysis of Transgenic Potato (*Solanum tuberosum* L. cv Desiree) Plants," *Plant Physiol.,* 107(2):469-477 (1995).
Hsieh et al., "A library of siRNA duplexes targeting the phosphoinositide 3-kinase pathway: determinants of gene silencing for use in cell-based screens," *Nucleic Acids Res.,* 32(3):893-901 (2004).
Huesken et al., "Design of a genome-wide siRNA library using an artificial neural network," *Nature Biotechnology,* 23(8): 995-1001 (2005).
Ichihara et al., "Thermodynamic instability of siRNA duplex is a prerequisite for dependable prediction of siRNA activities," *Nucleic Acids Res.,* 35(18):e123 (2007).
International Preliminary Report on Patentability issued on Sep. 11, 2014, in International Application No. PCT/IL13/50447.
International Search Report dated Mar. 12, 2013 in International Application No. PCT/US 12/54789.
International Search Report and the Written Opinion dated May 10, 2011, in International Application No. PCT/US 11/27528.
International Search Report and the Written Opinion dated Feb. 25, 2013, in International Application No. PCT/US 12/54883.
International Search Report and the Written Opinion dated Feb. 27, 2013, in International Application No. PCT/US 12/54814.
International Search Report and the Written Opinion dated Feb. 27, 2013, in International Application No. PCT/US 12/54842.
International Search Report and the Written Opinion dated Feb. 27, 2013, in International Application No. PCT/US 12/54862.
International Search Report and the Written Opinion dated Feb. 27, 2013, in International Application No. PCT/US 12/54894.
International Search Report and the Written Opinion dated Feb. 27, 2013, in International Application No. PCT/US 12/54974.
International Search Report and the Written Opinion dated Feb. 27, 2013, in International Application No. PCT/US 12/54980.
International Search Report and the Written Opinion dated Oct. 1, 2013, in International Application No. PCT/IL2013/050447.
International Search Report and the Written Opinion dated Jul. 15, 2014, in International Application No. PCT/US2014/025305.
International Search Report and the Written Opinion dated Jul. 22, 2014, in International Application No. PCT/IL2013/051083.
International Search Report and the Written Opinion dated Jul. 22, 2014, in International Application No. PCT/IL2013/051085.
International Search Report and the Written Opinion dated Jul. 24, 2014, in International Application No. PCT/US2014/026036.
International Search Report and Written Opinion dated Aug. 25, 2014, in International Application No. PCT/US2014/023503.
International Search Report and Written Opinion dated Aug. 27, 2014, in International Application No. PCT/US2014/023409.
Invitation to Pay Additional Fees dated May 6, 2014, in International Application No. PCT/IL2013/051083.
Invitation to Pay Additional Fees dated May 6, 2014, in International Application No. PCT/IL2013/051085.
Isaacs et al., "Engineered riboregulators enable post-transcriptional control of gene expression," *Nature Biotechnology,* 22(7):841-847 (2004).
Ji et al., "Regulation of small RNA stability: methylation and beyond," *Cell Research,* 22:624-636 (2012).
Jones-Rhoades et al., "MicroRNAs and Their Regulatory Roles in Plants," *Annu. Rev. Plant Biol.,* 57:19-53 (2006).
Josse et al., "A DELLA in Disguise: SPATULA Restrains the Growth of the Developing *Arabidopsis* Seedling," *Plant Cell,* 23:1337-1351 (2011).

Kam et al., "Nanotube Molecular Transporters: Internalization of Carbon Nanotube-Protein Conjugates into Mammalian Cells," *J. Am. Chem. Soc.,* 126(22):6850-6851 (2004).
Katoh et al., "Specific residues at every third position of siRNA shape its efficient RNAi activity," *Nucleic Acids Res.,* 35(4): e27 (2007).
Kertbundit et al., "In vivo random β-glucuronidase gene fusions in *Arabidopsis thaliana,*" *Proc. Natl. Acad. Sci. U S A.,* 88:5212-5216 (1991).
Khachigian, "DNAzymes: Cutting a path to a new class of therapeutics," *Curr Opin Mol Ther* 4(2):119-121 (2002).
Khodakovskaya et al., "Carbon Nanotubes Are Able to Penetrate Plant Seed Coat and Dramatically Affect Seed Germination and Plant Growth," *ACS Nano,* 3(10):3221-3227 (2009).
Klahre et al., "High molecular weight RNAs and small interfering RNAs induce systemic posttranscriptional gene silencing in plants," *Proc. Natl. Acad. Sci. USA,* PNAS, 99(18):11981-11986 (2002).
Kronenwett et al., "Oligodeoxyribonucleotide Uptake in Primary Human Hematopoietic Cells Is Enhanced by Cationic Lipids and Depends on the Hematopoietic Cell Subset," *Blood,* 91(3):852-862 (1998).
Kusaba, "RNA Interference in Crop Plants," *Curr Opin Biotechnol.,* 15(2):Abstract (2004).
Lavigne et al., "Enhanced antisense inhibition of human immunodeficiency virus type 1 in cell cultures by DLS delivery system," *Biochem Biophys Res Commun,* 237:566-571 (1997).
Lee et al., "Aptamer Database," *Nucleic Acids Research,* 32:D95-D100 (2004).
Lesnik et al., "Prediction of rho-independent transcriptional terminators in *Escherichia coli,*" *Nucleic Acids Research,* 29(17):3583-3594 (2001).
Li et al., "Establishment of a highly efficient transformation system for pepper (*Capicum annuum* L.)," *Plant Cell Reports,* 21: 785-788 (2003).
Li et al., "The FAST technique: a simplified *Agrobacterium*-based transformation method for transient gene expression analysis in seedlings of *Arabidopsis* and other plant species," *Plant Methods,* 5(6):1-15 (2009).
Liu et al., "Carbon Nanotubes as Molecular Transporters for Walled Plant Cells," *Nano Letters,* 9(3):1007-1010 (2009).
Liu et al., "DNAzyme-mediated recovery of small recombinant RNAs from a 5S rRNA-derived chimera expressed in *Escherichia coli,*" *BMC Biotechnology,* 10:85 (2010).
Lu et al., "RNA silencing in plants by the expression of siRNA duplexes," *Nucleic Acids Res.,* 32(21):e171 (2004).
Lu et al., "OligoWalk: an online siRNA design tool utilizing hybridization thermodynamics," *Nucleic Acids Research,* 36:W104-W108 (2008).
Luft, "Making sense out of antisense oligodeoxynucleotide delivery: getting there is half the fun," *J Mol Med,* 76:75-76 (1998).
Maher III et al., "Inhibition of DNA binding proteins by oligonucleotide-directed triple helix formation," *Science,* 245(4919):725-730 (1989).
Makkouk et al., "Virus Diseases of Peas, Beans, and Faba Bean in the Mediterranean region," *Adv Virus Res,* 84:367-402 (2012).
Mandal et al., "Adenine riboswitches and gene activation by disruption of a transcription terminator," *Nature Struct. Mol. Biol.,* 11(1):29-35 (2004).
Mandal et al., "Gene Regulation by Riboswitches," *Nature Reviews | Molecular Cell Biology,* 5:451-463 (2004).
Manoharan, "Oligonucleotide Conjugates as Potential Antisense Drugs with Improved Uptake, Biodistribution, Targeted Delivery, and Mechanism of Action," *Antisense & Nucleic Acid Drug Development,* 12:103-128 (2002).
Masoud et al., "Constitutive expression of an inducible β-1,3-glucanase in alfalfa reduces disease severity caused by the oomycete pathogen *Phytophthora megasperma* f. sp *medicaginis,* but does not reduce disease severity of chitincontaining fungi," *Transgenic Research,* 5:313-323 (1996).
Matveeva et al., "Prediction of antisense oligonucleotide efficacy by in vitro methods," *Nature Biotechnology,* 16:1374-1375 (1998).
Meinke, et al., "Identifying essential genes in *Arabidopsis thaliana,*" *Trends Plant Sci.,* 13(9):483-491 (2008).

(56) References Cited

OTHER PUBLICATIONS

Meins et al., "RNA Silencing Systems and Their Relevance to Plant Development," *Annu. Rev. Cell Dev. Biol.*, 21:297-318 (2005).
Misawa et al., "Functional expression of the *Erwinia uredovora* carotenoid biosynthesis gene crtI in transgenic plants showing an increase of β-carotene biosynthesis activity and resistance to the bleaching herbicide norflurazon," *The Plant Journal*, 4(5):833-840 (1993).
Misawa et al., "Expression of an *Erwinia* phytoene desaturase gene not only confers multiple resistance to herbicides interfering with carotenoid biosynthesis but also alters xanthophyll metabolism in transgenic plants," *The Plant Journal*, 6(4):481-489 (1994).
Miura et al., "The Balance between Protein Synthesis and Degradation in Chloroplasts Determines Leaf Variegation in *Arabidopsis* yellow variegated Mutants," *The Plant Cell*, 19:1313-1328 (2007).
Molnar et al., "Plant Virus-Derived Small Interfering RNAs Originate Predominantly from Highly Structured Single-Stranded Viral RNAs," *Journal of Virology*, 79(12):7812-7818 (2005).
Moriyama et al., "Double-stranded RNA in rice: a novel RNA replicon in plants," *Molecular & General Genetics*, 248(3):364-369 (1995).
Moriyama et al., "Stringently and developmentally regulated levels of a cytoplasmic double-stranded RNA and its high-efficiency transmission via egg and pollen in rice," *Plant Molecular Biology*, 31:713-719 (1996).
Morrissey et al., "Potent and persistent in vivo anti-HBV activity of chemically modified siRNAs," *Nat Biotechnol.* 23(8):1002-1007 (2005).
Moser et al., "Sequence-Specific Cleavage of Double Helical DNA by Triple Helix Formation," *Science*, 238:645-646 (1987).
Office Action issued on Oct. 8, 2014, in Mexican Patent Application MX/a/2012/010479.
Ongvarrasopone et al., "A Simple and Cost Effective Method to Generate dsRNA for RNAi Studies in Invertebrates," *Science Asia*, 33:35-39 (2007).
Paddison et al., "Stable suppression of gene expression by RNAi in mammalian cells," *Proc. Natl Acad. Sci. USA*, 99(3):1443-1448 (2002).
Parera et al., "Dehydration Rate after Solid Matrix Priming Alters Seed Performance of Shrunken-2 Corn," *J. Amer. Soc. Hort. Sci.*, 119(3):629-635 (1994).
Pei et al., "On the art of identifying effective and specific siRNAs," *Nature Methods*, 3(9):670-676 (2006).
Peretz et al., "A Universal Expression/Silencing Vector in Plants," *Plant Physiology*, 145:1251-1263 (2007).
Pornprom et al., "Glutamine synthetase mutation conferring target-site-based resistance to glufosinate in soybean cell selections," *Pest Manag Sci*, 2009; 65(2):216-222 (2009).
Preston et al., "Multiple effects of a naturally occurring proline to threonine substitution within acetolactate synthase in two herbicide-resistant populations of *Lactuca serriola*," *Pesticide Biochemistry and Physiology*, 84(3):227-235 (2006).
Rajur et al., "Covalent Protein—Oligonucleotide Conjugates for Efficient Delivery of Antisense Molecules," *Bioconjug Chem.*, 8:935-940 (1997).
Reddy et al., "Aminomethylphosphonic Acid Accumulation in Plant Species Treated with Glyphosate," *J. Agric. Food Chem.*, 56(6):2125-2130 (2008).
Reither et al., "Specificity of DNA triple helix formation analyzed by a FRET assay," *BMC Biochemistry*, 3:27 (2002).
Rey et al., "Diversity of Dicotyledenous-Infecting Geminiviruses and Their Associated DNA Molecules in Southern Africa, Including the South-West Indian Ocean Islands," *Viruses*, 4:1753-1791 (2012).
Reynolds et al., "Rational siRNA design for RNA interference," *Nature Biotechnology*, 22:326-330 (2004).
Ryan, "Human endogenous retroviruses in health and disease: a symbiotic perspective," *Journal of the Royal Society of Medicine*, 97:560-565 (2004).
Santoro et al., "A general purpose RNA-cleaving DNA enzyme," *Proc. Natl. Acad. Sci. USA*, 94:4262-4266 (1997).
Sathasivan et al., "Nucleotide sequence of a mutant acetolactate synthase gene from an imidazolinone-resistant *Arabidopsis thaliana* var. Columbia," *Nucleic Acids Research*, 18(8):2188-2193 (1990).
Schwab et al., "RNA silencing amplification in plants: Size matters," *PNAS*, 107(34):14945-14946 (2010).
Schwember et al., "Drying Rates following Priming Affect Temperature Sensitivity of Germination and Longevity of Lettuce Seeds," *HortScience*, 40(3):778-781 (2005).
Seidman et al., "The potential for gene repair via triple helix formation," *J Clin Invest.*, 112(4):487-494 (2003).
Selvarani et al., "Evaluation of seed priming methods to improve seed vigour of onion (*Allium cepa* cv. *aggregatum*) and carrot (*Daucus carota*)," *Journal of Agricultural Technology*, 7(3):857-867 (2011).
Sharma et al., "A simple and efficient *Agrobacterium*-mediated procedure for transformation of tomato," *J. Biosci.*, 34(3):423 433 (2009).
Sijen et al., "On the Role of RNA Amplification in dsRNA-Triggered Gene Silencing," *Cell*, 107:465-476 (2001).
Singh et al., "Absorption and translocation of glyphosate with conventional and organosilicone adjuvants," *Weed Biology and Management*, 8:104-111 (2008).
Steeves et al., "Transgenic soybeans expressing siRNAs specific to a major sperm protein gene suppress *Heterodera glycines* reproduction," *Funct. Plant Biol.*, 33:991-999 (2006).
Strat et al., "Specific and nontoxic silencing in mammalian cells with expressed long dsRNAs," *Nucleic Acids Research*, 34(13):3803-3810 (2006).
Sudarsan et al., "Metabolite-binding RNA domains are present in the genes of eukaryotes," *RNA*, 9:644-647 (2003).
Sun et al., "A Highly efficient Transformation Protocol for Micro-Tom, a Model Cultivar for Tomato Functional Genomics," *Plant Cell Physiol.*, 47(3):426-431 (2006).
Takasaki et al., "An Effective Method for Selecting siRNA Target Sequences in Mammalian Cells," *Cell Cycle*, 3:790-795 (2004).
Templeton et al., "Improved DNA: liposome complexes for increased systemic delivery and gene expression," *Nature Biotechnology*, 15:647-652 (1997).
Tepfer, "Risk assessment of virus resistant transgenic plants," *Annual Review of Phytopathology*, 40:467-491 (2002).
Thompson, et al., "CLUSTAL W: improving the sensitivity of progressive multiple sequence alignment through sequence weighting, position-specific gap penalties and weight matrix choice," *Nucl. Acids Res.*, 22(22):4673-4680 (1994).
Timmons et al., "Specific interference by ingested dsRNA," *Nature*, 395:854 (1998).
Tomari et al., "Perspective: machines for RNAi," *Genes & Dev.*, 19:517-529 (2005).
Töpfer et al., "Uptake and Transient Expression of Chimeric Genes in Seed-Derived Embryos," *Plant Cell*, 1:133-139 (1989).
Toriyama et al., "Transgenic Rice Plants After Direct Gene Transfer Into Protoplasts," *Bio/Technology*, 6:1072-1074 (1988).
Tran et al., "Control of specific gene expression in mammalian cells by co-expression of long complementary RNAs," *FEBS Lett.*;573(1-3):127-134 (2004).
Turina et al., "Tospoviruses in the Mediterranean Area," *Advances in Virus Research*, 84:403-437 (2012).
Tuschl, "RNA Interference and Small Interfering RNAs," *ChemBiochem.* 2(4):239-245 (2001).
Tuschl, "Expanding small RNA interference," *Nature Biotechnol.*, 20: 446-448 (2002).
Ui-Tei et al., "Guidelines for the selection of highly effective siRNA sequences for mammalian and chick RNA interference," *Nucleic Acids Res.*, 32(3): 936-948 (2004).
Unnamalai et al., "Cationic oligopeptide-mediated delivery of dsRNA for post-transcriptional gene silencing in plant cells," *FEBS Letters*, 566:307-310 (2004).
Unniraman et al., "Alternate Paradigm for Intrinsic Transcription Termination in Eubacteria," *The Journal of Biological Chemistry*, 276(45)(9):41850-41855 (2001).
Urayama et al., "Knock-down of *OsDCL2* in Rice Negatively Affects Maintenance of the Endogenous dsRNA Virus, *Oryza sativa* Endornavirus," *Plant and Cell Physiology*, 51(1):58-67 (2010).

(56) References Cited

OTHER PUBLICATIONS van de Wetering et al., "Specific inhibition of gene expression using a stably integrated, inducible small-interfering-RNA vector," *EMBO Rep.*, 4(6):609-615 (2003).
Vasil et al., "Herbicide Resistant Fertile Transgenic Wheat Plants Obtained by Microprojectile Bombardment of Regenerable Embryogenic Callus," *Bio/Technology*,10:667-674 (1992).
Vaucheret, "Post-transcriptional small RNA pathways in plants: mechanisms and regulations," *Genes Dev.*, 20:759-771 (2006).
Vencill et al., "Resistance of Weeds to Herbicides," *Herbicides and Environment*, 29:585-594 (2011).
Verma et al., "Modified oligonucleotides: synthesis and strategy for users," *Annu. Rev. Biochem.*, 67:99-134 (1998).
Vert et al., "An accurate and interpretable model for siRNA efficacy prediction," *BMC Bioinformatics*, 7:520 (2006).
Wakelin et al., "A target-site mutation is present in a glyphosate-resistant *Lolium rigidum* population," *Weed Res.* (Oxford), 46(5):432-440 (2006).
Walton et al., "Prediction of antisense oligonucleotide binding affinity to a structured RNA target," *Biotechnology and Bioengineering*, 65(1):1-9 (1999).
Wan et al., "Generation of Large Numbers of Independently Transformed Fertile Barley Plants," *Plant Physiol.*, 104:37-48 (1994).
Welch et al., "Expression of ribozymes in gene transfer systems to modulate target RNA levels," *Curr Opin Biotechnol.* 9(5):486-496 (1998).
Wilson, et al., "Transcription termination at intrinsic terminators: The role of the RNA hairpin," *Proc. Natl. Acad. Sci. USA*, 92:8793-8797 (1995).
Winkler et al., "Thiamine derivatives bind messenger RNAs directly to regulate bacterial gene expression," *Nature*, 419:952-956 (2002).
Written Opinion dated May 8, 2014, in International Application No. PCT/IL2013/050447.
Written Opinion mailed on Sep. 4, 2014, in Singapore Patent Application No. 201206152-9.
Yin et al., "Production of double-stranded RNA for interference with TMV infection utilizing a bacterial prokaryotic expression system," *Appl. Microbiol. Biotechnol.*, 84(2):323-333 (2009).
Zagnitko, "*Lolium regidum* clone LS1 acetyl-CoA carboxylase mRNA, partial cds; nuclear gene for plastid product," GenBank: AF359516.1, 2 pages (2001).
Zagnitko, et al., "An isoleucine/leucine residue in the carboxyltransferase domain of acetyl-CoA carboxylase is critical for interaction with aryloxyphenoxypropionate and cyclohexanedione inhibitors," *PNAS*, 98(12):6617-6622 (2001).
Zhang et al., "Transgenic rice plants produced by electroporation-mediated plasmid uptake into protoplasts," *The Plant Cell Rep.*, 7:379-384 (1988).
Zhang et al., "DEG: a database of essential genes," *Nucleic Acids Res.*, 32:D271-D272 (2004).
Zhang et al., "*Agrobacterium*-mediated transformation of *Arabidopsis thaliana* using the floral dip method," *Nature Protocols*, 1(2):1-6 (2006).
Zhang et al., "A novel rice gene, NRR responds to macronutrient deficiency and regulates root growth," *Mol Plant*, 5(1):63-72 (2012).
Chang et al., "Cellular Internalization of Fluorescent Proteins via Arginine-rich Intracellular Delivery Peptide in Plant Cells," *Plant Cell Physiol.*, 46(3): 482-488 (2005).
GenBank Accession No. GI:186478573, retrieved: Oct. 30, 2014, <http://www.ncbi.nlm.nih.gov/nuccore/186478573>.
Orbovic et al., "Foliar-Applied Surfactants and Urea Temporarily Reduce Carbon Assimilation of Grapefruit Leaves," J. Amer. Soc. Hort. Sci., 126(4): 486-490 (2001).
Schweizer et al., "Double-stranded RNA interferes with gene function at the single-cell level in cereals," *The Plant Journal*, 24(6): 895-903 (2000).
Silwet L-77 Spray Adjuvant for agricultural applications, Momentive Performance Materials, Mar. 2007.
The Seed Biology Place—Seed Technology and Biotechnology, Website Gerhard Leubner Lab, Royal Holloway, University of London, retrieved: May 19, 2015, <http://www.seedbiology.de/seedtechnology.asp>.
Waterhouse & Helliwell (2003), Exploring Plant Genomes by RNA-Induced Gene Silencing, Nature Reviews, Genetics, 4:29-38. [Published Jan. 2003].†
Tang et al., (2006), Efficient delivery of small interfering RNA to plant cells by a nanosecond pulsed laser-induced stress wave for posttranscriptional gene silencing. Plant Science, 171:375-381 [Published May 15, 2003].†
Fraley et al., (1982), Liposome-mediated delivery of tobacco mosaic virus RNA into tobacco protoplasts: A sensitive assay for monitoring liposome-protoplast interactions, Proc. Natl. Acad. Sci. USA., 79: 1859-1863. [Published Mar. 1982].†
Bart (2006) A novel system for gene silencing using siRNAs in rice leaf and stem-derived protoplasts, Plant Methods 2006, 2:13 [Published Jun. 29, 2006].†
Artymovich, K. (2009) Using RNA interference to increase crop yield and decrease pest damage. MMG 445 Basic Biotechnology eJournal. [Online] 5:1 Published: Nov. 29, 2009.†
Tenllado, F. et al., (2003) Crude extracts of bacterially expressed dsRNA can be used to protect plants against virus infections, BMC Biotechnology 2003, 3:3 [Published Mar. 20, 2003].†
Tenllado & Ruiz (2001), Double-Stranded RNA-Mediated Interference with PlantVirus Infection, Journal of Virology; 75(24): 12288-12297 [Published Dec. 2001].†
Sun et al., (2005) Antisense oligodeoxynucleotide inhibition as a potent strategy in plant biology: identification of SUSIBA2 as a transcriptional activator in plant sugar signaling, The Plant Journal 44(1)128-138. [Published Sep. 5, 2005].†
Basu et al., (2004) Weed genomics: new tools tounderstand weed biology, TRENDS in Plant Science 9 (8): 391-398 [Published Jul. 17, 2004].†
Roberts (2005), Fast-track applications: The potential for direct delivery of proteins and nucleic acids to plant cells for the discovery of gene function, Plant Methods 1 (12): 1-3 [Published Dec. 15, 2005].†
Busch et al., (2005) RNAi for discovery of novel cropprotection products. Pflanzenschutz-Nachrichten Bayer, vol. 58, No. 1, 34-50, ISSN 0340-1723. [Published 2005].†
Gao & Huang (2008) Nonviral Methods for siRNA Delivery, Molecular Pharmaceutics vol. 6, No. 3: 651-658 [Published Dec. 30, 2008].†
Al-Kaff et al., (2000) Plants rendered herbicide-susceptible by cauliflower mosaicvirus-elicited suppression of a 35S promoter-regulated transgene, Nature Biotechnology 18 (9), 995-999 [Published Sep. 2000].†
Unnamalai (2004) Cationic oligopeptide-mediated delivery of dsRNA for post-transcriptional gene silencing in plant cells, FEBS Letters 566 (1):307-310 [Published May 21, 2004].†

\* cited by examiner
† cited by third party

Figure 1

ATGGCTCAAGCTACTACCATCAACAATGGTGTCCATACTGGTCAATTGCACCATACTTTACCCAAAA
CCCAGTTACCCAAATCTTCAAAAACTCTTAATTTTGGATCAAACTTGAGAATTTCTCCAAAGTTCAT
GTCTTTAACCAATAAAAGAGTTGGTGGGCAATCATCAATTGTTCCCAAGATTCAAGCTTCTGTTGCT
GCTGCAGCTGAGAAACCTTCATCTGTCCCAGAAATTGTGTTACAACCCATCAAAGAGATCTCTGGTA
CTGTTCAATTGCCTGGGTCAAAGTCTTTATCCAATCGAATCCTTCTTTTAGCTGCTTTGTCTGAGGG
CACAACAGTGGTCGACAACTTGCTGTATAGTGATGATATTCTTTATATGTTGGACGCTCTCAGAACT
CTTGGTTTAAAAGTGGAGGATGATAGTACAGCCAAAAGGGCAGTCGTAGAGGGTTGTGGTGGTCTGT
TTCCTGTTGGTAAAGATGGAAAGGAAGAGATTCAACTTTTCCTTGGTAATGCAGGAACAGCGATGCG
CCCATTGACAGCTGCGGTTGCCGTTGCTGGAGGAAATTCAAGTTATGTGCTTGATGGAGTACCAAGA
ATGAGGGAGCGCCCCATTGGGGATCTGGTAGCAGGTCTAAAGCAACTTGGTTCAGATGTAGATTGTT
TTCTTGGCACAAATTGCCCTCCTGTTCGGGTCAATGCTAAAGGAGGCCTTCCAGGGGGCAAGGTCAA
GCTCTCTGGATCGGTTAGTAGCCAATATTTAACTGCACTTCTCATGGCTACTCCTTTGGGTCTTGGA
GACGTGGAGATTGAGATAGTTGATAAATTGATTTCTGTACCGTATGTTGAAATGACAATAAAGTTGA
TGGAACGCTTTGGAGTATCCGTAGAACATAGTGATAGTTGGGACAGGTTCTACATTCGAGGTGGTCA
GAAATACAAATCTCCTGGAAAGGCATATGTTGAGGGTGATGCTTCAAGTGCTAGCTACTTCCTAGCC
GGAGCCGCCGTCACTGGTGGGACTGTCACTGTCAAGGGTTGTGGAACAAGCAGTTTACAGGGTGATG
TAAAATTTGCCGAAGTTCTTGAGAAGATGGGTTGCAAGGTCACCTGGACAGAGAATAGTGTAACTGT
TACTGGACCACCCAGGGATTCATCTGGAAAGAAACATCTGCGTGCTATCGACGTCAACATGAACAAA
ATGCCAGATGTTGCTATGACTCTTGCAGTTGTTGCCTTGTATGCAGATGGGCCCACCGCCATCAGAG
ATGTGGCTAGCTGGAGAGTGAAGGAAACCGAACGGATGATTGCCATTTGCACAGAACTGAGAAAGCT
TGGGGCAACAGTTGAGGAAGGATCTGATTACTGTGTGATCACTCCGCCTGAAAAGCTAAACCCCACC
GCCATTGAAACTTATGACGATCACCGAATGGCCATGGCATTCTCTCTTGCTGCCTGTGCAGATGTTC
CCGTCACTATCCTTGATCCGGGATGCACCCGTAAAACCTTCCCGGACTACTTTGATGTTTTAGAAAA
GTTCGCCAAGCATTGA

SEQ ID NO:1

Figure 2

GGCCCATAGGCCTTTTTCTAAAATAGGCCCATTTAAGCTATTAACAATCTTCAAAAGTACCACATCG
CTTAGGTAAAGAAAGCAGCTGAGTTTATATATGGTTAGAGACGAAGTAGTGATTG*CGACGAGCGACG*
*TCTCGCCCTCATCGCAATCCACGCCATTGAGCTTGAGGCCATTGGCGACGGCCGAGAGGCGGTCGCT*
*T*AAGATTAGCATG*TCCTTGACGCGGAGTTCTTCCAGACCGTTCATCACGGTCGCCCCTTCCGCGAAG*
*GCGGCGGCGACAGCGAGAATCGGATATTCGTCGATCATCGAAGGCGCGCGGTCTTCCGGCACCGTG*A
CGCATAAAcacggtgccggaagaccgcgcgccttcgatgatcgacgaatatccgattctcgctgtcg
ccgccgcttcgcggaagggggcgaccgtgatgaacggtctggaagaactccgcgtcaaggaaagcga
ccgcctctcggccgtcgccaatggcctcaagctcaatggcgtggattgcgatgagggcgagacgtcg
ctcgtcgTTTTTTTTGGCAAAAA

SEQ ID NO:3

Figure 3
3A
3B
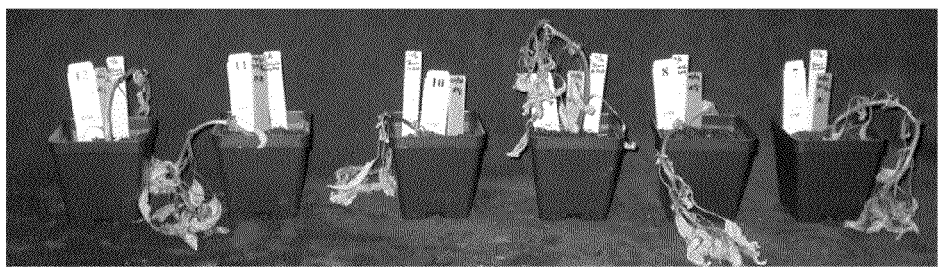
3C

Figure 5

```
ATGCCCCAAATCGGACTTGTATCTGCTGTTAATTTGAGAGTCCAAGGTAATTCAGCTTATCTTTGGA
GCTCGAGGTCTTCGTTGGGAACTGAAAGTCAAGATGTTTGCTTGCAAAGGAATTTGTTATGTTTTGG
TAGTAGCGACTCCATGGGGCATAAGTTAAGGATTCGTACTCCAAGTGCCACGACCCGAAGATTGACA
AAGGACTTTAATCCTTTAAAGGTAGTCTGCATTGATTATCCAAGACCAGAGCTAGACAATACAGTTA
ACTATTTGGAGGCGGCGTTATTATCATCATCGTTTCGTACTTCCTCACGCCCAACTAAACCATTGGA
GATTGTTATTGCTGGTGCAGGTTTGGGTGGTTTGTCTACAGCAAAATATCTGGCAGATGCTGGTCAC
AAACCGATATTGCTGGAGGCAAGAGATGTCCTAGGTGGGAAGGTAGCTGCATGGAAAGATGATGATG
GAGATTGGTACGAGACTGGGTTGCACATATTCTTTGGGGCTTACCCAAATATGCAGAACCTGTTTGG
AGAACTAGGGATTGATGATCGGTTGCAGTGGAAGGAACATTCAATGATATTTGCGATGCCTAACAAG
CCAGGGGAGTTCAGCCGCTTTGATTTTCCTGAAGCTCTTCCTGCGCCATTAAATGGAATTTTGGCCA
TACTAAAGAACAACGAAATGCTTACGTGGCCCGAGAAAGTCAAATTTGCTATTGGACTCTTGCCAGC
AATGCTTGGAGGGCAATCTTATGTTGAAGCTCAAGACGGTTTAAGTGTTAAGGACTGGATGAGAAAG
CAAGGTGTGCCTGATAGGGTGACAGATGAGGTGTTCATTGCCATGTCAAAGGCACTTAACTTCATAA
ACCCTGACGAGCTTTCGATGCAGTGCATTTTGATTGCTTTGAACAGATTTCTTCAGGAGAAACATGG
TTCAAAAATGGCCTTTTTAGATGGTAACCCTCCTGAGAGACTTTGCATGCCGATTGTGGAACATATT
GAGTCAAAAGGTGGCCAAGTCAGACTAAACTCACGAATAAAAAAGATCGAGCTGAATGAGGATGGAA
GTGTCAAATGTTTTATACTGAATAATGGCAGTACAATTAAAGGAGATGCTTTTGTGTTTGCCACTCC
AGTGGATATCTTGAAGCTTCTTTTGCCTGAAGACTGGAAAGAGATCCCATATTTCCAAAAGTTGGAG
AAGCTAGTGGGAGTTCCTGTGATAAATGTCCATATATGGTTTGACAGAAAACTGAAGAACACATCTG
ATAATCTGCTCTTCAGCAGAAGCCCGTTGCTCAGTGTGTACGCTGACATGTCTGTTACATGTAAGGA
ATATTACAACCCCAATCAGTCTATGTTGGAATTGGTATTTGCACCCGCAGAAGAGTGGATAAATCGT
AGTGACTCAGAAATTATTGATGCTACAATGAAGGAACTAGCGAAGCTTTTCCCTGATGAAATTTCGG
CAGATCAGAGCAAAGCAAAAATATTGAAGTATCATGTTGTCAAAACCCCAAGGTCTGTTTATAAAAC
TGTGCCAGGTTGTGAACCCTGTCGGCCCTTGCAAAGATCCCCTATAGAGGGTTTTTATTTAGCTGGT
GACTACACGAAACAGAAGTACTTGGCTTCAATGGAAGGTGCTGTCTTATCAGGAAAGCTTTGTGCAC
AAGCTATTGTACAGGATTACGAGTTACTTCTTGGCCGGAGCCAGAAGATGTTGGCAGAAGCAAGCGT
AGTTAGCATAGTGAACTAA
```

SEQ ID NO:2

Figure 10

```
>gi|93117609|gb|DQ469932.1| Nicotiana benthamiana
phytoene desaturase mRNA, complete cds
ATGCCCCAAATCGGACTTGTATCTGCTGTTAATTTGAGAGTCCAAGGTAATTCAGCTTATCTTTGGA
GCTCGAGGTCTTCGTTGGGAACTGAAAGTCAAGATGTTTGCTTGCAAAGGAATTTGTTATGTTTTGG
TAGTAGCGACTCCATGGGGCATAAGTTAAGGATTCGTACTCCAAGTGCCACGACCCGAAGATTGACA
AAGGACTTTAATCCTTTAAAGGTAGTCTGCATTGATTATCCAAGACCAGAGCTAGACAATACAGTTA
ACTATTTGGAGGCGGCGTTATTATCATCATCGTTTCGTACTTCCTCACGCCCAACTAAACCATTGGA
GATTGTTATTGCTGGTGCAGGTTTGGGTGGTTTGTCTACAGCAAAATATCTGGCAGATGCTGGTCAC
AAACCGATATTGCTGGAGGCAAGAGATGTCCTAGGTGGGAAGGTAGCTGCATGGAAAGATGATGATG
GAGATTGGTACGAGACTGGGTTGCACATATTCTTTGGGCTTACCCAAATATGCAGAACCTGTTTGG
AGAACTAGGGATTGATGATCGGTTGCAGTGGAAGGAACATTCAATGATATTTGCGATGCCTAACAAG
CCAGGGGAGTTCAGCCGCTTTGATTTTCCTGAAGCTCTTCCTGCGCCATTAAATGGAATTTTGGCCA
TACTAAAGAACAACGAAATGCTTACGTGGCCCGAGAAAGTCAAATTTGCTATTGGACTCTTGCCAGC
AATGCTTGGAGGGCAATCTTATGTTGAAGCTCAAGACGGTTTAAGTGTTAAGGACTGGATGAGAAAG
CAAGGTGTGCCTGATAGGGTGACAGATGAGGTGTTCATTGCCATGTCAAAGGCACTTAACTTCATAA
ACCCTGACGAGCTTTCGATGCAGTGCATTTTGATTGCTTTGA**ACAGATTTCTTCAGGAGAAACATGG
TTCAAAAATGGCCTTTTTAGATGGTAACCCTCCTGAGAGACTTTGCATGCCGATTGTGGAACATATT
GAGTCAAAAGGTGGCCAAGTCAGACTAAACTCACGAATAAAAAAGATCGAGCTGAATGAGGATGGAA
GTGTCAAATGTTTTATACTGAATAATGGCAGTACAATTAAA**GGAGATGCTTTTGTGTTTGCCACTCC
AGTGGATATCTTGAAGCTTCTTTTGCCTGAAGACTGGAAAGAGATCCCATATTTCCAAAAGTTGGAG
AAGCTAGTGGGAGTTCCTGTGATAAATGTCCATATATGGTTTGACAGAAAACTGAAGAACACATCTG
ATAATCTGCTCTTCAGCAGAAGCCCGTTGCTCAGTGTGTACGCTGACATGTCTGTTACATGTAAGGA
ATATTACAACCCCAATCAGTCTATGTTGGAATTGGTATTTGCACCCGCAGAAGAGTGGATAAATCGT
AGTGACTCAGAAATTATTGATGCTACAATGAAGGAACTAGCGAAGCTTTTCCCTGATGAAATTTCGG
CAGATCAGAGCAAAGCAAAAATATTGAAGTATCATGTTGTCAAAACCCCAAGGTCTGTTTATAAAAC
TGTGCCAGGTTGTGAACCCTGTCGGCCCTTGCAAAGATCCCCTATAGAGGGTTTTTATTTAGCTGGT
GACTACACGAAACAGAAGTACTTGGCTTCAATGGAAGGTGCTGTCTTATCAGGAAGCTTTGTGCAC
AAGCTATTGTACAGGATTACGAGTTACTTCTTGGCCGGAGCCAGAAGATGTTGGCAGAAGCAAGCGT
AGTTAGCATAGTGAACTAA
```

SEQ ID NO:2

Figure 12
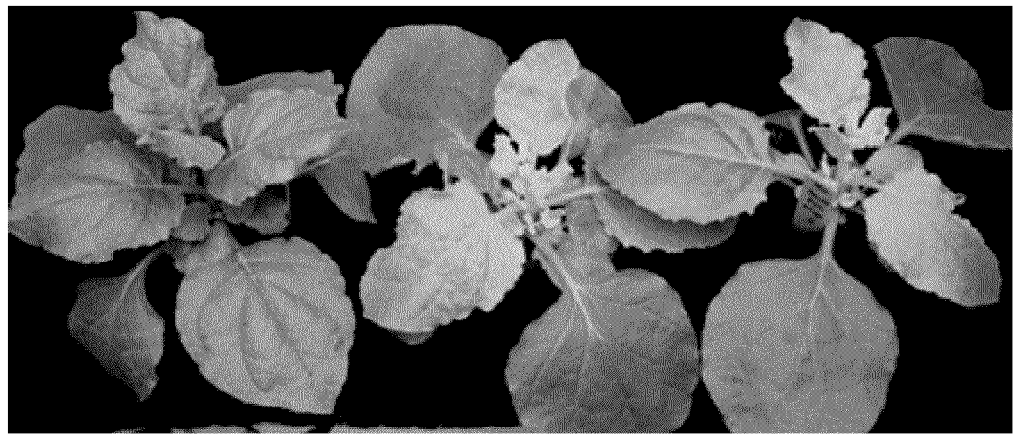
Control     200nt ds RNA     ssDNA oligos (1+2+3+4+5+6) SEQ ID NOs:16, 17, 20, 21, 24, 25, and 26
A
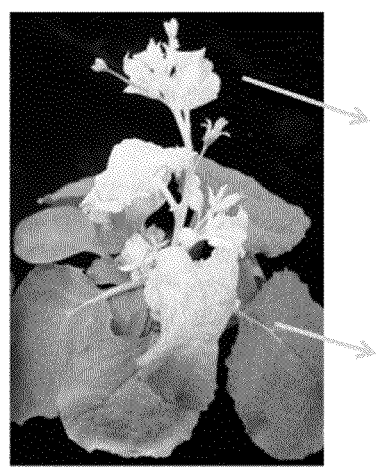
B

Figure 16

```
                             10                   20
Palmer       T-----CAA-------TTTCATCT-------ATTGGA-------AGTGAT      SEQ ID NO:37
             :::              ::  ::::       :::  ::         ::   :
Benthamiana  ATGCCCCAAATCGGACTTGTATCTGCTGTTAATTTGAGAGTCCAAGGTAA      SEQ ID NO:38
             10        20        30        40        50

30               40        50
Palmer       TT---------TTTGG--------GTCATTCTGTGAGAAATTTCAGTG--
             ::         :::::         :::  :::  :: :::  :     :::
Benthamiana  TTCAGCTTATCTTTGGAGCTCGAGGTC-TTCGTTGGGAACTGAAAGTCAA
             60        70        80        90

60
Palmer       -------------------TTAGTAAAGTTT----------------AT
                                ::  ::  :  ::::                ::
Benthamiana  GATGTTTGCTTGCAAAGGAATTTGTTATGTTTTGGTAGTAGCGACTCCAT
             100       110       120       130       140

70        80        90
Palmer       GGAGCA-AAGCAAAGAAATGGGC-----ACTGCC----------------
             :: ::: ::: ::: : :     :              : ::::
Benthamiana  GGGGCATAAGTTAAGGATTCGTACTCCAAGTGCCACGACCCGAAGATTGA
             150       160       170       180       190

100       110       120       130
Palmer       ---------------CTTTAAAGGTTGTTTGTATAGATTATCCTAGGCCA
                            :::::::::: :: ::  ::  :::::::::  :: :::
Benthamiana  CAAAGGACTTTAATCCTTTAAAGGTAGTCTGCATTGATTATCCAAGACCA
             200       210       220       230       240

140       150       160       170       180
Palmer       GAGCTTGAAAGTACATCCAATTTCTTGGAAGCCGCCTACTTATCTTCTAC
             ::::: ::  : ::::   ::  :  ::::: :: :: :  :::::  ::  :
Benthamiana  GAGCTAGACAATACAGTTAACTATTTGGAGGCGGCGTTATTATCATCATC
             250       260       270       280       290

190       200       210       220       230
Palmer       TTTTCGGAATTCGCCTCGTCCTCAGAAGCCATTAGAAGTTGTAATTGCTG
             :::::  :  :::   :  :: :: :        :: :::::   ::::  ::::::::
Benthamiana  GTTTCGTACTTCCTCACGCCCAACTAAACCATTGGAGATTGTTATTGCTG
             300       310       320       330       340

240       250       260       270       280
Palmer       GAGCAGGTTTGGCTGGTCTATCCACGGCAAAGTATTTAGCTGATGCAGGT
             :  :::::::::: ::::  :  :: ::  ::::: :::  ::: :::
Benthamiana  GTGCAGGTTTGGGTGGTTTGTCTACAGCAAAATATCTGGCAGATGCTGGT
                      350       360       370       380       390

290       300       310       320       330
Palmer       CACAAACCCATATTGTTGGAAGCACGAGATGTTTTAGGAGGAAAGGTTGC      SEQ ID NO:37
             :::::::::  ::::::  ::::  :::  :::::::  ::::  ::  :::::::  ::
Benthamiana  CACAAACCGATATTGCTGGAGGCAAGAGATGTCCTAGGTGGGAAGGTAGC      SEQ ID NO:38
             400       410       420       430       440
```

Figure 16 (continued)

```
                      340       350       360       370       380
Palmer       AGCGTGGAAGGATGAGGATGGTGACTGGTATGAGACTGGGCTACATATAT    SEQ ID NO:37
             ::  :::::  ::::: ::::: ::  :::::  ::::::::::  :  :: ::::
Benthamiana  TGCATGGAAAGATGATGATGGAGATTGGTACGAGACTGGGTTGCACATAT    SEQ ID NO:38
                 450       460       470       480       490

390       400       410       420       430
Palmer       TCTTTGGGGCATATCCAAATGTCCAAAATCTATTTGGAGAACTTGGTATA
             :::::::::::: ::  :::::: :  ::  ::  :::::::::: ::  ::
Benthamiana  TCTTTGGGGCTTACCCAAATATGCAGAACCTGTTTGGAGAACTAGGGATT
                 500       510       520       530       540

440       450       460       470       480
Palmer       AATGACCGACTGCAATGGAAGGAGCACTCTATGATTTTTGCAATGCCCAG
             ::::  ::  ::::  :::::::::: ::  :::::  :::::  :::::  :
Benthamiana  GATGATCGGTTGCAGTGGAAGGAACATTCAATGATATTTGCGATGCCTAA
                 550       560       570       580       590

490       500       510       520       530
Palmer       CAAGCCCGGTGAATTCAGTCGCTTTGATTTTCCCGAAATCCTGCCTGCAC
             ::::::  ::  ::  ::::::  :::::::::::::  :::         ::  :::::  :
Benthamiana  CAAGCCAGGGGAGTTCAGCCGCTTTGATTTTCCTGAAGCTCTTCCTGCGC
                 600       610       620       630       640

540       550       560       570       580
Palmer       CATTAAATGGCATATGGGCAATCCTAAGAAATAATGAAATGCTAACCTGG
             ::::::::::  ::  :::  ::  ::::   ::  :::::::::::  :::
Benthamiana  CATTAAATGGAATTTTGGCCATACTAAAGAACAACGAAATGCTTACGTGG
                 650       660       670       680       690

590       600       610       620       630
Palmer       CCAGAAAAAATCAAGTTTGCCATTGGCTTGTTGCCTGCTATGGCAGGCGG
             ::  ::  :::  ::::  :::::  ::::::   :::::  ::  :::        ::  ::
Benthamiana  CCCGAGAAAGTCAAATTTGCTATTGGACTCTTGCCAGCAATGCTTGGAGG
                 700       710       720       730       740

640       650       660       670       680
Palmer       ACAGTCATATGTTGAAGCACAAGATGGTTTGAGTGTCCAAGAGTGGATGA
             ::  ::  ::::::::::::  :::::  :::::  :::::     :  ::  ::::::::
Benthamiana  GCAATCTTATGTTGAAGCTCAAGACGGTTTAAGTGTTAAGGACTGGATGA
                 750       760       770       780       790

690       700       710       720       730
Palmer       GAAAACAAGGAGTACCCGATCGTGTAACTGATGATGTGTTTATTGCCATG
             ::::  :::::  ::  ::  :::  :  ::  ::  :::::  :::::  :::::::::
Benthamiana  GAAAGCAAGGTGTGCCTGATAGGGTGACAGATGAGGTGTTCATTGCCATG
                 800       810       820       830       840

740       750       760       770       780
Palmer       TCAAAGGCACTGAACTTCATAAATCCCGATGAACTTTCAATGCAGTGCAT    SEQ ID NO:37
             ::::::::::::: :::::::::::::::  ::  :::::::::  :::::::::::::
Benthamiana  TCAAAGGCACTTAACTTCATAAACCCTGACGAGCTTTCGATGCAGTGCAT    SEQ ID NO:38
                 850       860       870       880       890
```

Figure 16 (continued)

```
                    790        800        810        820        830
Palmer      CTTGATTGCTCTGAACCGATTCCTGCAGGAGAAACATGGTTCTAAGATGG    SEQ ID NO:37
            ::::::::::  :::::  ::::  ::  ::::::::::::::::::  ::  ::::
Benthamiana TTTGATTGCTTTGAACAGATTTCTTCAGGAGAAACATGGTTCAAAAATGG    SEQ ID NO:38
                    900        910        920        930        940

840        850        860        870        880
Palmer      CCTTCCTAGACGGAAACCCTCCAGAGAGGCTGTGCATGCCTATTGTTAAA
            ::::    ::::  ::  ::::::::::  :::::  ::  :::::::::  :::::  ::
Benthamiana CCTTTTTAGATGGTAACCCTCCTGAGAGACTTTGCATGCCGATTGTGGAA
                    950        960        970        980        990

890        900        910        920        930
Palmer      CACATCGAGTCACTAGGTGGTGAAGTTAAACTTAACTCTCGTATACAAAA
            ::  ::  ::::::    :::::::    ::::  :  :::  :::::  ::  :::  ::::
Benthamiana CATATTGAGTCAAAAGGTGGCCAAGTCAGACTAAAACTCACGAATAAAAAA
                    1000       1010       1020       1030       1040

940        950        960        970        980
Palmer      GATTCAGTTGGACCAGAGTGGAAGCGTGAAGAGTTTTTTGCTAAATAACG
            :::  ::  ::  ::    ::  ::::::  :::  ::  ::::::::::  ::::
Benthamiana GATCGAGCTGAATGAGGATGGAAGTGTCAAATGTTTTATACTGAATAATG
                    1050       1060       1070       1080       1090

990        1000       1010       1020       1030
Palmer      GGAGGGAAATACGAGGAGATGCCTATGTTTTTGCCACCCCAGTTGACATC
            :  ::    :::    :::::::::::  :  :::  ::::::::::  :::::  ::  :::
Benthamiana GCAGTACAATTAAAGGAGATGCTTTTGTGTTTGCCACTCCAGTGGATATC
                    1100       1110       1120       1130       1140

1040       1050       1060       1070       1080
Palmer      TTGAAGCTGTTACTACCTGATACTTGGAAGGAAATCTCATACTTCAAAAA
            ::::::::::  :  :  ::::::    :::::::  ::  :::  ::::  :::  ::::
Benthamiana TTGAAGCTTCTTTTGCCTGAAGACTGGAAAGAGATCCCATATTTCCAAAA
                    1150       1160       1170       1180       1190

1090       1100       1110       1120       1130
Palmer      ACTTGAGAAATTAGTGGGCGTTCCTGTGATTAATGTTCACATATGGTTTG
            :  :::::  ::::::::  ::::::::::::  :::::  ::  :::::::::::
Benthamiana GTTGGAGAAGCTAGTGGGAGTTCCTGTGATAAATGTCCATATATGGTTTG
                    1200       1210       1220       1230       1240

1140       1150       1160       1170       1180
Palmer      ACAGAAAATTAAAGAATACATATGACCATCTACTCTTCAGCAGGAGTCCT
            :::::::::  :  :::::  ::::  :::  ::  ::  ::  ::  ::::::::
Benthamiana ACAGAAAACTGAAGAACACATCTGATAATCTGCTCTTCAGCAGAAGCCCG
                    1250       1260       1270       1280       1290

1190       1200       1210       1220       1230
Palmer      CTTTTGAGTGTCTATGCTGATATGTCGGAGACATGCAAGGAATATAAGGA    SEQ ID NO:37
            :    :  ::::::  ::  :::::  :::::  :    :::::  ::::::::::  :    :
Benthamiana TTGCTCAGTGTGTACGCTGACATGTCTGTTACATGTAAGGAATATTACAA    SEQ ID NO:38
                    1300       1310       1320       1330       1340
```

Figure 16 (continued)

```
                1240       1250       1260       1270       1280
Palmer      TCCAAATAGATCCATGCTGGAATTGGTTTTTGCACCCGCGGAGGAATGGA  SEQ ID NO:37
            :: :::     :: :::  :::::::::::: :::::::::::: :: :: ::::
Benthamiana CCCCAATCAGTCTATGTTGGAATTGGTATTTGCACCCGCAGAAGAGTGGA  SEQ ID NO:38
                1350       1360       1370       1380       1390

1290       1300       1310       1320       1330
Palmer      TTTCACGAAGCGACACTGATATTATAGAGGCAACAATGAAAGAGCTTGCC
            :          :: :: :::  :  ::  ::::: :: ::  :::::::::  :: :: ::
Benthamiana TAAATCGTAGTGACTCAGAAATTATTGATGCTACAATGAAGGAACTAGCG
                1400       1410       1420       1430       1440

1340       1350       1360       1370       1380
Palmer      AAGCTTTTCCCGGATGAAATCGCTGCCGATGGAAGCAAGGCCAAGATCCT
            ::::::::::: ::::::::::    :  ::  :::      :::::  ::  :: ::     :
Benthamiana AAGCTTTTCCCTGATGAAATTTCGGCAGATCAGAGCAAAGCAAAAATATT
                1450       1460       1470       1480       1490

1390       1400       1410       1420       1430
Palmer      CAAATATCATGTCGTCAAAACTCCAAGGTCGGTTTATAAGACTGTACCGG
            ::  ::::::::::  ::::::::::  :::::::::  ::::::::::  :::::  :: :
Benthamiana GAAGTATCATGTTGTCAAAACCCCAAGGTCTGTTTATAAAACTGTGCCAG
                1500       1510       1520       1530       1540

1440       1450       1460       1470       1480
Palmer      ATTGTGAACCTTGTCGGCCGCTGCAAAGATCACCAATAGAGGGTTTCTAT
            ::::::::::  ::::::::  :::::::::::  :: ::::::::::::::  :::
Benthamiana GTTGTGAACCCTGTCGGCCCTTGCAAAGATCCCCTATAGAGGGTTTTTAT
                1550       1560       1570       1580       1590

1490       1500       1510       1520       1530
Palmer      TTAGCTGGTGATTACACAAAACAAAAATATTTGGCTTCTATGGAAGGTGC
            ::::::::::: :::::  :::::  :: ::  ::::::::::  :::::::::::
Benthamiana TTAGCTGGTGACTACACGAAACAGAAGTACTTGGCTTCAATGGAAGGTGC
                1600       1610       1620       1630       1640

1540       1550       1560       1570       1580
Palmer      TGTCTTATCTGGGAAGCTTTGTGCACAGGCTATCGTACAGGATTATGA--
            ::::::::::  ::  ::::::::::::::::  :::::  :::::::::::::  ::
Benthamiana TGTCTTATCAGGAAAGCTTTGTGCACAAGCTATTGTACAGGATTACGAGT
                1650       1660       1670       1680       1690

1590       1600       1610
Palmer      ----TCT--GCTG--------AGTTCTCG--AGCACAAAGAGAA-TTGGC
            :::  :: :          :: : : ::  ::  :::  :  :: ::
Benthamiana TACTTCTTGGCCGGAGCCAGAAGATGTTGGCAGAAGCAAGCGTAGTTAGC
                1700       1710       1720       1730       1740

Palmer      G-----------     SEQ ID NO:37

Benthamiana ATAGTGAACTAA     SEQ ID NO:38
                1750       1760
```

Figure 19
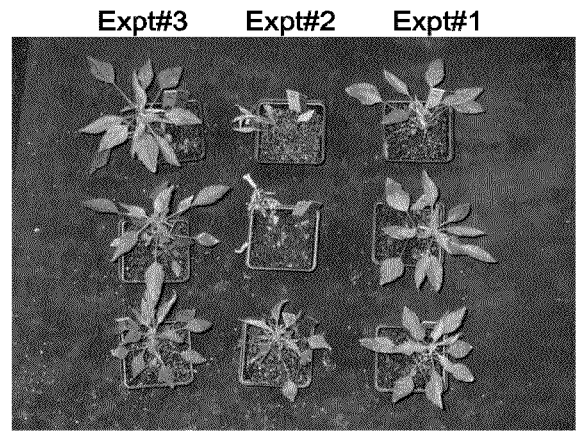
R31 (35 copies EPSPS)
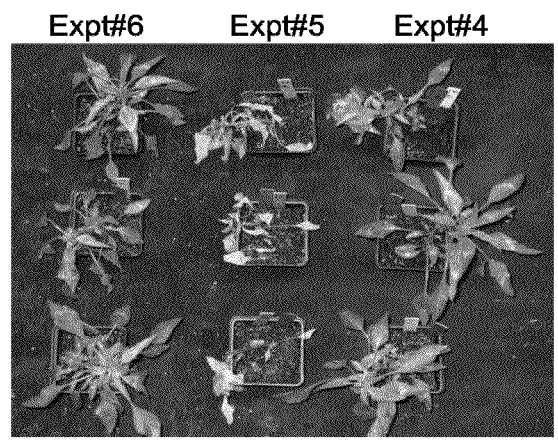
R34 (57 copies EPSPS)
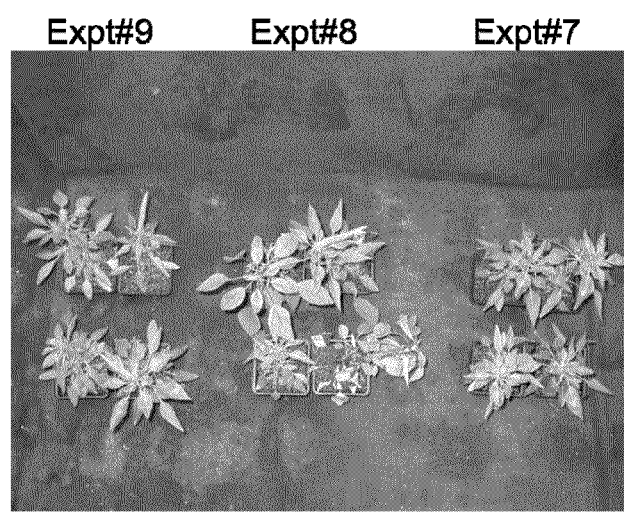
R28 (87 copies EPSPS)

Figure 20

ATGGCTCAAGCTACTACCATCAACAATGGTGTCCATACTGGTCAATTGCACCATACTTTACCCAAAA
CCCAGTTACCCAAATCTTCAAAAACTCTTAATTTTGGATCAAACTTGAGAATTTCTCCAAAGTTCAT
GTCTTTAACCAATAAAAGAGTTGGTGGGCAATCATCAATTGTTCCCAAGATTCAAGCTTCTGTTGCT
GCTGCAGCTGAGAAACCTTCATCTGTCCCAGAAATTGTGTTACAACCCATCAAAGAGATCTCTGGTA
CTGTTCAATTGCCTGGGTCAAAGTCTTTATCCAATCGAATCCTTCTTTTAGCTGCTTTGTCTGAGGG
CACAACAGTGGTCGACAACTTGCTGTATAGTGATGATATTCTTTATATGTTGGACGCTCTCAGAACT
CTTGGTTTAAAAGTGGAGGATGATAGTACAGCCAAAAGGGCAGTCGTAGAGGGTTGTGGTGGTCTGT
TTCCTGTTGGTAAAGATGGAAAGGAAGAGATTCAACTTTTCCTTGGTAATGCAGGAACAGCGATGCG
CCCATTGACAGCTGCGGTTGCCGTTGC*TGGAGGAAATTCAAGTTATGTGCTT*GATGGAGTACCAAGA
ATGAGGGAGCGCCCCATTGGGGATCTGGTAGCAGGTCTAAAGCAACTTGGTTCAGATGTAGATTGTT
TTCTTGGCACAAATTGCCCTCCTGTTCGGGTCAATGCTAAAGGAGGCCTTCCAGGGGGCAAGGTCAA
GCTCT*CTGGATCGGTTAGTAGCCAATATTT*AACTGCACTTCTCATGGCTACTCCTTTGGGTCTTGGA
GACGTGGAGATTGAGATAGTTGATAAATTGATTTCTGTACCGTATGTTGAAATGACAATAAAGTTGA
TGGAACGCTTTGGAGTATCCGTAGAACATAGTGATAGTTGGGACAGGTTCTACATTCGAGGTGGTCA
GAAATACAAATCTCCTGGAAAGGCATATGTTGAGGGTGATGCTTCAAGTGCTAGCTACTTCCTAGCC
GGAGCCGCCGTCACTGGTGGGACTGTCACTGTCAAGGGTTGTGGAACAAGCAGTTTACAGGGTGATG
TAAAATTTGCCGAAGTTCTTGAGAAGATGGGTTGCAAGGTCACCTGGACAGAGAATAGTGTAACTGT
TACTGGACCACCCAGGGATTCATCTGGAAAGAAACATCTGCGTGCTATCGACGTCAACATGAACAAA
ATGCCAGATGTTGCTATGACTCTTGCAGTTGTTGCCTTGTATGCAGATGGGCCCACCGCCATCAGAG
ATGTGGCTAGCTGGAGAGTGAAGGAAACCGAACGGATGATTGCCATTTGCACAGAACTGAGAAAGCT
TGGGGCAACAGTTGAGGAAGGATCTGATTACTGTGTGATCACTCCGCCTGAAAAGCTAAACCCCACC
GCCATTGAAACTTATGACGATCACCGAATGGCCATGGCATTCTCTCTTGCTGCCTGTGCAGATGTTC
CCGTCACTATCCTTGATCCGGGATGCACCCGTAAAACCTTCCCGGACTACTTTGATGTTTTAGAAAA
GTTCGCCAAGCATTGA

SEQ ID NO:40

Figure 21
A
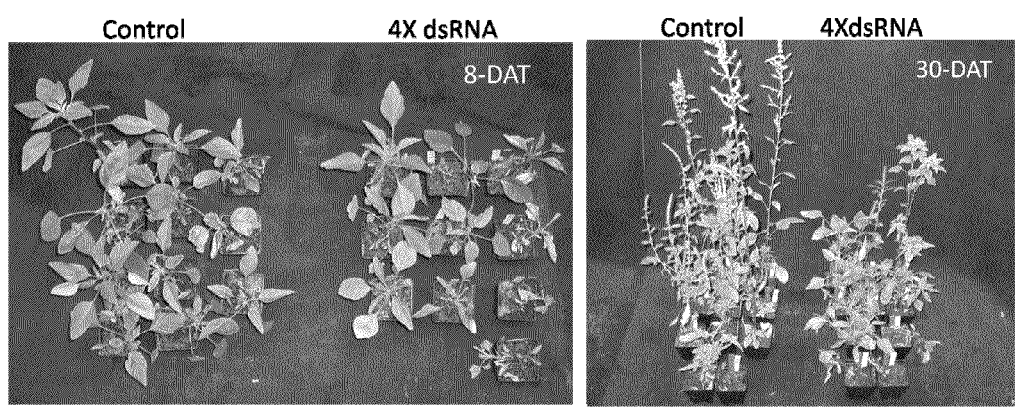
B

Figure 25
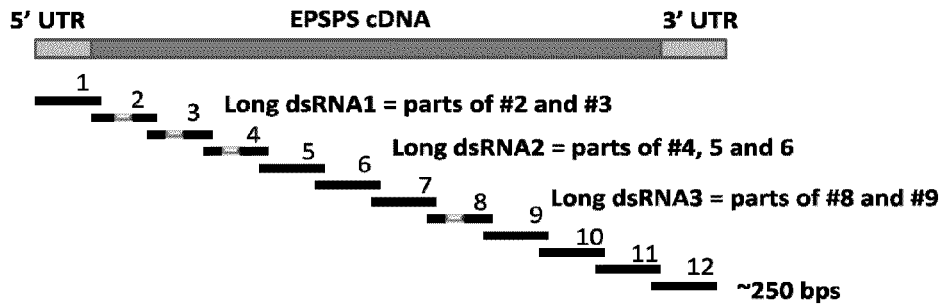
A
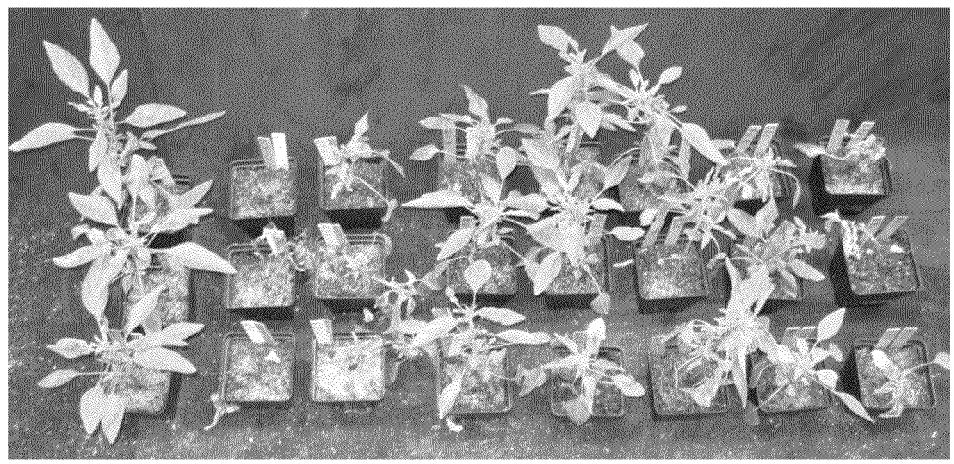
B
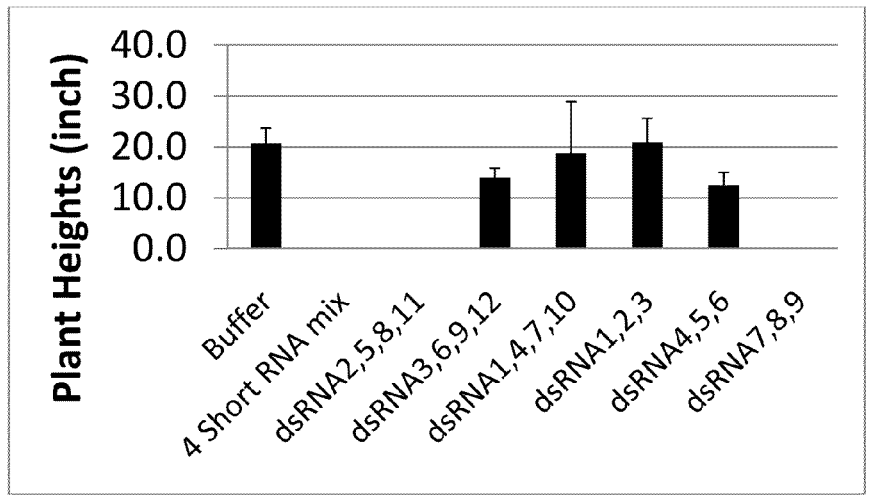
C

Figure 28
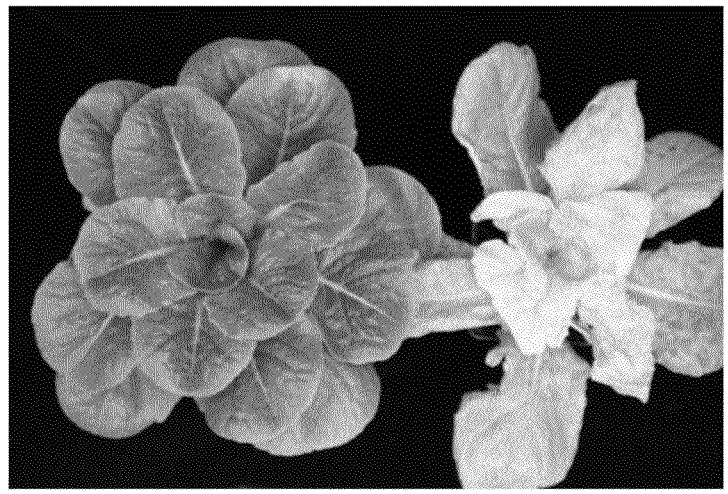
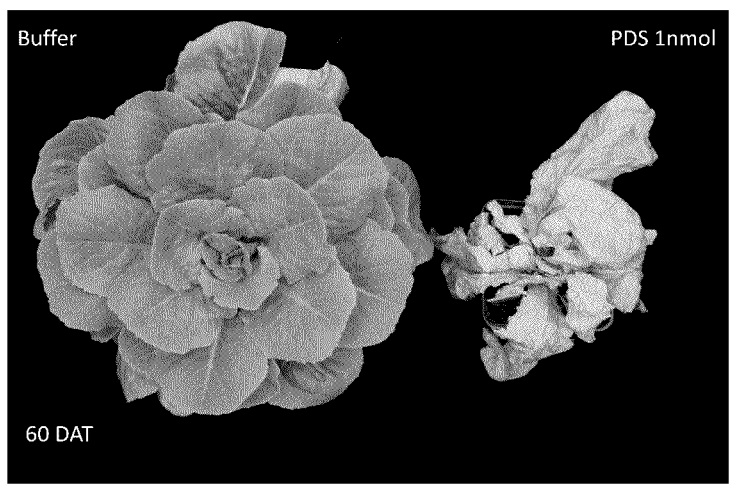

Figure 29
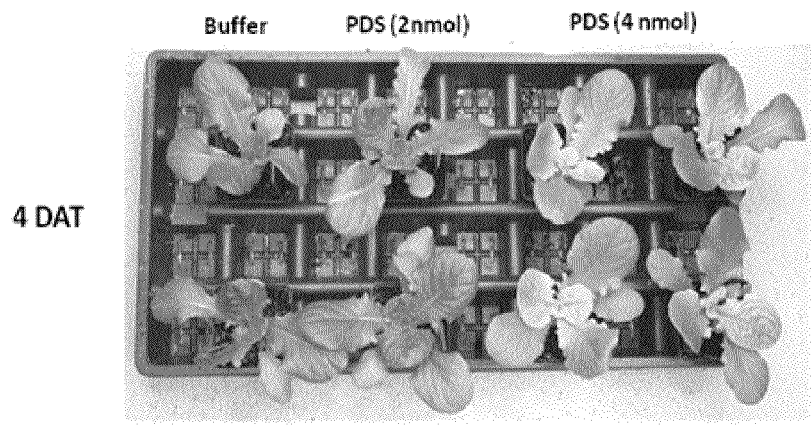
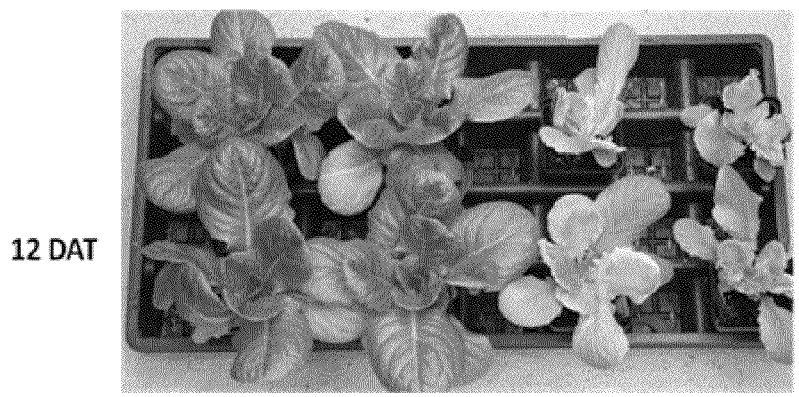
A
B

Figure 34

```
           810       820       830       840       850       860
PDS-2_ GTATGAACTTTCAGAATATTATACCGGATCAATATATTATGCT--GAAATATT--TTTCG
                    |||| ||||    ||   || |||  |    ||||
PDS-1_ GCTGTATCATATCTTCTTCTTTAGAACACTAATAAATTAAACTTCGAGATAATGATTTCT
           330       340       350       360       370       380

870       880       890       900       910
PDS-2_ GAC-----TTTAAATAATTTCTT-TATTTAAATTTATTTTTATACAAAAATAACTAAATT
       |||     | |||| || |  |  |||  | ||||     ||  | ||||||      ||||
PDS-1_ GACAAGAGTATAAACAAGTGCATCTATGAAGATTTGAGGTTGTCCAAAAAAGTGACAATT
           390       400       410       420       430       440

920       930       940       950       960       970
PDS-2_ TCAATTACTTTTAAA----ATTATGATTATTTTTCAATTACCACT-TATACATCCTGC--
          |   |   | ||||    |||    |||||| ||  |  ||  |  |||  || |  ||   |
PDS-1_ TTGGGTTCCTATAAACTGTATTTACATTATTGTT-ATTTGCAACTATAAAAATTTTAGAT
           450       460       470       480       490

980                 990       1000      1010
PDS-2_ TATTTTGAAT---------TTCACCCGAAA-GAAC-TACTACTATACGTGGATC---CTC
       ||||| ||           |||| |   ||| |||   ||   |||    |   |||   |||
PDS-1_ TATTTCCAAGCTCAGTTTCTTCAACTTAAATGAAGGTAGCACTTGAATTTCATCAGCCTC
           500       510       520       530       540       550

1020      1030      1040      1050      1060      1070
PDS-2_ AATGACCCAGTAACCCAAGTGGGAGATGTGTGCAAAGTGGTCAAATCTTAGAAGGAATGA
       |||||||||||||||| ||||||||| | ||||||||||||||||| |||||||||||
PDS-1_ TATGACCCAGTAACCCATGTGGGAGATGGGAGCAAAGTGGTCAAACTTTAGAAGGAAT
           560       570       580       590       600       610
```

PDS-1 promoter sequence (SEQ ID NO:319)

and

PDS-2 promoter sequence (SEQ ID NO:320)

Comparison of spermine (SPM), spermidine (SPMD), ammonium sulfate (AMS)

METHOD FOR CONTROLLING HERBICIDE-RESISTANT PLANTS

CROSS-REFERENCE TO RELATED APPLICATIONS AND INCORPORATION OF SEQUENCE LISTING

This application claims the benefit of priority of U.S. Provisional Patent Applications 61/311,762 filed 8 Mar. 2010, 61/349,807 filed 28 May 2010, and 61/381,556 filed 10 Sep. 2010, which are incorporated by reference in their entirety herein. The sequence listing that is contained in the file named "38-21_56855_D.txt", which is 133 kilobytes (measured in operating system MS-Windows) and was created on 7 Mar. 2011, is filed herewith and incorporated herein by reference.

FIELD OF THE INVENTION

Disclosed herein are polynucleotide molecules for regulating genes in plants and methods of making and using such molecules.

BACKGROUND

The failure of herbicides to control resistant weeds is a problem especially when such weeds are growing in field of herbicide resistant crops that may have lower herbicide resistance than the weed. Herbicide-resistant weeds are identified with a variety of modes of action. Resistance resulting from selection for multiple copies of genes producing herbicide targeted proteins in pigweed is reported by Gaines et al. (2010) *Proc. Natl. Acad. Sci. USA*, 107(3):1029-1034. Resistance resulting from mutations in genes producing herbicide targeted proteins in goosegrass, prickly lettuce, and ryegrass are reported by Baerson et al. (2002) *Plant Physiol.*, 129(3): 1265-1275; Preston et al. (2006) *Pesticide Biochem. Physiol.*, 84(3):227-235; and Wakelin et al. (2006) *Weed Res. (Oxford)*, 46(5):432-440. Vacuolar sequestration of glyphosate is an observed mechanism in glyphosate resistant horseweed; see Ge et al. (2010) *Pest Management Sci.*, 66:576-576. Resistance resulting from expression of enzymes that metabolize herbicides to an inactive chemical form in hairy crabgrass is reported by Hidayat et al. (1997) *Pesticide Biochem. Physiol.*, 57(2):137-146. Reddy et al. (2008) *J. Agric. Food Chem.*, 56(6):2125-2130 reported the accumulation of aminomethylphosphonic acid in plant species treated with glyphosate.

SUMMARY OF THE INVENTION

This invention provides polynucleotide molecules and methods for regulating genes in plants, e.g., by providing RNA for systemic regulation of genes. Various aspects of the invention provide polynucleotide molecules and methods for regulating endogenous genes and transgenes in a plant cell and polynucleotide molecules. The polynucleotides, compositions, and methods disclosed herein are useful for regulating endogenous genes of a plant pest or pathogen. In an aspect of the invention, the polynucleotide molecules are provided in compositions that can permeate or be absorbed into living plant tissue to initiate systemic gene silencing of endogenous genes or transgenes, or of their transcribed RNA. In some aspects of the invention polynucleotide molecules ultimately provide to a plant, or allow the production in cells in a plant, RNA that is capable of hybridizing under physiological conditions in a plant cell to RNA transcribed from a target endogenous gene or target transgene in the plant cell, thereby effecting regulation of the target gene, e.g., silencing or suppression of the target gene. In other aspects of the invention polynucleotide molecules disclosed herein are useful also for ultimately providing to a plant, or allowing the production in cells of a plant, RNA that is capable of hybridizing under physiological conditions to RNA transcribed from a target gene in a cell of an invertebrate pest or of a viral pathogen of the plant, thereby effecting regulation of the target gene, e.g., silencing or suppression of the target gene. In some aspects, the silencing or suppression of the target gene leads to the upregulation of another gene that is itself affected or regulated by the target gene's expression.

The compositions and methods of this invention are believed to operate through one or more of the several natural cellular pathways involved in RNA-mediated gene suppression as generally described in reviews by Brodersen and Voinnet (2006), *Trends Genetics*, 22:268-280; Tomari and Zamore (2005) *Genes & Dev.*, 19:517-529; Vaucheret (2006) *Genes Dev.*, 20:759-771; Meins et al. (2005) *Annu. Rev. Cell Dev. Biol.*, 21:297-318; and Jones-Rhoades et al. (2006) *Annu. Rev. Plant Biol.*, 57:19-53. RNA-mediated gene suppression generally involves a double-stranded RNA (dsRNA) intermediate that is formed intramolecularly within a single RNA molecule or intermolecularly between two RNA molecules. This longer dsRNA intermediate is processed by a ribonuclease of the RNase III family (Dicer or Dicer-like ribonuclease) to one or more shorter double-stranded RNAs, one strand of which is incorporated into the RNA-induced silencing complex ("RISC"). For example, the siRNA pathway involves the cleavage of a longer double-stranded RNA intermediate to small interfering RNAs ("siRNAs"). The size of siRNAs is believed to range from about 19 to about 25 base pairs, but the most common classes of siRNAs in plants include those containing 21 base pairs or 24 base pairs. See, Hamilton et al. (2002) *EMBO J.*, 21:4671-4679. As used herein, "oligonucleotide" means a polynucleotide molecule having a length of 18-25 nucleotides, similar to the size of processed small RNA molecules in gene silencing mechanisms. Various embodiments of this invention include compositions including oligonucleotides or polynucleotides or a mixture of both.

Aspects of the invention include compositions and methods for: providing single-stranded RNA molecules in a plant cell for systemic regulation of genes; herbicidal treatment with compositions including surfactant and a plant lethal agent which provides single-stranded RNA for suppression of an endogenous gene in a plant cell; topical coating onto a plant surface including a surfactant (e.g., an organosilicone surfactant) and an oligonucleotide or polynucleotide molecule for suppression of an endogenous gene in a plant cell; topically applied compositions for inducing systemic silencing of a target gene in a plant including (a) an agent for conditioning of a plant to permeation by polynucleotides and (b) polynucleotide molecules; and, herbicidal treatment with compositions including (a) an agent for conditioning of a plant to permeation by polynucleotide molecules, (b) polynucleotide molecules. Optionally these compositions can include a non-nucleotide herbicide.

In other aspects the invention provides methods for: controlling herbicide-resistant volunteer plants; investigating reverse genetics by modulating an endogenous gene in a plant by applying onto tissue of a growing plant a composition for providing single-stranded RNA molecules in a plant cell for systemic regulation of genes; inducing systemic silencing of a target gene including topical application of polynucleotides to a plant; inducing systemic silencing of a target gene in a plant by (a) conditioning of a plant to permeation by polynucleotides and (b) topically applying polynucleotides to the plant; investigating reverse genetics by modulating an endogenous gene in a plant by topically applying onto a living plant a topically applied composition including polynucleotide molecules and an agent for conditioning of a plant to permeation by such polynucleotide molecules.

In other aspects the invention provides a plant with exogenous DNA or RNA for suppressing an endogenous gene, where the exogenous DNA is not integrated into a chromosome of the plant, the exogenous RNA is not transcribed from DNA integrated into a chromosome of the plant, and the endogenous gene is suppressed by topical application of a polynucleotide to the plant. These and other aspects of the invention are described in greater detail in the following sections.

BRIEF DESCRIPTION OF THE DRAWINGS

FIG. 1 presents SEQ ID NO:1, a nucleotide sequence encoding Palmer amaranth EPSPS.

FIG. 2 presents SEQ ID NO:3 which is a nucleotide sequence of a synthesized Pol III gene.

FIG. 3 illustrates the morbidity of Palmer amaranth plants treated with a dsRNA. FIG. 3A depicts the plants 7 days after the glyphosate treatment. FIG. 3B depicts surfactant-treated plants that were treated with the long dsRNA solution followed by glyphosate treatment after 72 hours. FIG. 3C depicts surfactant-treated plants that were treated with the short dsRNA solution followed by glyphosate treatment after 72 hours.

FIG. 5 presents SEQ ID NO:2 which is a nucleotide sequence of a *Nicotiana benthamiana* phytoene desaturase.

FIG. 10 depicts the nucleotide sequence of a *Nicotiana benthamiana* phytoene desaturase (SEQ ID NO:2).

FIG. 12A illustrates apical leaf bleaching in *Nicotiana benthamiana* plants topically treated with buffer ("Control"), a 200-mer dsRNA polynucleotide with an RNA sequence corresponding to the segment consisting of nucleotides 914-1113 of SEQ ID NO:2 ("200 nt dsRNA"), and a combination of single-stranded DNA oligonucleotides and polynucleotides (SEQ ID NOs:16, 17, 20, 21, 24, 25, and 26) ("ssDNA oligos") as described in Example 10. FIG. 12B illustrates results of northern blot analysis of RNA isolated from *Nicotiana benthamiana* plants treated with buffer (control), the 200-mer dsRNA polynucleotide, and the ssDNA oligonucleotides. Also shown is RNA isolated from plants that had been stressed by being kept at 4 degrees Celsius and in the dark overnight prior to treatment with the 200-mer dsRNA polynucleotides.

FIG. 16 illustrates an alignment of the Palmer amaranth and *Nicotiana benthamiana* PDS DNA sequences showing about 71% identity (1252/1762) as described in Example 11.

FIG. 19 illustrates results of assays on different glyphosate-resistant Palmer amaranth lines (3 plants per replicate) treated with the conditions listed in Table 6, as described in Example 13. Photographs were taken at 7 days after glyphosate treatment (experiments 1-6) or at 9 days after glyphosate treatment (experiments 7-9).

FIG. 20 illustrates location of two small RNAs identified as abundant in EPSPS dsRNA-treated Palmer amaranth plants and which are shown as italicized underlined nucleotides at positions 564-588 and 743-767 of the full-length EPSPS (SEQ ID NO:40), as described in Example 14. The EPSPS sequence also shows the location of the four oligonucleotide-size "short" EPSPS dsRNA molecules (underlined, non-italicized text) and the three "long" double-stranded RNA polynucleotides (bolded text as described in Example 1.

FIG. 21A illustrates results of treating Palmer amaranth plants with surfactant followed by dsRNA at one of three application amounts, followed by herbicide, as described in Example 17. FIG. 21B illustrates results of assay 1 carried out on glyphosate-resistant Palmer amaranth grown from field-collected seeds as described in Example 17; plants are shown at 8 days and 30 days after treatment with herbicide.

FIG. 25A illustrates twelve dsRNA polynucleotides corresponding to DNA segments of approximately 250 bp each covering in a tiling manner the full coding sequence and part of the 5' and 3' untranslated regions of the Palmer EPSPS gene, as described in Example 21; the four oligonucleotide-size "short" EPSPS dsRNA molecules as described in Example 1 and FIG. 1 are located in the tiling segments 2, 3, 4, and 8 respectively, and are shown as light grey bars within those segments. FIG. 25B and FIG. 25C illustrates results of treating glyphosate-resistant Palmer amaranth plants with dsRNAs designed from these tiling segments or the four "short" dsRNA molecules or buffer.

FIG. 28 depicts the progression of bleaching and death of the lettuce plants treated with 1 nanomole ssDNA per plant at (from top to bottom) 37, 46, and 60 days after treatment, as described in Example 24.

FIG. 29A illustrates systemic silencing in lettuce plants evidenced by bleaching observed at 4 or 12 days after topical treatment with polynucleotides, as described in Example 24. FIG. 29B depicts the systemic silencing evidenced by bleaching observed at 4 after topical treatment with the four individual anti-sense ssDNAs ("HL287", SEQ ID NO:43; "HL288", SEQ ID NO:44; "HL289", SEQ ID NO:45; and "HL290", SEQ ID NO:46) or with a mixture of all four.

FIG. 30 also illustrates the stunting of the tomato plants treated with PDS polynucleotides (lower panel).

FIG. 34 illustrates an alignment of the *Nicotiana benthamiana* PDS locus 1 promoter (SEQ ID NO:319) and PDS locus 2 promoter (SEQ ID NO:320), as described in Example 30.

DETAILED DESCRIPTION OF THE INVENTION

Figure 4:
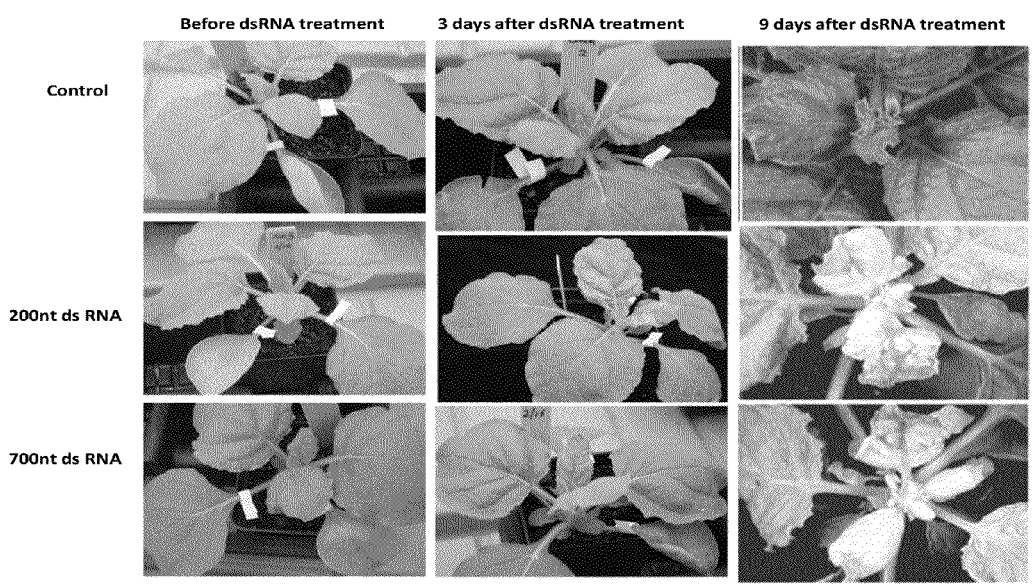
FIG. 4 illustrates the bleaching in *Nicotiana benthamiana* plants treated with a dsRNA composition.
Figure 6:
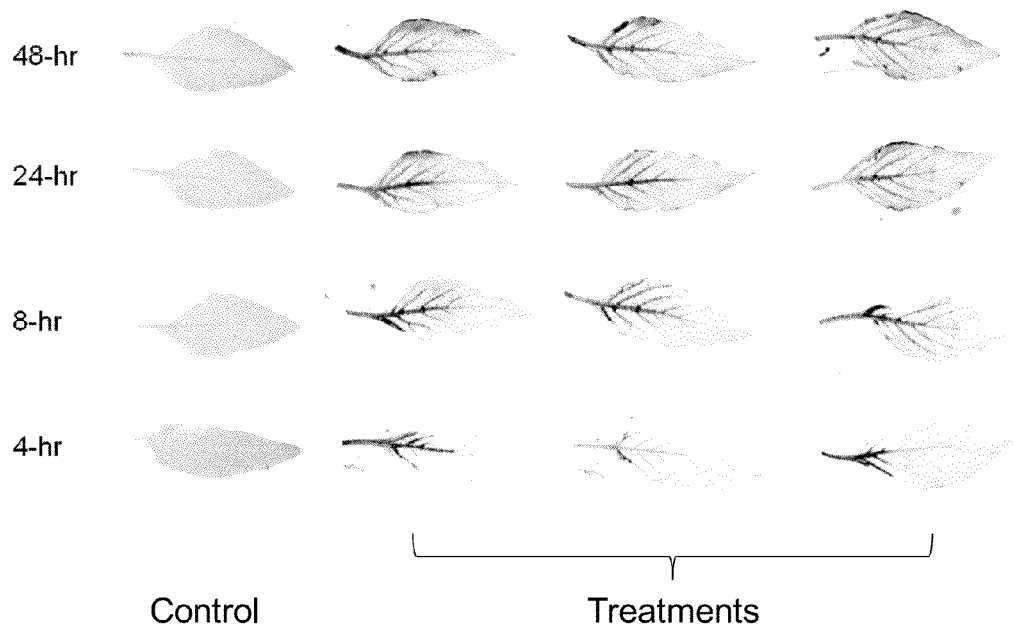
FIG. 6 illustrates 5'-Alexa Fluor 488-labelled anti-sense ssDNA oligonucleotides (SEQ ID NO:15) permeating glyphosate-resistant Palmer amaranth leaves as described in Example 9.

Unless otherwise stated, nucleic acid sequences in the text of this specification are given, when read from left to right, in the 5' to 3' direction. Nucleic acid sequences may be provided as DNA or as RNA, as specified; disclosure of one necessarily defines the other, as is known to one of ordinary skill in the art. Where a term is provided in the singular, the inventors also contemplate aspects of the invention described by the plural of that term. By "non-transcribable" polynucleotides is meant that the polynucleotides do not comprise a complete polymerase II transcription unit. As used here "solution" refers to homogeneous mixtures and non-homogeneous mixtures such as suspensions, colloids, micelles, and emulsions.

Polynucleotides

As used herein, "polynucleotide" refers to a nucleic acid molecule containing multiple nucleotides and generally refers both to "oligonucleotides" (a polynucleotide molecule of 18-25 nucleotides in length) and polynucleotides of 26 or more nucleotides. Embodiments of this invention include compositions including oligonucleotides having a length of 18-25 nucleotides (e.g., 18-mers, 19-mers, 20-mers, 21-mers, 22-mers, 23-mers, 24-mers, or 25-mers), or medium-length polynucleotides having a length of 26 or more nucleotides (e.g., polynucleotides of 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, about 65, about 70, about 75, about 80, about 85, about 90, about 95, about 100, about 110, about 120, about 130, about 140, about 150, about 160, about 170, about 180, about 190, about 200, about 210, about 220, about 230, about 240, about 250, about 260, about 270, about 280, about 290, or about 300 nucleotides), or long polynucleotides having a length greater than about 300 nucleotides (e.g., polynucleotides of between about 300 to about 400 nucleotides, between about 400 to about 500 nucleotides, between about 500 to about 600 nucleotides, between about 600 to about 700 nucleotides, between about 700 to about 800 nucleotides, between about 800 to about 900 nucleotides, between about 900 to about 1000 nucleotides, between about 300 to about 500 nucleotides, between about 300 to about 600 nucleotides, between about 300 to about 700 nucleotides, between about 300 to about 800 nucleotides, between about 300 to about 900 nucleotides, or about 1000 nucleotides in length, or even greater than about 1000 nucleotides in length, for example up to the entire length of a target gene including coding or non-coding or both coding and non-coding portions of the target gene). Where a polynucleotide is double-stranded, its length can be similarly described in terms of base pairs.

Polynucleotide compositions used in the various embodiments of this invention include compositions including oligonucleotides or polynucleotides or a mixture of both, including RNA or DNA or RNA/DNA hybrids or chemically modified oligonucleotides or polynucleotides or a mixture thereof. In some embodiments, the polynucleotide may be a combination of ribonucleotides and deoxyribonucleotides, e.g., synthetic polynucleotides consisting mainly of ribonucleotides but with one or more terminal deoxyribonucleotides or synthetic polynucleotides consisting mainly of deoxyribonucleotides but with one or more terminal dideoxyribonucleotides. In some embodiments, the polynucleotide includes non-canonical nucleotides such as inosine, thiouridine, or pseudouridine. In some embodiments, the polynucleotide includes chemically modified nucleotides. Examples of chemically modified oligonucleotides or polynucleotides are well known in the art; see, e.g., Verma and Eckstein (1998) *Annu. Rev. Biochem.*, 67:99-134. For example, the naturally occurring phosphodiester backbone of an oligonucleotide or polynucleotide can be partially or completely modified with phosphorothioate, phosphorodithioate, or methylphosphonate internucleotide linkage modifications, modified nucleoside bases or modified sugars can be used in oligonucleotide or polynucleotide synthesis, and oligonucleotides or polynucleotides can be labelled with a fluorescent moiety (e.g., fluorescein or rhodamine) or other label (e.g., biotin).

The polynucleotides can be single- or double-stranded RNA or single- or double-stranded DNA or double-stranded DNA/RNA hybrids or modified analogues thereof, and can be of oligonucleotide lengths or longer. In more specific embodiments of the invention the polynucleotides that provide single-stranded RNA in the plant cell are selected from the group consisting of (a) a single-stranded RNA molecule, (b) a single-stranded RNA molecule that self-hybridizes to form a double-stranded RNA molecule, (c) a double-stranded RNA molecule, (d) a single-stranded DNA molecule, (e) a single-stranded DNA molecule that self-hybridizes to form a double-stranded DNA molecule, and (f) a single-stranded DNA molecule including a modified Pol III gene that is transcribed to an RNA molecule, (g) a double-stranded DNA molecule, (h) a double-stranded DNA molecule including a modified Pol III gene that is transcribed to an RNA molecule, (i) a double-stranded, hybridized RNA/DNA molecule, or combinations thereof. In some embodiments these polynucleotides include chemically modified nucleotides or non-canonical nucleotides. In embodiments of the method the polynucleotides include double-stranded DNA formed by intramolecular hybridization, double-stranded DNA formed by intermolecular hybridization, double-stranded RNA formed by intramolecular hybridization, or double-stranded RNA formed by intermolecular hybridization. In one embodiment the polynucleotides include single-stranded DNA or single-stranded RNA that self-hybridizes to form a hairpin structure having an at least partially double-stranded structure including at least one segment that will hybridize under physiological conditions in the cell to RNA transcribed from the gene targeted for suppression. Not intending to be bound by any mechanism, it is believed that such polynucleotides are or will produce single-stranded RNA with at least one segment that will hybridize under physiological conditions in a cell to RNA transcribed from the gene targeted for suppression. In certain other embodiments the polynucleotides further includes a promoter, generally a promoter functional in a plant, e.g., a pol II promoter, a pol III promoter, a pol IV promoter, or a pol V promoter.

In some embodiments, the polynucleotide compositions are formulated with counter-ions or other molecules that are known to associate with nucleic acid molecules, e.g., tetraalkyl ammonium ions, trialkyl ammonium ions, sulfonium ions, lithium ions, and polyamines such as spermine, spermidine, or putrescine. In some embodiments, the polynucleotide compositions are formulated with a non-polynucleotide herbicide (e.g., the chemical herbicides disclosed herein in the section headed "Herbicide-Tolerance Proteins") or with a transferring agent or permeability-enhancing agent (see the section headed "Permeability-Enhancing Agents and Treatments").

The polynucleotides are designed to induce systemic regulation or suppression of an endogenous gene in a plant and are designed to have a sequence essentially identical or essentially complementary to the sequence (which can be coding sequence or non-coding sequence) of an endogenous gene of a plant or to the sequence of RNA transcribed from an endogenous gene of a plant. By "essentially identical" or "essentially complementary" is meant that the polynucleotides (or at least one strand of a double-stranded polynucleotide) are designed to hybridize under physiological conditions in cells of the plant to the endogenous gene or to RNA transcribed from the endogenous gene to effect regulation or suppression of the endogenous gene.

Embodiments of single-stranded polynucleotides functional in this invention have sequence complementarity that need not be 100% but is at least sufficient to permit hybridization to RNA transcribed from the target gene to form a duplex under physiological conditions in a plant cell to permit cleavage by a gene silencing mechanism. Thus, in embodiments the segment is designed to be essentially identical to, or essentially complementary to, a sequence of 18 or more contiguous nucleotides in either the target gene or messenger RNA transcribed from the target gene. By "essentially identical" is meant having 100% sequence identity or at least about 83, 84, 85, 86, 87, 88, 89, 90, 91, 92, 93, 94, 95, 96, 97, 98, or 99% sequence identity when compared to the sequence of 18 or more contiguous nucleotides in either the target gene or RNA transcribed from the target gene; by "essentially complementary" is meant having 100% sequence complementarity or at least about 83, 84, 85, 86, 87, 88, 89, 90, 91, 92, 93, 94, 95, 96, 97, 98, or 99% sequence complementarity when compared to the sequence of 18 or more contiguous nucleotides in either the target gene or RNA transcribed from the target gene. In some embodiments of this invention polynucleotide molecules are designed to have 100% sequence identity with or complementarity to one allele of a given target gene (e.g., coding or non-coding sequence of a gene for an herbicide-tolerance protein, an herbicide-deactivating protein, a stress-response gene, or an essential gene); in other embodiments the polynucleotide molecules are designed to have 100% sequence identity with or complementarity to multiple alleles of a given target gene.

In one aspect of the invention the polynucleotides are modified RNA polymerase III genes, e.g., genes that transcribe 7SL signal recognition particle RNA or U6 spliceosomal RNA (Pol III genes) or polynucleotides containing a functional Pol III promoter sequence. In one embodiment, the polynucleotides are modified Pol III genes containing sense and anti-sense DNA corresponding to RNA of the targeted gene identified for regulation replacing the DNA sequence originally transcribed by the Pol III gene.

The polynucleotides useful in this invention typically effect regulation or modulation (e.g., suppression) of gene expression during a period during the life of the treated plant of at least 1 week or longer and typically in systemic fashion. For instance, within days of treating a plant leaf with a polynucleotide composition of this invention, primary and transitive siRNAs can be detected in other leaves lateral to and above the treated leaf and in apical tissue.

Methods of making polynucleotides are well known in the art. Commercial preparation of oligonucleotides often provides 2 deoxyribonucleotides on the 3' end of the sense strand. Long polynucleotide molecules can be synthesized from commercially available kits, e.g., kits from Ambion have DNA ligated on the 5' end that encodes a bacterial T7 polymerase promoter that makes RNA strands that can be assembled into a dsRNA. Alternatively, dsRNA molecules can be produced from expression cassettes in bacterial cells that have regulated or deficient RNase III enzyme activity. Long polynucleotide molecules can also be assembled from multiple RNA or DNA fragments. In some embodiments design parameters such as Reynolds score and Tuschl rules are known in the art and are used in selecting polynucleotide sequences effective in gene silencing. In some embodiments random design or empirical selection of polynucleotide sequences is used in selecting polynucleotide sequences effective in gene silencing. In some embodiments the sequence of a polynucleotide is screened against the genomic DNA of the intended plant to minimize unintentional silencing of other genes.

The polynucleotide compositions of this invention are useful in compositions, such as solutions of polynucleotide molecules, at low concentrations, alone or in combination with other components (e.g., surfactants, salts, and non-polynucleotide herbicides) either in the same solution or in separately applied solutions. While there is no upper limit on the concentrations and dosages of polynucleotide molecules that can useful in the methods of this invention, lower effective concentrations and dosages will generally be sought for efficiency. The concentrations can be adjusted in consideration of the volume of spray applied to plant leaves. In one embodiment, a useful treatment for herbaceous plants using 25-mer oligonucleotide molecules is about 1 nanomole of oligonucleotide molecules per plant, e.g., from about 0.05 to 1 nanomole per plant. Other embodiments for herbaceous plants include useful ranges of about 0.05 to about 100 nanomoles, or about 0.1 to about 20 nanomoles, or about 1 nanomole to about 10 nanomoles of polynucleotides per plant. Very large plants, trees, or vines may require correspondingly larger amounts of polynucleotides. When using long dsRNA molecules that can be processed into multiple oligonucleotides, lower concentrations can be used. In the examples to below to illustrate embodiments of the invention the factor 1× when applied to oligonucleotide molecules is arbitrarily used to denote a treatment of 0.8 nanomoles of polynucleotide molecule per plant; 10×, 8 nanomoles of polynucleotide molecule per plant; and 100×, 80 nanomoles of polynucleotide molecule per plant. For example, in example 23 plants were treated with an aqueous solution comprising a 100× treatment of EPSPS dsRNA (264 micrograms or 80 nanomoles) per plant.

Single-Stranded RNA Molecules

This invention provides polynucleotide molecules for providing single-stranded RNA for systemic regulation of genes in a plant cell. More specifically, the invention also provides compositions and methods for inducing systemic regulation (e.g., systemic suppression or silencing) of a target gene in a plant by topical application to the plant of a polynucleotide molecule with a segment in a nucleotide sequence essentially identical to, or essentially complementary to, a sequence of 18 or more contiguous nucleotides in either the target gene or RNA transcribed from the target gene, whereby the composition permeates the interior of the plant and induces systemic regulation of the target gene by the action of single-stranded RNA that hybridizes to the transcribed RNA, e.g., messenger RNA. The polynucleotide molecule can be one or more polynucleotide molecules with a single such segment, multiples of such a segment, multiple different such segments, or combination thereof.

Transferring Agents, Permeability-Enhancing Agents and Treatments

The compositions and methods of this invention can comprise transferring agents or permeability-enhancing agents and treatments to condition the surface of plant tissue, e.g., leaves, stems, roots, flowers, or fruits, to permeation by the polynucleotide molecules into plant cells. The transfer of polynucleotides into plant cells can be facilitated by the prior or contemporaneous application of a polynucleotide-transferring agent to the plant tissue. In some embodiments the transferring agent is applied subsequent to the application of the polynucleotide composition. The polynucleotide transferring agent enables a pathway for polynucleotides through cuticle wax barriers, stomata and/or cell wall or membrane barriers and into plant cells. Suitable agents to facilitate transfer of the composition into a plant cell include agents that increase permeability of the exterior of the plant or that increase permeability of plant cells to oligonucleotides or polynucleotides. Such agents to facilitate transfer of the composition into a plant cell include a chemical agent, or a physical agent, or combinations thereof. Chemical agents for conditioning includes (a) surfactants, (b) an organic solvents or an aqueous solutions or aqueous mixtures of organic solvents, (c) oxidizing agents, (e) acids, (f) bases, (g) oils, (h) enzymes, or combinations thereof. Embodiments of the method can optionally include an incubation step, a neutralization step (e.g., to neutralize an acid, base, or oxidizing agent, or to inactivate an enzyme), a rinsing step, or combinations thereof. Embodiments of agents or treatments for conditioning of a plant to permeation by polynucleotides include emulsions, reverse emulsions, liposomes, and other micellar-like compositions. Embodiments of agents or treatments for conditioning of a plant to permeation by polynucleotides include counter-ions or other molecules that are known to associate with nucleic acid molecules, e.g., inorganic ammonium ions, alkyl ammonium ions, lithium ions, polyamines such as spermine, spermidine, or putrescine, and other cations. Organic solvents useful in conditioning a plant to permeation by polynucleotides include DMSO, DMF, pyridine, N-pyrrolidine, hexamethylphosphoramide, acetonitrile, dioxane, polypropylene glycol, other solvents miscible with water or that will dissolve phosphonucleotides in non-aqueous systems (such as is used in synthetic reactions). Naturally derived or synthetic oils with or without surfactants or emulsifiers can be used, e.g., plant-sourced oils, crop oils (such as those listed in the $9^{th}$ Compendium of Herbicide Adjuvants, publicly available on line at www.herbicide.adjuvants.com) can be used, e.g., paraffinic oils, polyol fatty acid esters, or oils with short-chain molecules modified with amides or polyamines such as polyethyleneimine or N-pyrrolidine.

Such agents for conditioning of a plant to permeation by polynucleotides are applied to the plant by any convenient method, e.g., spraying or coating with a powder, emulsion, suspension, or solution; similarly, the polynucleotide molecules are applied to the plant by any convenient method, e.g., spraying or wiping a solution, emulsion, or suspension.

Examples of useful surfactants include sodium or lithium salts of fatty acids (such as tallow or tallowamines or phospholipids) and organosilicone surfactants. Other useful surfactants include organosilicone surfactants including non-ionic organosilicone surfactants, e.g., trisiloxane ethoxylate surfactants or a silicone polyether copolymer such as a copolymer of polyalkylene oxide modified heptamethyl trisiloxane and allyloxypolypropylene glycol methylether (commercially available as SILWET L-77® brand surfactant having CAS Number 27306-78-1 and EPA Number: CAL. REG. NO. 5905-50073-AA, currently available from Momentive Performance Materials, Albany, N.Y.). When SILWET L-77® brand surfactant is used as a pre-spray treatment of plant leaves or other surfaces, concentrations in the range of about 0.015 to about 2 percent by weight (wt %) (e.g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt %) are efficacious in preparing a leaf or other plant surface for transfer of polynucleotide molecules into plant cells from a topical application on the surface.

Useful physical agents can include (a) abrasives such as carborundum, corundum, sand, calcite, pumice, garnet, and the like, (b) nanoparticles such as carbon nanotubes or (c) a physical force. Carbon nanotubes are disclosed by Kam et al. (2004) *J. Am. Chem. Soc.*, 126 (22):6850-6851, Liu et al. (2009) *Nano Lett.*, 9(3):1007-1010, and Khodakovskaya et al. (2009) *ACS Nano*, 3(10):3221-3227. Physical force agents can include heating, chilling, the application of positive pressure, or ultrasound treatment. Embodiments of the method can optionally include an incubation step, a neutralization step (e.g., to neutralize an acid, base, or oxidizing agent, or to inactivate an enzyme), a rinsing step, or combinations thereof. The methods of the invention can further include the application of other agents which will have enhanced effect due to the silencing of certain genes. For example, when a polynucleotide is designed to regulate genes that provide herbicide resistance, the subsequent application of the herbicide can have a dramatic effect on herbicide efficacy.

Agents for laboratory conditioning of a plant to permeation by polynucleotides include, e.g., application of a chemical agent, enzymatic treatment, heating or chilling, treatment with positive or negative pressure, or ultrasound treatment. Agents for conditioning plants in a field include chemical agents such as surfactants and salts.

Target Genes and Essential Genes

Compositions and methods of the invention are useful for modulating the expression of an endogenous or transgenic target gene in a plant cell. In various embodiments, a target gene includes coding (protein-coding or translatable) sequence, non-coding (non-translatable) sequence, or both coding and non-coding sequence. Compositions of the invention can include polynucleotides and oligonucleotides designed to target multiple genes, or multiple segments of one or more genes. The target gene can include multiple consecutive segments of a target gene, multiple non-consecutive segments of a target gene, multiple alleles of a target gene, or multiple target genes from one or more species. Examples of target genes include endogenous plant genes and transgenes expressed in plant cells. Other examples of target genes include endogenous genes of plant viral pathogens or endogenous genes of invertebrate plant pests.

Target genes can include genes encoding herbicide-tolerance proteins, non-coding sequences including regulatory RNAs, and essential genes, which are genes necessary for sustaining cellular life or to support reproduction of an organism. Embodiments of essential genes include genes involved in DNA or RNA replication, gene transcription, RNA-mediated gene regulation, protein synthesis, energy production, and cell division. One example of a compendium of essential genes is described in Zhang et al. (2004) *Nucleic Acids Res.*, 32:D271-D272, and is available at tubic.tju.edu.cn/deg/; version DEG 5.4 lists 777 essential genes for *Arabidopsis thaliana*. Examples of essential genes include translation initiation factor (TIF) and ribulose-1,5-bisphosphate carboxylase oxygenase (RuBisCO). Target genes can include genes encoding transcription factors and genes encoding enzymes involved in the biosynthesis or catabolism of molecules in plants such as, but not limited to, amino acids, fatty acids and other lipids, sugars and other carbohydrates, biological polymers, and secondary metabolites including alkaloids, terpenoids, polyketides, non-ribosomal peptides, and secondary metabolites of mixed biosynthetic origin.

Compositions and Methods

Single-stranded RNA molecules of this invention can be provided directly to the plant cell as RNA or provided indirectly, e.g., where a polynucleotide molecule in the treatment composition causes in cells of a plant the production of the single-stranded RNA that is capable of hybridizing to the target gene's transcript. In many embodiments compositions of polynucleotide molecules further include one or more permeability enhancing agents to facilitate transfer of the polynucleotide molecules into a plant cell, such as agents for conditioning of a plant to permeation by polynucleotides. In aspects of the invention methods include one or more applications of the polynucleotide composition and one or more applications of a permeability-enhancing agent for conditioning of a plant to permeation by polynucleotides. When the agent for conditioning to permeation is an organosilicone surfactant, embodiments of the polynucleotide molecules are double-stranded RNA oligonucleotides, single-stranded RNA oligonucleotides, double-stranded RNA polynucleotides, single-stranded RNA polynucleotides, double-stranded DNA oligonucleotides, single-stranded DNA oligonucleotides, double-stranded DNA polynucleotides, single-stranded DNA polynucleotides, chemically modified RNA or DNA oligonucleotides or polynucleotides or mixtures thereof.

An aspect of the invention provides a method for inducing systemic silencing of a target gene in a plant including (a) conditioning of a plant to permeation by polynucleotides and (b) topical application of polynucleotide molecules to the plant, where the polynucleotide molecules include at least one segment of 18 or more contiguous nucleotides cloned from or otherwise identified from the target gene in either anti-sense or sense orientation, whereby the polynucleotide molecules permeate the interior of the plant and induce systemic silencing of the target gene. The conditioning and polynucleotide application can be performed separately or in a single step. When the conditioning and polynucleotide application are performed in separate steps, the conditioning can precede or can follow the polynucleotide application within minutes, hours, or days. In some embodiments more than one conditioning step or more than one polynucleotide molecule application can be performed on the same plant. In embodiments of the method, the segment can be cloned or identified from (a) coding (i.e., protein-encoding), (b) non-coding, or (c) both coding and non-coding parts of the target gene. Non-coding parts include DNA (or the RNA encoded by the DNA) encoding RNA regulatory sequences (e.g., promoters, introns, 5' or 3' untranslated regions, and microRNAs, trans-acting siRNAs, natural anti-sense siRNAs, and other small RNAs with regulatory function) or encoding RNAs having structural or enzymatic function (e.g., ribozymes, ribosomal RNAs, t-RNAs, aptamers, and riboswitches).

In various embodiments of the method for inducing systemic silencing of a target gene in a plant the target gene is (a) an endogenous gene of the plant, (b) an endogenous gene of a viral pathogen of the plant, (c) an endogenous gene of an invertebrate pest of the plant, (d) an endogenous gene of a symbiont of an invertebrate pest of the plant, or (e) an man-made gene inserted into a transgenic plant. In embodiments where the target gene is endogenous to a plant, the target gene (a) is an endogenous gene of the plant that is essential for maintaining the growth or life of the plant, (b) encodes a protein that provides herbicide resistance to the plant, or (c) transcribes to an RNA regulatory molecule. In embodiments of the method for inducing systemic silencing of a target gene in a plant, the conditioning includes application of a chemical agent, abrasion, wounding, enzymatic treatment, heating or chilling, treatment with positive or negative pressure, ultrasound treatment, or combinations thereof. In some embodiments, the conditioning includes application of a surfactant, such as organosilicone surfactants, e.g., a silicone polyether copolymer such as a copolymer of polyalkylene oxide modified heptamethyl trisiloxane and allyloxypolypropylene glycol methylether (commercially available as SILWET L-77® brand surfactant). In embodiments of the method, the conditioning includes application of (a) a surfactant, (b) an organic solvent or an aqueous solution or aqueous mixture of an organic solvent, (c) a polypropylene glycol or an aqueous solution or aqueous mixture of polypropylene glycol, (d) nanoparticles, (e) an oxidizing agent, (f) an acid or a base, or (g) an oil, or of a combination thereof. Embodiments of the method can optionally include an incubation step, a neutralization step (e.g., to neutralize an acid, base, or oxidizing agent, or to inactivate an enzyme), a rinsing step, or combinations thereof.

The invention provides topical compositions for inducing systemic silencing of a target gene in a plant including (a) an agent for conditioning of a plant to permeation by polynucleotides and (b) polynucleotide molecules with at least one segment of 18 or more contiguous nucleotides essentially identical or complementary to the sequence of nucleotides of the target gene in either anti-sense or sense orientation. Such compositions can be used for the various methods disclosed herein including methods for investigating reverse genetics by modulating an endogenous gene in a plant, and as herbicidal compositions for the disclosed methods of weed control and volunteer plant control. Another aspect of the invention provides a plant including exogenous DNA or RNA for suppressing an endogenous gene, wherein the exogenous DNA is not integrated into a chromosome of the plant and the exogenous RNA is not transcribed from DNA integrated into a chromosome of the plant, and wherein the endogenous gene is suppressed by topical application of a polynucleotide to the plant. Alternatively, the exogenous DNA or RNA can be designed for suppressing an endogenous plant gene involved in responding to a pest or pathogen to provide control of plant pests or diseases. Such plant can be grown from seed or produced by a cutting, cloning, or grafting process (i.e., a plant not grown from a seed). Such plant is a row crop plant, a fruit, a vegetable, a tree, or an ornamental plant. For example, in embodiments of the inventions disclosed herein the plant is a row crop plant (e.g., corn, soybean, cotton, canola, sugar beet, alfalfa, sugarcane, rice, and wheat), or is a vegetable (e.g., tomato, sweet pepper, hot pepper, melon, watermelon, cucumber, eggplant, cauliflower, broccoli, lettuce, spinach, onion, peas, carrots, sweet corn, Chinese cabbage, leek, fennel, pumpkin, squash or gourd, radish, Brussels sprouts, tomatillo, garden beans, dry beans, or okra), or is an culinary plant (e.g., basil, parsley, coffee, or tea,), or is a fruit (e.g., apple, pear, cherry, peach, plum, apricot, banana, plantain, table grape, wine grape, citrus, avocado, mango, or berry), or is a tree grown for ornamental or commercial use (e.g., a fruit or nut tree, or is an ornamental plant (e.g., an ornamental flowering plant or shrub or turf grass). Embodiments of a plant produced by a cutting, cloning, or grafting process (i.e., a plant not grown from a seed) include fruit trees and plants including citrus, apples, avocados, tomatoes, eggplant, cucumber, melons, watermelons, and grapes as well as various ornamental plants.

Methods for Investigating Reverse Genetics

In yet another aspect, the invention provides a method for investigating reverse genetics by regulating or modulating an endogenous target gene in a plant; such method includes applying onto tissue of a growing plant a composition for providing (directly or indirectly) single-stranded RNA of this invention for systemic regulation of genes in a plant cell. In embodiments of such a method, messenger RNA encoding a protein or regulatory RNA gene is targeted by a polynucleotide of the invention, effecting modulation of the gene during a period of at least 1 week during the life of the plant, e.g., to identify traits that can be imparted by topical application of polynucleotides. The method can further include additional steps, e.g., exposing the plant to an array of compounds to identify herbicide interactions or exposing the plant to abiotic stress (e.g., water deficit stress, nutrient deficit stress, heat stress, cold stress, salinity stress) or to biotic treatments (e.g., challenge with an insect or nematode pest or with a viral, fungal, or bacterial pathogen or exposure to a chemical compound or biological treatment) to identify responses by the plant to the stress or treatment. In another aspect of the invention libraries of plants with a variety of transiently silenced genes are screened against libraries of compounds (e.g., herbicides, phytohormones, endogenous or exogenous defense elicitors such as salicylic acid or harpins, deficiencies of molecules providing a plant nutrient such as nitrogen, phosphorous, potassium, sulfur, calcium, magnesium, iron, and zinc) to identify interactions with such compounds. Examples of plants useful in such screens include *Amaranthus palmeri* and *Nicotiana benthamiana*.

Methods for Transgene Silencing

In still yet another aspect of the invention, this method can be used to silence a transgene being expressed in a plant, thus providing a negative control that is an event-independent measurement of a transgene's contribution to plant performance or effect on a trait. Imparting a negative control effect may require multiple successive treatments with the polynucleotide molecules of this invention during the life cycle of a plant.

Specific Applications

In a related aspect the compositions and methods of the invention are also useful for transiently silencing one or more genes in a growing plant cell or whole plant to effect a desired phenotype in response to culture conditions, environmental or abiotic or biotic stress, or change in market demand during the growing season or in the post-harvest environment. For example, compositions and methods of the invention are useful for transiently suppressing a biosynthetic or catabolic gene in order to produce a plant or plant product with a desired phenotype, such as a desired nutritional composition of a crop plant product, e.g., suppressing a FAD2 gene to effect a desired fatty acid profile in soybean or canola or other oilseed or suppressing a lignin biosynthetic genes such as COMT and CCOMT to provide more easily digestible forage plants. Similarly, compositions and methods of the invention are useful for transiently suppressing an RNA regulatory molecule such as a microRNA (miRNA) or an endogenous miRNA decoy such as an endogenous miRNA, miRNA precursor, or miRNA decoy as disclosed in US Patent Application Publication 2009/0070898 which is incorporated herein by reference. Embodiments of the invention are useful for suppressing an endogenous plant gene involved in responding to a pest or pathogen, thus providing control of plant pests or diseases. The polynucleotides, compositions, and delivery methods disclosed herein are further useful in suppressing an endogenous target gene of an invertebrate pest of a plant, e.g., lepidopteran or coleopteran pests which can ingest RNA from the plant, thus providing control of plant pests or pest-induced diseases, e.g., by use of a topical spray for crop plants, vegetables, or fruit trees with DNA or RNA molecules targeting an invertebrate essential gene or a gene of a symbiont of the invertebrate pest. The polynucleotides, compositions, and delivery methods disclosed herein are further useful in providing control of a viral pathogen, e.g., by use of a topical anti-viral spray for crop plants, vegetables, or fruit trees with DNA or RNA molecules targeting a viral gene.

Herbicidal Compositions and Methods

An aspect of the invention provides a liquid herbicidal composition comprising polynucleotide molecules as a plant lethal agent which provides at least one species of single-stranded RNA which can hybridize under physiological conditions in a plant cell to RNA transcribed from endogenous gene(s) in the plant cell. In some embodiments, the target gene encodes a protein that provides tolerance to an herbicide or encodes a gene essential for maintaining the growth or life of the plant. The liquid herbicidal composition can further include permeability-enhancing agents, non-nucleotide herbicides, or combinations thereof and can be used in a multi-step treatment with the non-nucleotide herbicide and/or the permeability-enhancing agents applied separately. An embodiment of the liquid herbicidal composition is a liquid including an organosilicone surfactant as permeability-enhancing agent and oligonucleotides or polynucleotides as plant lethal agent which provide to cells of the plant single-stranded RNA capable of hybridizing under physiological conditions in the plant cells to RNA transcribed from a target gene in the plant cell to effect silencing of the target gene. In one embodiment a liquid herbicidal composition effective against glyphosate-resistant plants includes an organosilicone surfactant such as SILWET L-77® brand surfactant and polynucleotide molecules for providing single-stranded RNA capable of hybridizing under physiological conditions in the plant cells to the RNA transcript of an endogenous or transgenic EPSPS gene encoding an EPSPS protein that provides tolerance to glyphosate. When the polynucleotide molecule is designed to hybridize under physiological conditions in a plant cell to mRNA encoding an endogenous, protein or non-protein coding RNA that essential for maintaining plant growth or life and to effect gene silencing and reduction of the essential protein, the polynucleotide molecule can function as a plant lethal agent, i.e., a nucleotide herbicide. These herbicidal compositions including polynucleotide molecules can be adapted for topical coating onto leaves of a growing plant or for application onto roots or cut stems, e.g., of hydroponically grown or pot-grown plants.

An aspect of the invention provides a composition adapted for topical coating onto leaves or other surfaces of a living plant including a permeability-enhancing agent, e.g., a surfactant such as an organosilicone surfactant, and oligonucleotides or polynucleotides that provide (directly or indirectly) single-stranded RNA that can hybridize under physiological conditions in a plant cell to RNA transcribed from an endogenous plant gene in the cell. In one embodiment the endogenous plant gene is an endogenous plant gene encoding a protein that provides herbicide tolerance to herbicides such as glyphosate, dicamba, or sulfonylurea. Examples of such proteins that provide herbicide tolerance are disclosed below in the section "Herbicide-Tolerance Proteins".

Another aspect of the invention provides a method for controlling herbicide-resistant volunteer plants growing in a field of herbicide-resistant crop plants including applying onto the leaves or other surface of the volunteer plants a composition that provides to, or allows the production in, cells of the volunteer plants a single-stranded RNA molecule that is capable of hybridizing under physiological conditions in cells of the volunteer plants to RNA that is transcribed from an endogenous gene in the cells, wherein the endogenous gene (i) is an essential gene for maintaining the growth or life of the volunteer plant, (ii) encodes a protein that provides herbicide resistance to the volunteer plant, or (iii) transcribes to an RNA regulatory agent (e.g., promoters, also miRNA precursors, miRNAs, trans-acting siRNAs, and other non-coding RNAs having a regulatory function such as aptamers and riboswitches). The composition that provides to, or allows the production in, cells of the volunteer plants a single-stranded RNA molecule that is capable of hybridizing under physiological conditions in cells of the volunteer plants to RNA that is transcribed from an endogenous gene in the cells includes at least one polynucleotide molecule selected from the group consisting of (a) a single-stranded RNA molecule, (b) a single-stranded RNA molecule that self-hybridizes to form a double-stranded RNA molecule, (c) a double-stranded RNA molecule, (d) a single-stranded DNA molecule, (e) a single-stranded DNA molecule that self-hybridizes to form a double-stranded DNA molecule, and (f) a single-stranded DNA molecule including a modified Pol III gene that is transcribed to an RNA molecule, (g) a double-stranded DNA molecule, (h) a double-stranded DNA molecule including a modified Pol III gene that is transcribed to an RNA molecule, and (i) a double-stranded, hybridized RNA/DNA molecule; In embodiments for silencing or suppression of an endogenous gene of a volunteer plant that encodes a protein that provides herbicide resistance to the volunteer plant, the method can include applying onto the volunteer plant a quantity of the herbicide for which the protein provides resistance. Compositions and methods of the invention are useful in controlling herbicide-tolerant (resistant) weeds or volunteer herbicide-tolerant (resistant) transgenic plants that may be growing in crop fields, e.g., a field of herbicide-resistant crop plants such as corn, soybean, cotton, canola, sugar beet, alfalfa, sugarcane, rice, wheat, as well as fruit and vegetable crops. In some such embodiments the weed or the volunteer plant is pigweed (e.g., Palmer amaranth) and other amaranth species, mare's tail (horseweed), waterhemp, giant ragweed, common ragweed, johnsongrass, goosegrass, ryegrass, hairy crabgrass, prickly lettuce, velvetleaf, alfalfa, corn, soybean, canola, cotton, sugar beet, sugarcane, rice, or wheat. In some such embodiments the endogenous gene encodes a protein that provides herbicide tolerance; examples of such proteins are disclosed herein in the section "Herbicide-Tolerance Proteins". In other such embodiments single-stranded RNA selectively suppresses a gene in a specific plant species but not in others, to permit selective control of that plant species. In still other such embodiments a non-selective, single-stranded RNA molecule suppresses a common gene in multiple plant species, permitting broader control across a group or taxon of plants. In more specific embodiments the method further includes applying onto the weed or volunteer plant a quantity of non-nucleotide herbicide (e.g., glyphosate, dicamba, glufosinate or sulfonylurea) for which the protein targeted by an RNA molecule provides resistance allowing dual modes of action through reducing production of the target protein by action of the RNA molecule and inhibiting the function of protein that is produced by action of the non-nucleotide herbicide; the herbicide can be applied in a separate (earlier or later) step from, or together with, the nucleotide composition. Applying a polynucleotide composition concurrently with, or followed by, application of a conventional non-nucleotide herbicide in some cases provides weed or volunteer plant control with synergistic effect (i.e., where the combined effect is greater than the sum of effects of the treatments made separately).

Herbicide-Tolerance Proteins

Natural (non-transgenic) and transgenic plants exhibiting herbicide tolerance (resistance) often have a gene that encodes a protein that is responsible for the herbicide tolerance, e.g., a transgene that provides the tolerance, a mutated endogenous gene that provides the tolerance or multiple copies of an endogenous gene that is normally targeted by an herbicide. A strategy for control of such plants is to apply an agent that suppresses, or at least reduces the expression of, the gene encoding the protein that imparts herbicide tolerance. Examples of a protein that provides tolerance to an herbicide include e.g., a 5-enolpyruvylshikimate-3-phosphate synthase (EPSPS), a glyphosate oxidoreductase (GOX), a glyphosate decarboxylase, a glyphosate-N-acetyl transferase (GAT), a dicamba monooxygenase, a phosphinothricin acetyltransferase, a 2,2-dichloropropionic acid dehalogenase, an acetohydroxyacid synthase, an acetolactate synthase, a haloarylnitrilase, an acetyl-coenzyme A carboxylase, a dihydropteroate synthase, a phytoene desaturase, a protoporphyrin IX oxygenase, a hydroxyphenylpyruvate dioxygenase, a para-aminobenzoate synthase, a glutamine synthase, a cellulose synthase, a beta-tubulin, and a serine hydroxymethyltransferase.

Examples of nucleic acids encoding proteins conferring tolerance to herbicides include 5-enolpyruvylshikimate-3-phosphate synthases (EPSPS; see, e.g., U.S. Pat. Nos. 5,627,061, 5,633,435 RE39,247, 6,040,497, and 5,094,945, and PCT International Application Publications WO04074443 and WO04009761), glyphosate oxidoreductase (GOX; U.S. Pat. No. 5,463,175), glyphosate decarboxylase (PCT International Application Publication WO05003362, U.S. Pat. No. 7,405,347, and U.S. Patent Application Publication 2004/0177399), glyphosate-N-acetyl transferase (GAT; U.S. Pat. No. 7,714,188) conferring tolerance to glyphosate; dicamba monooxygenase conferring tolerance to auxin-like herbicides such as dicamba (U.S. Pat. No. 7,105,724); phosphinothricin acetyltransferase (pat or bar) conferring tolerance to phosphinothricin or glufosinate (U.S. Pat. No. 5,646,024); 2,2-dichloropropionic acid dehalogenase conferring tolerance to 2,2-dichloropropionic acid (Dalapon) (PCT International Application Publication WO9927116); acetohydroxyacid synthase or acetolactate synthase conferring tolerance to acetolactate synthase inhibitors such as sulfonylurea, imidazolinone, triazolopyrimidine, pyrimidyloxybenzoates and phthalide (U.S. Pat. No. 6,225,105); haloarylnitrilase (Bxn) for conferring tolerance to bromoxynil (U.S. Pat. No. 4,810,648); modified acetyl-coenzyme A carboxylase for conferring tolerance to cyclohexanedione (sethoxydim) and aryloxyphenoxypropionate (haloxyfop) (U.S. Pat. No. 6,414,222); dihydropteroate synthase (sul I) for conferring tolerance to sulfonamide herbicides (U.S. Pat. No. 5,719,046); 32 kDa photosystem II polypeptide (psbA) for conferring tolerance to triazine herbicides (Hirschberg et al., 1983, Science, 222:1346-1349); anthranilate synthase for conferring tolerance to 5-methyltryptophan (U.S. Pat. No. 4,581,847); dihydrodipicolinic acid synthase (dap A) for conferring to tolerance to aminoethyl cysteine (PCT International Application Publication WO8911789); phytoene desaturase (crtI) for conferring tolerance to pyridazinone herbicides such as norflurazon (Japan Patent JP06343473); hydroxyphenylpyruvate dioxygenase, a 4-hydroxyphenylacetic acid oxidase and a 4-hydroxyphenylacetic 1-hydrolase (U.S. Pat. No. 7,304,209) for conferring tolerance to cyclopropylisoxazole herbicides such as isoxaflutole (U.S. Pat. No. 6,268,549); modified protoporphyrinogen oxidase I (protox) for conferring tolerance to protoporphyrinogen oxidase inhibitors (U.S. Pat. No. 5,939,602); aryloxyalkanoate dioxygenase (AAD-1) for conferring tolerance to an herbicide containing an aryloxyalkanoate moiety (WO05107437); a serine hydroxymethyltransferase (US Patent Application Publication 2008/0155716), a glufosinate-tolerant glutamine synthase (US Patent Application Publication 2009/0018016). Examples of such herbicides include phenoxy auxins (such as 2,4-D and dichlorprop), pyridyloxy auxins (such as fluroxypyr and triclopyr), aryloxyphenoxypropionates (AOPP) acetyl-coenzyme A carboxylase (ACCase) inhibitors (such as haloxyfop, quizalofop, and diclofop), and 5-substituted phenoxyacetate protoporphyrinogen oxidase IX inhibitors (such as pyraflufen and flumiclorac). The nucleotide sequences of the nucleic acids encoding herbicide-tolerance proteins and the sequences of the herbicide-tolerance proteins, as disclosed in the U.S. patent and patent application publications cited in this paragraph are incorporated herein by reference.

Aspects of this invention provide polynucleotides and methods that directly or indirectly provide to a plant cell RNAs that hybridize to RNA encoding such herbicide-tolerance proteins at a level to be lethal to the plant or at least at a level to reduce herbicide tolerance. Due to the sequence degeneracy of the DNA encoding herbicide-tolerance proteins it is possible to design a polynucleotide for use in this invention that is specifically effective in a particular plant. Due to conservation of domains of DNA among a multitude of plants it is possible to design a polynucleotide for use in this invention that is effective across a variety of plants.

In an embodiment the polynucleotide is admixed with the corresponding herbicide to potentiate the activity of the herbicide by providing improved herbicidal activity. In an embodiment the polynucleotide is utilized separately from the herbicide but in combination with an application of the herbicide as a pre- or post-treatment. In embodiments the organosilicone surfactant is advantageously combined with the herbicide and the polynucleotide or is combined with one or the other when the compositions are applied in a sequential manner. Plants in a greenhouse setting can be treated using a track sprayer or laboratory sprayer with a 11001XR spray nozzle to deliver the sample solution at a determined rate (e.g., 140 L/ha) at 0.25 MPa pressure. In the field the treatment solution can be applied with a $CO_2$ pressurized backpack sprayer calibrated to deliver the appropriate rate of the composition with a 11015 flat fan spray nozzle with a customized single nozzle assembly (to minimize waste) at a spray pressure of 0.25 MPa; the single nozzle sprayer provides an effective spray swath of 60 cm above the canopy of 3 to 12 inch tall growing plants.

Example 1

This example illustrates the utility of the polynucleotide molecules of this invention in controlling herbicide resistant weeds. Genotypes of glyphosate-resistant Palmer amaranth were identified as having multiple copies, e.g., from 4 to more than 100 copies, of the gene encoding 5-enolpyruvylshikimate-3-phosphate synthase (EPSPS) which is targeted by the glyphosate compounds in herbicide treatments.

With reference to SEQ ID NO:1 as shown in FIG. 1, four oligonucleotide-size "short" dsRNA molecules were designed with an anti-sense strand that is capable of hybridizing to the mRNA transcribed from the Palmer amaranth EPSPS gene at positions 14-38 (short dsRNA-1), positions 153-177 (short dsRNA-2), 345-369 (short dsRNA-3), and 1105-1129 (short dsRNA-4), as indicated by underlined nucleotides in FIG. 1. The four designed short dsRNAs were purchased from Integrated DNA Technologies (IDT); the dsRNAs had a two nucleotide overhang at the 3' end of the anti-sense strand, and had two deoxynucleotides as the terminal nucleotides at the 3' end of the sense strand.

With reference to SEQ ID NO:1 and FIG. 1, three "long" double-stranded RNA polynucleotides were designed with one strand that is capable of hybridizing to the mRNA transcribed from the Palmer amaranth EPSPS gene at positions 16-170 (long dsRNA-1), 451-722 (long dsRNA-2), and 1109-1328 (long dsRNA-3) as indicted by the bolded nucleotides in FIG. 1. The three designed long dsRNAs were made using an Ambion MEGAscript® RNAi Kit, Cat. No. 1626.

Vegetative clones of glyphosate-resistant Palmer amaranth with 16 copies of the endogenous gene encoding EPSPS (Gaines, et al. (2010) *Proceedings of the National Academy of Sciences* 107(3): 1029-1034) were grown in 3.5 inch square pots with SunGro® Redi-earth seedling mix containing 3.5 kg/cubic meter Osmocote® 14-14-14 fertilizer in a greenhouse with 14-hour photoperiod and a daytime temperature of 30 degrees centigrade and night temperature of 20 degrees centigrade; the plants were watered with deionized water as necessary.

A pretreatment surfactant solution for leaf dip was prepared by diluting SILWET L-77® brand organosilicone surfactant with distilled water to 0.1% (v/v). A pretreatment 5% (w/v) carborundum solution was prepared by mixing 2 g carborundum (400 grit) in 40 ml distilled water. A treatment buffer solution was prepared with 10 mM sodium phosphate and 0.01% (v/v) SILWET L-77® brand organosilicone surfactant in DEPC water (Omega Bio-Tek) and adjusted to pH 6.8. A short dsRNA solution was prepared with equimolar amounts of each of the four short dsRNAs (identified above) in treatment buffer solution at a concentration of 0.005 nanomoles of each short dsRNA per microliter. A long dsRNA solution was prepared with equimolar amounts of each of the three long dsRNAs in treatment buffer at a concentration of 0.0006 nanomoles of each of long dsRNA per microliter. A mixed (short/long) dsRNA solution was prepared with 0.005 nanomoles of each of the four short dsRNAs and 0.0006 nanomoles of each of the three long dsRNAs per microliter.

Vegetative clones of glyphosate-resistant Palmer amaranth with 16 copies of the endogenous gene encoding EPSPS were pre-treated with carborundum solution or surfactant solution to condition the leaves to transfer or permeation of dsRNA. For carborundum solution pre-treatment leaf abrasion was effected by gently rubbing 0.5 ml of the carborundum solution on the upper surface of a leaf, rinsing with water and blotting dry. For surfactant solution pre-treatment four, fully-expanded, mature source leaves were dipped in the surfactant solution and allowed to dry. After leaf pre-treatment by carborundum solution or surfactant solution, the conditioned leaves were treated with either buffer solution (as a control) or 40 microliters of a dsRNA solution (applying 10 microliters of dsRNA solution on each of 4 leaves per plant). Treatment with the short dsRNA solution applied about 0.8 nanomoles of short dsRNA molecules (0.2 nanomoles of each short dsRNA) to each treated plant. Treatment with the long dsRNA solution applied about 0.072 nanomoles of long dsRNA molecules (0.024 nanomoles of each long dsRNA) to each treated plant. Treatment with the mixed (short/long) dsRNA solution applied about 0.8 nanomoles of the short dsRNA molecules and about 0.072 nanomoles of the long dsRNA molecules to each treated plant. Except for controls, all plants were sprayed with a glyphosate herbicide solution (1682 g acid equivalent per hectare of Roundup® Weather-MAX® brand herbicide) immediately, 48, or 72 hours after dsRNA treatment and evaluated at least after 7 days post-glyphosate treatment.

Results:

Six surfactant-treated, control plants (no dsRNA molecule treatment) survived glyphosate treatment. See FIG. 3A for a picture of the plants 7 days after the glyphosate treatment.

Two of four carborundum abrasive-treated, control plants (no dsRNA molecule treatment) were killed by glyphosate treatment.

Six surfactant-treated plants that were treated with glyphosate immediately after application of the mixed (short/long) dsRNA solution survived but were stunted.

Six surfactant-treated plants that were treated only with the mixed (short/long) dsRNA solution and no glyphosate survived. Five of six surfactant-treated plants that were treated with the mixed (short/long) dsRNA solutions followed by glyphosate treatment were killed.

Five of six surfactant-treated plants that were treated with glyphosate 48 hours after application of the mixed (short/long) dsRNA solution were killed.

Three of four carborundum-treated plants that were treated with glyphosate 48 hours after application of the mixed (short/long) dsRNA solution were killed.

Five of six surfactant-treated plants, that were treated with the long dsRNA solution, followed by glyphosate treatment after 72 hours, were killed; see FIG. 3B. Six of six surfactant-treated plants, that were treated with the short dsRNA solution, followed by glyphosate treatment after 72 hours, were killed; see FIG. 3C.

Example 2

This example illustrates the utility of the polynucleotide molecules of this invention for improving the control of glyphosate herbicide-sensitive weeds. The mixed (short/long) dsRNA solutions prepared in Example 1 were applied to glyphosate-sensitive velvetleaf plants (a total of 40 microliters applied to two leaves) that had been pre-treated with the surfactant solution used in Example 1. Control plants were treated with buffer only following pre-treatment with the surfactant solution. 48 hours after dsRNA treatment the plants were treated with glyphosate herbicide solution (53 g acid equivalent per hectare of Roundup® WeatherMAX® brand glyphosate herbicide). A two-fold increase in glyphosate activity as estimated by observing plant growth (measured as plant height) was observed in the plants treated with the polynucleotide composition and herbicide as compared to control plants treated with buffer and herbicide. The plants treated with the polynucleotide composition and herbicide survived with severe stunting; the control plants treated with buffer and herbicide survived and fully recovered. Similar results were obtained with other glyphosate herbicide-sensitive weeds, i.e., glyphosate herbicide-sensitive waterhemp, redroot pigweed, giant ragweed, prickly lettuce, tobacco, and dandelion.

Example 3

This example illustrates the utility of the polynucleotide molecules of this invention for controlling weeds in transgenic glyphosate-resistant crops. Transgenic alfalfa, canola, corn, cotton, rice, soybean, sugarcane, sugar beet, and wheat plants having recombinant DNA for expressing a bacterial EPSPS (see U.S. Pat. RE39,247 for a description of glyphosate-resistant "class II" EPSPS genes) are treated with (a) the surfactant solution used in Example 1, (b) the mixed (short/long) dsRNA solution prepared in Example 1, and (c) glyphosate herbicide solution (1682 g acid equivalence per hectare Roundup® WeatherMAX®) 48 hours after dsRNA treatment. After 30 days all transgenic glyphosate-resistant crop plants survive and exhibit no stunting.

Example 4

This example illustrates the utility of the polynucleotide molecules of the invention as herbicidal agents. Two dsRNA polynucleotide molecules were designed to target overlapping segments of mRNA encoding phytoene desaturase in tobacco (*Nicotiana benthamiana*). With reference to SEQ ID NO:2 and FIG. 5, a dsRNA targeting a 192 nt length (shown in bold in FIG. 5) and a 685 nt length (shown in underline in FIG. 5) of the mRNA were made using an Ambion® MEGAscript® kit. Separate dsRNA solutions were prepared. Tobacco plant leaves were pretreated with surfactant solution prepared as in Example 1 and then treated with either one of the dsRNA solutions applying about 0.6 micromoles of dsRNA per plant. On day 9 after dsRNA treatment phytoene desaturase silencing was apparent from visible leaf bleaching on apical leaves; see FIG. 4. At 15 days after treatment with dsRNA one half of the treated plants appeared to be dead and the other half of the plants had most of the above ground tissues bleached. Northern blot analysis indicates the presence of siRNAs corresponding to the dsRNAs used in treatment.

Example 5

This example further illustrates the utility of polynucleotide molecules of the invention as herbicidal agents. dsRNA oligonucleotide molecules are designed to target RNA encoding EPSPS for each of the following plants: ragweed (*Ambrosia artemisiifolia*), giant ragweed (*Ambrosia trifida*), Johnsongrass (*Sorghum halepense*), hairy fleabane (*Conzya bonariensis*), sourgrass (*Digitaria insularis*), liverseedgrass (*Urochloa panicoides*), euphorbia (*Euphorbia heterophylla*), junglerice (*Echinochloa colona*), lambsquarters (*Chenopodium album*), green foxtail (*Setaria viridis*), foxtail millet (*Setaria italic*), barnyard grass (*Echinochloa crus-galli*), crabgrass (*Digitaria sanguinalis*), cocklebur (*Xanthium strumarium*), blackgrass (*Alopecurus myosuroides*), wild oat (*Avena fatua*), sicklepod (*Senna obtusifolia*), morning glories (*Ipomoea* sp.), field bindweed (*Convolvulus arvensis*), shattercane (*Sorghum bicolor*), dayflower (*Commelina*), Spiderwort (*Tradescantia* sp.), ryegrass (*Lolium* sp.), goosegrass (*Eleusine indica*), horseweed (*Conzya canadensis*), buckhorn plantain (*Plantago lanceolata*), pigweed (*Amaranthus palmeri*), rough-fruit amaranth (*Amaranthus tuberculatus*), tumble pigweed (*Amaranthus albus*), smooth pigweed (*Amaranthus hybridus*), redroot pigweed (*Amaranthus retroflexus*), waterhemp (*Amaranthus rudis/tuberculatus*), slender amaranth (*Amaranthus viridis*), Thunberg's amaranth (*Amaranthus thumbergii*), spiny amaranth (*Amaranthus spinosis*), (*Amaranthus rubra*), (*Amaranthus lividus*), Mediterranean amaranth (*Amaranthus graecizans*), rough amaranth (*Amaranthus chlorostachys*), Powell amaranth (*Amaranthus powellii*), Mat amaranth (*Amaranthus blitoides*), Kochia (*Kochia scoparia*), Yellow starthistle (*Centaurea solstitialis*), and Velvetleaf (*Abutilon theophrasti*). Plant leaves are pretreated with surfactant solution prepared as in Example 1 and treated with dsRNA solutions at a treatment of about 1 nanomole per plant. After 15 days treated plants are dead, dying, or stunted.

Example 6

This example further illustrates the utility of polynucleotide molecules of the invention as herbicidal agents. dsRNA oligonucleotide molecules are designed to target RNA encoding acetolactate synthase and phytoene desaturase for each of the plants listed in Example 5. Plant leaves are pretreated with surfactant solution prepared as in Example 1 and treated with dsRNA solutions at a treatment of about 1 nanomole per plant. After 15 days treated plants are dead, dying, or stunted.

Example 7

This example further illustrates the utility of the polynucleotide molecules of the invention as herbicidal agents. The method of Example 4 is repeated to provide short dsRNA oligonucleotides that are designed to target RNA encoding each of the following proteins in Palmer amaranth: a 5-enolpyruvylshikimate-3-phosphate synthase (EPSPS), an acetyl-coenzyme A carboxylase, a dihydropteroate synthase, a protoporphyrin IX oxygenase, a hydroxyphenylpyruvate dioxygenase, a glutamine synthase, D1 protein, a translation initiation factor (TIF), a ribulose-1,5-bisphosphate carboxylase oxygenase (RuBisCO), and a DNA-dependent ATPase (ddATPase). Leaves of separate glyphosate-resistant Palmer amaranth plants are treated with the surfactant solution prepared as in Example 1 and separately each of the dsRNA oligonucleotide molecules in the manner of Example 1 at a treatment of 1 nanomole of dsRNA per plant. After 30 days the treated plants are dead, dying, or stunted.

Example 8

This example illustrates the utility of employing a synthetic Pol III gene in compositions and methods of this invention. With reference to SEQ ID NO:3 and FIG. 2, a synthetic Pol III gene is created using elements from an *Arabidopsis thaliana* U6 snRNA gene to provide a dsDNA molecule with two copies of RGCCCR elements (bold and underlined), an upstream sequence element (USE) having the sequence "TCCCACATCG" (SEQ ID NO:4, bold and underlined), a TATA box (bold and underlined), a "G" nucleotide (bold and underlined), anti-sense DNA (italics) corresponding to a bacterial DNA encoding an EPSPS protein (see U.S. Pat. RE39, 247) that imparts resistance to glyphosate herbicide when expressed in transgenic corn plants, an "AAGATTAG-CACGG" element (SEQ ID NO:5, bold and underlined) embedded in the anti-sense DNA, an "ACGCATAAAAT" element (SEQ ID NO:6, bold and underlined) followed by sense DNA (lower case) and a "TTTTTT" terminator element (SEQ ID NO:7, bold and underlined). A solution of 0.1 wt % SILWET L-77® brand organosilicone surfactant and a solution of multiple copies of the dsDNA molecule are sprayed onto leaves of volunteer glyphosate-resistant corn plants growing in a field of glyphosate-resistant soybean plants, followed 7 days later by treatment with Roundup Weather-MAX® brand glyphosate herbicide. 15 days later the corn plants are dead and the soybean plants are thriving; control glyphosate-resistant corn plants treated only with surfactant and glyphosate herbicide are thriving.

Example 9

This example illustrates an aspect of the invention. In this example, polynucleotide molecules were applied to and permeated into plant tissue thereby inducing systemic regulation, i.e., silencing, of a target gene (an endogenous EPSPS). More specifically, a composition including single-stranded DNA (ssDNA) oligonucleotides suppressed the expression of an endogenous EPSPS in glyphosate-tolerant Palmer amaranth (*Amaranthus palmeri*).

The anti-sense ssDNA oligonucleotides were designed using IDT SciTools software (available at idtdna.com/Scitools/Applications/Anti-sense/Anti-sense.aspx). The oligonucleotides included four ssDNA oligonucleotides anti-sense to *Amaranthus palmeri* EPSPS (SEQ ID NOs:8, 9, 10, and 11), two chemically modified (phosphorothioate modified) ssDNA oligonucleotides anti-sense to *Amaranthus palmeri* EPSPS (SEQ ID NOs:12 and 13), a control ssDNA oligonucleotide anti-sense to a control gene, barley (*Hordeum vulgare*) seed protein, GenBank ID X97636 (SEQ ID NO:14), and a chemically modified (5'-labelled with Alexa Fluor 488 from Invitrogen) ssDNA oligonucleotide anti-sense to *Amaranthus palmeri* EPSPS (SEQ ID NO:15), as indicated in Table 1.

TABLE 1

Anti-sense ssDNA oligonucleotides

| Name | SEQ ID NO: | Sequence (5' to 3') | Note |
|---|---|---|---|
| Anti-sense_PO1 | 8 | ACCCTCCACGACTGCCCTTT | |
| Anti-sense_PO2 | 9 | GTTTCCTTCACTCTCCAGC | |
| Anti-sense_PO3 | 10 | GTAGCTTGAGCCATTATTGT | |
| Anti-sense_PO4 | 11 | GTTGATGGTAGTAGCTTGAG | |
| Anti-sense_PS1 | 12 | ACCCTCCACGACTGCCCTTT | phosphorothioate modification of the three 5'-terminal and three 3'-terminal nucleotides |
| Anti-sense_PS2 | 13 | GTTTCCTTCACTCTCCAGC | phosphorothioate modification of the three 5'-terminal and three 3'-terminal nucleotides |
| Anti-sense_ck | 14 | AAGCGGTTGAGCACTGAA | Control sequence, barley seed protein, GenBank ID X97636 |
| Anti-sense_PO1_488 | 15 | ACCCTCCACGACTGCCCTTT | 5'-labelled with Alexa Fluor 488 |

Oligonucleotide uptake was demonstrated with the fluorescently labelled ssDNA oligonucleotides (SEQ ID NO:15) confirming that ssDNA oligonucleotides permeated the leaf tissue. Petioles of detached leaves of glyphosate-resistant Palmer amaranth were placed in 200 mM sucrose solution with fluorescently labelled ssDNA oligonucleotides (SEQ ID NO:15). Leaf images were taken by Bio-Rad PharosFX imager equipped with a 488 nm laser from 4 h up to 48 h after uptake through petiole. Leaves incubated with 200 mM sucrose alone served as control. A slightly time-dependent vascular uptake of the fluorescently labelled ssDNA oligonucleotides was observed (see FIG. 6). Fluorescently labelled ssDNA oligonucleotides were released from vascular tissue into cells as early as 8 h after treatment and were observed to accumulate at the leaf edge at 24 h and 48 h, suggesting a transpiration effect.

EPSPS suppression was demonstrated with detached leaves of glyphosate-resistant Palmer amaranth using the petiole uptake technique. Petioles of detached leaves of glyphosate-resistant Palmer amaranth were placed in 200 mM sucrose solution with oligonucleotides according to the treatments listed in Table 2. Control leaves were permeated with the anti-sense control (SEQ ID NO:14), and additionally treated with or without 50 micrograms/mL glyphosate. EPSPS mRNA, EPSPS protein, and shikimate levels were measured after 48 h incubation. To assess the effects of anti-sense ssDNA oligonucleotides on EPSPS mRNA, total leaf RNA was isolated and quantitative real-time RT-PCR was performed to compare EPSPS mRNA levels. To assess the effects of anti-sense ssDNA oligonucleotides on EPSPS protein, total leaf soluble protein was isolated, separated by SDS-PAGE, and EPSPS protein levels measured by Western blot using antibodies against maize EPSPS TIPA. Effects of anti-sense ssDNA oligonucleotides on shikimate accumulation as an indication of suppression of EPSPS were assessed in two experiments: in experiment 1, the oligonucleotide-treated leaves were incubated with 50 microgram/mL glyphosate for an additional 48 h either by petiole uptake (control leaves were permeated with the anti-sense control (SEQ ID NO:14), and additionally treated with or without 50 micrograms/mL glyphosate); in experiment 2, leaf disc assays were performed on the oligonucleotide-treated leaves, and shikimate levels measured by HPLC (controls in this case were leaves that had not been treated with oligonucleotides but incubated with 50 microgram/mL glyphosate).

TABLE 2

List of treatments using anti-sense ssDNA oligonucleotides

| Treatment | Anti-sense ssDNAs | Final concentration |
|---|---|---|
| #1 | Anti-sense_PO1 (SEQ ID NO: 8) | 5 microM |
| #2 | Anti-sense_PO2 (SEQ ID NO: 9) | 5 microM |
| #3 | Anti-sense_PS1 (SEQ ID NO: 12) | 5 microM |
| #4 | Anti-sense_PS2 (SEQ ID NO: 13) | 5 microM |
| #5 | Anti-sense_PS1, PS2 (SEQ ID NOs: 12, 13) | 10 microM each (20 microM total) |
| #6 | Anti-sense_PO1, PO2, PO3, PO4 (SEQ ID NOs: 8, 9, 10, 11) | 5 microM each (20 microM total) |
| Control | Anti-sense_ck (SEQ ID NO: 14) | 5 microM or 20 microM |

Figure 7:
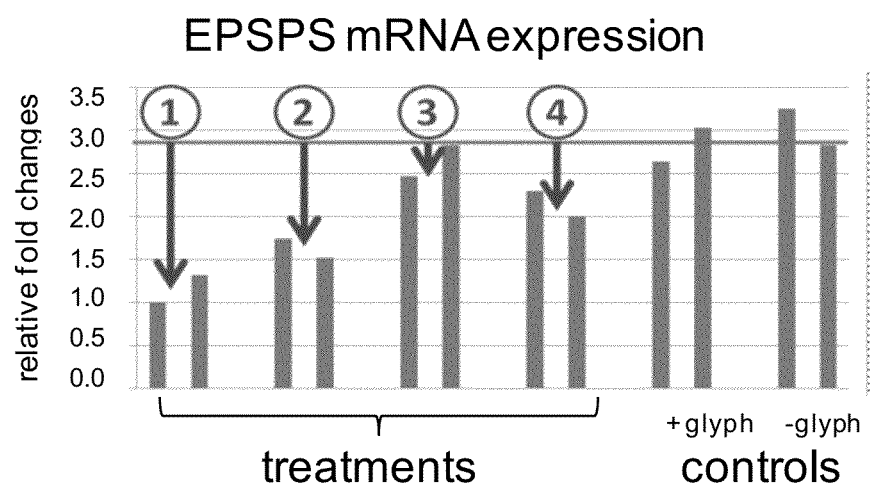
FIG. 7 depicts results of EPSPS mRNA measured in glyphosate-resistant Palmer amaranth leaves treated with anti-sense ssDNA oligonucleotides for EPSPS as described in Example 9. Bars represent replicate experiments for each of treatments #1-#4 (indicated by the numbers enclosed in circles and referring to Table 2) and for controls (leaves permeated with anti-sense ssDNA oligonucleotides for a barley seed protein, SEQ ID NO:14, treated with or without glyphosate).
Figure 8:
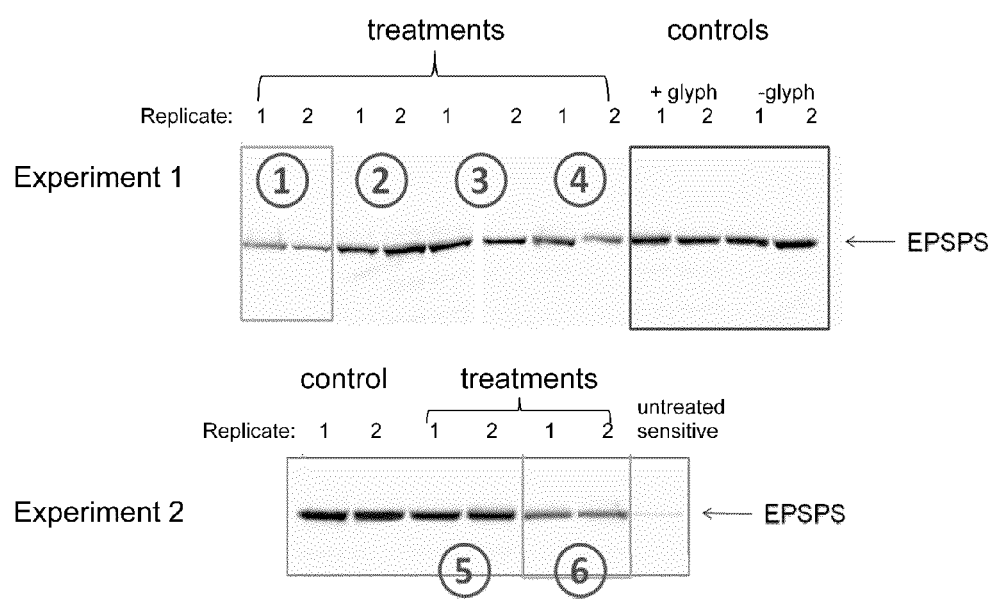
FIG. 8 depicts results of EPSPS protein measured in glyphosate-resistant Palmer amaranth leaves topically treated with anti-sense ssDNA oligonucleotides for EPSPS as described in Example 9; treatments are indicated by the numbers enclosed in circles and refer to Table 2.
Figure 9:
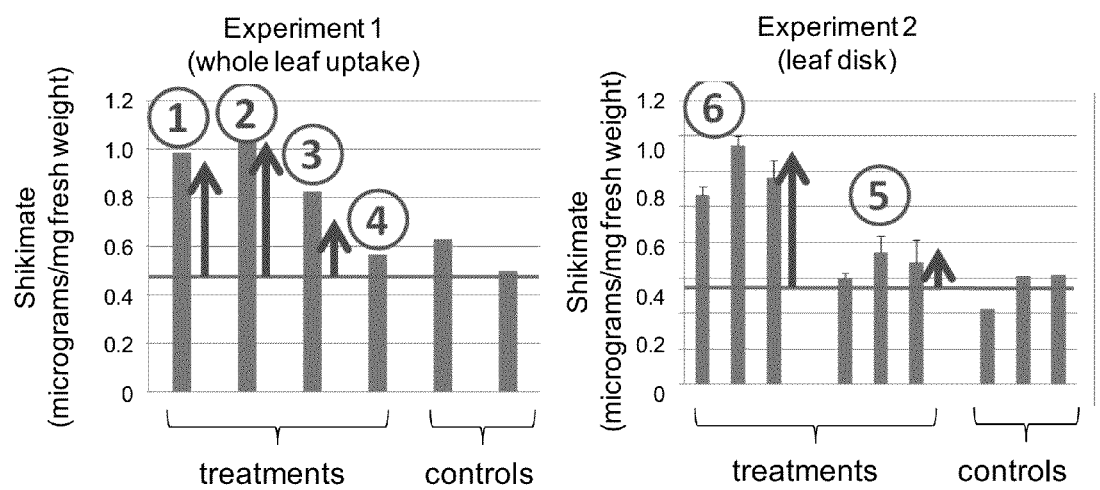
FIG. 9 depicts results of shikimate accumulation measured in glyphosate-resistant Palmer amaranth leaves treated with anti-sense ssDNA oligonucleotides for EPSPS in two experiments as described in Example 9; treatments are indicated by the numbers enclosed in circles and refer to Table 2.

Results for EPSPS mRNA expression, EPSPS protein levels, and shikimate levels are shown in FIGS. 7, 8, and 9, respectively. These results demonstrate that treatment with the anti-sense ssDNA oligonucleotides systematically regulated or suppressed the target gene by decreasing levels of the target gene transcript (EPSPS mRNA) or of the protein (EPSPS) encoded by the target gene in the plant tissue. In this particular experiment, treatments #1 and #6 appeared to be more efficacious in suppressing levels of EPSPS mRNA and protein and in increasing glyphosate efficacy as evidenced by the increased accumulation of shikimate. These results also indicate that glyphosate efficacy is improved by suppressing EPSPS mRNA and protein in glyphosate-resistant Palmer amaranth.

Example 10

This example illustrates an aspect of the invention. In this example, growing plants were treated with a topically applied composition for inducing systemic silencing of a target gene in a plant including (a) an agent for conditioning of a plant to permeation by polynucleotides and (b) polynucleotides including at least one polynucleotide strand including at least one segment of 18 or more contiguous nucleotides of the target gene in either anti-sense or sense orientation. More specifically, tobacco (*Nicotiana benthamiana*) plants were treated with (a) a topically applied surfactant solution for conditioning of the plant to permeation by polynucleotides and (b) a composition including topically applied DNA oligonucleotides or polynucleotides having at least one strand including at least one segment of 18 or more contiguous nucleotides of the target gene in either anti-sense or sense orientation, whereby systemic regulation or suppression of the target gene (a phytoene desaturase, "PDS") was achieved.

Figure 11:
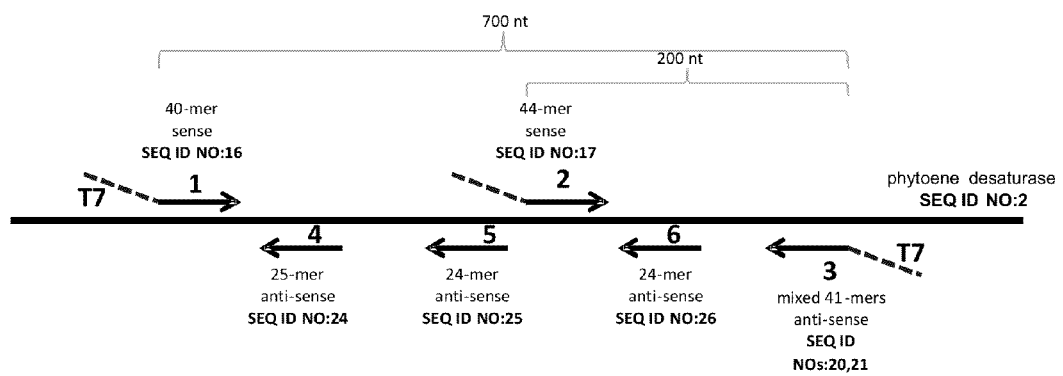
FIG. 11 schematically depicts the location of the sequences of assayed oligonucleotides and polynucleotides (see Table 3) in relation to the phytoene synthase sequence (SEQ ID NO:16) as described in Example 10.

The target gene used was a *Nicotiana benthamiana* phytoene desaturase (SEQ ID NO:2), shown in FIG. 10; the segment consisting of nucleotides 421-1120 of SEQ ID NO:2 (underlined text in FIG. 10) was used to design a 700-mer dsRNA polynucleotide ("PDS 700-mer") and the segment consisting of nucleotides 914-1113 of SEQ ID NO:2 (bolded underlined text in FIG. 10) was used to design a 200-mer dsRNA polynucleotide ("PDS 200-mer"). Sequences of other polynucleotides or oligonucleotides used in the treatments are listed in Table 3. FIG. 11 schematically depicts the location of the sequences of these oligonucleotides and polynucleotides in relation to the phytoene synthase (SEQ ID NO:2) sequence. Non-plant sequences obtained from corn rootworm ("CRW"), SEQ ID NOs:27, 28, 29, and 30 were used as non-homologous controls. Some of the polynucleotides included a T7 promoter sequence (indicated by lowercase text in Table 3) that is a promoter recognized by a bacteriophage T7 RNA polymerase.

TABLE 3

| Description | sense/anti-sense | sequence | Number of nucleotides | SEQ ID NO: |
|---|---|---|---|---|
| oligo 1 with T7 promoter | S | taatacgactcactataggGCAAGAGATGTCCTAGGTGGG | 40 | 16 |
| oligo 2 with T7 promoter | S | taatacgactcactataggACAGATTTCTTCAGGAGAAACATGG | 44 | 17 |
| oligo 1 w/o T7 promoter | S | GCAAGAGATGTCCTAGGTGGG | 21 | 18 |
| oligo 2 w/o T7 promoter | S | ACAGATTTCTTCAGGAGAAACATGG | 25 | 19 |
| oligo 3 mix with T7 promoter | AS | taatacgactcactataggCATCTCCTTTAATTGTACTGCC (SEQ ID NO: 20) and taatacgactcactataggTTTAATTGTACTGCCATTATTC (SEQ ID NO: 21) | 41 (SEQ ID NO: 20), 41 (SEQ ID NO: 21) | 20, 21 |
| oligo 3 mix w/o T7 promoter | AS | CATCTCCTTTAATTGTACTGCC (SEQ ID NO: 22) and TTTAATTGTACTGCCATTATTC (SEQ ID NO: 23) | 22 (SEQ ID NO: 22), 22 (SEQ ID NO: 23) | 22, 23 |

TABLE 3-continued

| Description | sense/<br>anti-<br>sense | sequence | Number of<br>nucleotides | SEQ<br>ID<br>NO: |
|---|---|---|---|---|
| oligo 4 w/o T7 promoter | AS | CACTTCCATCCTCATTCAGCTCGAT | 25 | 24 |
| oligo 5 w/o T7 promoter | AS | ACACCTCATCTGTCACCCTATCAG | 24 | 25 |
| oligo 6 w/o T7 promoter | AS | CAGTCTCGTACCAATCTCCATCAT | 24 | 26 |
| CRW oligo mixture with T7 promoter | S and AS | taatacgactcactatagggATCCATGATATCGTGAACATC (SEQ ID NO: 27) and taatacgactcactatagggGCAAAGAAAAATGCGTCG (SEQ ID NO: 28) | 41 (SEQ ID NO: 27), 38 (SEQ ID NO: 28) | 27, 28 |
| CRW oligo mixture w/o T7 promoter | S and AS | ATCCATGATATCGTGAACATC (SEQ ID NO: 29) and GCAAAGAAAAATGCGTCG (SEQ ID NO: 29) | 21 (SEQ ID NO: 29), 18 (SEQ ID NO: 30) | 29, 30 |

The following procedure was used for all assays described in this example. Four-week old *Nicotiana benthamiana* plants were used in all assays. Plants were treated with 0.1% SILWET L-77® brand surfactant solution freshly made with ddH2O. Two fully expanded leaves per plant (one cotyledon, one true leaf) were dipped into the SILWET L-77® brand surfactant solution for a few seconds, and allowed to dry for 15-30 minutes before application of the polynucleotide composition. Final concentration for each oligonucleotide or polynucleotide was 25 microM (in 0.01% SILWET L-77® brand surfactant, 5 mM sodium phosphate buffer, pH 6.8) unless otherwise stated. 20 microliters of the solution was applied to the top surface of each of the two pre-treated leaves to provide a total of 40 microliters (1 nmol oligonucleotide or polynucleotide) for each plant. Leaf bleaching was observed 3 days post treatment.

FIG. 12A illustrates results of an assay where a 200-mer dsRNA polynucleotide with an RNA sequence corresponding to the "PDS 200-mer" segment (nucleotides 914-1113 of SEQ ID NO:2) and a combination of single-stranded DNA oligonucleotides and polynucleotides (SEQ ID NOs:16, 17, 20, 21, 24, 25, and 26) were separately applied to tobacco plants. The 200-mer dsRNA polynucleotide was applied at a concentration of 0.6 microM. Bleaching of apical leaves was observed after topical treatment with the polynucleotides and oligonucleotides, indicating systemic regulation or suppression of the target phytoene desaturase gene.

FIG. 12B illustrates results of northern blot analysis of RNA isolated from *Nicotiana benthamiana* plants treated with buffer (control), the 200-mer dsRNA polynucleotide, and the ssDNA oligonucleotides. Also shown is RNA isolated from plants that had been stressed by being kept at 4 degrees Celsius and in the dark overnight prior to treatment with the 200-mer dsRNA polynucleotides.

Figure 13:
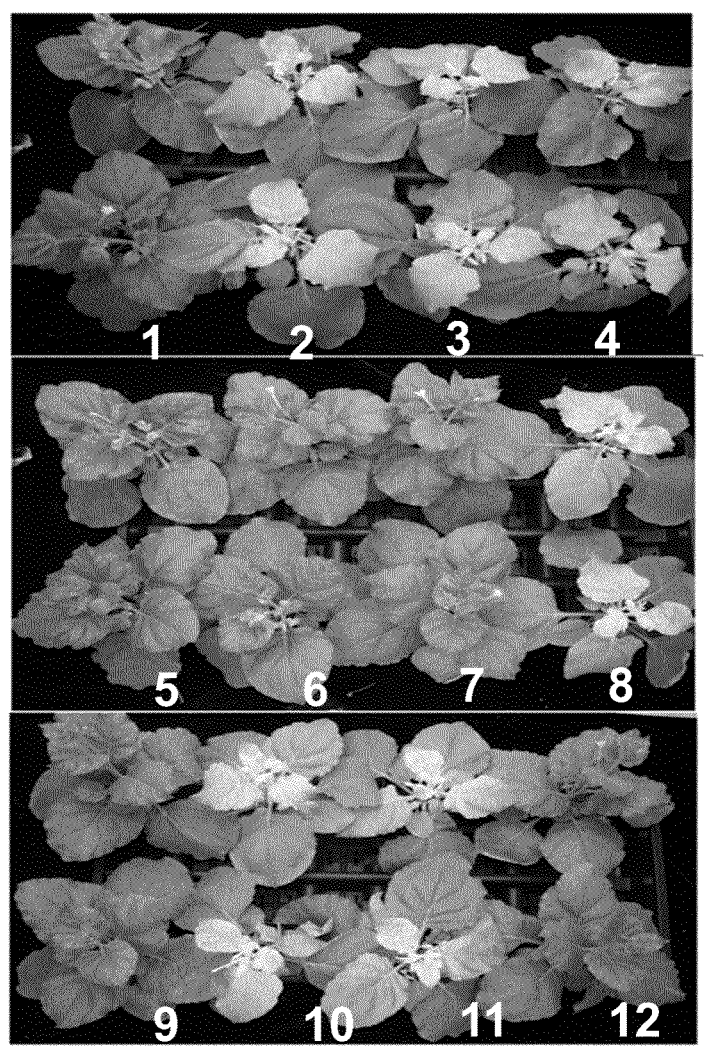
FIG. 13 illustrates apical leaf bleaching in *Nicotiana benthamiana* plants topically treated in duplicate with various combinations of polynucleotides or oligonucleotides (numbers refer to the treatments listed in Table 4) as described in Example 10. The control (Treatment 13 in Table 4) plants are not shown.

FIG. 13 illustrates phenotypes observed at day 12 after treatment in another assay of the effect from twelve combinations of polynucleotides or oligonucleotides (see Table 4). Table 4 also lists observations of visible bleaching of the plants at day 5 after treatment and the results of chlorophyll measurements taken at days 7 and 12 after treatment. Chlorophyll measurements are an indication of suppression of the target gene phytoene desaturase, and measurements were taken at 6 spots on the apical area, focussing on visibly bleached leaves or (in plants without visible bleaching) on leaves in equivalent locations on the plants; lower chlorophyll measurement values indicate suppression of phytoene desaturase. These results show that the combinations of oligonucleotides and polynucleotides in treatments 2, 3, 4, 8, and 11 were effective in systematically regulating (suppressing) the target gene in the treated plants; treatment 1 also effected systematic regulation (suppression) of the target gene to a lesser extent. The 200-mer dsRNA polynucleotide was also effective in systematically regulating (suppressing) the target gene in the treated plants. Oligonucleotides from a non-homologous (corn rootworm) gene (treatments 5 and 6) did not suppress the target phytoene desaturase gene. These results demonstrate that both sense and anti-sense single-stranded DNA oligonucleotides and polynucleotides were effective in systematically regulating (suppressing) the target gene in the treated plants. In this particular example, sense oligonucleotides with the T7 promoter (treatment 1) effected a weak systematic suppression of the phytoene desaturase gene, whereas sense oligonucleotides without the T7 promoter (treatment 7) did not suppress the phytoene desaturase gene. In this particular example, anti-sense oligonucleotides with the T7 promoter (treatment 2) as well as anti-sense oligonucleotides without the T7 promoter (treatment 8) both provided strong bleaching, indicating strong systemic regulation of the target phytoene desaturase gene.

TABLE 4

| Treatment | Description | SEQ ID NO: | Comment | Bleaching (day 5) | Chlorophyll (day 7) | Chlorophyll (day 12) |
|---|---|---|---|---|---|---|
| 1 | Oligos 1 and 2 | 16, 17 | Sense oligos with T7 promoter | weak | 18.6 | 17.5 |

TABLE 4-continued

| Treatment | Description | SEQ ID NO: | Comment | Bleaching (day 5) | Chlorophyll (day 7) | Chlorophyll (day 12) |
|---|---|---|---|---|---|---|
| 2 | Oligo 3 | 20, 21 | Anti-sense oligos with T7 promoter | strong | 12.7 | 1.6 |
| 3 | Oligos 1, 2, and 3 | 16, 17, 20, 21 | Sense and anti-sense oligos with T7 promoter | strong | 11.5 | 2.6 |
| 4 | Oligos 1, 2, 3, 4, 5 and 6 | 16, 17, 20, 21, 24, 25, 26 | Sense and anti-sense oligos with T7 promoter, plus anti-sense oligos without T7 promoter | strong | 15.1 | 2.5 |
| 5 | CRW oligo mixture with T7 promoter | 27, 28 | Sense and anti-sense oligos with T7 promoter | not yet | 30.8 | 37.3 |
| 6 | CRW oligo mixture without T7 promoter | 29, 30 | Sense and anti-sense oligos without T7 promoter | not yet | 34.2 | 38.2 |
| 7 | Oligos 1 and 2 without T7 promoter | 18, 19 | Sense oligos without T7 promoter | not yet | 32.0 | 41.1 |
| 8 | Oligo 3 without T7 promoter | 22, 23 | Anti-sense oligos without T7 promoter | strong | 11.3 | 3.2 |
| 9 | Oligos 1, 2, and 3 w/o T7 promoter and oligos 4, 5, & 6 | 18, 19, 22, 23, 24, 25, 26 | Sense and anti-sense oligos without T7 promoter | not yet | 30.2 | 34.4 |
| 10 | 200-mer dsRNA polynucleotide | RNA sequence corresponding to the "PDS 200-mer" segment consisting of nucleotides 914-1113 of SEQ ID NO:2 | Sense and anti-sense dsRNA polynucleotide | strong | 11.3 | 4.0 |
| 11 | 1/10th of Experiment 4 oligonucleotide mixture | 16, 17, 20, 21, 24, 25, 26 | Sense and anti-sense oligos with T7 promoter, plus anti-sense oligos without T7 promoter | strong | 11.4 | 4.5 |
| 12 | 1/100th of Experiment 4 oligonucleotide mixture | 16, 17, 20, 21, 24, 25, 26 | Sense and anti-sense oligos with T7 promoter, plus anti-sense oligos without T7 promoter | not yet | 31.0 | 38.0 |
| 13 | Control | (none) | Buffer only | not yet | 31.2 | 38.4 |

Figure 14:
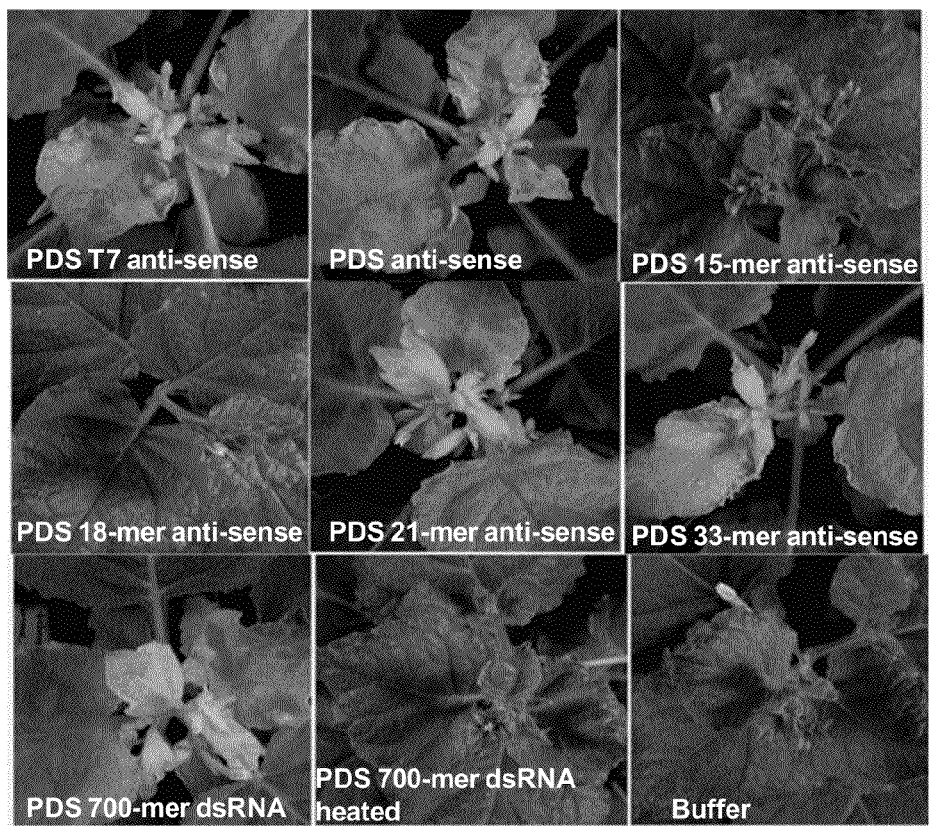
FIG. 14 illustrates apical leaf bleaching in *Nicotiana benthamiana* plants topically treated with the polynucleotides listed in Table 5 as described in Example 10.

Table 5 shows six polynucleotides: a 40-mer segment ("PDS 40-mer sense ssDNA", SEQ ID NO:31) consisting of the 5'-most 40 nucleotides of the "PDS 700-mer" (nucleotides 1081-1120 of SEQ ID NO:2), and four anti-sense single-stranded DNA polynucleotides and one sense single-stranded DNA polynucleotide synthesized based on the "PDS 40-mer sense ssDNA" sequence (SEQ ID NO:31). FIG. 14 illustrates results of topical treatment of tobacco plants with the polynucleotides and oligonucleotides. Strong bleaching of apical leaves indicating systemic regulation or suppression of the target gene phytoene desaturase was observed after topical treatment with the PDS 21-mer anti-sense ssDNA and PDS 33-mer anti-sense ssDNA, as well as after topical treatment with the PCR-amplified and column-purified 700-mer dsRNA polynucleotide ("PDS 700-mer dsRNA"), previously assayed PDS anti-sense 22-mer oligonucleotides with a T7 promoter (SEQ ID NOs:20 and 21) ("PDS T7 anti-sense"), or previously assayed PDS anti-sense 22-mer oligonucleotides without a T7 promoter (SEQ ID NOs:22 and 23) ("PDS anti-sense"). Little or no visible bleaching of apical leaves was observed after topical treatment with the buffer only ("Buffer"), or after topical treatment with heat-denatured (5 minutes at 95 degrees Celsius, then stored on ice) 700-mer dsRNA polynucleotide ("PDS 700-mer dsRNA heated"), the PDS 15-mer anti-sense ssDNA, or the PDS 18-mer anti-sense ssDNA.

TABLE 5

| Description | Sequence | SEQ ID NO: |
|---|---|---|
| PDS 40-mer sense ssDNA | TGTTTTATACTGAATAATGGCAGTACAATTAAAGGAGATG | 31 |
| PDS 15-mer anti-sense ssDNA | CATCTCCTTTAATTG | 32 |
| PDS 18-mer anti-sense ssDNA | CATCTCCTTTAATTGTAC | 33 |
| PDS 21-mer anti-sense ssDNA | CATCTCCTTTAATTGTACTGC | 34 |
| PDS 33-mer anti-sense ssDNA | CATCTCCTTTAATTGTACTGCCATTATTCAGTA | 35 |
| PDS 21-mer sense ssDNA | GCAGTACAATTAAAGGAGATG | 36 |

Figure 15:
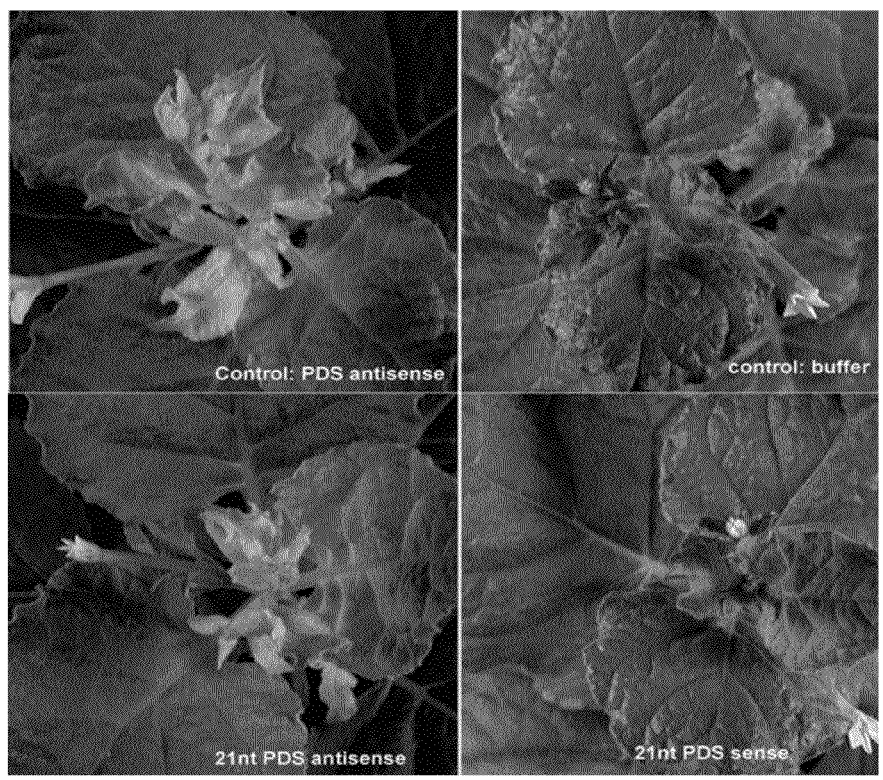
FIG. 15 illustrates apical leaf bleaching observed in *Nicotiana benthamiana* plants after topical treatment with the PDS 21-mer anti-sense ssDNA (SEQ ID NO:34, "21nt PDS anti-sense") or with previously assayed PDS anti-sense 22-mer oligonucleotides without a T7 promoter (SEQ ID NOs:22 and 23) ("PDS anti-sense"). Little or no visible bleaching of apical leaves was observed after topical treatment with the buffer only or after topical treatment with PDS 21-mer sense ssDNA (SEQ ID NO:36, "21nt PDS sense") as described in Example 10.

Results of another assay are shown in FIG. 15, strong bleaching of apical leaves indicating systemic regulation or suppression of the target gene phytoene desaturase was observed after topical treatment with the PDS 21-mer anti-sense ssDNA (SEQ ID NO:34, "21nt PDS anti-sense") or with previously assayed PDS anti-sense 22-mer oligonucleotides without a T7 promoter (SEQ ID NOs:22 and 23) ("PDS anti-sense"). Little or no visible bleaching of apical leaves was observed after topical treatment with the buffer only ("control: buffer"), or after topical treatment with PDS 21-mer sense ssDNA (SEQ ID NO:36, "21nt PDS sense").

Example 11

This example illustrates treatment of growing plants with a topically applied composition for inducing systemic silencing of a target gene in a plant including (a) an agent for conditioning of a plant to permeation by polynucleotides and (b) polynucleotides including at least one polynucleotide strand including at least one segment of 18 or more contiguous nucleotides of the target gene in either anti-sense or sense orientation. More specifically, this example demonstrates the target specificity (sequence specificity) of the polynucleotides.

Palmer amaranth phytoene desaturase (PDS) has the sequence TCAATTTCATCTATTGGAAGT-GATTTTTTGGGTCATTCTGT-GAGAAATTTCAGTGTTAGTAAAGTTTATG GAG-CAAAGCAAAGAAATGGGCACTGCCCTTTAAAGGT TGTTTGTATAGATTATCCTAGGCCAGAGCTT GAAAG-TACATCCAATTTCTTGGAAGCCGC-CTACTTATCTTCTACTTTTCGGAAT-TCGCCTCGTCCTCAG AAGCCATTAGAAGTTGTAATTGCTGGAG-CAGGTTTGGCTGGTCTATCCACG-GCAAAGTATTTAGCTGA TGCAGGTCACAAAC-CCATATTGTTGGAAGCACGAGATGTTT TAGGAGGAAAGGTTGCAGCGTGGAAGGATGAGGA TGGTGACTGGTATGAGACTGGGCTACATATATTCTTT GGGGCATATCCAAATGTCCAAAATCTATTTGGAGAA CTTGGTATAAATGACCGACTGCAATGGAAGGAGCAC TCTATGATTTTTGCAATGCCCAGCAAGCCCGGTGAA TTCAGTCGCTTTGATTTCCCGAAATCCTGCCTGCA CCATTAAATGGCATATGGGCAATCCTAAGAAATAAT GAAATGCTAACCTGGCCAGAAAAAATCAAGTTTGC CATTGGCTTGTTGCCTGCTATGGCAGGCGGACAGT CATATGTTGAAGCACAAGATGGTTTGAGTGTCCAA GAGTGGATGAGAAAACAAGGAGTACCCGATCGTGT AACTGATGATGTGTTTATTGCCATGTCAAAGGCACT GAACTTCATAAATCCCGATGAACTTTCAATGCAGTG CATCTTGATTGCTCTGAACCGATTCCTGCAGGAGAA ACATGGTTCTAAGATGGCCTTCCTAGACGGAAACCC TCCAGAGAGGCTGTGCATGCCTATTGTTAAACACAT CGAGTCACTAGGTGGTGAAGTTAAACTTAACTCTCG TATACAAAAGATTCAGTTGGACCAGAGTGGAAGCGT GAAGAGTTTTTTGCTAAATAACGGGAGGGAAATAC GAGGAGATGCCTATGTTTTTGCCAC-CCCAGTTGACATCTTGAA GCTGTTACTACCT-GATACTTGGAAGGAAATCTCATACT-TCAAAAAACTTGAGAAATTAGTGGGCGTTC CTGTGATTAATGTTCACATATGGTTTGA-CAGAAAATTAAAGAATACATATGAC-CATCTACTCTTCAGCA GGAGTCCTCTTTTGAGT-GTCTATGCTGATATGTCGGAGACATGCAAGGAATATA AGGATCCAAATAGA TCCATGCTGGAATTG-GTTTTTGCACCCGCGGAGGAATG-GATTTCACGAAGCGACACTGATATTATAGA GGCAA-CAATGAAAGAGCTTGCCAAGCTTTTCCCGGATGAA ATCGCTGCCGATGGAAGCAAGGCCAAG ATCCT-CAAATATCATGTCGTCAAAACTCCAAG-GTCGGTTTATAAGACTGTACCGGATTGT-GAACCTTGT CGGCCGCTGCAAAGATCACCAATA-GAGGGTTTCTATTTAGCTGGTGATTACA-CAAAACAAAAATATTT GGCTTCTATGGAAGGTGCT-GTCTTATCTGGGAAGCTTTGTGCACAGGCTATCGTA CAGGATTATGATCT GCTGAGTTCTCGAGCACAAA-GAGAATTGGCG (SEQ ID NO:37). A 678 base pair dsRNA polynucleotide with an anti-sense strand capable of hybridizing to the RNA encoded by the nucleotides at positions 317-994 (shown as underlined text) in SEQ ID NO:37 and a 198 base pair dsRNA polynucleotide with an anti-sense strand capable of hybridizing to the RNA encoded by the nucleotides at positions 797-994 (shown as italicized and underlined text) in SEQ ID NO:37 were synthesized.

*Nicotiana benthamiana* phytoene desaturase has the sequence ATGCCCCAAATCGGACTTGTATCTGCT-GTTAATTTGAGAGTCCAAGGTAAT-TCAGCTTATCTTTGGAGC TCGAGGTCTTCGTTGG-GAACTGAAAGTCAAGATGTTTGCTTGCAAAGGAAT TTGTTATGTTTTGGTAGT AGCGACTCCATGGGGCAT-AAGTTAAGGATTCGTACTCCAAGTGC-CACGACCCGAAGATTGACAAAGG ACTTTAATCCTT-TAAAGGTAGTCTGCATTGATTATCCAAGACCAGAGC TAGACAATACAGTTAACTATT TGGAGGCGGCGTTAT-TATCATCATCGTTTCGTACTTCCT-CACGCCCAACTAAACCATTGGAGATTGTTA TTGCTGGTGCAGGTTTGGGTGGTTTGTC-TACAGCAAAATATCTGGCAGATGCTGGT-CACAAACCGATA TTGCTGGAG GCAAGAGATGTCCTAGGTGGGAAGGTAGCTGCAT
GGAAAGATGATGATGGAGATTGGTACGAGACTGGG
TTGCACATATTCTTTGGGGCTTACCCAAATATGCAG
AACCTGTTTGGAGAACTAGGGATTGATGATCGGTTG
CAGTGGAAGGAACATTCAATGATATTTGCGATGCCT
AACAAGCCAGGGGAGTTCAGCCGCTTTGATTTTCCT
GAAGCTCTTCCTGCGCCATTAAATGGAATTTTGGCC
ATACTAAAGAACAACGAAATGCTTACGTGGCCCGAG
AAAGTCAAATTTGCTATTGGACTCTTGCCAGCAATG
CTTGGAGGGCAATCTTATGTTGAAGCTCAAGACGGT
TTAAGTGTTAAGGACTGGATGAGAAAGCAAGGTGT
GCCTGATAGGGTGACAGATGAGGTGTTCATTGCCA
TGTCAAAGGCACTTAACTTCATAAACCCTGACGAG
CTTTCGATGCAGTGCATTTTGATTGCTTTGAACAGA
TTTCTTCAGGAGAAACATGGTTCAAAAATGGCCTTT
TTAGATGGTAACCCTCCTGAGAGACTTTGCATGCCG
ATTGTGGAACATATTGAGTCAAAAGGTGGCCAAGTC
AGACTAAACTCACGAATAAAAAAGATCGAGCTGAA
TGAGGATGGAAGTGTCAAATGTTTTATACTGAATAA
TGGCAGTACA ATTAAAGGAGATGCTTTTGT-
GTTTGCCACTCCAGTGGATATCT-
TGAAGCTTCTTTTGCCTGAAGACTGG AAAGAGATC-
CCATATTTCCAAAAGTTGGAGAAGCTAGTGGGAGT
TCCTGTGATAAATGTCCATATATG GTTTGACA-
GAAAACTGAAGAACACATCTGATAATCT-
GCTCTTCAGCAGAAGCCCGTTGCTCAGTGTGT
ACGCTGACATGTCTGTTACATGTAAG-
GAATATTACAACCCCAATCAGTCTATGT-
TGGAATTGGTATTTG CACCCGCAGAAGAGTG-
GATAAATCGTAGTGACTCAGAAATTATTGATGCTAC
AATGAAGGAACTAGC GAAGCTTTTCCCTGAT-
GAAATTTCGGCAGATCAGAGCAAAG-
CAAAAATATTGAAGTATCATGTTGTCA AAAC-
CCCAAGGTCTGTTTATAAAACTGTGCCAGGTTGT
GAACCCTGTCGGCCCTTGCAAAGATCCCCT ATA-
GAGGGTTTTTATTTAGCTGGTGACTA-
CACGAAACAGAAGTACTTGGCTTCAATG-
GAAGGTGCTGT
CTTATCAGGAAAGCTTTGTGCACAAGC-
TATTGTACAGGATTACGAGTTACTTCT-
TGGCCGGAGCCAGA AGATGTTGGCAGAAG-
CAAGCGTAGTTAGCATAGTGAACTAA (SEQ ID
NO:38). A 685 base pair dsRNA polynucleotide with an
anti-sense strand capable of hybridizing to the RNA encoded
by the nucleotides at positions 421-1105 (shown as underlined text) in SEQ ID NO:38 and a 192 base pair dsRNA
polynucleotide with an anti-sense strand capable of hybridizing to the RNA encoded by the nucleotides at positions
914-1105 (shown as italicized and underlined text) in SEQ ID
NO:38 were synthesized.

An alignment of the Palmer amaranth and *Nicotiana benthamiana* PDS DNA sequences was performed using a global pairwise alignment (stretcher) and is illustrated in FIG. 16; with this method the two sequences showed about 71% identity (1252/1762).

Palmer amaranth plants having 16 copies of EPSPS and 5-8 inches high were treated with 0.1% SILWET L-77® brand surfactant solution freshly made with ddH2O. Four fully expanded leaves per plant were dipped into the SILWET L-77® brand surfactant solution for a few seconds, and allowed to dry for 30 minutes to 1 hour before application of the polynucleotide composition. Individual polynucleotide solutions were made for each of the 678 bp Palmer PDS dsRNA, 198 bp Palmer PDS dsRNA, the 685 bp *Nicotiana benthamiana* PDS dsRNA, and the 192 bp *Nicotiana benthamiana* PDS dsRNA (0.6 micromolar polynucleotide in 0.01% SILWET L-77® brand surfactant, 5 mM sodium phosphate buffer, pH 6.8). 10 microliters of polynucleotide solution (or buffer as a control) was applied to the top surface of each of the four pre-treated leaves per plant to provide a total of 40 microliters for each plant. Plants were kept in a growth chamber, and leaf bleaching was observed 3 days post treatment. Plants topically treated with either 678 bp Palmer PDS dsRNA or 198 bp Palmer PDS dsRNA, showed bleaching of leaves (indicating silencing of the endogenous phytoene desaturase) but Palmer amaranth plants topically treated with either 685 by *Nicotiana benthamiana* PDS dsRNA or 192 bp *Nicotiana benthamiana* PDS dsRNA did not show bleaching of leaves. This sequence specificity demonstrates that the polynucleotide compositions and methods of the invention are useful in selective control of a given species or taxon having a specific target gene sequence, e.g., in controlling herbicide-resistant volunteer plants growing in a field of crop plants resistant to the same herbicide.

Figure 17:
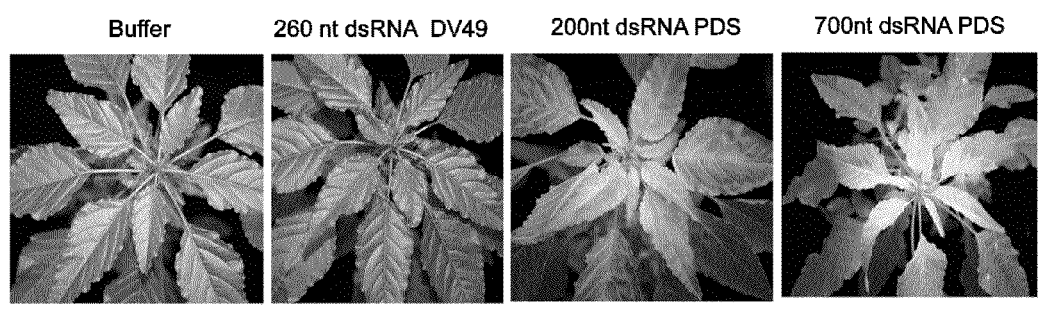
FIG. 17 illustrates apical leaf bleaching observed in Palmer amaranth plants topically treated with 678 bp or 198 bp Palmer PDS dsRNA but not in Palmer amaranth plants topically treated with a 260 base pair dsRNA of corn root worm gene as described in Example 11.

In a separate assay, Palmer amaranth plants topically treated with 678 bp Palmer PDS dsRNA (labelled "700 nt dsRNA PDS") or 198 bp Palmer PDS dsRNA (labelled "200 nt dsRNA PDS") showed bleaching of leaves (indicating silencing of the endogenous phytoene desaturase) but Palmer amaranth plants topically treated with a 260 base pair dsRNA of an invertebrate gene (labelled "260 nt dsRNA DV49", from corn root worm *Diabrotica virgifera*) did not result in a bleaching phenotype, indicating no silencing of the endogenous phytoene desaturase (FIG. 17). This sequence specificity demonstrates that the polynucleotide compositions and methods of the invention are useful in selective control of a given species or taxon.

Example 12

This example describes use of a topically applied composition including at least one polynucleotide strand including at least one segment of 18 or more contiguous nucleotides of a target gene in either anti-sense or sense orientation to induce systemic silencing of a target gene in a plant. More specifically this example demonstrates using a single treatment with a phytoene desaturase (PDS) oligonucleotide to induce systemic silencing in different plant organs including leaves, stems, and flowers.

Figure 18:
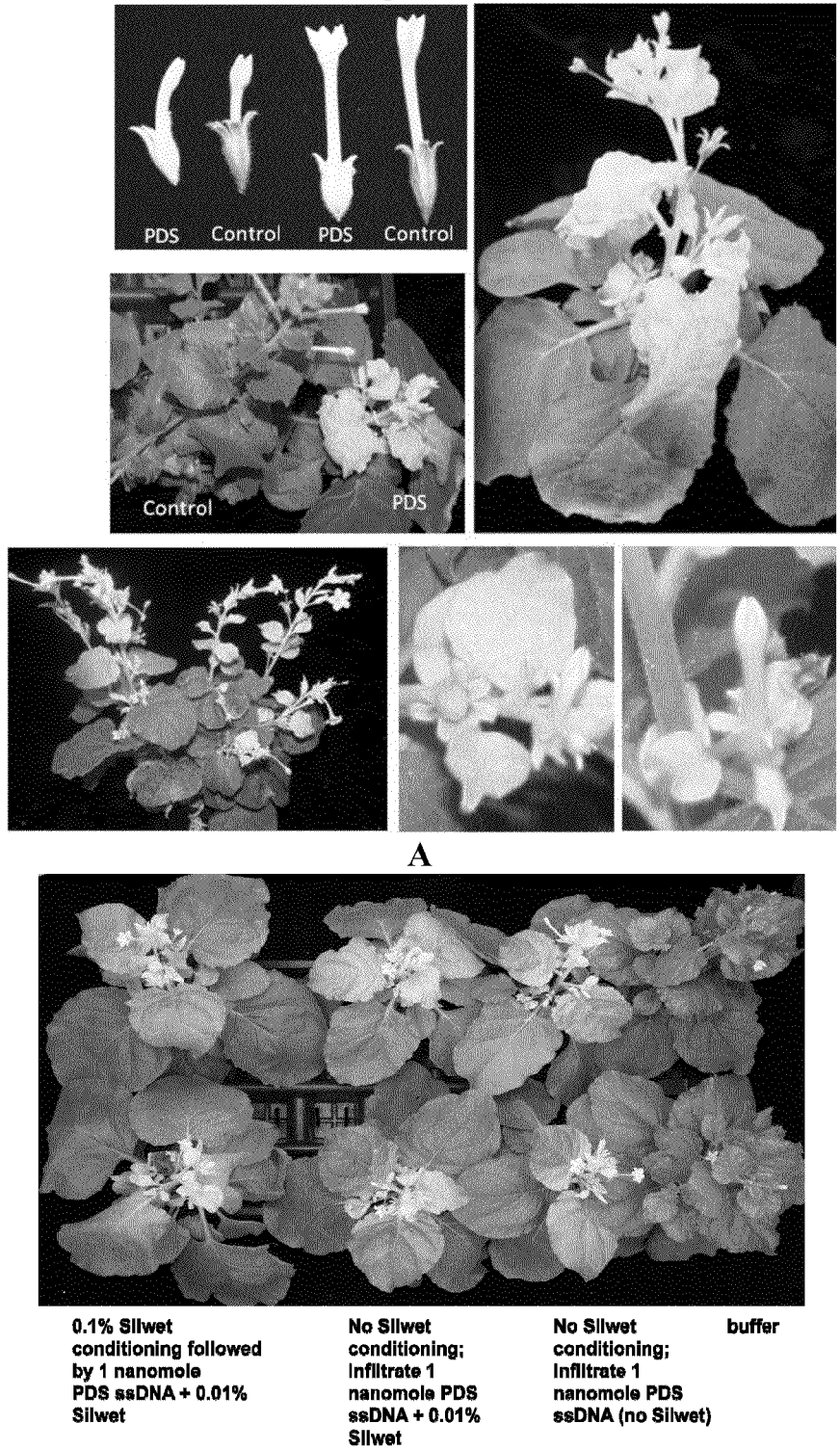
FIG. 18A illustrates bleaching of apical leaves, stems, and flowers of *Nicotiana benthamiana* plants topically treated first with a surfactant solution and then with an ssDNA PDS oligonucleotide to induce systemic silencing of phytoene desaturase as described in Example 12.
FIG. 18B illustrates bleaching of apical leaves, stems, and flowers of *Nicotiana benthamiana* plants topically treated with an ssDNA PDS oligonucleotide to induce systemic silencing of phytoene desaturase, with or without conditioning with a surfactant solution, as described in Example 12.

Four-week old tobacco (*Nicotiana benthamiana*) plants were used in all treatments. Two fully expanded leaves (one cotyledon, one true leaf) were conditioned by dipping into freshly made surfactant solution (0.1% SILWET L-77® brand surfactant in double-distilled water) for a few seconds and allowed to dry for 15-30 minutes. Twenty microliters of a single-stranded DNA (ssDNA) 22-mer oligonucleotide with the sequence GGCAGTACAATTAAAGGAGATG (SEQ ID NO:39), corresponding to the nucleotides at positions 1099-1120 of *Nicotiana benthamiana* phytoene desaturase (SEQ ID NO:2) was applied as a 25 micromolar solution in 0.01% SILWET L-77® brand surfactant in 5 millimolar sodium phosphate buffer, pH 6.8 to the top surface of each conditioned leaf for a total of 40 microliters (1 nanomole oligonucleotide) per plant. Control plants were treated with the SILWET® brand surfactant solution without the DNA oligonucleotide. Plants were observed for bleaching 3 days post-treatment. Apical leaves, stems, and flowers of plants treated with the ssDNA oligonucleotide all displayed bleaching indicating systemic silencing of PDS (FIG. 18A).

Flowers of both control and ssDNA-treated plants were allowed to set seed. Seeds were collected from mature fruits, weighed, and allowed to germinate. Seed weights were identical (about 11 mg per 100 seeds) and seed morphology appeared similar between the ssDNA-treated and the control plants. A reduced amount of seed produced per fruit and a reduction in germination rate (4 out of 100 seeds germinated) was observed in seeds from the ssDNA-treated plants, compared to the amount of seed per fruit and germination rate (95 out of 100 seeds germinated) of seeds from control plants.

In a separate assay using a similar procedure, tobacco plants were conditioned by dipping in 0.1% SILWET L-77® brand surfactant in double-distilled water, allowed to dry for 15-30 minutes, and treated with the PDS ssDNA 22-mer (SEQ ID NO:39) applied as a 25 micromolar solution in 0.01% SILWET L-77® brand surfactant in 5 millimolar sodium phosphate buffer, pH 6.8 to the top surface of each conditioned leaf for a total of 40 microliters (1 nanomole oligonucleotide) per plant. Other plants were not conditioned with a surfactant treatment, but were treated only with 1 nanomole of the PDS ssDNA 22-mer (SEQ ID NO:39) applied either by infiltration with a needleless syringe (shown in FIG. 18B) or by hand application of drops to the leaf surface (not shown in FIG. 18B), and either as a 25 micromolar solution in 0.01% SILWET L-77® brand surfactant in 5 millimolar sodium phosphate buffer, pH 6.8 or as a 25 micromolar solution in 5 millimolar sodium phosphate buffer, pH 6.8 (without surfactant). Negative control plants were treated with the SILWET® brand surfactant buffer solution without the DNA oligonucleotide. Results are depicted in FIG. 18B. All plants treated only with direct application of the PDS ssDNA (without conditioning by SILWET L-77® brand surfactant treatment), whether applied by infiltration or by hand application of drops, displayed bleaching of apical leaves, stems, and flowers, indicating systemic silencing of PDS.

Example 13

This example illustrates methods and topically applied compositions for inducing systemic silencing including the use of agents for conditioning of a plant to permeation by polynucleotides. More specifically, this example describes use of polynucleotides of the invention to control herbicide-resistant Palmer amaranth.

Palmer amaranth plants having lower (fewer than 30) copy numbers of 5-enolpyruvylshikimate-3-phosphate synthase (EPSPS) are susceptible to treatment with dsRNA designed to silence EPSPS followed by treatment with glyphosate (see details in Example 1). However, Palmer amaranth plants having high copy numbers of EPSPS (i.e., 30 or more copies of EPSPS) are resistant to glyphosate treatment and are a challenge for weed resistance management. For example, in one assay (results not shown) on glyphosate resistant high-copy Palmer amaranth using treatments similar to those described in Example 1 but where either dose of dsRNA was increased up to ten-fold (i.e., 8 nanomoles of short dsRNAs described in Example 1 per plant) or where a proprietary glyphosate formulation ("Roundup® WeatherMAX® brand herbicide") combined with a tallowamine surfactant was used, glyphosate activity was improved (estimated by observing plant growth measured as plant height) but the resistant plants were not killed.

Three different glyphosate resistant high-copy Palmer amaranth lines (3 plants per replicate) were treated with dsRNA using the treatment conditions listed in Table 6, where the dsRNA delivery vehicle, permeabilization or conditioning agent, and order of steps were varied. Results are depicted in FIG. 19. Treatment with "4x" glyphosate (i.e., treatment with 3360 g acid equivalent per hectare of Roundup® WeatherMAX® brand herbicide which is four-fold the standard rate of application of 840 g acid equivalent per hectare) alone did not kill 35-copy (experiment 3) or 57-copy (experiment 6) Palmer amaranth.

In one set of experiments (1-3, Table 6), including 2% ammonium sulfate in an aqueous dsRNA delivery vehicle comprising 0.1% tallowamine surfactant and 10% glycerol (experiment 2) improved the efficacy of a 10-fold dose of dsRNA followed by a 4x glyphosate application. Improved efficacy of a 10-fold dose of dsRNA followed by glyphosate application was also observed when ammonium sulfate was included in a dsRNA delivery vehicle without a tallowamine surfactant (experiment 8).

In another set of experiments (4-6, Table 6), applying the SILWET L-77® brand surfactant prior to applying the dsRNA in a delivery vehicle containing ammonium sulfate was effective, whereas combining the SILWET L-77® brand surfactant with the dsRNA in the dsRNA delivery vehicle containing ammonium sulfate was not effective. Applying glyphosate ("Roundup® WeatherMAX® brand herbicide") at 72 hours (experiment 7) was less effective than applying glyphosate at 48 hours (experiment 2) after treatment with dsRNA.

TABLE 6

| Palmer amaranth line | EPSPS Copy number | Experiment number | EPSPS dsRNA relative concentration | dsRNA delivery vehicle | Step 2 | Step 3* |
|---|---|---|---|---|---|---|
| R31 | 35 | 1 | 10x | 0.1% tallowamine surfactant + 10% glycerol | 1% SILWET L-77 ® brand surfactant | 4x WeatherMAX ® (48 h) |
| | | 2 | 10x | 2% ammonium sulfate + 0.1% tallowamine surfactant + 10% glycerol | 1% SILWET L-77 ® brand surfactant | 4x WeatherMAX ® (48 h) |
| | | 3 | Buffer only (control) | 2% ammonium sulfate + 0.1% tallowamine surfactant + 10% glycerol | 1% SILWET L-77 ® brand surfactant | 4x WeatherMAX ® (48 h) |

TABLE 6-continued

| Palmer amaranth line | EPSPS Copy number | Experiment number | Step 1 | Step 2 | | Step 3* |
| --- | --- | --- | --- | --- | --- | --- |
| | | | | EPSPS dsRNA relative concentration | dsRNA delivery vehicle | |
| R34 | 57 | 4 | — | 10× | 1% SILWET L-77 ® brand surfactant + 2% ammonium sulfate | 4× WeatherMAX ® (48 h) |
| | | 5 | 1% SILWET L-77 ® brand surfactant | 10× | 2% ammonium sulfate | 4× WeatherMAX ® (48 h) |
| | | 6 | 1% SILWET L-77 ® brand surfactant | Buffer only (control) | 2% ammonium sulfate | 4× WeatherMAX ® (48 h) |

| Palmer amaranth line | EPSPS Copy number | Experiment number | Step 1 | | Step 2 | Step 3* |
| --- | --- | --- | --- | --- | --- | --- |
| | | | EPSPS dsRNA relative concentration | dsRNA delivery vehicle | | |
| R28 | 87 | 7 | 10× | 2% ammonium sulfate + 0.1% tallowamine surfactant + 10% glycerol | 1% SILWET L-77 ® brand surfactant | 4× WeatherMAX ® (72 h) |

| Palmer amaranth line | EPSPS Copy number | Experiment number | Step 1 | Step 2 | | Step 3* |
| --- | --- | --- | --- | --- | --- | --- |
| | | | | EPSPS dsRNA relative concentration | dsRNA delivery vehicle | |
| R28 | 87 | 8 | 1% SILWET L-77 ® brand surfactant | 10× | 2% ammonium sulfate | 4× WeatherMAX ® (72 h) |
| | | 9 | 1% SILWET L-77 ® brand surfactant | Buffer only (control) | 2% ammonium sulfate | 4× WeatherMAX ® (72 h) |

*glyphosate (as the commercial formulation "Roundup ® WeatherMAX ® brand herbicide", which contains 660 g/L glyphosate K+ salt in a carrier including the MON56151 tallowamine surfactant blend of tallowamine (16-18C) and cocoamine (12-14C) in the ratio of 55:45) is listed at the amount used (where 1× = 840 g acid equivalent per hectare of Roundup ® WeatherMAX ® brand herbicide, 4× = 3360 g acid equivalent per hectare of Roundup ® WeatherMAX ® brand herbicide) and hours after application of dsRNA Example 14

This example illustrates methods and topically applied compositions for inducing systemic silencing including the use of agents for conditioning of a plant to permeation by polynucleotides.

Two small RNAs identified through small RNA sequencing were found to be abundant in and unique to Palmer amaranth plants that had been treated with four oligonucleotide-size "short" EPSPS dsRNA molecules as described in Example 1. These two small RNAs were respectively mapped to nucleotide positions 743-764 and 566-585 of the full-length EPSPS having the sequence shown in FIG. 20 (SEQ ID NO:40). Two 25 nucleotide long oligonucleotide-size "short" dsRNA molecules were designed with an anti-sense strand that is capable of hybridizing to the mRNA transcribed from the Palmer amaranth EPSPS gene at nucleotide positions 743-767 ("short dsRNA-5") and 564-588 ("short dsRNA-6"), as indicated by the italicized underlined nucleotides in SEQ ID NO:40 shown in FIG. 20, which also shows the four oligonucleotide-size "short" EPSPS dsRNA molecules (underlined, non-italicized text) and the three "long" double-stranded RNA polynucleotides (bolded text as described in Example 1.

Application of a mixture of the four oligonucleotide-size "short" EPSPS dsRNA molecules (described in Example 1) followed by application of glyphosate replicating the treatment procedure described in Example 1 resulted in 4 out of 4 Palmer amaranth plants with 16 copies of EPSPS being killed. Using the same treatment procedure but applying short dsRNA-5 and short dsRNA-6 together resulted in 0 out of 4 Palmer amaranth plants being killed. Adding either or both short dsRNA-5 and short dsRNA-6 to the mixture of the four oligonucleotide-size "short" EPSPS dsRNA molecules (described in Example 1) resulted in 4 out of 4 Palmer amaranth plants being killed, i.e., no antagonistic effect of short dsRNA-5 and short dsRNA-6 was observed.

Example 15

This example illustrates methods and topically applied compositions for inducing systemic silencing including the use of agents for conditioning of a plant to permeation by polynucleotides. More specifically, this example describes use of salicylic acid and polynucleotides.

Salicylic acid (SA) induces virus resistance in tobacco; see, e.g., Chivasa et al. (1997) *Plant Cell,* 19:547-557. Glyphosate-resistant Palmer amaranth plants having 49 or 63 copies EPSPS were pretreated with 15 millimolar SA. A solution of the four oligonucleotide-size "short" EPSPS dsRNA molecules (described in Example 1) was applied by hand at 1, 5, or 24 hours after treatment with SA, followed 72 hours later by spraying with glyphosate (1682 g acid equivalent per hectare of Roundup® WeatherMAX® brand herbicide). No improvement of the effects of the dsRNAs and glyphosate activity (estimated by observing plant growth measured as plant height) was observed for any of the SA treatments at 7 days after glyphosate treatment.

Example 16

This example illustrates methods and topically applied compositions for inducing systemic silencing including the use of agents for conditioning of a plant to permeation by polynucleotides. More specifically, this example describes variations in the order and timing of application of polynucleotides and surfactant solution.

These assays were conducted on Palmer amaranth plants with high copy numbers (56, 63, or 100 copies) of EPSPS, using a protocol including the following steps: (1) application of dsRNA (a solution of the four oligonucleotide-size "short" EPSPS dsRNA molecules described in Example 1) in a solution containing tallowamine surfactant and glycerol; (2) application of 1% SILWET L-77® brand silicone surfactant; and (3) application of glyphosate (1682 g acid equivalent per hectare of Roundup® WeatherMAX® brand herbicide). Spacing of the timing of the application of the polynucleotides and application of SILWET® brand surfactant was assessed, with the SILWET® brand surfactant spray applied at 30 minutes, 1 hour, or 2 hours after application of the dsRNA solution. In this set of assays, the three different times of the SILWET® brand surfactant solution application all produced similar results, i.e., stunting of growth of most of the high copy plants that were treated with the dsRNA solution, as compared to control high copy plants which were treated with a control solution containing only tallowamine surfactant and glycerol.

Example 17

This example illustrates methods and topically applied compositions for inducing systemic silencing including the use of agents for conditioning of a plant to permeation by polynucleotides. More specifically, this example describes application of polynucleotides of the invention by low-volume spray and the use of a silicone surfactant and ammonium sulfate.

A solution of dsRNA (a solution of the four oligonucleotide-size "short" EPSPS dsRNA molecules described in Example 1) in a solution containing 2% ammonium sulfate was applied by low-volume spray to Palmer amaranth having 16 copies of EPSPS, followed by spraying with glyphosate (1682 g acid equivalent per hectare of Roundup® WeatherMAX® brand herbicide), resulting in the Palmer amaranth plants being killed.

Six Palmer amaranth plants per treatment were treated with a three-step procedure using low-volume spray: (1) spraying 1% SILWET L-77® brand surfactant; (2) spraying 2 milliliters of a dsRNA solution containing equal amounts of the four oligonucleotide-size "short" EPSPS dsRNA molecules described in Example 1 at one of 3 doses (1× or 0.8 nanomoles per plant, 2× or 1.6 nanomoles per plant, or 4× or 3.2 nanomoles per plant); and (3) spraying glyphosate (1682 g acid equivalent per hectare of Roundup® WeatherMAX® brand herbicide) at a rate of 159 liters/acre. Nine days after the glyphosate spray, all six plants sprayed with 4×(3.2 nanomoles per plant) dsRNA were killed, and the plants sprayed with 2×(1.6 nanomoles per plant) dsRNA or 1× (0.8 nanomoles per plant) dsRNA were stunted (FIG. 21A).

Several assays were carried out on glyphosate-resistant Palmer amaranth grown from field-collected seeds. Plants were treated with various protocols described below, with some plants being treated topically with a dsRNA solution and control plants being treated with the buffer (dsRNA vehicle); application was by low-volume spray. Unless otherwise noted, the dsRNA solution contained equal amounts of the four oligonucleotide-size "short" EPSPS dsRNA molecules described in Example 1 in buffer at a "4×" dose (3.2 nanomoles per plant); the buffer consisted of 10 millimolar sodium phosphate and 0.01% (v/v) SILWET L-77® brand organosilicone surfactant in diethylpyrocarbonate (DEPC) water (Omega Bio-Tek) and adjusted to pH 6.8; and herbicide was a glyphosate herbicide applied at 840 g acid equivalent per hectare of Roundup® WeatherMAX® brand herbicide at a rate of 159 liters/acre. Results are provided in Table 7.

Assays 1 and 2: These assays were carried out on glyphosate-resistant Palmer amaranth grown from seeds obtained from a soil sample from a farm location with known glyphosate-resistant Palmer amaranth stands. For assay 1, ten plants per treatment were treated as follows: (1) spraying 1% SILWET L-77® brand surfactant; (2) spraying 2 milliliters of the dsRNA solution; and (3) spraying glyphosate. For assay 2, eighteen plants per treatment were treated using the same procedure as in assay 1.

Assay 3: This assay compared treatments applied at different developmental stages and used seedlings grown from Palmer amaranth seeds from a Macon County, Ga. site and selected for glyphosate resistance. The buffer included 2% ammonium sulfate. Twelve small (3-leaf stage) or twelve large (5-leaf stage) seedlings per treatment were treated as follows: (1) spraying 1% SILWET L-77® brand surfactant; (2) spraying 2 milliliters of the dsRNA solution; and (3) spraying glyphosate. This treatment provided better control (killed more plants) on small seedlings as compared to the larger seedlings. The dsRNA treatment killed or stunted more glyphosate-resistant plants than treatment with buffer and herbicide achieved, although at 16 days after treatment not all dsRNA-treated plants were killed.

Assays 4 and 5: These assays used Palmer amaranth plants grown from seeds in soil from a Pemiscot, Mo. farm. The buffer included 2% ammonium sulfate. Eleven small (3-leaf stage) seedlings per treatment were treated as follows: (1) spraying 1% SILWET L-77® brand surfactant; (2) spraying 2 milliliters of the dsRNA solution; and (3) spraying glyphosate. For assay 5, twelve plants per treatment were treated using the same procedure as in assay 4.

Assay 6: This assay used Palmer amaranth plants grown from seeds in soil from the "Ivy2" farm. The buffer included 2% ammonium sulfate. Eighteen small (3-leaf stage) seedlings per treatment were treated as follows: (1) spraying 1% SILWET L-77® brand surfactant; (2) applying 2 milliliters of the dsRNA solution, either by hand or by spraying; and (3) spraying glyphosate. In this assay the method of application (hand drop or spraying) provided similar results.

Assay 7: This assay used 3- to 4-leaf stage Palmer amaranth seedlings grown from F3 seeds selected for glyphosate resistance and more resistant to glyphosate than plants in assays 1-6. The buffer included 2% ammonium sulfate. Eighteen plants per treatment were treated as follows: (1) spraying 1% SILWET L-77® brand surfactant; (2) spraying 2 milliliters of the dsRNA solution; and (3) spraying glyphosate.

TABLE 7

| Assay Number | killed plants/total plants | | Comments |
| --- | --- | --- | --- |
| | dsRNA-treated | control | |
| 1 | 2/10 | 0/10 | dsRNA-treated survivors stunted compared to controls (FIG. 21B) |
| 2 | 7/18 | 4/18 | dsRNA-treated survivors stunted at 8 and 30 days after treatment, compared to controls |
| 3 (large seedlings) | 5/12 | 3/12 | dsRNA/ammonium sulfate-treated survivors more stunted after treatment, compared to controls |
| 3 (small seedlings) | 9/12 | 6/12 | |
| 4 | 7/11 | 2/11 | dsRNA/ammonium sulfate-treated survivors more stunted after treatment, compared to controls |
| 5 | 8/12 | 3/12 | |
| 6 (hand drop) | 14/18 | — | |
| 6 (spray) | 13/18 | 9/18 | |
| 7 | 8/18 | 2/18 | |

Example 18

This example illustrates methods and topically applied compositions for inducing systemic silencing including the use of agents for conditioning of a plant to permeation by polynucleotides.

Figure 22:
FIG. 22 illustrates results obtained from treating Palmer amaranth with tallowamine surfactant and ammonium sulfate or with transfection reagents, as described in Example 18.

In these assays, the dsRNA solution contained equal amounts of the four oligonucleotide-size "short" EPSPS dsRNA molecules described in Example 1 at a "10×" dose (8 nanomoles per plant) in a solution containing either 0.2% tallowamine surfactant and 2% ammonium sulfate (identified in FIG. 22 as "tallowamine/AMS"), or one of the following transfection reagents: (a) a polyamine (JetPRIME™, Polyplus-transfection SA, Illkirch, France), (b) a magnetic nanoparticle (SilenceMag, OZ Biosciences, Marseille, France), (c) a peptide (N-TER™ Nanoparticle, Sigma-Aldrich, St. Louis, Mo.), (d) a lipid (siPORT™ NeoFX™, Ambion, Foster City, Calif.), or (e) a cationic lipid/polymer (TransIT®, Minis Bio, Madison, Wis.). Plants were treated as follows: (1) hand-applying dsRNA solution; (2) spraying 1% SILWET L-77® brand surfactant; and (3) spraying with glyphosate applied at 840 g acid equivalent per hectare of Roundup® WeatherMAX® brand herbicide at a rate of 159 liters/acre. This protocol when used with dsRNA in the tallowamine surfactant/ammonium sulfate solution kills glyphosate-resistant Palmer amaranth having 35 copies EPSPS. Results are depicted in FIG. 22. Stunting or death of the plants was observed for plants treated with dsRNA in solutions containing polyamine (JetPRIME™), peptide (N-TER™ Nanoparticle), cationic lipid/polymer (TransIT®), or tallowamine surfactant/ammonium sulfate.

Example 19

This example illustrates methods using compositions including topically applied polynucleotides for inducing systemic silencing in a plant. More specifically, this example describes use of different types of polynucleotides for inducing systemic silencing.

Sense single-stranded DNAs (ssDNAs) and anti-sense single-stranded RNAs (ssRNAs) corresponding to the Palmer amaranth EPSPS gene at positions 14-38, positions 153-177, 345-369, and 1105-1129 (indicated by underlined nucleotides in FIG. 1) were purchased from Integrated DNA Technologies. The sense ssDNAs and anti-sense ssRNAs were annealed by heating equal moles of mixed ssDNAs and ssRNAs at 95 degrees Celsius for 5 minutes and slowly cooled over 1.5-2 hours to room temperature to yield the DNA/RNA hybrids.

16-copy glyphosate-resistant Palmer amaranth plants were used in the assays which used this procedure: (1) spraying 1% SILWET L-77® brand surfactant; (2) hand-applying on four mature leaves of each plant a total of 0.8 nanomoles of either the Palmer EPSPS dsRNAs (as described in Example 1) or of the Palmer EPSPS DNA/RNA hybrids; and (3) spraying with glyphosate applied at 840 g acid equivalent per hectare of Roundup® WeatherMAX® brand herbicide at a rate of 159 liters/acre.

Figure 23:
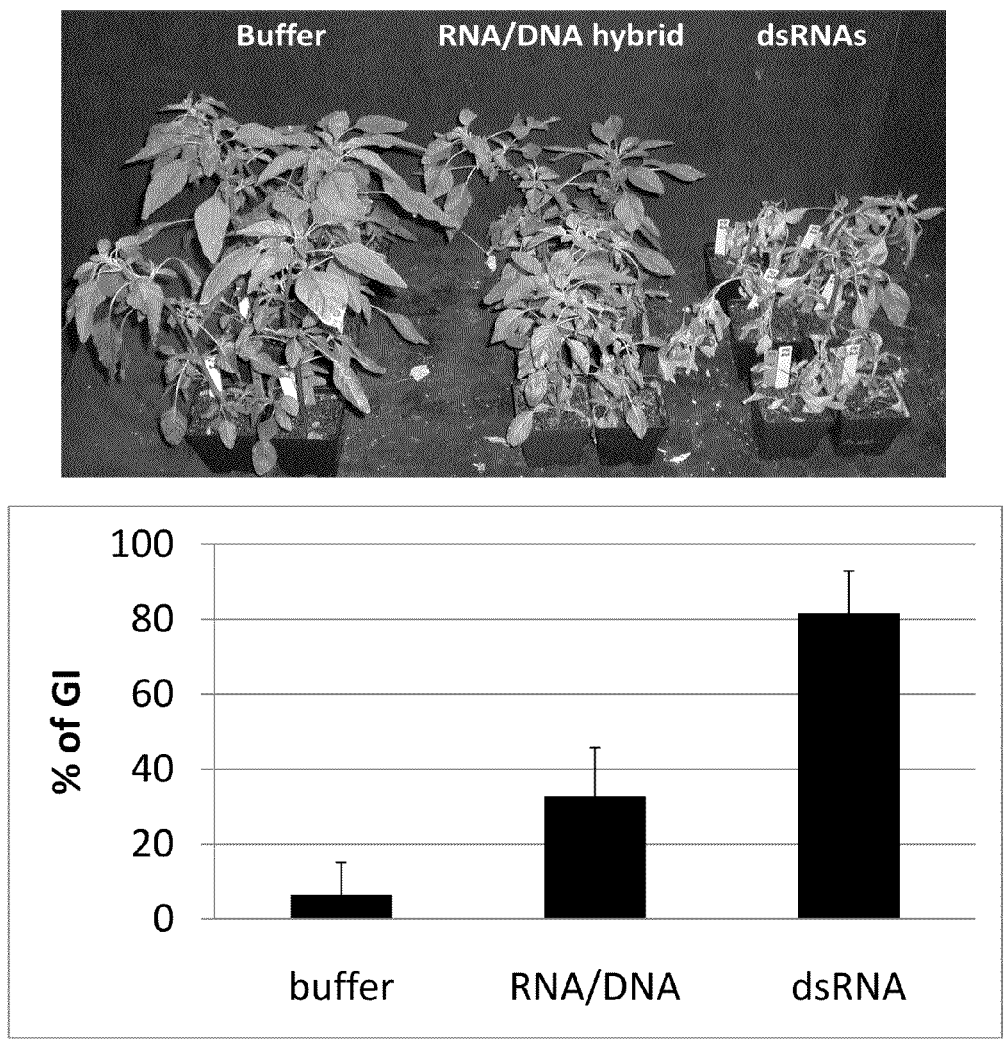
FIG. 23 illustrates results of treating glyphosate-resistant Palmer amaranth plants with either EPSPS dsRNAs or EPSPS DNA/RNA hybrids, as described in Example 19.

Results are depicted in FIG. 23. Seven days after the herbicide spraying, 4 out of 6 dsRNA-treated plants were dead and the remaining 2 were dying, whereas plants sprayed with the DNA/RNA hybrid were stunted in growth (glyphosate injury) compared to the control.

Example 20

This example illustrates methods using compositions including topically applied polynucleotides for inducing systemic silencing in a plant. More specifically, this example describes use of different types of polynucleotides for inducing systemic silencing.

Figure 24:
FIG. 24 illustrates results of treating glyphosate-resistant Palmer amaranth plants with either EPSPS dsRNA or EPSPS ssDNA polynucleotides, as described in Example 20. The upper photography was taken at 8 days after herbicide spray and the lower (bar) graph presents the results as a glyphosate injury (GI) scored 8 days after herbicide spray.

Six glyphosate-resistant Palmer amaranth plants having 16 copies of EPSPS were used per treatment in this assay. A 0.8 nanomoles ("1×") per plant treatment of dsRNA, a ten-fold greater amount (8 nanomoles per plant treatment, "10×") of ssDNA polynucleotides (described in Example 19) and buffer alone as a control, were applied to separate plants by hand in buffer containing 2% ammonium sulfate, followed 48 hours later by spraying with glyphosate applied at 840 g acid equivalent per hectare of Roundup® WeatherMAX® brand herbicide at a rate of 159 liters/acre. FIG. 24 depicts the results. Both polynucleotide treatments gave better control of the Palmer amaranth compared to plants treated only with buffer and herbicide. Of the plants treated with the 10× ssDNA treatment, two of six were killed, and the remaining four were stunted in growth by 30%. Of the plants treated with the 1× dsRNA treatment, all six plants were killed by 8 days after WM spray or 10-day after dsRNA treatment.

Example 21

This example illustrates methods using compositions including topically applied polynucleotides for inducing systemic silencing in a plant. More specifically, this example describes selection of a polynucleotide sequence for inducing systemic silencing in a plant.

Twelve dsRNAs of approximately 250 bp each and having one strand of the dsRNA corresponding to the EPSPS tiled DNA sequences of SEQ ID NOS:41-52 (Table 8) were designed to cover in a tiling fashion the full coding sequence and part of the 5' and 3' untranslated regions of the Palmer amaranth EPSPS gene, as depicted in FIG. 25A.

TABLE 8

| Tiling segment number (see FIG. 25A) | Sequence | SEQ ID NO. |
|---|---|---|
| 1 | CGCCAGGGCTGCAGACGCGTTACGTANTCGGATCCAGAATTCGTGATTAAC GTCACAGCATGTCATGTAAAACACGCGAATCAGACCGGTCCACTCTTGTTT TAATTTGAGACAATTTTGATGTTGAGTCATCCCACACCAACCCCAAAAAAT TCAACAACAAACTCTTATAATGATTCCCTCTACTCTACTAGAGTCTACACC AACCCACTTTCTCTTTGCCCACCAAAACTTTGGTTTGGTAAGAACT | 41 |
| 2 | CACCAACCCACTTTCTCTTTGCCCACCAAAACTTTGGTTTGGTAAGAACTA AGCCCTCTTCTTTCCCTTCTCTCTCTTAAAAGCCTAAAATCCACCTAACTTT TTCAGCCAACAAACAACGCCAAATTCAGAGGAAGAATAATGATGGCTCAA GCTACTACCATCAACAATGGTGTCCATACTGGTCAATTGCACCATACTTTA CCCAAAACCCAGTTACCCAAATCTTCAAAAACTCTTAATT | 42 |
| 3 | CCATACTTTACCCAAAACCCAGTTACCCAAATCTTCAAAAACTCTTAATTTT GGATCAAACTTGAGAATTTCTCCAAAGTTCATGTCTTTAACCAATAAAAGA GTTGGTGGGCAATCATCAATTGTTCCCAAGATTCAAGCTTCTGTTGCTGCT GCAGCTGAGAAACCTTCATCTGTCCCAGAAATTGTGTTACAACCCATCAAA GAGATCTCTGGTACTGTTCAATTGCCTGGGTCAAAGTCTTTATCC | 43 |
| 4 | TCAAAGAGATCTCTGGTACTGTTCAATTGCCTGGGTCAAAGTCTTTATCCA ATCGAATCCTTCTTTTAGCTGCTTTGTCTGAGGGCACAACAGTGGTCGACA ACTTGCTGTATAGTGATGATATTCTTTATATGTTGGACGCTCTCAGAACTCT TGGTTTAAAAGTGGAGGATGATAGTACAGCCAAAAGGGCAGTCGTAGAGG GTTGTGGTGGTCTGTTTCCTGTTGGTAAAGATGGAAAGGAAGAGAT | 44 |
| 5 | GAGGGTTGTGGTGGTCTGTTTCCTGTTGGTAAAGATGGAAAGGAAGAGATT CAACTTTTCCTTGGTAATGCAGGAACAGCGATGCGCCCATTGACAGCTGCG GTTGCCGTTGCTGGAGGAAATTCAAGTTATGTGCTTGATGGAGTACCAAGA ATGAGGGAGCGCCCCATTGGGGATCTGGTAGCAGGTCTAAAGCAACTTGG TTCAGATGTAGATTGTTTTCTTGGCACAAATTGCCCTCCTGTTCGGG | 45 |
| 6 | TGGTTCAGATGTAGATTGTTTTCTTGGCACAAATTGCCCTCCTGTTCGGGTC AATGCTAAAGGAGGCCTTCCAGGGGGCAAGGTCAAGCTCTCTGGATCGGT TAGTAGCCAATATTTAACTGCACTTCTCATGGCTACTCCTTTGGGTCTTGGA GACGTGGAGATTGAGATAGTTGATAAATTGATTTCTGTACCGTATGTTGAA ATGACAATAAAGTTGATGGAACGCTTTGGAGTATCCGTAGAACAT | 46 |
| 7 | TTGAAATGACAATAAAGTTGATGGAACGCTTTGGAGTATCCGTAGAACAT AGTGATAGTTGGGACAGGTTCTACATTCGAGGTGGTCAGAAATACAAATCT CCTGGAAAGGCATATGTTGAGGGTGATGCTTCAAGTGCTAGCTACTTCCTA GCCGGAGCCGCGTCACTGGTGGGACTGTCACTGTCAAGGGTTGTGGAAC AAGCAGTTTACAGGGTGATGTAAAATTTGCCGAAGTTCTTGAGAAGAT | 47 |
| 8 | ACAAGCAGTTTACAGGGTGATGTAAAATTTGCCGAAGTTCTTGAGAAGAT GGGTTGCAAGGTCACCTGGACAGAGAATAGTGTAACTGTTACTGGACCAC CCAGGGATTCATCTGGAAAGAAACATCTGCGTGCTATCGACGTCAACATG AACAAAATGCCAGATGTTGCTATGACTCTTGCAGTTGTTGCCTTGTATGCA GATGGGCCCACCGCCATCAGAGATGTGGCTAGCTGGAGAGTGAAGGAAA | 48 |
| 9 | AGATGGGCCCACCGCCATCAGAGATGTGGCTAGCTGGAGAGTGAAGGAAA CCGAACGGATGATTGCCATTTGCACAGAACTGAGAAAGCTTGGGGCAACA GTTGAGGAAGGATCTGATTACTGTGTGATCACTCCGCCTGAAAAGCTAAAC CCCACCGCCATTGAAACTTATGACGATCACCGAATGGCCATGGCATTCTCT CTTGCTGCCTGTGCAGATGTTCCCGTCACTATCCTTGATCCGGGATGC | 49 |
| 10 | CTCTTGCTGCCTGTGCAGATGTTCCCGTCACTATCCTTGATCCGGGATGCAC CCGTAAAACCTTCCCGGACTACTTTGATGTTTTAGAAAAGTTCGCCAAGCA TTGATGAGTAGCTATATACGAGATCCTTAAATTGTACGCCGAAGGTTTTGA TTTGAGTCTAATAGTAGATAAAAGGCTATAAATAAACTGGCTTTCTGCTTG AGTAATTATGAAATTCTTTGTATTATGTTTGTGAGATTTGAAGTAGCTTATA | 50 |
| 11 | TAATTATGAAATTCTTTGTATTATGTTTGTGAGATTTGAAGTAGCTTATAAA TTACAATGTACTAAAGTCTAGAAATAAGTTATGTATCTTTTAAATCAATGA GAAATGCATACTTGAAAGGCTTGACCTTGTATTTGTGACCTAAAGAGTACT AACTTTGGAGTTTCCAACTCATTTGTTTATCTCATTTTTTTTAATTTTGAT TTAAATTGTTTATTTTTATGAGTAATCATGTATCTTTCTTATTCTAACCAAA TGTAATACTCCTTC | 51 |
| 12 | TATGAGTAATCATGTATCTTTCTTATTCTAACCAAATGTAATACTCCTTCCA ACTCTCTTTAAACGTCCACACTCTGGGCACAGAGTGTAATAGTGTGGTGGT TGGAGTCTTTTAAGTGATTATAATAATTGTAAATGTGGTAGTTAGAATATT TTAAGTAATGTAGGTGGGGTATTATGGTCTTGTTGAACATAGGATATTTAG GTAAAAAATCTATGCAAAAAAAGGAAAGTAAGCAAATAAAGCGAATTGA CCTGAAAAGAAAAGTGGACATGTATAGTGAGTTGGAGGAAGTATTTT | 52 |

The four oligonucleotide-size "short" EPSPS dsRNA molecules as described in Example 1 and FIG. 1 are located in the tiling segments 2, 3, 4, and 8 respectively, and are shown as light grey bars within those segments. The polynucleotides were synthesized in vitro transcription using a pBR322 vector with the EPSPS polynucleotides inserted at EcoRI and BamHI cloning sites; plasmid DNA was isolated with Qiagen Maxi prep kits and digested with EcoRI and BamHI restriction enzymes. The digested DNA solution was used in the treatment of the plants without further purification.

Glyphosate-resistant Palmer amaranth plants having 16 copies of EPSPS were treated as follows: spraying with 1% SILWET L-77® brand surfactant; (2) hand application of a dsRNA solution (containing polynucleotides selected from the twelve tiling segments or the four "short" dsRNA molecules described in Example 1 at the rate of 0.01 nanomole DNA/plant) or buffer as a control; and (3) 48 hours later spraying with glyphosate applied at 840 g acid equivalent per hectare of Roundup® WeatherMAX® brand herbicide at a rate of 159 liters/acre. Above-ground height of the treated plants was observed 11 days after herbicide treatment; plants that were dead or dying were assigned a height of zero. Results are depicted in FIGS. 25B and 25C. The dsRNA polynucleotides combinations showing the greatest efficacy in this assay included the four "short" dsRNA molecules described in Example 1, the combination of tiling segments 2, 5, 8, and 11, and the combination of tiling segments 7, 8, and 9.

Example 22

This example illustrates methods using compositions including topically applied polynucleotides for inducing systemic silencing in a plant. More specifically, this example describes topical application of polynucleotides following application of herbicide to a plant.

Figure 26:
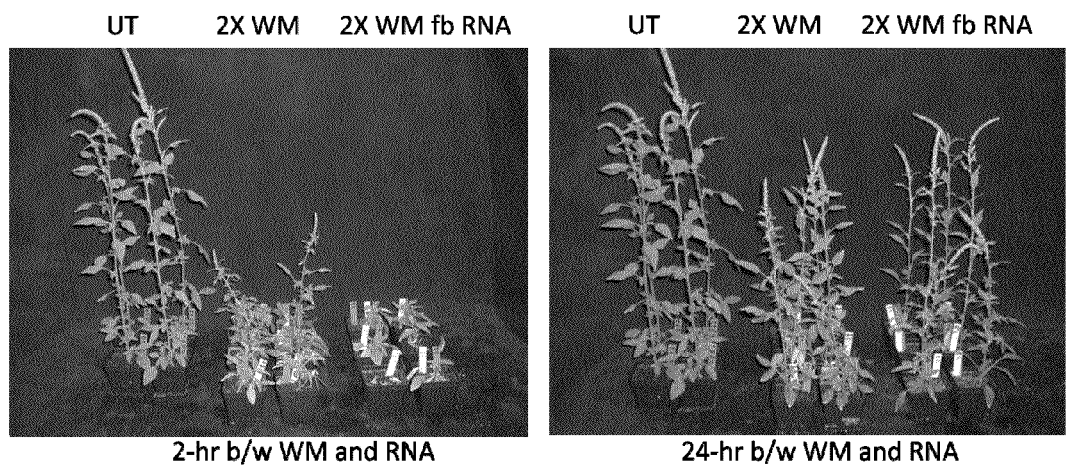
FIG. 26 illustrates results of treating glyphosate-resistant Palmer amaranth plants with glyphosate followed by spraying with 1% SILWET L-77® brand surfactant followed by application of EPSPS dsRNA in buffer containing 2% ammonium sulfate, as described in Example 22. Untreated ("UT") control plants were treated only with the 1% SILWET L-77® brand surfactant spray but not with herbicide or dsRNA. Plants were photographed and rated at 16 days after treatment.

In one assay, glyphosate-resistant Palmer amaranth plants having 16 copies of EPSPS were sprayed with glyphosate applied at 840 g acid equivalent per hectare of Roundup® WeatherMAX® brand herbicide at a rate of 159 liters/acre. Two or 24 hours after herbicide application, the plants were treated by spraying with 1% SILWET L-77® brand surfactant. Fifteen to 20 minutes after SILWET® brand surfactant treatment, the plants were treated by hand application of either 0.8 nanomoles ("1x") per plant of the four oligonucleotide-size "short" EPSPS dsRNA molecules as described in Example 1 in buffer containing 2% ammonium sulfate or buffer containing 2% ammonium sulfate. In this assay, untreated ("UT") control plants were treated only with the 1% SILWET L-77® brand surfactant spray but not with herbicide or dsRNA. Results are depicted in FIG. 26. In this assay, application of 1% SILWET® brand surfactant resulted in improved glyphosate activity by 60% when applied 2 hours after herbicide spraying and by 20% when applied 24 hours after herbicide spraying. In this assay, application of 1% SILWET® brand surfactant followed by EPSPS dsRNA resulted in improved glyphosate activity by at least 80% when applied 2 hours after herbicide spraying and by 20% when applied 24 hours after herbicide spraying.

In another assay, Palmer amaranth plants grown from seeds in soil from a farm site in Macon, Ga. were sprayed with glyphosate applied at 840 g acid equivalent per hectare of Roundup® WeatherMAX® brand herbicide at a rate of 159 liters/acre. Three days after herbicide treatment, 9 of 40 plants were killed and 3 were severely stunted. Surviving plants were sprayed with 1% SILWET L-77® brand surfactant, followed by topical application by hand of either 8 nanomoles ("10x") per plant of the four oligonucleotide-size "short" EPSPS dsRNA molecules as described in Example 1 or buffer as a control. Three days later, 3 more plants in the dsRNA-treated group were dead and 2 more plants in the buffer-treated group were dead. At this point (6 days after the original herbicide treatment and 3 days after the SILWET® brand surfactant/dsRNA or buffer treatment), half of the surviving plants in each group were sprayed with a second application of glyphosate (applied at the same dose as in the first application). Two weeks after this second herbicide treatment, the remaining dsRNA-treated plants showed 80% injury and the remaining buffer-treated plants showed 40% injury.

Example 23

This example illustrates methods using compositions including topically applied polynucleotides for inducing systemic silencing in a plant. More specifically, this example describes a single-step topical application of a single composition including polynucleotides, surfactant, and herbicide for controlling herbicide-resistant weeds.

This assay was carried out on a field population of glyphosate-resistant Palmer amaranth plants that were known to have very high copy numbers of EPSPS (plants from this study site have been reported to have from 5 to more than 160 copies of EPSPS by Gaines et al. (2010) Proc. Natl. Acad. Sci. USA, 107:1029-1034). The polynucleotides used in this assay were an equimolar mixture of the four oligonucleotide-size "short" EPSPS dsRNA molecules as described in Example 1.

Four to six inch tall plants in a treatment area of 1 foot by 5 feet were sprayed in a single treatment with either 264 micrograms ("100x") or 52.8 micrograms ("20x") of the EPSPS dsRNAs in a solution that also contained 1% SILWET L-77® brand surfactant, 2% ammonium sulfate, and glyphosate (applied at 1682 g acid equivalent per hectare of Roundup® WeatherMAX® brand herbicide at a rate of 159 liters/acre). For comparison, other plants in treatment areas of 1 foot by 5 feet were sprayed with glyphosate (in a solution that also contained 1% SILWET L-77® brand surfactant and 2% ammonium sulfate) applied at the same rate.

Figure 27:
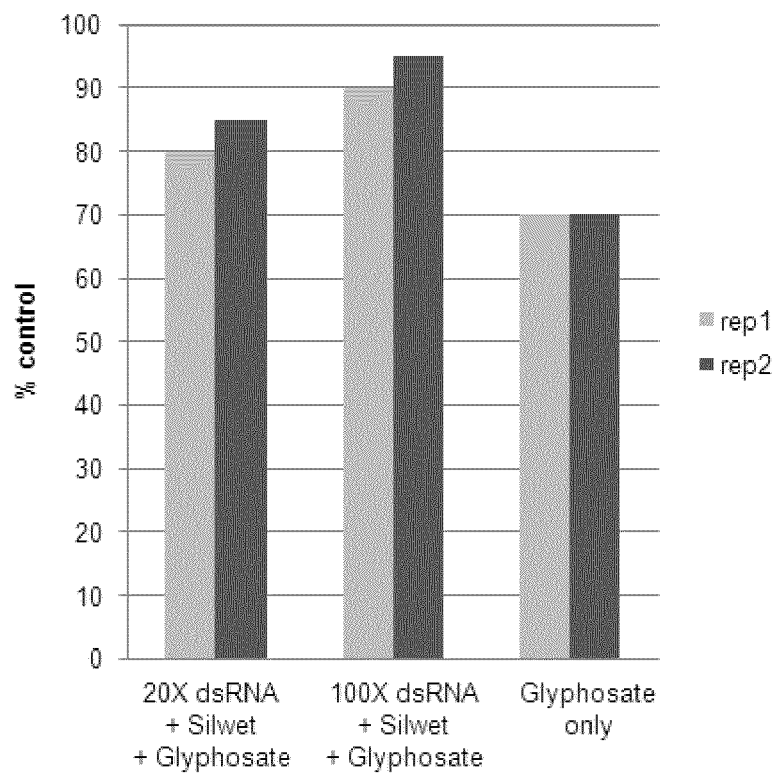
FIG. 27 illustrates results of treating a field population of high copy number glyphosate-resistant Palmer amaranth with a composition containing a 20× or 100× amount of EPSPS dsRNA polynucleotides, surfactant, ammonium sulfate, and herbicide or with a composition containing, surfactant, ammonium sulfate, and herbicide, as described in Example 23. For each treatment, two replicate 1 foot by 5 foot plots were treated.

Results are depicted in FIG. 27. Treating the plants with only glyphosate (applied at 1682 g acid equivalent per hectare of Roundup® WeatherMAX® brand herbicide at a rate of 159 liters/acre) in a solution that also contained SILWET L-77® brand surfactant and ammonium sulfate resulted in about 70% control (death of plants). The one-step treatment using a composition containing the 20x EPSPS dsRNA polynucleotides, surfactant, ammonium sulfate, and herbicide resulted in about 80-85% control of the glyphosate-resistant Palmer amaranth, which is the approximate control rate obtained by spraying with glyphosate applied at 6720 g acid equivalent per hectare of Roundup® WeatherMAX® brand herbicide at a rate of 159 liters/acre (i.e., at 8 times the standard application rate of about 840 g acid equivalent per hectare of Roundup® WeatherMAX® brand herbicide at a rate of 159 liters/acre). The one-step treatment using a composition containing the 100xEPSPS dsRNA polynucleotides, surfactant, ammonium sulfate, and herbicide resulted in about 90-95% control of the glyphosate-resistant Palmer amaranth, which is the approximate control rate obtained by spraying with glyphosate applied at 13440 g acid equivalent per hectare of Roundup® WeatherMAX® brand herbicide at a rate of 159 liters/acre (i.e., at 16 times the standard application rate of about 840 g acid equivalent per hectare of Roundup® WeatherMAX® brand herbicide at a rate of 159 liters/acre).

Example 24

This example illustrates a method for inducing systemic regulation of a target gene in a vegetable plant by topical application to the vegetable of a polynucleotide molecule including a segment with a nucleotide sequence essentially identical to, or essentially complementary to, a sequence of 18 or more contiguous nucleotides in either the target gene or RNA transcribed from the target gene, whereby the molecule permeates the interior of the vegetable plant and induces systemic regulation of the target gene. In this example, growing vegetable plants were treated with a topically applied composition for inducing systemic silencing of a target gene in a vegetable or fruit crop plant including (a) an agent for conditioning of a plant to permeation by polynucleotides and (b) polynucleotides including at least one polynucleotide strand including at least one segment of 18 or more contiguous nucleotides of the target gene in either anti-sense or sense orientation. More specifically, this example demonstrates the use of topically applied polynucleotides to induce systemic silencing of a phytoene desaturase (PDS) gene in a vegetable crop plant, i.e., lettuce (*Lactuca sativa*).

Lettuce PDS has the sequence ATGTCTCTGTTTGGAAATGTTTCT-GCCATTAACTCAAGTGGAAAGTGTATAGTAATGAATCTTTCAAGC1 ACACAAAT-CACTTCAAGAGATTGTTTCAAGATTAC-CTCAGGGCAAAAAGATGTTTTGTCATTTGGATG CTGTGATGCTATGGGTAACAGATTG-CAATTCCCAAGTGCTCGTTCTTTTACACCAAGATCAAAGAAGA ATGTCTC-CCCTCTAAAGGTAGTTTGTGTTGAT-TATCCAAGACCAGATCTTGATAACACATCTAATTTCT TGGAAGCTGCTCACTTGTCTTCAACCT-TCAGAACTTCCCCACGCCCATCTAAGCCATTGAAGATTGTAA TTGCTGGTG-CAGGTTTAGCTGGTTTATCAACT-GCTAAGTATTTAGCTGATGCAGGTCACAAGCCAATTT TACTAGAAGCAAGAGATGTTCTTGGTG-GAAAGGTGGCAGCTTGGAAAGATGATGATGGAGATTGGTA TGAGACAGGTT-TACACATATTCTTTGGAGCTTAC-CCAAATGTACAAAATTTATTTGGAGAGCTAGGAA TTAATGATAGATTACAGTGGAAGGAG-CATTCTATGATATTTGCAATGCCAAATAAGCCTGGAGAATTT AGTAG-GTTTGACTTCCCAGATGTTTTACCTG-CACCATTGAATGGAATTTTTGCTATATTGAGGAACAAT GAAATGCTGACGTGGCCTGAGAAAGT-GAAGTTTGCAATTGGGCTGTTGCCTGCAATGTTAGGTGGACA GGCTTATGT-TGAGGCCCAAGATGGGCTTAGTGTTCAG-GACTGGATGAGAAAGCAAGGTATACCTGATC GAGTTACTACTGAAGTGTTTATTGCAAT-GTCAAAAGCATTAAACTTTATAAATCCAGATGAACTTTCAA TGCAATGTATTCT-CATTGCTCTAAACCGTTTTCTTCAG-GAAAAGCATGGTTCCAAGATGGCATTTTTAG ATGGGAGCCCACCAGAAAGACTTTG-CAAGCCAATTGTTGACCACATCGAGTCACTCGGTGGCCAAGTC AGAGTCAACT-CACGAATACAAAAAATTGAGTTAAA-CAAAGACGGAACTGTCCGGAACTTTCTATTGAG TGATGGGAATGTTCTAGAAGCTGATGCT-TATGTTTTCGCTACCCCTGTTGACATTCTCAAGCTTCTTTTA CCCGAAGAATG-GAAACCAATTCCATATTTCAAAAAATTA-GAGAAGTTAGTCGGTGTTCCTGTTATAAA CGTTCATATATGGTTTGACAGAAAGCT-GAAAAACACATATGATCACTTACTTTTCAGTAGGTCACCTCT GCTGAGTGTG-TATGCTGACATGTCAGTGACATGTAAG-GAATATTATGATCCGAATAAGTCAATGTTGG AGTTGGTTCTTGCTCCAGCTGAGGAATG-GATTTCAAGAAGTGACACTGATATTATTGATGCAACAATG AGT-GAACTTTCAAGGCTTTTTCCTGAT-GAAATTGCAGCTGATCAAAGTAAAGCAAAAATCTTGAAATA TAAAGTTGTTAAAACACCAAGGTCTGTT-TATAAAACTGTTCCAGATTGTGAACCATGTCGACCCCTACA AAGATCTCCAAT-TCAAGGATTTTATTTATCTGGTGAT-TATACTAAACAAAAGTATTTGGCTTCAATGGG GGGTGCTGTTTTATCTGGAAAAATTTGT-GCACAAGCTATTTTACAAGATTATGAGATGCTTGCTACA (SEQ ID NO:53). Polynucleotide single-stranded DNAs of 21-45 nucleotides in length with the following sequences were synthesized: taatacgactcactatagggtttggagcttacccaaATGtac ("HL286", sense orientation, SEQ ID NO:54), taatacgactcactatagggag-gccacgtcagcatttcattgttc ("HL287", anti-sense orientation, SEQ ID NO:55), ccattcaATGgtgcaggtaaaac ("HL288", anti-sense orientation, SEQ ID NO:56), catagaATGctccttccactg ("HL289", anti-sense orientation, SEQ ID NO:57), and caaataaattttgtacatttgggtaagctccaa ("HL290", anti-sense orientation, SEQ ID NO:58). An ssDNA solution was made with an equal mixture of all five polynucleotides in 0.01% SILWET L-77® brand surfactant in 5 millimolar sodium phosphate buffer, pH 6.8.

Lettuce variety LS49 "Green Tower" was used in the assays. Two fully expanded leaves of each plant were dipped into a freshly made 0.1% SILWET L-77® brand surfactant in double-distilled water solution for a few seconds. The leaves were allowed to dry for 15-30 minutes. Each plant was then treated by applying 20 microliters ssDNA solution to the top surface of two SILWET® brand surfactant-treated leaves (total 40 microliters per plant). Table 9 lists the assay conditions used and the observed bleaching of plants topically treated with ssDNA polynucleotides. FIG. 28 depicts the progression of bleaching and death of the lettuce plants treated with 1 nanomole ssDNA per plant at (from top to bottom) 37, 46, and 60 days after treatment.

TABLE 9

| Developmental stage | Amount of each ssDNA applied (nanomoles/plant) | Earliest observation of bleaching |
| --- | --- | --- |
| 4 weeks post-germination, plants have 2 fully expanded leaves | 1 | 3 weeks post-treatment |
| 5 weeks post-germination, plants have 4 fully expanded leaves | 4 | 4 days post-treatment |

The assays were repeated with 2 or 4 nanomoles ssDNA applied per plant. FIG. 29A depicts the systemic silencing evidenced by bleaching observed at 4 or 12 days after topical treatment with the polynucleotides.

The assays were repeated using each individual anti-sense ssDNAs ("HL287", SEQ ID NO:55; "HL288", SEQ ID NO:56; "HL289", SEQ ID NO:57; and "HL290", SEQ ID NO:58) with 8 nanomoles polynucleotide applied per plant; positive control plants were treated with a mixture of the four individual anti-sense ssDNAs at 2 nanomoles each (for a total of 8 nanomoles polynucleotide applied per plant) and negative control plants were treated only with buffer. FIG. 29B depicts the systemic silencing evidenced by bleaching observed at 4 after topical treatment with the anti-sense ssDNAs.

Example 25

This example illustrates an aspect of the invention. In this example, growing plants were treated with a topically applied composition for inducing systemic silencing of a target gene in a plant including (a) an agent for conditioning of a plant to permeation by polynucleotides and (b) polynucleotides including at least one polynucleotide strand including at least one segment of 18 or more contiguous nucleotides of the target gene in either anti-sense or sense orientation. More specifically, this example demonstrates the use of topically applied polynucleotides to induce systemic silencing of a phytoene desaturase (PDS) gene in a vegetable crop, i.e., tomato (*Solanum lycopersicum*).

Tomato PDS has the sequence (SEQ ID NO: 59)
GGGTTTATCTCGCAAGTGTGGCTATGGTGGGACGTGTCAAATTTTGGA

TTGTAGCCAAACATGAGATTTGATTTAAAGGGAATTGGCCAAATCACC

GAAAGCAGGCATCTTCATCATAAATTAGTTTGTTTATTTATACAGAAT

TATACGCTTTTACTAGTTATAGCATTCGGTATCTTTTTCTGGGTAACT

GCCAAACCACCACAAATTTCAAGTTTCCATTTAACTCTTCAACTTCAA

CCCAACCAAATTTATTTGCTTAATTGTGCAGAACCACTCCCTATATCT

TCTAGGTGCTTTCATTCGTTCCGAGTAAAATGCCTCAAATTGGACTTG

TTTCTGCTGTTAACTTGAGAGTCCAAGGTAGTTCAGCTTATCTTTGGA

GCTCGAGGTCGTCTTCTTTGGGAACTGAAAGTCGAGATGGTTGCTTGC

AAAGGAATTCGTTATGTTTTGCTGGTAGCGAATCAATGGGTCATAAGT

TAAAGATTCGTACTCCCCATGCCACGACCAGAAGATTGGTTAAGGACT

TGGGGCCTTTAAAGGTCGTATGCATTGATTATCCAAGACCAGAGCTGG

ACAATACAGTTAACTATTTGGAGGCTGCATTTTTATCATCAACGTTCC

GTGCTTCTCCGCGCCCAACTAAACCATTGGAGATTGTTATTGCTGGTG

CAGGTTTGGGTGGTTTGTCTACAGCAAAATATTTGGCAGATGCTGGTC

ACAAACCGATACTGCTGGAGGCAAGGGATGTTCTAGGTGGAAAGGTAG

CTGCATGGAAAGATGATGATGGAGATTGGTACGAGACTGGTTTGCATA

TATTCTTTGGGGCTTACCCAAATATTCAGAACCTGTTTGGAGAATTAG

GGATTAACGATCGATTGCAATGGAAGGAACATTCAATGATATTTGCAA

TGCCAAGCAAGCCAGGAGAATTCAGCCGCTTTGATTTCTCCGAAGCTT

TACCCGCTCCTTTAAATGGAATTTTAGCCATCTTAAAGAATAACGAAA

TGCTTACATGGCCAGAGAAAGTCAAATTTGCAATTGGACTCTTGCCAG

CAATGCTTGGAGGGCAATCTTATGTTGAAGCTCAAGATGGGATAAGTG

TTAAGGACTGGATGAGAAAGCAAGGTGTGCCGGACAGGGTGACAGATG

AGGTGTTCATTGCTATGTCAAAGGCACTCAACTTTATAAACCCTGACG

AACTTTCAATGCAGTGCATTTTGATCGCATTGAACAGGTTTCTTCAGG

AGAAACATGGTTCAAAAATGGCCTTTTTAGATGGTAATCCTCCTGAGA

GACTTTGCATGCCGATTGTTGAACACATTGAGTCAAAAGGTGGCCAAG

TCAGACTGAACTCACGAATAAAAAGATTGAGCTGAATGAGGATGGAA

GTGTCAAGAGTTTTATACTGAGTGACGGTAGTGCAATCGAGGGAGATG

CTTTTGTGTTTGCCGCTCCAGTGGATATTTTCAAGCTTCTATTGCCTG

AAGACTGGAAAGAGATTCCATATTTCCAAAAGTTGGAGAAGTTAGTCG

GAGTACCTGTGATAAATGTACATATATGGTTTGACAGAAAACTGAAGA

ACACATATGATCATTTGCTCTTCAGCAGAAGCTCACTGCTCAGTGTGT

ATGCTGACATGTCTGTTACATGTAAGGAATATTACAACCCCAATCAGT

CTATGTTGGAATTGGTTTTTGCACCTGCAGAAGAGTGGATATCTCGCA

GCGACTCAGAAATTATTGATGCAACGATGAAGGAACTAGCAACGCTTT

TTCCTGATGAAATTTCAGCAGATCAAAGCAAAGCAAAAATATTGAAGT

ACCATGTTGTCAAAACTCCGAGGTCTGTTTATAAAACTGTGCCAGGTT

GTGAACCCTGTCGGCCTTTACAAAGATCCCCAATAGAGGGGTTTTATT

TAGCCGGTGACTACACGAAACAGAAATACTTGGCTTCAATGGAAGGCG

CTGTCTTATCAGGAAAGCTTTGTGCTCAAGCTATTGTACAGGATTATG

AGTTACTTGTTGGACGTAGCCAAAAGAAGTTGTCGGAAGCAAGCGTAG

TTTAGCTTTGTGGTTATTATTTAGCTTCTGTACACTAAATTTATGATG

CAAGAAGCGTTGTACACAACATATAGAAGAAGAGTGCGAGGTGAAGCA

AGTAGGAGAAATGTTAGGAAAGCTCCTATACAAAAGGATGGCATGTTG

AAGATTAGCATCTTTTTAATCCCAAGTTTAAATATAAAGCATATTTTA

TGTACCACTTTCTTTATCTGGGGTTTGTAATCCCTTTATATCTTTATG

CAATCTTTACGTTAGTTAAAAAAAAAAAAAAAAAAAAAAAAACTCGA.

A 201 nucleotide dsRNA polynucleotide with an anti-sense strand capable of hybridizing to the RNA encoded by the sequence TCGCAGCGACTCAGAAATTATTGATG-CAACGATGAAGGAACTAGCAACGCTTTTTCCTGATGAAATTT CAGCAGAT-CAAAGCAAAGCAAAAATATTGAAGTAC-CATGTTGTCAAAACTCCGAGGTCTGTTTATAAA ACTGTGCCAGGTTGTGAACCCTGTCGGC-CTTTACAAAGATCCCCAATAGAGGGGTTTTATTTAG (SEQ ID NO:60) which correspond to the nucleotides at positions 1724-1923 of the mRNA transcribed from the tomato PDS gene sequence (SEQ ID NO:59) was synthesized by RT PCR using oligonucleotide primers with the sequences TAATACGACTCAC-TATAGGGTCGCAGCGACTCAGAAATTATTG (SEQ ID NO:61, sense primer) and TAATACGACTCACTATAGGGGTAAAGGC-CGACAGGGTTCACAACC (SEQ ID NO:62, anti-sense primer). A 2.5 micromolar dsRNA solution was made with the 201 nucleotide dsRNA polynucleotide (SEQ ID NO:60) in 0.01% SILWET L-77® brand surfactant in 5 millimolar sodium phosphate buffer, pH 6.8.

Figure 30:
FIG. 30 illustrates bleaching of leaves (right top panel) and flowers (right middle panel) of tomato plants treated with tomato phytoene desaturase polynucleotides, as described in Example 25.

Three-week old tomato seedlings were treated as follows. Two fully expanded leaves were dipped into a freshly made 0.1% SILWET L-77® brand surfactant solution in double-distilled water for a few seconds. The leaves were allowed to dry for 30 minutes to 1 hour. Each plant was then treated by applying 20 microliters dsRNA solution to the top surface of two SILWET® brand surfactant-treated leaves (total 40 microliters per plant). Control plants were treated with buffer. The plants were kept in a growth chamber for observation. FIG. 30 depicts the systemic silencing of the target gene PDS as evidenced by bleaching of the dsRNA-treated plants 30 days after topical treatment. The dsRNA-treated plants were severely stunted, compared to control plants.

Example 26

This example illustrates an improvement to herbicidal compositions adapted for topical coating onto the exterior surface of a growing plant where the plant lethal agent includes polynucleotides having a sequence essentially identical or complementary to sequences of one or more plant genes or sequence of transcribed DNA from the plant genes. The polynucleotides effect systemic suppression of the plant gene in plant organs or tissues other than those that received the topical polynucleotide application. More specifically this example illustrates an herbicidal composition adapted for topical coating onto the exterior surface of a growing plant comprising surfactant and at least one plant lethal agent including combinations of polynucleotides having sequence targeting the 5-enolpyruvylshikimate-3-phosphate synthase (EPSPS) gene, a transcription initiation factor (TIF), and DNA-dependent ATPase (ddATPase) in Palmer amaranth.

The herbicidal composition includes at least one of the following 21-base-pair double-stranded RNA polynucleotides:

```
(1) nDsRNA1: sense strand
                              (SEQ ID NO: 63)
CUACCAUCAACAAUGGUGUCC
and
anti-sense strand
                              (SEQ ID NO: 64)
GGACACCAUUGUUGAUGGUAG (2) nDsRNA3: sense strand
                              (SEQ ID NO: 65)
GUCGACAACUUGCUGUAUAGU
and
anti-sense strand
                              (SEQ ID NO: 66)
ACUAUACAGCAAGUUGUCGAC (3) nDsRNA4: sense strand
                              (SEQ ID NO: 67)
GGUCACCUGGACAGAGAAUAG
and
anti-sense strand
                              (SEQ ID NO: 68)
CUAUUCUCUGUCCAGGUGACC (4) nDsNA5: sense strand
                              (SEQ ID NO: 69)
AAUGCCAGAUGUUGCUAUGAC
and
anti-sense strand
                              (SEQ ID NO: 70)
GUCAUAGCAACAUCUGGCAUU
```

A mixture of multiple polynucleotides is advantageous for preventing selection of resistance in the treated plants. In an embodiment, the herbicidal composition includes a mixture of all four of the above dsRNA polynucleotides having SEQ ID NOS: 63-70. In another embodiment, the herbicidal composition includes single-stranded DNA polynucleotides with deoxyribonucleotide sequences corresponding to one or more of the dsRNA sequences SEQ ID NOS: 63-70. In another embodiment, the herbicidal composition includes RNA/DNA hybrids with nucleotide sequences corresponding to one or more of the dsRNA sequences SEQ ID NOS: 63-70. In another embodiment, the herbicidal composition includes dsRNA polynucleotides where the 2' hydroxyls are methylated for stability.

The herbicidal composition includes a surfactant such as SILWET L-77® brand surfactant (or other effective surfactants such as those provided in Example 36). Optionally, the herbicidal composition can include one or more additives such as a salt, chelating agent, or a humectant (such as those provided in Example 35) to improve herbicidal performance, e.g., by enhancing transfer of the polynucleotide into the interior of the plant, enhancing efficacy of the polynucleotides, or potentiating the herbicidal activity of the non-polynucleotide herbicide.

Optionally the herbicidal composition includes polynucleotides designed to regulate multiple genes in the plant. In an embodiment, the herbicidal composition includes polynucleotides having sequence essentially identical or complementary to the sequence of a second gene or to the sequence of RNA transcribed from the second gene, wherein the regulation of the second gene provides a synergistic enhancement of the herbicidal activity of the composition.

In an embodiment, the herbicidal composition includes polynucleotides having sequence essentially identical or complementary to the sequence of the endogenous Palmer amaranth 5-enolpyruvylshikimate-3-phosphate synthase (EPSPS) gene or to the sequence of RNA transcribed from the endogenous EPSPS gene as well as polynucleotides having sequence essentially identical or complementary to the sequence of the endogenous Palmer translation initiation factor (TIF) gene or to the sequence of RNA transcribed from the endogenous TIF gene. Translation initiation factor (TIF) is a nuclear-encoded chloroplast protein that is essential for initiating protein synthesis and is expressed throughout a plant. *Arabidopsis thaliana* has an orthologue named AT1G17220.1 (described on the publicly available database The *Arabidopsis* Information Resource found online at www.arabidopsis.org/servlets/TairObject?type=locus&name=AT1G17220) and assigned GenBank accession number GI:186478573, which has been identified as a chloroplast localized protein with similarity to bacterial translation initiation factor 2; see also Miura et al. (2007) *Plant Cell*, 19:1313-1328 for a description of this gene. TIF sequences were identified from Palmer amaranth (*Amaranthus palmeri*); one TIF gene was identified to have the sequence of SEQ ID NO:71. Examples of polynucleotides for suppression of this TIF gene in *Amaranthus palmeri* are listed in Table 10.

TABLE 10

| Poly-nucleotide | Position in TIF sequence | Sequence | SEQ ID NO. |
| --- | --- | --- | --- |
| Palmer amaranth TIF | Entire sequence of SEQ ID NO: 71 | ATGGCAACAATGGCTTCCCTAGTGAGTTTGGGAAGCTCTGGAG CAACTTGCTCAGGGCAATTGGAGGTTTCCTTTTCATTGGTTAAG AAAATTACATTGCCTAGAAGAAATTGTAGTTGCAATTTTAGGCA ATTAGGAGGGGGAGGAGATGGCGTTACGTTTCGGTGTGTAGA CTTTCTGTCACTACTGATTATGTTTCTGAGCAAGGAAATGCTGT TTCTCTTGAAAATGCATATAGTGAGAGTAAAGAAGAGGGTCTC ATCTTGAAGCCTTCTCCTAAGCCGGTTTTGAAATCCGGGTCTGA TGGAAATCGGAAATTTGGGGAGAGTTCGGTGGCGTTTTCGAGT AATGGGAAATTGGATAATGTAGAGGAGAGGAAGAAGGTTATTG ATTCATTGGATGAGGTATTAGAAAAGGCCGAGAGATTAGAAAC GGCGAACTTACAAGCAGATAATAGAAAGGATAGCACAAATGTA AATAAACCGTCTCCGAGTGTAAGTAGTTCAACCAATGGTAAAC | 71 |

TABLE 10-continued

| Poly-nucleotide | Position in TIF sequence | Sequence | SEQ ID NO. |
|---|---|---|---|
| | | CTGTAAATAATTTGAACAAAGGGAAGCCTAAAGCTGCGAAGAG<br>CGTTTGGAGAAAGGGAAATCCAGTTTCTACTGTGCAAAAAGTA<br>GTGCAAGAATCTCCGAAGATTGAAAAGGTTGAGAGAGTGGAAG<br>CTCGAACGACCAGCCAATCGTCTGAAACGATAAGACCCCCAGT<br>GCCACTACAGAGGCCTGAGATTAAGTTGCAGGCAAAGCCTTCT<br>ACTGCTCCTCCACCCATGCCTAAGAAGCCGGTTTTGAAGGATGT<br>GGGGATGTCCTCCAGAGCTGATGGGAAGGACCAGTCTGTGAAA<br>TCTAAAGAGAGGAAGCCTATTCTAGTGGACAAATTTGCCACCA<br>AGAAGGCATCAGTTGATCCGTCGATTGCTCAAGCAGTAATTGC<br>CCCACCAAAACCTGCTAAATTTCCTTCTGGAAAGTTTAAAGATG<br>ATTATCGGAAGAAGGGTCTTGCAGCTGGTGGGCCGAAGAGGCG<br>TATGGTCAATGATGATGATATTGAAATGCATGAAGACACTTCA<br>GAGCTCGGTCTTTCTATTCCTGGTGCTGCTACGGCTCGGAAAGG<br>CAGGAAATGGAGTAAGGCAAGTCGCAAGGCTGCCAGACGCCA<br>AGCAGCTAGAGATGCCGCTCCTGTTAAAGTGGAAATCTTAGAG<br>GTTGAAGAAAAGGGCATGTCGACCGAAGAATTAGCATACAACT<br>TGGCTATTAGCGAAGGTGAAATTCTTGGGTACCTGTATTCTAAG<br>GGGATAAAACCAGATGGTGTGCAAACTCTTGACAAGGCAATGG<br>TAAAGATGATATGTGAAAGATATGACGTGGAGGTTTTGGACGC<br>ACTTTCTGAACAAATGGAAGAAATGGCTCGAAAGAAGGAAATT<br>TTCGACGAAGATGACCTTGACAAGCTTGAAGATAGGCCTCCTG<br>TGCTTACTATAATGGGTCATGTAGATCATGGCAAGACGACCCTT<br>CTGGATTATATACGGAAGAGCAAGGTTGCTGCTTCTGAAGCTG<br>GTGGGATTACACAAGGTATTGGTGCTTATAAAGTGGAAGTACC<br>GGTTGATGGCAAGTTGCTGCCTTGTGTCTTTCTTGACACTCCCG<br>GACACGAGGCGTTCGGGGCAATGAGGGCTCGTGGAGCAAGAGT<br>GACAGATATTGCTATTATAGTTGTAGCTGCTGACGATGGGATCC<br>GTCCTCAAACAAATGAAGCCATAGCACATGCAAAAGCAGCTGG<br>TGTACCTATTGTGGTTGCAATTAATAAGATTGACAAGGATGGG<br>GCTAATCCGGACCGTGTGATGCAAGAGCTTTCATCAATTGGTCT<br>AATGCCAGAGGATTGGGGTGGTGATACCCCAATGGTCAAGATA<br>AGTGCTCTAAAAGGTGAAAATGTGGACGAGTTACTCGAGACAG<br>CCATGCTTGTCGCCGAGTTGCAAGAGTTAAAGGCTAATCCTCAG<br>AGGAACGCTAAGGGCACTGTAATTGAGGCTGGTCTTCATAAAT<br>CAAAAGGACCCATTGCCACTTTTATTGTGCAGAATGGTACCCTC<br>AAACAAGGGGATACTGTAGTTTGTGGGGAAGCATTTGGGAAGG<br>TTCGTGCCCTATTTGATCACGGAGGGAATCGCGTTGATGAAGCT<br>GGTCCATCTATTCCCGTGCAGGTTATTGGATTGAATAATGTTCC<br>TTTTGCCGGTGATGAGTTCGAGGTAGTGAGTTCCCTTGATATAG<br>CTCGTGAAAAGGCAGAGGTCCGTGCAGAGTCTTTACGAAATGA<br>GCGTATAGCTGCTAAGGCCGGAGACGGAAAGGTTACGCTGTCA<br>TCCTTGGCATCGGCTGTTTCTTCAGGGAAGATGGCTGGTTTGGA<br>TTTGCACCAGTTAAATATCATTTTGAAGGTTGATGTTCAGGGAT<br>CAATCGAGGCATTGAGGCAAGCTCTAGAAGTTCTTCCTCAAGA<br>TAACGTCACTTTGAAGTTTCTCTTACAAGCGACCGGAGATGTTA<br>CTACAAGTGATGTTGATCTTGCAGTTGCTAGTAAAGCTATTATC<br>TTGGGGTTCAATGTGAAGGCACCAGGTTCTGTCGAAAAATTAG<br>CAGATAACAAAGGTGTTGAAATTCGGCTTTATAAAGTCATTTAT<br>GATCTAATTGACGACATGCGGAGTGCAATGGAAGGAATGCTAG<br>ATCCCGTTGAGGAACAAGTTGCAATTGGTTCAGCCGAAGTGCG<br>GGCTACATTCAGTAGTGGTAGTGGCCGTGTCGCTGGATGCATG<br>GTGACCGAGGGAAAGATTACCAAAGGCTGTGGGATTCGAGTGA<br>TACGGAAGGGAAAAACTGTCCACGTTGGAGTTCTTGATTCGTTG<br>CGTCGAGTAA | |
| 200 bp DNA | 341-541 | TTTCGAGTAATGGGAAATTGGATAATGTAGAGGAGAGGAAGAA<br>GGTTATTGATTCATTGGATGAGGTATTAGAAAAGGCCGAGAGA<br>TTAGAAACGGCGAACTTACAAGCAGATAATAGAAAGGATAGCA<br>CAAATGTAAATAAACCGTCTCCGAGTGTAAGTAGTTCAACCAA<br>TGGTAAACCTGTAAATAATTTGAACAAA | 72 |
| 160 bp dsRNA | 342-501 | Sense:<br>UUCGAGUAAUGGGAAAUUGGAUAAUGUAGAGGAGAGGAAGA<br>AGGUUAUUGAUUCAUUGGAUGAGGUAUUAGAAAAGGCCGAG<br>AGAUUAGAAACGGCGAACUUACAAGCAGAUAAUAGAAAGGA<br>UAGCACAAAUGUAAAUAAACCGUCUCCGAGUGUAAGU | 73 |
| | | Anti-sense:<br>ACUUACACUCGGAGACGGUUUAUUUACAUUUGUGCUAUCCUU<br>UCUAUUAUCUGCUUGUAAGUUCGCCGUUUCUAAUCUCUCGGC<br>CUUUUCUAAUACCUCAUCCAAUGAAUCAAUAACCUUCUUCCU<br>CUCCUCUACAUUAUCCAAUUUCCCAUUACUCGAA | 74 |

TABLE 10-continued

| Poly-nucleotide | Position in TIF sequence | Sequence | SEQ ID NO. |
|---|---|---|---|
| anti-sense DNA TIF_AS1 | 555-576 | ATTTCTCCAAACGCTCTTCGCA | 75 |
| anti-sense DNA TIF_AS2 | 342-363 | ATCCAATTTCCCATTACTCGAA | 76 |
| anti-sense DNA TIF_AS3 | 412-433 | GTTTCTAATCTCTCGGCCTTTT | 77 |
| anti-sense DNA TIF_AS4 | 488-509 | TTGAACTACTTACACTCGGAG | 78 |
| anti-sense DNA TIF_AS5 | 368-389 | TAACCTTCTTCCTCTCCTCTA | 79 |
| anti-sense DNA TIF_AS6 | 790-811 | GTCCTTCCCATCAGCTCTGGA | 80 |
| anti-sense DNA TIF_AS7 | 1052-1073 | CGTAGCAGCACCAGGAATAG | 81 |
| anti-sense DNA TIF_AS8 | 1655-1676 | CAGCAGCTACAACTATAATAG | 82 |

In an embodiment, the herbicidal composition includes a mixture of at least two of the above EPSPS dsRNA polynucleotides having SEQ ID NOS: 63-70 and also at least one polynucleotide having sequence essentially identical or complementary to the sequence of the endogenous Palmer translation initiation factor (TIF) gene or to the sequence of RNA transcribed from the endogenous TIF gene, such as those provided in Table 10. In a specific embodiment, the herbicidal composition includes a mixture of the four EPSPS dsRNA polynucleotides having SEQ ID NOS: 63-70 and a 160 base-pair TIF double-stranded RNA polynucleotide having the sense sequence of UUCGAGUAAUGGGAAAUUG-GAUAAUGUAGAGGAGAGGAAGAAGGUUA-UUGAUUC AUUGGAUGAGGUAUUAGAAAAGGC-CGAGAGAUUAGAAACGGCGAACUUACAAGC AGAUAAUAGAAAGGAUAGCACAAAU-GUAAAUAAACCGUCUCCGAGUGUAAGU (SEQ ID NO. 73) and the anti-sense sequence of ACUUACACUCG-GAGACGGUUUAUUUACAUUUGUGCUAUC-CUUUCUAUUAUCUGC UUGUAAGUUCGCCGUUUC-UAAUCUCUCGGCCUUUUCUAAUACCUCAUCCAAUGAA UCAAUAACCUUCUUCCUCUCCUCUACA-UUAUCCAAUUUCCCAUUACUCGAA (SEQ ID NO. 74).

In some embodiments, the polynucleotides are designed to regulate multiple target genes, resulting in a synergistic effect on herbicide activity. For example, a synergistic effect on herbicide activity was obtained by treatment of a plant with polynucleotides designed to suppress a translation initiation factor (TIF) and 5-enolpyruvylshikimate-3-phosphate synthase (EPSPS) followed by treatment with the non-polynucleotide herbicide glyphosate.

The polynucleotides listed in Table 11 were produced by synthesis or by in vitro transcription.

TABLE 11

| Name | Comments | Nucleotide sequences |
|---|---|---|
| IDT [1] | Palmer/EPSPS dsRNA with two 2-deoxyribonucleotides (in bold underlined text) at 3' end of sense strand (25-mer) and a 2-nucleotide overhang at 3' end of anti-sense strand (27-mer); chemically | Sense: CUACCAUCAACAAUGGUGUCCAUAC (SEQ ID NO. 83) Anti-sense: GUAUGGACACCAUUGUUGAUGGUAGUA (SEQ ID NO. 84) |
| IDT [2] | | Sense: AGUUGGUGGGCAAUCAUCAAUUGTT (SEQ ID NO. 85) Anti-sense: AACAAUUGAUGAUUGCCCACCAACUCU (SEQ ID NO. 86) |

TABLE 11-continued

| Name | Comments | Nucleotide sequences |
|---|---|---|
| IDT [3] | synthesized by IDT | Sense:<br>GGUCGACAACUUGCUGUAUAGUGAT<br>(SEQ ID NO. 87)<br>Anti-sense:<br>AUCACUAUACAGCAAGUUGUCGACCUC<br>(SEQ ID NO. 88) |
| IDT [4] | | Sense:<br>UGCAAGGUCACCUGGACAGAGAATA<br>(SEQ ID NO. 89)<br>Anti-sense:<br>UAUUCUCUGUCCAGGUGACCUUGCAAC<br>(SEQ ID NO. 90) |
| IDT [5] | Palmer/EPSPS dsRNA (21-mer) with blunt ends; chemically synthesized by IDT | Sense:<br>AACAUGAACAAAAUGCCAGAU<br>(SEQ ID NO. 91)<br>Anti-sense:<br>AUCUGGCAUUUUGUUCAUGUU<br>(SEQ ID NO. 92) |
| IDT blunt [1] | Palmer/EPSPS dsRNA (27-mer) with blunt ends; synthesized via in vitro T7 transcription | 1S-Anti-sense<br>GUAUGGACACCAUUGUUGAUGGUAGUA<br>(SEQ ID NO. 93)<br>1S-Sense<br>UACUACCAUCAACAAUGGUGUCCAUAC<br>(SEQ ID NO. 94) |
| IDT blunt [2] | | 2S-Anti-sense<br>AAUAAUUGAUGAUUGCCCACCAACUCU<br>(SEQ ID NO. 95)<br>2S-Sense<br>AGAGUUGGUGGGCAAUCAUCAAUUAUU<br>(SEQ ID NO. 96) |
| IDT blunt [3] | | 3S-Anti-sense<br>AUCACUAUACAGCAAGUUGUCGACCAC<br>(SEQ ID NO. 97)<br>3S-Sense<br>GUGGUCGACAACUUGCUGUAUAGUGAU<br>(SEQ ID NO. 98) |
| IDT blunt [4] | | 4S-Anti-sense<br>UAUUCUCUGUCCAGGUGACCUUGCAAC<br>(SEQ ID NO. 99)<br>4S-Sense<br>GUUGCAAGGUCACCUGGACAGAGAAUA<br>(SEQ ID NO. 100) |
| 3OH [1] | Palmer/EPSPS dsRNA (27-mer) with 3'-overhangs; synthesized via in vitro T7 transcription | 1S-Anti-sense<br>gGUAUGGACACCAUUGUUGAUGGUAGUAC<br>(SEQ ID NO. 101)<br>1S-Sense<br>GCUACCAUCAACAAUGGUGUCCAUACCAC<br>(SEQ ID NO. 102) |
| 3OH [2] | | 2S-Anti-sense<br>gAAGAAUUGAUGAUUGCCCACCAACUCAC<br>(SEQ ID NO. 103)<br>2S-Sense<br>GAGUUGGUGGGCAAUCAUCAAUUAUUCAC<br>(SEQ ID NO. 104) |
| 3OH [3] | | 3S-Anti-sense<br>gAUCACUAUACAGCAAGUUGUCGACAC<br>(SEQ ID NO. 105)<br>3S-Sense<br>GUCGACAACUUGCUGUAUAGUGAUCAC<br>(SEQ ID NO. 106) |
| 3OH [4] | | 4S-Anti-sense<br>gUAUUCUCUGUCCAGGUGACCUUGCACAC<br>(SEQ ID NO. 107)<br>4S-Sense<br>GUGCAAGGUCACCUGGACAGAGAAUACAC<br>(SEQ ID NO. 108) |
| IDT HP [1] | Palmer/EPSPS single strand of RNA designed to self-hybridize | 1S-<br>GUAUGGACACCAUUGUUGAUGGUAGUAGAAAUACUACCAUCAACAA<br>UGGUGUCCAUAC<br>(SEQ ID NO. 109) |

TABLE 11-continued

| Name | Comments | Nucleotide sequences |
|---|---|---|
| IDT HP [2] | into a hairpin, containing anti-sense sequence on the 5' arm | 2S-<br>AUAAUUGAUGAUUGCCCACCAACUCUGAAAAGAGUUGGUGGGCAAUC<br>UCAAUUAUU<br>(SEQ ID NO. 110) |
| IDT HP [3] | and anti-sense sequence on the 3' arm, with an intermediate | 3S-<br>AUCACUAUACAGCAAGUUGUCGACCACGAAAGUGGUCGACAACUUG<br>CUGUAUAGUGAU<br>(SEQ ID NO. 111) |
| IDT HP [4] | GAAA tetranucleotide loop; chemically synthesized by IDT | 4S-<br>UAUUCUCUGUCCAGGUGACCUUGCAACGAAAGUUGCAAGGUCACC<br>UGGACAGAGAAUA<br>(SEQ ID NO. 112) |
| [TIF] | Palmer/translation initiation factor (TIF) dsRNA (160-mer) synthesized via in vitro T7 transcription | Sense:<br>UUCGAGUAAUGGGAAAUUGGAUAAUGUAGAGGAGAGGAAGAAGGUU<br>AUUGAUUCAUUGGAUGAGGUAUUAGAAAAGGCCGAGAGAUUAGAAA<br>CGGCGAACUUACAAGCAGAAUAUAGAAAGGAUAGCACAAAUGUAAAU<br>AAACCGUCUCCGAGUGUAAGU<br>(SEQ ID NO. 73)<br>Anti-sense:<br>ACUUACACUCGGAGACGGUUUAUUUACAUUUGUGCUAUCCUUUCUAU<br>UAUCUGCUUGUAAGUUCGCCGUUUCUAAUCUCUCGGCCUUUUCUAAU<br>ACCUCAUCCAAUGAAUCAAUAACCUUCUUCCUCUCCUCUACAUUAUC<br>CAAUUUCCCAUUACUCGAA<br>(SEQ ID NO. 74) |
| [ddATPase] | Palmer/DNA-dependent ATPase (ddATPase) dsRNA (168-mer) synthesized via in vitro T7 transcription | Sense:<br>GAUCACAAAUUUGCCGGUUUAUGAUCAAAUACGGAACAUAAGACAGA<br>UACACUUGAACACCAUGAUUCGCAUUGGGGGUGUGGUUACUCGUCGU<br>UCUGGAGUAUUCCCUCAGUUGAUGCAGGUGAAGUAUGACUGCAAUAA<br>AUGUGGGGCUAUCCUGGGUCCCUUUUU<br>(SEQ ID NO. 113)<br>Anti-sense:<br>AAAAAGGGACCCAGGAUAGCCCCACAUUUAUUGCAGUCAUACUUCAC<br>CUGCAUCAACUGAGGGAAUACUCCAGAACGACGAGUAACCACACCCC<br>CAAUGCGAAUCAUGGUGUUCAAGUGUAUCUGUCUUAUGUUCCGUAUU<br>UGAUCAUAAACCGGCAAAUUUGUGAUC<br>(SEQ ID NO. 114) |

Solutions of the polynucleotides were prepared and applied to the leaves of Palmer amaranth using the protocols described in Table 12.

TABLE 12

| Protocol number (description) | Protocol |
|---|---|
| 1 (1-step hand) | 1. Apply mixture of polynucleotides in 1% SILWET L-77 ® brand surfactant, 2% ammonium sulfate in 10 millimolar sodium phosphate buffer, pH 6.8 (or control buffer solution of 1% SILWET L-77 ® brand surfactant, 2% ammonium sulfate in 10 millimolar sodium phosphate buffer, pH 6.8) by hand pipetting<br>2. 48 or 72 hours later, spray glyphosate ("2X Wmax" or 1682 g acid equivalent per hectare of Roundup ® WeatherMAX ® brand herbicide) by regular sprayer (10 gallons/acre) |
| 2 (1-step sprayer) | 1. Spray mixture of polynucleotides in 1% SILWET L-77 ® brand surfactant, 2% ammonium sulfate in 10 millimolar sodium phosphate buffer, pH 6.8 (or control buffer solution of SILWET L-77 ® brand surfactant, 2% ammonium sulfate in 10 millimolar sodium phosphate buffer, pH 6.8) by Milli sprayer<br>2. 48 or 72 hours later, spray glyphosate ("2X Wmax" or 1682 g acid equivalent per hectare of Roundup ® WeatherMAX ® brand herbicide) by regular sprayer (10 gallons/acre) |
| 3 (2-step hand) | 1. Spray 1% SILWET L-77 ® brand surfactant as 1st step by regular sprayer or Milli sprayer;<br>2. Apply mixture of polynucleotides in 1% SILWET L-77 ® brand surfactant, 2% ammonium sulfate in 10 millimolar sodium phosphate buffer, pH 6.8 (or control buffer solution of 1% SILWET L-77 ® brand surfactant, 2% ammonium sulfate in 10 millimolar sodium phosphate buffer, pH 6.8) by hand pipetting<br>3. 48 or 72 hours later, spray glyphosate ("2X Wmax" or 1682 g acid equivalent per hectare of Roundup ® WeatherMAX ® brand herbicide) by regular sprayer (10 gallons/acre) |
| 4 (2-step sprayer) | 1. Spray 1% SILWET L-77 ® brand surfactant as 1st step by regular sprayer or Milli sprayer;<br>2. Spray mixture of polynucleotides in 1% SILWET L-77 ® brand surfactant, 2% ammonium sulfate in 10 millimolar sodium phosphate buffer, pH 6.8 (or control buffer solution of 1% SILWET L-77 ® brand surfactant, 2% ammonium sulfate in 10 millimolar sodium phosphate buffer, pH 6.8) by Milli sprayer |

TABLE 12-continued

| Protocol number (description) | Protocol |
|---|---|
| 5 (tank mix) | 3. 48 or 72 hours later, spray glyphosate ("2X Wmax" or 1682 g acid equivalent per hectare of Roundup ® WeatherMAX ® brand herbicide) by regular sprayer (10 gallons/acre) Spray mixture of polynucleotides in 1% SILWET L-77 ® brand surfactant, 2% ammonium sulfate in 10 millimolar sodium phosphate buffer, pH 6.8 containing glyphosate at 1682 g acid equivalent per hectare of Roundup ® WeatherMAX ® brand herbicide (or control buffer solution of 1% SILWET L-77 ® brand surfactant, 2% ammonium sulfate in 10 millimolar sodium phosphate buffer, pH 6.8 containing glyphosate at 1682 g acid equivalent per hectare of Roundup ® WeatherMAX ® brand herbicide) by Milli sprayer. |

Combinations of polynucleotides were tested as indicated in Table 13.

TABLE 13

| Polynucleotides applied in combination | SEQ ID NO. | Protocol | Amount applied of each polynucleotide (g/acre) | Total polynucleotide applied (g/acre) | EPSPS copy number* | Results** |
|---|---|---|---|---|---|---|
| IDT [1] | 83, 84, | 1 | 0.29 | 0.87 | 112 | 75% killed |
| IDT [3] | 87, 88 | | 0.29 | | | (27 DAT) |
| IDT [4] | 89, 90 | | 0.29 | | | |
| IDT [1] | 83, 84, | 1 | 0.29 | 1.4 | 112 | 100% killed |
| IDT [3] | 87, 88 | | 0.29 | | | (27 DAT) |
| IDT [4] | 89, 90 | | 0.29 | | | |
| [TIF] | 73, 74 | | 0.50 | | | |
| IDT [1] | 83, 84, | 1 | 0.29 | 1.37 | 112 | 11.2% |
| IDT [3] | 87, 88 | | 0.29 | | | stunted |
| IDT [4] | 89, 90 | | 0.29 | | | (27 DAT) |
| [ddATPase] | 113, 114 | | 0.50 | | | |
| IDT [1] | 83, 84, | 1 | 0.29 | 1.87 | 112 | 100% killed |
| IDT [3] | 87, 88 | | 0.29 | | | (27 DAT) |
| IDT [4] | 89, 90 | | 0.29 | | | |
| [TIF] | 73, 74 | | 0.50 | | | |
| [ddATPase] | 114, 114 | | 0.50 | | | |
| IDT [1] | 83, 84, | 1 | 0.29 | 1.2 | 112, 36 | 0% control |
| IDT [2] | 85, 86 | | 0.29 | | | (11 DAT); |
| IDT [3] | 87, 88 | | 0.29 | | | 0% control |
| IDT [4] | 89, 90 | | 0.29 | | | (31 DAT) |
| IDT [1] | 83, 84, | 1 | 1.4 | 5.8 | 112, 36 | 0% control |
| IDT [2] | 85, 86 | | 1.4 | | | (11 DAT); |
| IDT [3] | 87, 88 | | 1.4 | | | 15% stunted |
| IDT [4] | 89, 90 | | 1.4 | | | (31 DAT) |
| IDT [1] | 83, 84, | 1 | 2.9 | 12 | 112, 36 | 0% control |
| IDT [2] | 85, 86 | | 2.9 | | | (11 DAT); |
| IDT [3] | 87, 88 | | 2.9 | | | 35% stunted |
| IDT [4] | 89, 90 | | 2.9 | | | (31 DAT) |
| IDT [1] | 83, 84, | 1 | 5.8 | 23 | 112, 36 | 51% stunted |
| IDT [2] | 85, 86 | | 5.8 | | | (11 DAT); |
| IDT [3] | 87, 88 | | 5.8 | | | 100% |
| IDT [4] | 89, 90 | | 5.8 | | | stunted (31 DAT) |
| IDT [1] | 83, 84, | 2 | 0.29 | 1.2 | 33, 54 | 9% stunted |
| IDT [2] | 85, 86 | | 0.29 | | | (6 DAT) |
| IDT [3] | 87, 88 | | 0.29 | | | |
| IDT [4] | 89, 90 | | 0.29 | | | |
| IDT [1] | 83, 84, | 2 | 5.8 | 23 | 33, 54 | 100% killed |
| IDT [2] | 85, 86 | | 5.8 | | | (6 DAT) |
| IDT [3] | 87, 88 | | 5.8 | | | |
| IDT [4] | 89, 90 | | 5.8 | | | |
| IDT [1] | 83, 84, | 2 | 0.29 | 0.87 | 33, 54 | 20% stunted |
| IDT [3] | 87, 88 | | 0.29 | | | (6 DAT) |
| IDT [4] | 89, 90 | | 0.29 | | | |
| IDT [1] | 83, 84, | 2 | 5.8 | 17 | 33, 54 | 100% killed |
| IDT [3] | 87, 88 | | 5.8 | | | (6 DAT) |
| IDT [4] | 89, 90 | | 5.8 | | | |
| IDT [5] | 91, 92 | 1 | 0.29 | 0.29 | 34, 36, 54 | 14.1% stunted (22 DAT) |
| IDT [5] (22 DAT) | 91, 92 | 1 | 2.9 | 2.9 | 34, 36, 54 | 100% kill |

TABLE 13-continued

| Polynucleotides applied in combination | SEQ ID NO. | Protocol | Amount applied of each polynucleotide (g/acre) | Total polynucleotide applied (g/acre) | EPSPS copy number* | Results** |
|---|---|---|---|---|---|---|
| IDT [1] | 83, 84, | 1 | 2.9 | 12 | 34, 36, 54 | 100% killed |
| IDT [2] | 85, 86 | | 2.9 | | | (22 DAT) |
| IDT [3] | 87, 88 | | 2.9 | | | |
| IDT [4] | 89, 90 | | 2.9 | | | |
| IDT [1] | 83, 84, | 1 | 2.9 | 14 | 34, 36, 54 | 100% killed |
| IDT [2] | 85, 86 | | 2.9 | | | (22 DAT) |
| IDT [3] | 87, 88 | | 2.9 | | | |
| IDT [4] | 89, 90 | | 2.9 | | | |
| IDT [5] | 91, 92 | | 2.9 | | | |
| IDT [1] | 83, 84, | 1 | 2.9 | 8.7 | 34, 36, 54 | 100% killed |
| IDT [3] | 87, 88 | | 2.9 | | | (22 DAT) |
| IDT [4] | 89, 90 | | 2.9 | | | |
| IDT [1] | 83, 84, | 1 | 2.9 | 12 | 34, 36, 54 | 100% killed |
| IDT [3] | 87, 88 | | 2.9 | | | (22 DAT) |
| IDT [4] | 89, 90 | | 2.9 | | | |
| IDT [5] | 91, 92 | | 2.9 | | | |
| IDT [5] | 91, 92 | 1 | 0.29 | 0.29 | 33, 54, 55 | 71% stunted (18 DAT) |
| IDT [5] | 91, 92 | 1 | 2.9 | 2.9 | 33, 54, 55 | 100% killed (18 DAT) |
| IDT [1] | 83, 84, | 1 | 0.29 | 1.4 | 33, 54, 55 | 100% killed |
| IDT [2] | 85, 86 | | 0.29 | | | (18 DAT) |
| IDT [3] | 87, 88 | | 0.29 | | | |
| IDT [4] | 89, 90 | | 0.29 | | | |
| IDT [5] | 91, 92 | | 0.29 | | | |
| IDT [1] | 83, 84, | 1 | 0.29 | 1.2 | 33, 54, 55 | 100% killed |
| IDT [2] | 85, 86 | | 0.29 | | | (18 DAT) |
| IDT [3] | 87, 88 | | 0.29 | | | |
| IDT [4] | 89, 90 | | 0.29 | | | |
| IDT HP [1] | 109 | 3 | 0.29 | 1.2 | 16, 33 | 100% killed |
| IDT HP [2] | 110 | | 0.29 | | | (18 DAT) |
| IDT HP [3] | 111 | | 0.29 | | | |
| IDT HP 4] | 112 | | 0.29 | | | |
| IDT [1] | 83, 84, | 3 | 0.29 | 1.2 | 16, 33 | 100% killed |
| IDT [2] | 85, 86 | | 0.29 | | | (18 DAT) |
| IDT [3] | 87, 88 | | 0.29 | | | |
| IDT [4] | 89, 90 | | 0.29 | | | |
| IDT [1] | 83, 84, | 3 | 0.29 | 0.87 | 16, 36 | 100% killed |
| IDT [3] | 87, 88 | | 0.29 | | | (18 DAT) |
| IDT [4] | 89, 90 | | 0.29 | | | |
| IDT [1] | 83, 84, | 3 | 5.8 | 17 | 16, 36 | 100% killed |
| IDT [3] | 87, 88 | | 5.8 | | | (18 DAT) |
| IDT [4] | 89, 90 | | 5.8 | | | |
| IDT [1] | 83, 84, | 3 | 29 | 87 | 16, 36 | 100% killed |
| IDT [3] | 87, 88 | | 29 | | | (18 DAT) |
| IDT [4] | 89, 90 | | 29 | | | |
| IDT [1] | 83, 84, | 3 | 0.29 | 1.1 | 16, 36 | 100% killed |
| IDT [2] | 85, 86 | | 0.29 | | | (18 DAT) |
| IDT [3] | 87, 88 | | 0.29 | | | |
| IDT [4] | 89, 90 | | 0.29 | | | |
| 3'-OH [1] | 101, 102 | 3 | Not applicable | 22-26 microliters (by volume) | 16 | 100% killed (10 DAT) |
| 3'-OH [2] | 103, 104 | | | | | |
| 3'-OH [3] | 105, 106 | | | | | |
| 3'-OH [4] | 107, 108 | | | | | |
| IDT Blunt [1] | 93, 94 | 3 | 0.29 | 1.1 | 16 | 75% killed |
| IDT Blunt [2] | 95, 96 | | 0.29 | | | (10 DAT) |
| IDT Blunt [3] | 97, 98 | | 0.29 | | | |
| IDT Blunt [4] | 99, 100 | | 0.29 | | | |
| IDT Blunt [1] | 93, 94 | 3 | 5.8 | 23 | 16 | 100% killed |
| IDT Blunt [2] | 95, 96 | | 5.8 | | | (10 DAT) |
| IDT Blunt [3] | 97, 98 | | 5.8 | | | |
| IDT Blunt [4] | 99, 100 | | 5.8 | | | |
| IDT [1] | 83, 84, | 3 | 29 | 87 | 16 | 34% stunted |
| IDT [2] | 85, 86 | | 29 | | | (14 DAT) |
| IDT [3] | 87, 88 | | 29 | | | |
| IDT [2] | 85, 86 | 3 | 29 | 87 | 16 | 48% stunted |
| IDT [3] | 87, 88 | | 29 | | | (14 DAT) |
| IDT [4] | 89, 90 | | 29 | | | |
| IDT [1] | 83, 84, | 3 | 29 | 87 | 16 | 25% stunted |
| IDT [2] | 85, 86 | | 29 | | | (14 DAT) |
| IDT [4] | 89, 90 | | 29 | | | |
| IDT [1] | 83, 84, | 3 | 29 | 58 | 16 | 44% stunted |
| IDT [4] | 89, 90 | | 29 | | | (14 DAT) |

TABLE 13-continued

| Polynucleotides applied in combination | SEQ ID NO. | Protocol | Amount applied of each polynucleotide (g/acre) | Total polynucleotide applied (g/acre) | EPSPS copy number* | Results** |
|---|---|---|---|---|---|---|
| IDT [3] | 87, 88 | 3 | 29 | 58 | 16 | 41% stunted |
| IDT [4] | 89, 90 |   | 29 |   |   | (14 DAT) |
| IDT [2] | 85, 86 | 3 | 29 | 58 | 16 | 40% stunted |
| IDT [4] | 89, 90 |   | 29 |   |   | (14 DAT) |
| IDT [1] | 83, 84 | 3 | 29 | 29 | 16 | 51% stunted |
|   |   |   |   |   |   | (13 DAT) |
| IDT [2] | 85, 86 | 3 | 29 | 29 | 16 | 0% control |
|   |   |   |   |   |   | (13 DAT) |
| IDT [3] | 87, 88 | 3 | 29 | 29 | 16 | 51% stunted |
|   |   |   |   |   |   | (13 DAT) |
| IDT [4] | 89, 90 | 3 | 29 | 29 | 16 | 51% stunted |
|   |   |   |   |   |   | (13 DAT) |
| IDT [1] | 83, 84, | 3 | 29 | 116 | 16 | 75% killed |
| IDT [2] | 85, 86 |   | 29 |   |   | (13 DAT) |
| IDT [3] | 87, 88 |   | 29 |   |   |   |
| IDT [4] | 89, 90 |   | 29 |   |   |   |

*where more than one copy number is listed, the treated plants were a mixture of copy numbers
**DAT = days after treatment;
"0% control" means no difference between treated and control plants was observed;
stunting % is calculated as [100 − (average height of the test plants/average height of control plants) * 100]

Double-stranded 25-mer RNA polynucleotide sequences for suppression of the TIF gene in *Amaranthus palmeri* were designed as listed in Table 14.

TABLE 14

| Name | Sequence | SEQ ID NO: |
|---|---|---|
| TIF_dsRNA1 | antisense: 5'-UUUUCUAAUACCUCAUCCAAUGAAU-3' | 115 |
|   | sense: 5'-AUUCAUUGGAUGAGGUAUUAGAAAA-3' | 116 |
| TIF_dsRNA2 | antisense: 5'-UAUCUGCUUGUAAGUUCGCCGUUUC-3' | 117 |
|   | sense: 5'-GAAACGGCGAACUUACAAGCAGAUA-3' | 118 |
| TIF_dsRNA3 | antisense: 5'-GGAGACGGUUUAUUUACAUUUGUGC-3' | 119 |
|   | sense: 5'-GCACAAAUGUAAAUAAACCGUCUCC-3' | 120 |
| TIF_dsRNA4 | antisense: 5'-UAUUUACAGGUUUACCAUUGGUUGA-3' | 121 |
|   | sense: 5'-UCAACCAAUGGUAAACCUGUAAAUA-3' | 122 |

The TIF 25-mer dsRNA polynucleotides were tested on both high (112) copy and low (16) copy EPSPS glyphosate-resistant Palmer amaranth.

High-copy plants were treated with a mixture of 4 short EPSPS dsRNAs (short dsRNA-1, short dsRNA-3, short dsRNA-4, as described in Example 1 and IDT [5] (SEQ ID NOS:91-92 as described in Table 11) at 11.5 grams/acre and one individual TIF dsRNA at 5.8 grams/acre, or with each individual TIF 25-mer dsRNA at 5.8 grams/acre; polynucleotide solutions were formulated in 10 millimolar sodium phosphate buffer (pH 6.8) containing 2% ammonium sulfate and 1% SILWET L-77® brand surfactant. Thirty minutes after polynucleotide treatment, plants were either sprayed with glyphosate (1682 g acid equivalent per hectare of Roundup® WeatherMAX® brand herbicide) or not.

Low-copy plants were treated with a mixture of 4 short EPSPS dsRNAs (short dsRNA-1, short dsRNA-3, short dsRNA-4, as described in Example 1, and IDT [5] (SEQ ID NOS:91-92 as described in Table 11)) at 0.23 grams/acre and one individual TIF dsRNA at 5.8 grams/acre, or with each individual TIF 25-mer dsRNA at 5.8 grams/acre; polynucleotide solutions were formulated in 10 millimolar sodium phosphate buffer (pH 6.8) containing 2% ammonium sulfate and 1% SILWET L-77® brand surfactant. Thirty minutes after polynucleotide treatment, plants were either sprayed with glyphosate (1682 g acid equivalent per hectare of Roundup® WeatherMAX® brand herbicide) or not.

Figure 31:
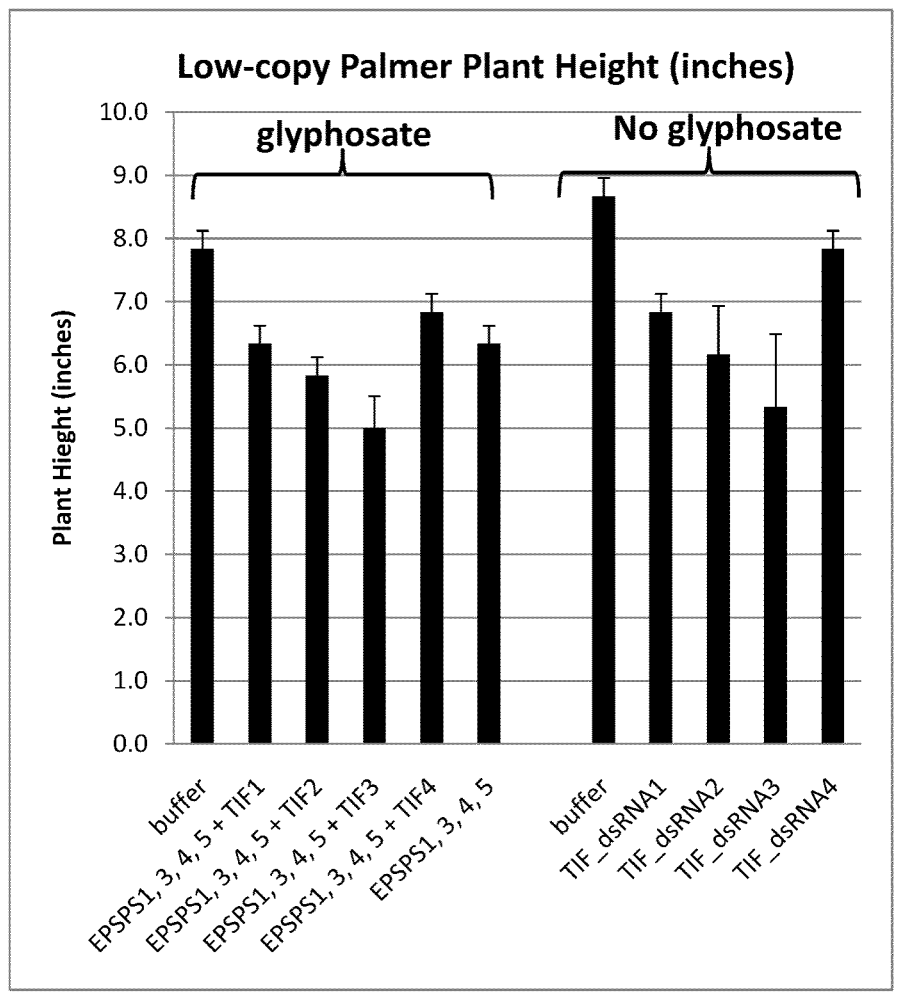
FIG. 31 illustrates enhancement of glyphosate herbicidal activity in low-copy number Palmer amaranth of the EPSPS polynucleotides by TIF polynucleotides and that the TIF polynucleotides have herbicidal activity on their own, as described in Example 26. EPSPS polynucleotides "1, 3, 4" refer to "short" dsRNAs having an anti-sense strand that is capable of hybridizing to the mRNA transcribed from the Palmer amaranth EPSPS gene (SEQ ID NO:1) at positions 14-38 (short dsRNA-1), 345-369 (short dsRNA-3), and 1105-1129 (short dsRNA-4), respectively as indicated by underlined nucleotides in FIG. 1 (see Example 1). EPSPS "5" refers to IDT [5] (SEQ ID NOS:91-92 as described in Table 11).
Figure 32:
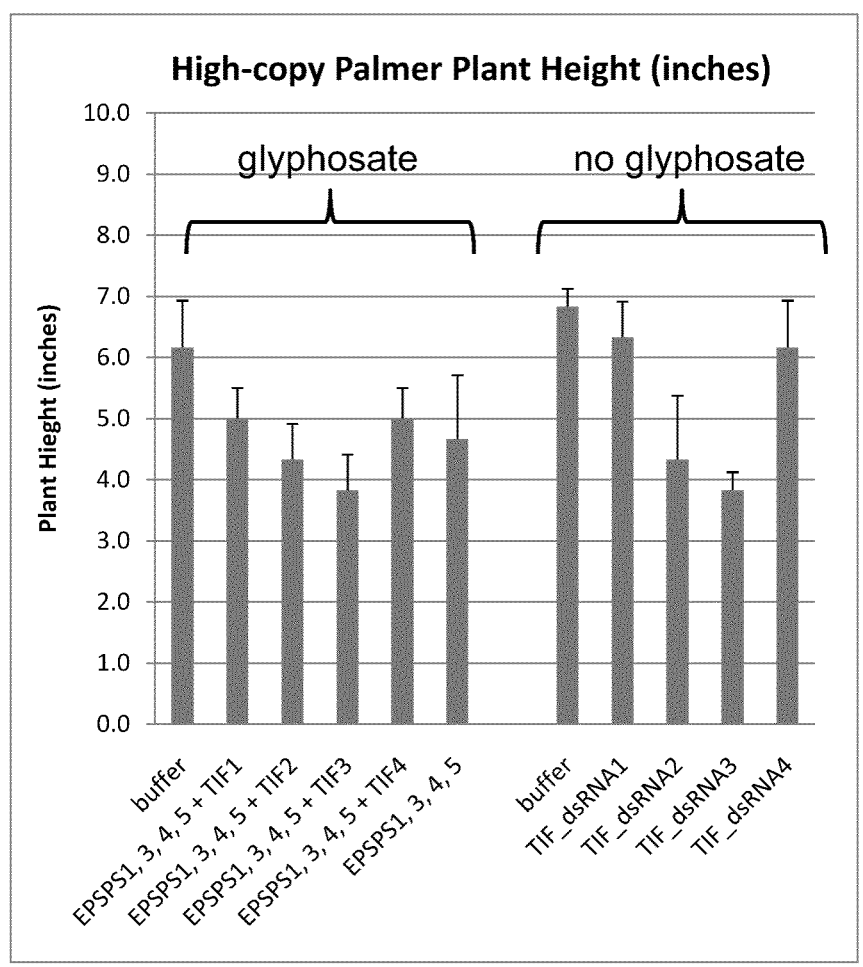
FIG. 32 illustrates enhancement of glyphosate herbicidal activity in high-copy number Palmer amaranth of the EPSPS polynucleotides by TIF polynucleotides and that the TIF polynucleotides have herbicidal activity on their own, as described in Example 26. EPSPS polynucleotides "1, 3, 4" refer to "short" dsRNAs having an anti-sense strand that is capable of hybridizing to the mRNA transcribed from the Palmer amaranth EPSPS gene (SEQ ID NO:1) at positions 14-38 (short dsRNA-1), 345-369 (short dsRNA-3), and 1105-1129 (short dsRNA-4), respectively as indicated by underlined nucleotides in FIG. 1 (see Example 1). EPSPS "5" refers to IDT [5] (SEQ ID NOS:91-92 as described in Table 11).

Results are depicted in FIGS. 31 and 32 and show that the TIF polynucleotides enhance the activity of the EPSPS polynucleotides and that the TIF polynucleotides have herbicidal activity on their own.

Example 27

Aspects of the invention include polynucleotide compositions and methods of use for potentiating the activity of a non-polynucleotide herbicide in a plant. For example, a polynucleotide composition designed to regulate an herbicide target gene, or an herbicide deactivation gene, or a stress response gene, or a combination of such target genes, is applied to a weed or to a volunteer plant, concurrently or followed or preceded by application of a non-polynucleotide herbicide (typically a conventional chemical herbicide), resulting in potentiation of the activity of the non-polynucleotide herbicide. The combination of a polynucleotide composition with a non-polynucleotide herbicide (e.g., a conventional chemical herbicide) provides a synergistic effect, i.e., the herbicidal effect of the combination is greater than the sum of the herbicidal effect of the polynucleotide composition and the herbicidal effect of the non-polynucleotide herbicide.

Examples of conventional chemical herbicides and their corresponding herbicide target genes are provided in Table 15.

TABLE 15

| Herbicide examples | Target gene (herbicide target gene) |
|---|---|
| glyphosate | 5-enolpyruvylshikimate-3-phosphate synthase (EPSPS) |
| Lactofen, flumioxazin, etc | protoporphyrinogen oxidase (PPO) |
| Mesotrione, isoxaflutole | 4-hydroxyphenyl-pyruvate-dioxygenase (HPPD) |
| Quizalofop, clethodim | acetyl coenzyme A carboxylase (ACCase) |
| Norflurazone, clomazone | phytoene desaturase (PDS) |
| glufosinate | glutamine synthase (GS) |
| Rimsulfuron, chlorsulfuron | acetolactate synthase (ALS) |
| Atrazine, diuron, bromoxynil, metribuzin | D1 protein of photosystem II (PSII) |
| Dinitroaniline, pendimethalin | tubulin |
| Dichlobenil, isoxaben | Cellulose synthase |

Examples of conventional chemical herbicides and their corresponding herbicide deactivation genes are provided in Table 16.

TABLE 16

| Herbicide examples | Target gene (herbicide deactivation gene) |
|---|---|
| Acetochlor, metolachlor | glutathione S-transferase (GST) |
| Many including SU herbicides | Mono-oxygenases including cytochromes P450 (see, e.g., a cytochrome P450 for conferring resistance to HPPD inhibitors, benzothia-diazinones, sulfonylureas, and other classes of herbicides, described in U.S. patent application publication 2009/0011936) |
| Thiazopyr | esterases (e.g., esterases involved in apoptosis or senescence) |

TABLE 16-continued

| Herbicide examples | Target gene (herbicide deactivation gene) |
|---|---|
| 2,4-D, metribuzin, Glyphosate, paraquat | glucosyl transferases; malonyl transferases Cellular compartmentation and sequestration genes (e.g., ABC transporters) |

Example 28

This example illustrates a method for inducing systemic regulation of a target endogenous gene in a growing plant including topically coating onto leaves of the growing plant polynucleotides having sequence essentially identical to, or essentially complementary to, a sequence of 18 or more contiguous nucleotides in either the target endogenous gene or messenger RNA transcribed from the target endogenous gene, whereby the polynucleotides permeate the interior of the growing plant and induce systemic regulation of the target endogenous gene.

Double-stranded RNA or anti-sense ssDNA polynucleotides were designed for the herbicide targeted genes 5-enolpyruvylshikimate-3-phosphate synthase (EPSPS), phytoene desaturase (PDS), protoporphyrin IX oxygenase (PPO), phenylalanine ammonia lyase (PAL), hydroxyphenylpyruvate dioxygenase (HPPD), acetyl-coenzyme A carboxylase (ACCase), acetolactate synthase (ALS), and glutamine synthase (GS). For each herbicide targeted gene, a solution containing a mixture of 8 anti-sense ssDNA polynucleotides in 2% ammonium sulfate in 10 millimolar sodium phosphate buffer, pH 6.8, was applied at a rate of 2.32 g/acre following application of 0.5% SILWET L-77® brand surfactant spray (10 gallons/acre). The tested polynucleotides and resulting phenotype observations are listed in Table 17.

TABLE 17

| Gene | Name | Size (nt) | Sequence | SEQ ID NO: | Phenotype |
|---|---|---|---|---|---|
| EPSPS | | | (See sequences provided in working Examples 1, 9, 13, 14, 21, 26) | — | Topical dsRNA followed by glyphosate killed glyphosate-resistant Palmer (up to 60 copies of EPSPS) within 7-10 days |
| PDS | PDS sense | 185 | GACGGAAACCCUCCAGAGAGGCUGU GCAUGCCUAUUGUUAAACACAUCGA GUCACUAGGUGGUGAAGUUAAACUU AACUCUCGUAUACAAAAGAUUCAGU UGGACCAGAGUGGAAGCGUGAAGAG UUUUUUGCUAAAUAACGGGAGGGAA AUACGAGGAGAUGCCUAUGUUUUUG CCACCCCAGU | 123 | Topical dsRNA caused bleaching and stunting phenotype, and is systemic. |
| | PDS anti-sense | 185 | ACUGGGGUGGCAAAAACAUAGGCAU CUCCUCGUAUUUCCCUCCCGUUAUUU AGCAAAAAACUCUUCACGCUUCCAC UCUGGUCCAACUGAAUCUUUUGUAU ACGAGAGUUAAGUUUAACUUCACCA CCUAGUGACUCGAUGUGUUUAACAA UAGGCAUGCACAGCCUCUCUGGAGG GUUUCCGUC | 124 | |
| PPO | PPO_OLIGO1 | 21 | GTGATATTACCTCCAACACGAT | 125 | Topical anti-sense DNAs caused stunting of plant growth. |
| | PPO_OLIGO2 | 21 | ATAGTAAGCACAGGATCGGAG | 126 | |
| | PPO_OLIGO3 | 21 | CTTTCAATCCACTGTCAACCG | 127 | |
| | PPO_OLIGO4 | 21 | ATCAAGCGTTCGAAGACCTCAT | 128 | |
| | PPO_OLIGO5 | 21 | CAGCAATGGCGGTAGGTAACA | 129 | |
| | PPO_OLIGO6 | 21 | GCAATTGCCCGAATCCTTTTA | 130 | |
| | PPO_OLIGO7 | 21 | TAGCTCAATATCAAGGTCCTA | 131 | |
| | PPO_OLIGO8 | 21 | TCATAAGCACCCTCTATACAC | 132 | |

TABLE 17-continued

| Gene | Name | Size (nt) | Sequence | SEQ ID NO: | Phenotype |
|---|---|---|---|---|---|
| PAL | PAL_OLIGO1 | 21 | TTCTTAACCTCGTCGAGATG | 133 | Topical anti-sense |
|  | PAL_OLIGO2 | 21 | ATACCCGAGTATCCTTGCAAA | 134 | DNAs caused |
|  | PAL_OLIGO3 | 21 | TAGGGCCCACGGCCTTGGAGT | 135 | stunting of plant |
|  | PAL_OLIGO4 | 21 | AGCGGATATAACCTCAGCTAG | 136 | growth. |
|  | PAL_OLIGO5 | 21 | CTTCGTGGCCCAACGAATGAC | 137 | |
|  | PAL_OLIGO6 | 21 | CAAGCTCGGGTCCCTGCTTGC | 138 | |
|  | PAL_OLIGO7 | 21 | GGAAGGTAGATGACATGAGTT | 139 | |
|  | PAL_OLIGO8 | 21 | GATGGCATAGTTACCACTGTC | 140 | |
| HPPD | HPPD_OLIGO1 | 21 | TCCGTAGCTTACATACCGAAG | 141 | Topical anti-sense |
|  | HPPD_OLIGO2 | 21 | TCCAAGTGAATAGGAGAAACA | 142 | DNAs caused |
|  | HPPD_OLIGO3 | 21 | AGCAGCTTCTGCGTCTTCTAC | 143 | stunting of plant |
|  | HPPD_OLIGO4 | 21 | ACAGCACGCACGCCAAGACCG | 144 | growth. |
|  | HPPD_OLIGO5 | 21 | CGATGTAAGGAATTTGGTAAA | 145 | |
|  | HPPD_OLIGO6 | 21 | CGAGGGGATTGCAGCAGAAGA | 146 | |
|  | HPPD_OLIGO7 | 21 | GTAGGAGAATACGGTGAAGTA | 147 | |
|  | HPPD_OLIGO8 | 21 | GACCCCAAGAAAATCGTCTGC | 148 | |
| ACCase | ACCA_OLIGO1 | 20 | GTCTTACAAGGGTTCTCAA | 149 | Topical anti-sense |
|  | ACCA_OLIGO2 | 21 | ATCTATGTTCACCTCCCTGTG | 150 | DNA caused |
|  | ACCA_OLIGO3 | 21 | ATAAACCATTAGCTTTCCCGG | 151 | stunting of plant |
|  | ACCA_OLIGO4 | 21 | TTTATTGGAACAAGCGGAGTT | 152 | growth. |
|  | ACCA_OLIGO5 | 21 | TATAGCACCACTTCCCGATAG | 153 | |
|  | ACCA_OLIGO6 | 21 | GCACCACGAGGATCACAAGAA | 154 | |
|  | ACCA_OLIGO7 | 21 | CCACCCGAGAAACCTCTCCAA | 155 | |
|  | ACCA_OLIGO8 | 21 | CAGTCTTGACGAGTGATTCCT | 156 | |
| ALS | ALS-OLIGO1 | 22 | GTTCTTCAGGGCTAAATCGGGA | 157 | No significant |
|  | ALS-OLIGO2 | 22 | GTTCAAGAGCTTCAACGAGAAC | 158 | phenotype |
|  | ALS-OLIGO3 | 22 | ATACAAACTCCAACGCGTCCAG | 159 | |
|  | ALS-OLIGO4 | 22 | CTCTTGGAAAGCATCAGTACCA | 160 | |
|  | ALS-OLIGO5 | 22 | CTAGAAAGATACCCACCCAATT | 161 | |
|  | ALS-OLIGO6 | 22 | ACTAGAATTCAAACACCCACCC | 162 | |
|  | ALS-OLIGO7 | 22 | TTTCTGCTCATTCAACTCCTCC | 163 | |
|  | ALS-OLIGO8 | 22 | TATGTATGTGCCCGGTTAGCTT | 164 | |
| GS (gluta-mine synthase) | GS_OLIGO1 | 21 | TCATATCCAAGCCAGATCCTC | 165 | No significant |
|  | GS_OLIGO2 | 21 | TGCATCACACATCACCAAGAT | 166 | phenotype |
|  | GS_OLIGO3 | 21 | GTACTCCTGTTCAATGCCATA | 167 | |
|  | GS_OLIGO4 | 21 | ATTGATACCAGCATAGAGACA | 168 | |
|  | GS_OLIGO5 | 21 | AGCAATTCTCTCTAGAATGTA | 169 | |
|  | GS_OLIGO6 | 21 | CATCATTCCTCATCGACTTAG | 170 | |
|  | GS_OLIGO7 | 21 | CTCTCGTTGCCCTCTCCATAA | 171 | |
|  | GS_OLIGO8 | 21 | CAACGCCCCAGGAGAAAGTTC | 172 | |

The herbicidal activity of ssDNA polynucleotides that target the enzymes 4-hydroxyphenylpyruvate (HPPD) and protoporphyrinogen oxidase (PPO), and a transcription initiation factor (TIF), and their effect on the herbicide activity when used in combination with the herbicides mesotrione, fomesafen, and atrazine in Palmer amaranth was investigated. The polynucleotides used in this experiment were 8 HPPD anti-sense ssDNA oligonucleotides (SEQ ID NOS:141-148), 8 PPO anti-sense oligonucleotides (SEQ ID NOS:125-132), and 8 TIF anti-sense ssDNA oligonucleotides (SEQ ID NOS: 75-82, see Example 26).

Glyphosate-sensitive Palmer amaranth (*Amaranthus palmeri*) plants were grown in 4-inch square pots with Sun Gro® Redi-Earth seedling mix containing 3.5 kg/cubic meter Osmocote® 14-14-14 fertilizer in a greenhouse with 14 h photoperiod and a daytime temperature of 30 degrees Celsius and night temperature of 20 degrees Celsius. The plants were sub-irrigated as necessary.

Plants at 10 to 15 cm height were pre-treated manually with 40 microliters (4 fully expanded mature leaves were treated with 10 microliters of solution per leaf on each plant) of a buffer-surfactant solution (as a control; 0.5% SILWET L-77® brand surfactant and 2% ammonium sulfate), or a buffer-surfactant-ssDNA polynucleotide mixture of the anti-sense oligonucleotides targeting HPPD, PPO, or TIF. Some plants were left untreated and were used as controls. Twenty-four hours later, untreated plants, buffer-surfactant treated plants, and buffer-surfactant-ssDNA treated plants were treated using a track-sprayer equipped with a 9501E nozzle and calibrated to deliver 93 liters of solution per hectare with a HPPD inhibitor, mesotrione (4 pounds active ingredient per gallon;), or with a PPO inhibitor, fomesafen (2 pounds active ingredient per gallon), or with a Photosystem II inhibitor, atrazine (90% active ingredient) as indicated in Table 18. Crop oil concentrate (COC) at 1% was added to all herbicide treatments. A low rate of each herbicide (mesotrione: 13 g per acre, equivalent to ⅛× of the recommended field rate; fomesafen: 16 g per acre, equivalent to 1/22× of the recommended field rate; and atrazine: 170 g per acre, equivalent to ⅛× of the recommended field rate,) was used to be able to detect any improvement of herbicide activity by the oligonucleotide mixture.

TABLE 18

| Treatment number | Pre-treatment | Active Ingredient | Rate (grams per hectare of active ingredient) |
|---|---|---|---|
| 0 | Buffer-surfactant | — | |
| 1 | Untreated | Mesotrione | 13 |
| 2 | Buffer-surfactant | Mesotrione | 13 |
| 3 | Buffer-surfactant-ssDNA-HPPD | | |
| 4 | Buffer-surfactant-ssDNA-HPPD | Mesotrione | 13 |
| 5 | Untreated | Fomesafen | 16 |
| 6 | Buffer-surfactant | Fomesafen | 16 |
| 7 | Buffer-surfactant-ssDNA-PPO | | |
| 8 | Buffer-surfactant-ssDNA-PPO | Fomesafen | 16 |
| 9 | Untreated | Atrazine | 170 |
| 10 | Buffer-surfactant-ssDNA-TIF | | |
| 11 | Buffer-surfactant-ssDNA-TIF | Atrazine | 170 |

Figure 33:
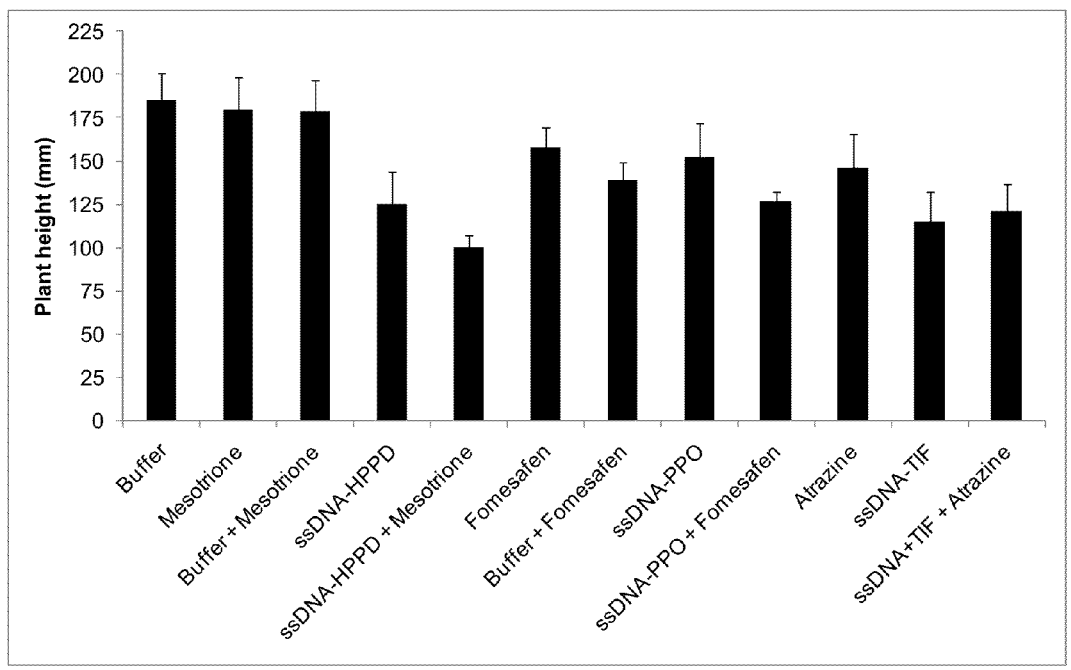
FIG. 33 illustrates the herbicidal effect on Palmer amaranth after treatment with the indicated combinations of non-polynucleotide herbicides and polynucleotides, as described in Example 28.

Plant height was determined at four days after herbicide treatment. Data were collected from one experiment with four replications per treatment. Results (expressed as Palmer amaranth plant height as affected by the buffer-surfactant solution, ssDNA, and herbicide treatment combinations) are presented in Table 19 and FIG. 33. Plants treated with HPPD anti-sense ssDNA oligonucleotides, PPO anti-sense ssDNA oligonucleotides, and TIF anti-sense ssDNA oligonucleotides showed growth stunting, measuring 125, 153, and 115 mm, respectively, while the plants treated with buffer-surfactant (control) measured 185 mm (FIG. 33). Treatment with HPPD anti-sense ssDNA oligonucleotides, PPO anti-sense ssDNA oligonucleotides, and TIF anti-sense ssDNA oligonucleotides respectively caused a 32%, 18%, and 38% growth reduction relative to the buffer-surfactant control.

No major differences in plant height were observed between plants treated with buffer-surfactant followed by herbicide, and plants treated with herbicide only. The plants treated with HPPD anti-sense ssDNA oligonucleotides followed by mesotrione showed the greatest reduction in plant growth, measuring 100 mm, a 46% reduction compared to the buffer-surfactant treated plants. The plants treated with PPO anti-sense ssDNA oligonucleotides followed by fomesafen measured 126 mm, a 32% reduction compared to the buffer-surfactant treated plants. The plants treated with TIF anti-sense ssDNA oligonucleotides followed by atrazine measured 121 mm, a 34% reduction compared to the buffer-surfactant treated plants.

TABLE 19

| Treatment number | Pre-treatment | Active Ingredient | Rate (grams per hectare of active ingredient) | Plant height (mm) | Standard Error |
|---|---|---|---|---|---|
| 0 | Buffer | — | — | 185 | 15 |
| 1 | Untreated | Mesotrione | 13 | 180 | 18 |
| 2 | Buffer | Mesotrione | 13 | 179 | 18 |
| 3 | ssDNA-HPPD | | | 125 | 19 |
| 4 | ssDNA-HPPD | Mesotrione | 13 | 100 | 7 |
| 5 | Untreated | Fomesafen | 23 | 158 | 12 |
| 6 | Buffer | Fomesafen | 23 | 139 | 10 |
| 7 | ssDNA-PPO | | | 153 | 20 |
| 8 | ssDNA-PPO | Fomesafen | 23 | 126 | 6 |
| 9 | Untreated | Atrazine | 170 | 146 | 19 |
| 10 | ssDNA-TIF | | | 115 | 17 |
| 11 | ssDNA-TIF | Atrazine | 170 | 121 | 16 |

Example 29

This example illustrates tested sequences of double-stranded RNA polynucleotides designed for different essential genes to ascertain the effect of the tested sequence on observable phenotype. For each essential gene, a solution containing the dsRNA polynucleotide in 2% ammonium sulfate in 10 millimolar sodium phosphate buffer, pH 6.8, was applied to Palmer amaranth at a rate of 240 picomole per plant following application of 0.5% SILWET L-77® brand surfactant spray (10 gallons/acre). The tested polynucleotides and resulting phenotype observations are listed in Table 20.

TABLE 20

| Gene | Name | Size (nt) | Sequence | SEQ ID NO: | Phenotype |
|---|---|---|---|---|---|
| Translation initiation factor (TIF) | sense | 160 | UUCGAGUAAUGGGAAAUUGGAUAAUGUA GAGGAGAGGAAGAAGGUUAUUGAUUCAU UGGAUGAGGUAUUAGAAAAGGCCGAGAG AUUAGAAACGGCGAACUUACAAGCAGAU AAUAGAAAGGAUAGCACAAAUGUAAAUA AACCGUCUCCGAGUGUAAGU | 73 | Topical dsRNA caused stunting of plant growth. |
| | anti-sense | 160 | ACUUACACUCGGAGACGGUUUAUUUACA UUUGUGCUAUCCUUUCUAUUAUCUGCUU GUAAGUUCGCCGUUUCUAAUCUCUCGGCC UUUUCUAAUACCUCAUCCAAUGAAUCAA UAACCUUCUUCCUCUCCUCUACAUUAUCC AAUUUCCCAUUACUCGAA | 74 | |
| DNA-dependent ATPase (ddATPase) | sense | 168 | GAUCACAAAUUUGCCGGUUUAUGAUCAA AUACGGAACAUAAGACAGAUACACUUGA ACACCAUGAUUCGCAUUGGGGGUGUGGU UACUCGUCGUUCUGGAGUAUUCCCUCAGU UGAUGCAGGUGAAGUAUGACUGCAAUAA AUGUGGGGCUAUCCUGGGUCCCUUUUU | 113 | Topical dsRNA caused stunting of plant growth. |

TABLE 20-continued

| Gene | Name | Size (nt) | Sequence | SEQ ID NO: | Phenotype |
|---|---|---|---|---|---|
| | anti-sense | 168 | AAAAAGGGACCCAGGAUAGCCCCACAUUU AUUGCAGUCAUACUUCACCUGCAUCAACU GAGGGAAUACUCCAGAACGACGAGUAAC CACACCCCCAAUGCGAAUCAUGGUGUUCA AGUGUAUCUGUCUUAUGUUCCGUAUUUG AUCAUAAACCGGCAAAUUUGUGAUC | 114 | |
| Hydroxy-3-Methylbut-2-enyl diphophate synthase (HMEDS) | sense | 200 | CUGAAGCUGGUGAAGGUGAAGAUGGACG AAUGAAAUCUGCGAUUGGAAUUGGGACC CUUCUUCAGGAUGGCUUGGGAGAUACGA UCAGGGUGUCUCUAACGAACCACCAGAA GAGGAGAUAGACCCUUGCAGAAGGUUGG CAAAUCUUGGAACAAAAGCAGCUGAAAU UCAGCAAGGAGUGGCACCAUUUGAAG | 173 | No significant phenotype. |
| | anti-sense | 200 | CUUCAAAUGGUGCCACUCCUUGCUGAUU UCAGCUGCUUUUGUUCCAAGAUUUGCCA ACCUUCUGCAAGGGUCUAUCUCCUCUUCU GGUGGUUCUGUUAGAGACACCCUGAUCG UAUCUCCCAAGCCAUCCUGAAGAAGGGUC CCAAUUCCAAUCGCAGAUUUCAUUCGUCC AUCUUCACCUUCACCAGCUUCAG | 174 | |
| Fertilization independent endosperm/ TF (FIE) | sense | 183 | UCCCAUCAAAGUUCCCUACAAAAUAUGUG CAGUUUCCUAUCUUCCUUGCCGCCAUUCA UACAAACUAUGUUGAUUGUACAAGGUGG CUUGGUGAUUUUGUUCUUUCUAAGAGUG UUGGACAAUGAGAUUGUACUGUGGGAGCC AAUUAUGAAGGAGCAAUCUCCUGGAGAG GGUUCAGUUGACA | 175 | No significant phenotype. |
| | anti-sense | 183 | UGUCAACUGAACCCUCUCCAGGAGAUUGC UCCUUCAUAAUUGGCUCCCACAGUACAAU CUCAUUGUCAACACUCUUAGAAAGAACA AAAUCACCAAGCCACCUUGUACAAUCAAC AUAGUUUGUAUGAAUGGCGGCAAGGAAG AUAGGAAACUGCACAUAUUUUGUAGGGA ACUUUGAUGGGA | 176 | |
| 26S proteasome ATPase subunit RPT5B (RPTB) | sense | 143 | UUGUGCUUAAAACAUCGACCAGACAGAC AAUAUUUCUUCCUGUUGUUGGACUAGUU GAUCCUGAUACGCUGAAACCUGGUGAUU UAGUUGGUGUCAACAAAGAUAGUUAUCU UAUCCUGGACACUCUGCCGUCGGAAUAUG AU | 177 | No significant phenotype. |
| | anti-sense | 143 | AUCAUAUUCCGACGGCAGAGUGUCCAGG AUAAGAUAACUAUCUUUGUUGACACCAA CUAAAUCACCAGGUUUCAGCGUAUCAGG AUCAACUAGUCCAACAACAGGAAGAAAU AUUGUCUGUCUGGUCGAUGUUUUAAGCA CAA | 178 | |
| ligase 1 (LIG1) | sense | 159 | CGCUGCAGUUGGUGAAGUAGAUCCCGGC AAGGGGAUUUCACUCCGGUUUCCACGUCU GGUUCGUAUCCGAGAGGAUAAAUCUCCA GAGGACGCCACAUCAUCUGAGCAGGUGGC GGAUAUGUACAGAUCUCAAGCAAACAAU CCACACCGCAAAAAGAG | 179 | No significant phenotype. |
| | anti-sense | 159 | CUCUUUUUGCGGUGUGGAUUGUUUGCUU GAGAUCUGUACAUAUCCGCCACCUGCUCA GAUGAUGUGGCGUCCUCUGGAGAUUUAU CCUCUCGGAUACGAACCAGACGUGGAAAC CGGAGUGAAAUCCCCUUGCCGGGAUCUAC UUCACCAACUGCAGCG | 180 | |
| tRNA synthetase (tS) | sense | 159 | UAAAGAUGGCGGAAAAAUCGACUAUGAU AAAUUGAUUGACAAAUUCGGCUGUCAGC GACUUGAUUUAUCGCUCAUUCAGAGAAU UGAGCGCAUCACUGCUCGUCCUGCUCAUG UAUUCUUCGCCGCAACGUUUUCUUCGCU CACCGUGAUUUGAAUGA | 181 | No significant phenotype. |
| | anti-sense | 159 | UCAUUCAAAUCACGGUGAGCGAAGAAAA CGUUGCGGCGAAGAAAAUACAUGAGCAGG ACGAGCAGUGAUGCGCUCAAUUCUCUGA AUGAGCGAUAAAUCAAGUCCUGACAGC CGAAUUUGUCAAUCAAUUUAUCAUAGUC GAUUUUUCCGCCAUCUUUA | 182 | |

TABLE 20-continued

| Gene | Name | Size (nt) | Sequence | SEQ ID NO: | Phenotype |
|---|---|---|---|---|---|
| Ubiquitin specific protease 14 (UBP) | sense | 150 | UGAAGCUGAUGCUGAAGGAAAGGAUAUU GAUGCUAGUGAAGUAGUUCGCCCAAGGG UGCCAUUAGAAGCUUGCCUAGCUAGCUAC UCAGCUCCGGAGGAGGUGAUGGACUUCU ACAGCACUGCAUUGAAGGCAAAGGCAAC UGCUACAAA | 183 | No significant phenotype. |
| | anti-sense | 150 | UUUGUAGCAGUUGCCUUUGCCUUCAAUG CAGUGCUGUAGAAGUCCAUCACCUCCUCC GGAGCUGAGUAGCUAGGCAAGCUU CUAAUGGCACCCUUGGGCGAACUACUUCA CUAGCAUCAAUAUCCUUUCCUUCAGCAUC AGCUUCA | 184 | |
| Serine hydroxy-methiy-transferase 2 (SHMT) | sense | 155 | ACACCUGCCCUAACAUCUCGGGGUUUUCU CGAAGAAGAUUUUGUUAAAGUGGCCGAG UAUUUUGAUGCUGCUGUUAAGCUGGCUC UAAAAAUCAAGGCUGACACAAAAGGAAC AAAGUUGAAGGACUUCGUUGCCACCUUG CAGUCUGGUGUUUU | 185 | No significant phenotype. |
| | anti-sense | 155 | AAAACACCAGACUGCAAGGUGGCAACGA AGUCCUUCAACUUUGUUCCUUUUGUGUC AGCCUUGAUUUUUAGAGCCAGCUUAACA GCAGCAUCAAAAUACUCGGCCACUUUAAC AAAAUCUUCUUCGAGAAAACCCCGAGAU GUUAGGGCAGGUGU | 186 | |
| Methionine-tRNA ligase/synthase (MtS) | sense | 159 | UGAACUACGAAGCAGGCAAAUUCUCCAA AAGUAAAGGCAUUGGAGUUUUUGGGAAU GACGCCAAGAAUUCUAAUAUACCUGUAG AAGUGUGGAGAUACUAUCUGCUAACAAA CAGGCCUGAGGUAUCAGACACAUUGUUC ACUUGGGCGGAUCUUCAAG | 187 | No significant phenotype. |
| | anti-sense | 159 | CUUGAAGAUCCGCCCAAGUGAACAAUGU GUCUGAUACCUCAGGCCUGUUUGUUAGC AGAUAGUAUCUCCACACUUCUACAGGUA UAUUAGAAUUCUUGGCGUCAUUCCCAAA AACUCCAAUGCCUUUACUUUUGGAGAAU UUGCCUGCUUCGUAGUUCA | 188 | |

Example 30

This example illustrates polynucleotides which are designed to target a particular low sequence homology region and are useful e.g., for selecting a specific allele of a target gene or a gene of a specific species. Polynucleotides designed to target non-coding sequence are useful in regulating non-coding RNAs that are involved in gene regulations, e.g., regulating non-coding RNAs that are processed to siRNAs in an RNAi-regulated pathway. FIG. 34 depicts an alignment of the Nicotiana benthamiana PDS locus 1 promoter (SEQ ID NO:319) and PDS locus 2 promoter (SEQ ID NO:320); in the case of locus 1 which contains multiple transcription start sites, the promoter sequence used in this alignment is the one with the most 5' transcription start site. The Nicotiana benthamiana PDS 1 and PDS2 genes were found to have low sequence homology in the promoter region but high sequence homology in the coding region.

Polynucleotides designed to target different parts of the PDS1 and PDS2 promoters are listed in Table 21.

TABLE 21

| Mix | Polynucleotide | promoter target | Sequence | SEQ ID NO. | position/dir |
|---|---|---|---|---|---|
| 2 | HL419 | PDS promoter 1 motif target | TCCCATCTCCCACATGGGTTACTG | 189 | 590-567 |
| 2 | HL420 | PDS promoter 1 motif target | CAGTAACCCATGTGGGAGATGGGA | 190 | 567-590 |
| 2 | HL421 | PDS promoter 1 motif target | GGCTGATGAAATTCAAGTGCTA | 191 | 557-536 |
| 2 | HL422 | PDS promoter 1 motif target | AAACTGAGCTTGGAAATAATC | 192 | 517-497 |
| 2 | HL423 | PDS promoter 1 motif target | GAACCCAAAATTGTCACTTTTT | 193 | 448-427 |

TABLE 21-continued

| Mix | Poly-nucleo-tide | promoter target | Sequence | SEQ ID NO. | position/dir |
|---|---|---|---|---|---|
| 3 | HL424 | PDS promoter 1 motif target | ATGCACTTGTTTATACTCTTGTCA | 194 | 403-438 |
| 3 | HL425 | PDS promoter 1 motif target | ATTTATTAGTGTTCTAAAGAA | 195 | 357-337 |
| 3 | HL426 | PDS promoter 1 motif target | TGTAGTAGCTTATAAGATTAGCTT | 196 | 287-264 |
| 3 | HL427 | PDS promoter 1 motif target | GTTGTCCCTTTTATGGGTCTTT | 197 | 240-183 |
| 3 | HL428 | PDS promoter 1 motif target | CCCGTGCAATTTCTGGGAAGC | 198 | 86-66 |
| 5 | HL429 | PDS promoter 2motif target | ATTAGTTTTTTATACACGAAAGAT | 199 | 1313-1336 |
| 5 | HL430 | PDS promoter 2motif target | ATCTTTCGTGTATAAAAACTAAT | 200 | 1336-1313 |
| 5 | HL431 | PDS promoter 2motif target | TTGGTGGTTTGGCCACTTCCGT | 201 | 1291-1270 |
| 5 | HL432 | PDS promoter 2motif target | TTTGTTTGCTATTTAGCTGGA | 202 | 1256-1236 |
| 5 | HL433 | PDS promoter 2motif target | CAATTTGCAGCAACTCGCACTGGA | 203 | 1205-1182 |
| 6 | HL434 | PDS promoter 2motif target | TCCCACCATTGGCTATTCCGAC | 204 | 1156-1135 |
| 6 | HL435 | PDS promoter 2motif target | CTGTCTCTCTTTTTAATTTCT | 205 | 1105-1085 |
| 6 | HL436 | PDS promoter 2motif target | CCACTTTGCACACATCTCCCACTT | 206 | 1056-1033 |
| 6 | HL437 | PDS promoter 2motif target | GAGGATCCACGTATAGTAGTAG | 207 | 1016-995 |
| 6 | HL438 | PDS promoter 2motif target | TTTAAATAAAGAAATTATTTA | 208 | 889-869 |
| 1 | HL439 | PDS promoter1 | TAATACGACTCACTATAGGGCTTGAGTTTATAACGAAGCT | 209 | |
| 1 | HL440 | PDS promoter1 | TAATACGACTCACTATAGGGCTTCTAATTTTCAAGGACG | 210 | |
| 1 | HL441 | PDS promoter1 | AGCTTCTAATTTTCAAGGACGATA | 211 | Antisense |
| 1 | HL442 | PDS promoter1 | GTCATGTGACTCCACTTTGATTTTG | 212 | Antisense |
| 1 | HL443 | PDS promoter1 | CTCAATTCCGATAAATTTAAGAAAT | 213 | Antisense |
| 1 | HL444 | PDS promoter1 | CGAAGCTATTGGACCGACCTAATTTC | 214 | Sense |
| 1 | HL445 | PDS promoter1 | GGAATTGAGGGCTTCCCAGAAATTGC | 215 | Sense |
| 1 | HL446 | PDS promoter1 | ATGACTTTTTGATTGGTGAAACTAA | 216 | Sense |
| 4 | HL447 | PDS promoter2 | TAATACGACTCACTATAGGTGGAACTCCAACACACAAAAAATTTC | 217 | Sense |
| 4 | HL448 | PDS promoter2 | TAATACGACTCACTATAGGTTGAAAAATAATCATAATTTTA | 218 | Antisense |
| 4 | HL449 | PDS promoter2 | GCATAATATATTGATCCGGTAT | 219 | Antisense |
| 4 | HL450 | PDS promoter2 | CTGAAAGTTCATACATAGGTACTC | 220 | Antisense |
| 4 | HL451 | PDS promoter2 | GGTACTCCAATTTTCAGTATAT | 221 | Antisense |
| 4 | HL452 | PDS promoter2 | CTGAAAATTGGAGTACCTATGTAT | 222 | Sense |

TABLE 21-continued

| Mix | Polynucleotide | promoter target | Sequence | SEQ ID NO. | position/dir |
|---|---|---|---|---|---|
| 4 | HL453 | PDS promoter2 | ATGTATGAACTTTCAGAATATTATACC | 223 | Sense |
| 4 | HL454 | PDS promoter2 | TACCGGATCAATATATTATGCT | 224 | Sense |

Figure 35:
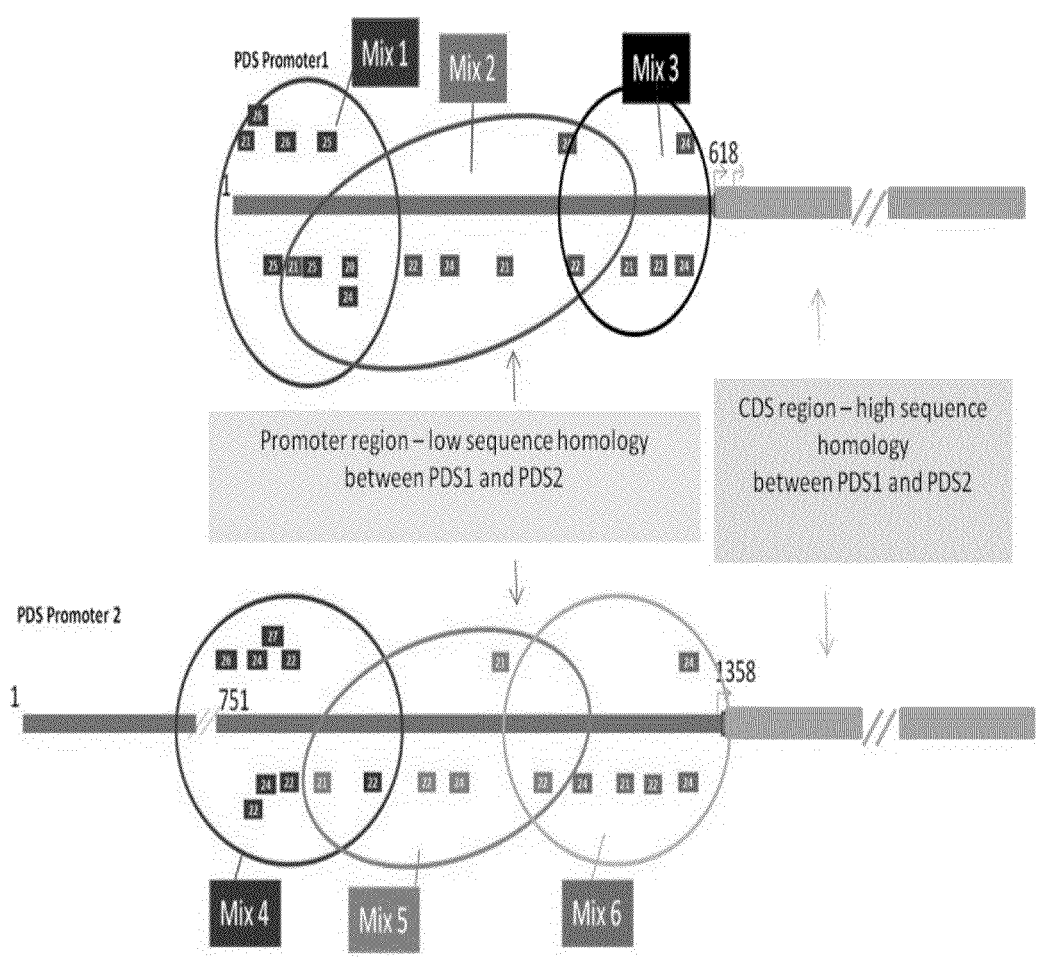
FIG. 35 schematically illustrates the *Nicotiana benthamiana* PDS locus 1 and locus 2 promoters and the regions targeted by mixtures of polynucleotides, as described in Example 30.

Six different combinations of polynucleotides (1 nanomole/plant of each applied polynucleotide) as listed in Table 21 and illustrated in FIG. 35 were tested on 4-week-old *Nicotiana benthamiana* plants using a procedure similar to that described in Example 12. Polynucleotide solutions were prepared in 0.01% (v/v) SILWET L-77® brand surfactant and 2% (w/v) ammonium sulfate in 5 millimolar sodium phosphate, pH 6.8. Two fully expanded leaves per plant were dipped into 0.1% SILWET L-77® brand surfactant solution freshly made with ddH2O for a few seconds, and allowed to dry. About 30 minutes later, 20 microliters of polynucleotide solution was applied to each of the two pre-treated leaves. Positive control plants were similarly treated with a DNA oligonucleotide targeting a conserved segment of the coding region of PDS1 and PDS2; negative control plants were similarly treated with a DNA oligonucleotide designed to silence green fluorescent protein (GFP). All six combinations of polynucleotides designed to target the PDS 1 or PDS2 promoter regions induced systemic silencing in the treated plants as evidenced by bleaching. Treatment with either dsRNA or dsDNA polynucleotides of approximately 200 bp and targeting the PDS 1 or PDS2 promoter regions also induced systemic silencing in the treated plants as evidenced by bleaching.

The following additional genomic sequences (including promoter and transcribed intron and exon sequence) listed in Table 22 were identified for *Amaranthus palmeri* genes for use in designing polynucleotides for topical application:

TABLE 22

| Gene Name | Sequence | SEQ ID NO. |
|---|---|---|
| ACC1 | TTCAAAATGAATTTAAAATTATATAAAAATCAATATGGA CACAAGACCGGATATCAATCCGACCCGAAATAGTTGACT TGAAATCAACCTGATGACCCGAATGAACACCTCTAGTTA TCACTAACAAGGGTCAGATTGCGTACATCAAACCCCTCA AATCCTGCTTAGGTGGGAGCTTGTCAATGGCTTAGGGGT AACGGGAATGTGTGCTATGTACATTGTGCATCTATTC TTATGCTTATTTATGTTGAGTTAGTTTTTTTTTGGATC AAATATAAAGAGCTTAACTTTTGTATTTCTTGATGTGG TGTAGTGGTGATGAAGATCAGGCTGAGAGAATCTAAATT GGCCAAAATTCTGAGAGAACAAGAAGTGAGTTCAGCCCT TCGTGCTGCTGGTGTTGGTGTGATTAGTTGCATCATACA GAGAGATGAAGGGCGAACTCCGATGAGGCATTCATTCTA TTGGTCAGCAGAAAAACAATATTATAGTGAGGAGCCTTT ACTACGTCATTTGGAACCCCCTCTATCTATGTATCTCGA GCTGGTACTAGTCTCTGAACCGATTGCCTTTCTTCTGCT TTGTTATTTTGTGTGATATTTCGACTTAAGTCTAATTTA CATCGTTTTGTACATTTGTTATC | 225 |
| ACC3 | TTTTGCTTTTTTACTATTATTTCCTTCTTTTCAAGGATT TGAGTTGTTTATTGCTGACTGCTTCCTATGTATTACCCA TATGTCTCTGTATAGGCATTACGGGAGCTGTACCTACAT CTAACTCCTATACAACGTGTGAATATTGCCCGGCATCCT AATCGCCCCACTTTTCTTGACCACGTATTCAGCATCACA GAAAAGGTTTCTGATTTATTATAATTTTTGTCATTTGTA TTCACTCTTCAATAAAGTACATCCATTATCAATCTTTAC GGAGGTTGTTCACACAACTTCTTGTTTCATTTTGCATAA TTAGTTTGTGGAACTACATGGAGATCGTGCTGGTTATGA TGACCCTGCTATAGTTACTGGCCTTGGTACGATAGATGG TAGGCGTTATATGTTCATTGGTCATCAAAAGGGAAGAAA TACGAAGGAAAATATTGCACGGAATTTCGGGATGCCTAC TCCTCATGGGTAAATGCTTTACTATAATGTTTTACTTTA ATTTAATTACCTATGTTATTTAGGATGAAAATGAATACT TTTCTTATTACTATTACTTAGGTTCCTAATGCACAAAAA CCGTAATTATTAATGTACCCTAATGGAATTAACACATGG TAATTAAGCTCTCCGCTTTGTGTAATTAATCCAATTTTT TAGAGAGTCAAATAGTTCAGGTTAAACTAGAGCTTTTCA TACCCAAATAATAAAACCAAGGGTAAATTTCCAAAA | 226 |
| ACC4 | ATGTGATCAATTAAAGAAAAAGTCTAATTATATGAGCCC GTCTCACAGTGACGGAGCTATCATAGAGCCCATGGGGTC ACGTGCCCTTCGGGGTTTTTAGAAAAAATTCAAAGTATA CTTTTCTATTAATAAGAGTAAAAATGTAAAATTAATATT AAACTCTTTTGATAATAAATACTCTCTCACTTTAGTAAT TTTGTCTTATTTATTTATTTTATCTCATGTGTTTAATAA GGTCAGTTGACTTATTTTGTTCCATTTTCTTTTATGGTA TGCCGTATTTAAAATTTTAGCAAGTAAAGATAAAATAGT TGTTAATCTTACAAATAAAACTCTATCGAAATTTCATCC ATTAGTTAATGTCCCCAAAAAGTCCGAACTACAAATCGA CCACTGTCATCACATGGTGAGATAGTCTCATATAAAACG AGTTCAGTTATTAAAGGAAAATAGGAAACACGAAACAGT TAATTTAGGCGGGGCCTATGTATTATCCAAATGTGATAC TCCAGTCCACATTACTCAGTCCTTCCAATTGAACAGTTG GCTTAATCTACCAAGCGCGTGGCCATAAATGCCTCTAAC ACTTTTCAATCTCTCAGATAACTCTCACACCACTTATCA TCACAATTCACAATTACTCTAATTCTTTTTATTCCTTTC CATGTCGCTAATTTTCTACTGATTCAGGTTTTATTCTCA GCTTTTATCAATTTTATTTCATGCTTTTTATGTCAATTT CTTGTTTCGCATTTTGTCTTCCACTTGCTGTCTGTTTTA TTAATCAATTTTGTATGATTGTTGGAATAATTGTATGTA TTTTTCATGATTTTCCTCTTATGGAGGTTCATAATGTAT TGCTAGATTTGTTTACTTTCAC | 227 |
| ACC5 | AATTTGAGCGGGAAAATTTTAATATCATTAAATAGTCTT TGCTTTAGTATATAGAATAGTTAAAATTAATAGTCAAAC TTATTGTAATAGCATGCACTAATCTATAATAATCTTATC CTGAAAGCTATAATAAAATTATAAAAAAATATATGTGAA AAACTAATTTGAGCGGGAAATTTTAACCAAGGGCTAAC ACGTATCATTAAATAGTCTTTTACTTTAGTATATAGAATG ATAATTAACGATCATAAAACAAAATTGTCACTTTCAGTA GCAAACTTACAAAATGAGCAGAGTACCTCATATCATAAA ATTGCTTCTTTCTCATTTGTTGTGTTGCTCTCATTTTAG GAGTTCATCGTTTATATCGTCGTCTTACCACTCAATCAC TTTTAGATTTATTAGTAGCACTTCCTCAATCTACAGCAG CAATTTCTACAGTTCAACAACCTC | 228 |
| ACC6 | GGAAAATTTACCTAGAATAATCCAATTTATTCGTGATTT TTCTACAAATTCCAACTTCAAGGGGTATTTGCCTAAAGT AATTAAACTTGGATACCCCGATGACCTGCTATAGTAGAT AATTTACCAGAAATTAAAAATGAAAATTAATTTAAAAT TAGAGAAAAATTTTGAAATTTCATATAAAAAATTTTAAA TAATAAAAAAATATAAATTTTTTTGAACATTTTATTTT AATCTATCTTTTTTGAAAAAATAAAACTTAGTTATAGCA AGTGATCTGGTCACCGGGTTTACTCTAGGAAAATATCCC TCAAAGTTGAGATTATTCATGGTTAATAAATAGGTGAGA TTATTATAGAAAATTACGAATAAATTGGATTATTGTTG GTAATTTTTTTTCAAAACTATCCCTAGGAAGGACCTTA TTAGTGATTCTCCCTCTACTTTGGAGGAGTATATTGTGG ACTTCCCATCTTCCTTAATTGTATTGTAACTTTTAACTA | 229 |

TABLE 22-continued

| Gene Name | Sequence | SEQ ID NO. |
|---|---|---|
| | TTGATTCTTTAAAAAAAGAACTTATAAAATTGTAGGGT TAATAAAATCTAAGATTTTATCTAATTTCACTTTGATTA TTCCGATTTTGTATTCACATTATTTTAAATGACATTCGT CAAATAAAAAAAAATAGTTTCATTGCATTCCAATTTTGT TGACTAGGGGGATTAAAGAAAGAATAGTATCAATAATCG TAATGTAGCAAGTAGTACAAAAGAAGTATATTTCAATAT GTCAAACTTTGATCTCGTTGTAACTTGTAATTTGTACGA TGCGGTGTGAATGACATACTTCACCTTTTTCATTATTTT ATACTGGTAGTGACATGGGATTATTATTGCGATATTTGC AGTAATGAAAATTTTTTTGGTTGTTGCTTTTACAAACAA AAATTCTACCGAATTTTTTATTAATTTAATTCAACACGT TGGTGTTACCCATGATTTATAGGTCTGGGTCCGCCACTG CTAGCTAACATTAAACAATTTAACAAACTCAATACACCA ACCTAAAAATAAAATTTTTTGGCCATAATTTTTAGAATT TTTAGTTTTTAAACATTATATTTGGGAATTTTTTTCCTT TTTATATATATAAAATAAAAAAAAATCCAAAAAAGGGGA CACACATTAATACACACTTGAAAGCATCGATGATATCGA AGAAAAACCAGATGGGGTGCCCAATTATCTTCGTCTCCT TCGATATTATCGAATTCATTAACAACATTATATCAAAAA CCAACCAAATTACCAACTTTCGAAACCAATATTCGCCGT ATTTTTCTCTATTCAACAATCCCTACAATGGCGGCATTG CCAGCTTCTTCTTCCTGCAATTTCGGAATCACCCACT TGCAATTTTCTTCCTATTCAAAAAATCACTACCACTCGC TTTTCTAAGGTTTCATTCGGTTTTACTCCCAAGCCTAAAT TTGGCCTTTTCTCCAAGGTTTATTTTCTATCTCTTTTT AATTGGTTAATCAATTGGATTGTTGAATTTTTCAGGGTT TAACGGTATAATATTTGTGGTTTTTTCGAGTACATTCT GGGTTTGTAGTATTGGATTTGGCATTGCTTTTAATTTTT GAGATTGGGTTTTTGGGTTTTATTTGGTTCTTGTGATT CAAGGTTATTGATTTGCTGCATTAAACTGTATTTATGGA ATGATGTCAATTAACTGTTACATTACATTGCTTTATGGT TTTCATCATGCTGATTAGTGATTACTGTGTTTGAATCTC TTGCTTCTCTATGTACTATTTAATCTGATACAACAAGTA CAACCTAGAAAACAGGTTAAAGGGAAATCTATAAGCTTA GTAAATTAACACTTGAAAGAAGCTAATGACGAGAGAGG GGTCTTTTTGGAGAAGGCAGTTTTCATATTATTGCTCAG TTCTCTAGTCAGCTTTACTTCACTTAGACACTCTTAAG TAGAGGTCATAGGTGTTCAGAATAGATCCAAAGACCCGA TATTTACCGGACTTTGTAAACACCTTAACCCGACTTCAA AATGAATTTACAATCATATAAAAGCAATATGGACTTAAA CCGATTTTGAACCGACCTTGACCGGTTGATCCGAATGAA TGCCTCTACTCTTAAGCATGTCAACTGTAATATGAAATA GAATTATAATATAAACTAAGTTCATGTTTTCTTCAACTA CAAATGAAATTTTATGACCCAAATAATGTGTGAATACCC CCAGCAATAGGTTGAATGGCATTTAGTTCAGTTGATTTT AGCAGACCACATCTGCCCTCACATTTCATTGTTCAGTTT AGTTGTTAGTAGCTGTACATAATAGACTAATTAAGTTGT CATTTTGATCCATGTTATGGTTGTCTGGGATAAACGGAT TGGAATTGTATAATAAAAGTTTGGGTTAGTTTATTTTGC TCTAGGAGGGGTTTGTCATATGTGCACTCTGTTGGCAA CCCGACAATGCAAAACATTTTCATACTTGGTACGTTGTT GCGTGTTTTGTGCCCTTCGTATTTTGTAACTGTTGATGA ATGTGTAAAAATATACTACATGATCATATGCTAGTAGGT CTTCTTCACCTAGTAAAGAAATTTTTCTAACACGAGAAG TTCAAAACATATTCCCATTACCATTATCCAACATCAGTA CCCGAGTCCAAGTAACATAGGGTGTCCCTTTATGATAGT ATAAGAATTGGTGCATGAAAAACGCGTGATTGTAGCGAG GATAGTAGGCGGGAGAGGTACAGGATTTGAAAATTTTGA ATTGCTAAAACGCTATCAGGATCTTGTTTTTCTTACTTT GATGTTGCTTTTTGAAATTTGATTCCAAATTGTTAAATT ATTGAGACTAATTCCTGTTGATCCTGTCGTGAACTTTGT AGAATCTTTCAGGCCGCATTCTCACAGTGAAGGCTCAAT TAAACAAGGTGAGTCTTTTTTGTCTTAACTCTTATGCA GTTCATTATCTCTTCTACTGATGAGAAAACCACTATTTG GCCTAATTCTAATTTCCTTCTAGGTTGCTTTGGATGGTT CAAATCATGCTCCATCACCTTCGCACGAAAAATCTGGGC TACCAGCCCAAGAAAAGAAGAACGATGAGCCGTCTAGTG AATCTTCCTGCAGCATCAGTGTCTGAAGAACGAGTCT CCGAATTCTTGAGCCAAGTTGCCGGTCTTGTCAAGTATG TAACATTCTTTATTTTCATTCTTCCACACACTCGCAATT TGGATAACAGATGTCTTTAGAGACGTCTGTGGGAACAAG GGAGAAATGAGTCTAGAGGTTGCTAGAGAGACGAGATA AATACTCATATATATGAATATTTCATAATCCACATTAAA AAAATACAATTGAATTTGCATTATGGTGAACTACCAAAG AATCGAATATTTTTAATACTCCATGTTTTGTGGTCTAG ACTTGTGGATTCTAGAGACATTGTAGAGTTGCAATTAAA | |
| ALS1 | ACAAACTGGACTGTGAGATATTGATCCGCAAGCAGGAAGC TATTCCTCAACCACAAATTCCTAATCCTACACATGTCGT TGCAATGCAACCACCACCACCTGCTGTAGCGTCTGCCCC AGCTCCCGTCTCTTCACCAGCCACTCCTCGTCCTGCGTT ACCTGCCCCAGCGCCTGCTGCCACGTCAGCTAAGCCATC ACTTCCACCTCTCAAGAGCCCTATGTCAGGCACATTCTA CCGTAGTCCAGCTCCTGGCGAGCCGCCTTTCGTGAAGGT AAGTGTATACCCCTTTTTTAGTGTTGTATTTCTGTGTTA TATCAATTTTTGCATTTTGTGAAGCTGAAAATAAATCTT TCATTTTCCATAGGTTGGAGATAAAGTTAAGAAAGGACA AGTCATATGCATTATCGAGGCTATGAAGTTGATGAATGA AATCGAGGTACGTATGTTATTGCTTTAAACTTCATGCCT TAGGCCGTGAAGTT | |
| ALS1 | ACAAAAAGCACAAATTCAATAATATACTCTTTAAGTTTG TTTATCTTCTAATTAGTTCGGTTAAAACGGTTCCCCACT TTCTTCTCCGACTCTCAACATTATCTTCCCCTATTCATT TTCTTCCACCCTCTCTAATGGCGGCTGTTTCCTTCAAT ATCAATGGTGGAAAGATTGGAACTTTATGTTCAAGCACAC GAATTCGTTTGTGGGTTTGTAAGAAAATTTCATTTTAGA ACTCATACTTCTATATTTGAAAAACATATGCCAAAAACT TCAAGGTTTAAAGCAATGGAAGTTTCTGCAAATGCAACA GTAAATATAGTTCCTGTTTCAGCTCATTCAGGTAATTT TATTTCTCGAAAATTTCCGATTTACAATTAAATTAATCT TGTTTTGTAGGTAATGAATTGCAGAAGAAATAGATGGAT TCTTATTTGTTTATTGGTATTTGTTTATAAATTTTTGTT TATATTAGTTTCTGAATTGTGATTATTCTGATTGTATGT CAAGGTTTAGGTTGTTATTAATAAATGTAAATTGGATTG ATTGAAGTTGCAATAAGGTGATGGCGTGATGCTGATTGT TGTAAATTTT | 230 |
| ALS2 | CAACAATGAGAATTTAGAATCCATATCAATCTTGATATT CAAGGGTATTTAAGTAATTAAAGAACAACCATTGTTAAG CGCCTCCACTATCTTCTTCTTCATTCTCCATTCTCG CTTAGCTTTCCTCTCGCACTAATTACCTCCATTGCAAC CTTTCAAGCTTTCAACAATGGCGTCCACTTCTTCAAACC CACCATTTTCCTCTTTTACTAAACCTAACAAAATCCCTA ATCTGCAATCATCCATTTACGCTATCCCTTTGTCCAATT CTCTTAAACCCACTTCTTCTTCTTCAATCCTCCGCCGCC CCCTTCAAATCATCATCTTCTTCTCAATCACCTAAAC CTAAACCTCCTTCCGCTACTATAACTCAATCACCTTCAT CTCTCACCGATGATAAACCCTCTTCATTTTGTTTCCCGAT TTAGCCCTGAAGAACCCAGAAAAGGTTGCGATGTTCTCG TTGAAGCTCTTGAACGTGAAGGTGTTACCGATGTTTTTG CTTACCCTGGTGGAGCATCCATGGAAATCCATCAAGCTC TTACTCGTTCTAATATCAAGAAATGTTCTTCCTCGAC ATGAACAAGGTGGGGTTTTCGCTGCTGAAGGCTACGCTC GTGCTACTGGACGCGTTGGAGTTTGTATTGCCACTTCTG GTCC | 231 |
| EPSPS1 | ATTTGGATAACTTTTTCCTTTGATTCGAATCGGATTATT TTTAATACAGTATTATGAACTGATTAATGAAAGTGGAG GAAGTTTCAATTTTTAAAGTTGTAGGTGTAATGTTTTCT CATTTTGGATATGAAAGTGGAGGAAGTTTCAATTTCGAA TCATGTTTGCCAGTTGATTCAATGAATGCTCTTGGAAAT GACCAAGAGTTCAAGGCTTCTTGTTATAAAACATTTCAA TTTTGATCTAAGAATGAACTATTTAGAACTTAAAGTAAT TAAATTATTAGTTATAACTTATAAAAAAATTCAATTTTA ACCTTAAATTTATAAATTATGACCTTAAAAAGATCAAGT ATTGAACGCATATTTAGAAAAATTATAATTCGGCTTATC AGTCTCATATTGAGACGGTCTCGTCCAAGACAAGTTGTA TCATTATATAATCAAATATAATTATGAGTGTATTCATG TAGGTTTCAACTCCCATAGGTGAAAGATATGTGT AGCATCTTTGTGAAAGTCAGCCTATAACTTGGTTCTAAA ATTTTGAAGCATAACCATATAGTCCCTCGAATTCATTCA AGTTGTCCAATTTACTTTTTATACTTGCCGAGACAACA TTTAAACCCTTAATATTCTAATTAATCTTAATTAAAA TTATGAAAATTTGATATTAATAATCTTTGTATTGAAACG AATTTAACAAGATCTCACATGACTATGTTTAACTTATA GATTAAAAAAAAATACAAATTAAGAGTGATAAGTGAATA GTGCCCCAAAACAAATCATTAGTAGCAACTTAGATGAATTGGAG GTAATATTAGGTAGCAAGTGATCACTTTAACATCAAAAT TGATCACTTATAGGTTCAAATTGAACTTTACTTTAAT TGATATGTTTAAATACTACTTTAAATTGAAATTGATATT TTTAAGGTCAAAATTGAAACCTTTAAGGATTATAATTGAA AATTGGCAGAAGAAAACAAAGAGAAAGAATATAAGACA | 232 |

TABLE 22-continued

| Gene Name | Sequence | SEQ ID NO. |
|---|---|---|
| | CGCAAATTGTACCGATCTACTCTTATTTCAATTTGAGAC GGTCTCGCCCAAGACTAGATGTTCGGTCATCCTACACCA ACCCCAAAAAATTCAACAACAAAGTCTTATAATGATTCC CTCTAATCTACTACAGTCTACACCAACCCACTTTCTCTT TGCCCACCAAAACTTTGGTTTGGTAAGAACTAAGCCCTC TTCTTTCCCTTCTCTCTCTTAAAAGCCTGAAAAATCC ACCTAACTTTTTTTTAAGCCAACAAACAACGCCAAATTC AGAGAAAGAATAATGGCTCAAGCTACTACCATCAACAAT GGTGTCCAAACTGGTCAATTGCACCATACTTTACCCAAA TCCCAGTTACCCAAATCTTCAAAAACTCTTAATTTTGGA TCAAACTTGAGAATTTCTCCAAAGTTCATGTCTTTAACC AATAAAAAAGAGTTGGTGGGCAATCATTCAATTGTTCCC AAGATTCAAGCTTCTGTTGCTGCTGCAGCTGAGAAACCT TCATCTGTCCCAGAAATTGTGTTACAACCCATCAAAGAG ATCTCTGGTACTGTTCAATTGCCTGGGTCAAAGTCTTTA TCCAATCGAATCCTTCTTTTAGCTGCTTTGTCTGAGGTA TTTATTTCTCAACTGCGAAAACAATCTCTATTTGATATT GGAATTTATATTACATACTCCATCTTGTTGTAATTGCAT TAGTAGATACTTATGTTTTGACCTTTGTTCATTTGTTTG TTGAATTGGTAGTGTTGAGAATTTGAATGTAATTATTTG TTTTTCATGTGAATTTAATCTGATTAAATCCACTTCTT ATTTATGTTAAGTTGCAATGATGTTTGCCAAATGGTTAT CATTGAAGGATAAGTTTGCCTACTTTTGACCCTCCCAAC TTCGCGGTGGTAGAGCCATTTTATGTTATTGGGGAAAT TAGAAAGATTTATTTGTTTTGCCTTTCGAATAGTAGCG TTCGTGATTCTGATTTGGGTGTCTTTATAGATATGATAT ATGGGTTATTCATGTAATGTGTAGGTTTATGCATTATGT TGGATGCATGTCTGGTGTTATTGCTGTAAATGGATGAAT GTTGTTATTTGGAGACATTTTTTCATTCATTTTTTCCCT TTTTAATTGGAACTGGAAGAGGGAAAGTTATTGGGAGTA ATTAAAAGGTTGTGAGTTCGATACACTGCATCAAAGACG AAGAACTTGACATAGATGTTGAAGGCTAATCCTTATCAC TGCTTGAATTCAATATGTATCTGAAAATTTTACCCCTCT ATATGCATCTGTTTTTGCTAATAAAGTGTTTTTGGACTA TCATGTTTTGTGATGCTTAAGAGGGTGATATTACTGAGA TAAATGGAAATATCAAATAACATCTATTGTGAAGT | |
| EPSPS2 | CAAGCTTCAATTATCGTTTTCAAAATAAGTATTTCAAAG TCTATAAAGATATTGTATAAGTTTTAGTTCAAATTTAAT AAGTTTTTTTTTTTTTTTTTTTTTTTGAAAATCC AAATTGAATAAGTTAATARTTAAATTATGACATATAATT ATGACATATAATTTGACCATGATATTTTACAATCTAACT TAATTTTGAACTTATTATTTCTAATATTCAATTATCGTT CTAAAAATAAGTATTTAAATTGTATAGATATATTGTATA ACATTTAGTTCAAATTTAATTATTGATAGTTTTATTGAC TATTTATTTGGKGTTTGAAATTCATCCATAGAATGATAG AATAACACCATTTTTTATATAACTTCGTTCTAAAATTTT GAAGCATAACCATATACTCCCTCCAATTCATCCAAGTTG TCCAATTTACTTTTTCATACTTGCCGAGGCAACATTTAA ACCCTTAATATTTCTAATTAATGTTAATTAAAAATTATG AAAATTTGATATTAATAATCCTTGTATTGAAACAAATCT AACAAGATCCCACATGACTATGTTTTAACTTATAGATTA AGAATAAAATACAAATTAAGAGTAATAAGTGAATAGTGT CCCAAAACAAATAGGACAACTTGATAATTGGAGGTAG TATTAGGTAGCAAGTGATCACTTTAACATCAAAATTGAT CAGTTACAGGTCAAATTGAAACTTTTACTTTAATTGAT ATGTTTAAATACTACTTTAAATTGAAATTGATATTCTTA AGGTCAAAATTGAAAACTTTAAGATTATAATTGAAAAAT GCCCAGAAGATGAAAAAACAGAGAGAAGACATGTAAGAC ACGCAAATTGAACCAGTCTACTCTTGTTTCAATTTGAGA CGGTCTCGCCCAAGACCAGATGTTCAGTCATCCTACACC AACCCCAAAAAATTCAACAACAAACTCTTATAATGATTC CCTCTAATCTACTAGAGTCTACACCAACCCACTTTCTCT TTGCCCACCAAAACTTTGGTTTGGTGAGAACTAAGCCCT CTTCTTTCCCTTCTCTCTCTTAAAAGCCTAAAACCCACC AACTTTTTCAGCCAAGAAACAACGCGAAATTCAGAGGAA GAATAATGGCTCAAGCTACTACCATCAACAATGGTGTCC ATACTGGTCAATTGCACCATACTTTACCCAAAACCCAGT TACCCAAATCTTCAAAAACTCTTAATTTTGGATCAAACT TGAGAATTTCTCCAAAGTTCATGTCTTTAACCAATAAAA GAGTTGGTGGGCAATCATTCAATTGTTCCCAAGATTCAA CTTCTGTTGCTGCTGCAGCTGAGAAACCTTCATCTGTCC CAGAAATTGTGTTACAACCCATCAAAGAGATCTCTGGTA CTGTTCAATTGCCTGGGTCAAAGTCTTTATCCAATCGAA TCCTTCTTTTAGCTGCTTTGTCTGAGGGCACAACAGTGG TCGACAACTTGCTGTATAGTGATGATATTCTTTATATGT | 233 |
| | TGGACGCTCTCAGAACTCTTGGTTTAAAAGTGGAGGATG ATAGTACAGCCAAAAGGGCAGTCGTAGAGGGTTGTGGTG GTCTGTTTCCTGTTGGTAAAGATGGAAAGGAAGAGATTC AACTTTTCCTTGGTAATGCAGGAACAGCGATGCGCCCAT TGACAGCTGCGGTTGCCGTTGCTGGAGGAAATTCAAGTT ATGTGCTTGATGGAGTACCAAGAATGAGGGAGCGCCCCA TTGGGGATCTGGTAGCAGGTCTAAAGCAACTTGGTTCAG ATGTAGATTGTTTTCTTGGCACAAATTGCCCTCCTGTTC GGGTCAATGCTAAAGGAGGCCTTCCAGGGGGCAAGGTCA AGCTCTCTGGATCGGTTAGTAGCCAATATTTAACTGCAC TTCTCATGGCTACTCCTTTGGGTCTTGGAGACGTGGAGA TTGAGATAGTTGATAAATTGATTTCTGTACCGTATGTTG AAATGACAATAAAGTTGATGGAACGCTTTGGAGTATCCG TAGAACATAGTGATAGTTGGGACAGGTTCTACATTCGAG GTGGTCAGAAATACAAATCTCCTGGAAAGGCATATGTTG AGGGTGATGCTTCAAGTGCTAGCTACTTCCTAGCCGGAG CCGCCGTCACTGGTGGGACTGTCACTGTCAAGGGTTGTG GAACAAGCAGTTTACAGGTATAATGTTAACCCTTACCCT TCACATTGTTCTGCTAAATTCTAGAGGACCCTTTCAATT CTGGGTGGGATAAGCACGGCAATTTGACCGCAAAAAAT TGCAAAATTATTCTGCTGATAGAACATCTCGAGATGAGA TCATATTGAGTTTTGGCGTCAACATAAACCTAATCAAAT AATGAAAATACAAACATCATATGGTTTCTTTTGTCTTT ATGACTAGACACTCTCTATTATTCCTTGATTGGGATCTT AATTTGAATTGCTGTGTAGCCTACACCTCATGTTCAGAT TTTGTTCGTATACCAGACTTTTCTTGATTGGGATCTTAT TTGTCCCCTGGATTTTGCATAGGGTGATGTAAAATTTGC CGAAGTTCTTGAGAAGATGGGTTGCAAGGTCACCTGGAC AGAGAAATAGTGACTGTTACTGGACCACCCAGGGATTC ATCTGGAAAGAAACATCTGCGTGCTATCGACGTCAACAT GAACAAAATGCCAGATGTTGCTATGACTCTTGCAGTTGT TGCCTTGTATGCAGATGGGCCCACCGCCATCAGAGATGT GGCTAGCTGGAGAGTGAAGGAAACCGAACGGATGATTGC CATTTGCACAGAACTGAGAAAGCTTGGGCAACAGTTGA GGAAGGATCTGATTACTGTCGATCACTCCGCCTGAAAA GCTAAACCCCACCGCCATTGAAACTTATGACGATCACCG AATGGCCATGGCATTCTCTCTTGCTGCCTGTGCAGATGT TCCCGTCACTATCCTTGATCCGGGATGCACCCGTAAAAC CTTCCCGGACTACTTTGATGTTTTAGAAAAGTTCGCCAA GCATTGA | |
| GS3 | TCTTAATTTGTATTTTATTATTAATCTATAAGTTAAAAC ATAGTCAAGTGAGATCTTGTTTGATTCGTCTCTATGCAA GGATTTTCATATCAACTTTTCATAATTTTTGATTATACA CAATTACAAATATTAACGAACGAATAAGTGCATTAAAAA GAGTGCAAAAAGCAAACTGACACTTGTGTTGAATAGGA GGGAGTATACATTAAGATGAATCTAACGAGATCTCACAT GGATATAATTTGTCTTCTATATATGTCTAAAAAATCTTG ATCAAATTTCTCTTTCCAAAATAGAATATTCTAAATGGG AAGAACATTAAGAAAACGGAGGGAGTACTTATAAGTTAAG ATAGTTGGGGTATTAGGTAAAAAAATCTATGCCAAAA GTAGAAAGTGGACAATTAGAGTGACTTTACTAAATAAGG AAAGTGGACATTTAAATGAATCGGAGGGAGCATATTAA CTTTATTTTCAAAGTGTGAAACATAATCATATTTAGGTA AAAAAATTATCAATTTAACGTCAAAATTGATCACAAATA GGTTAAAATTGAAATTTTTTATGTTAATTGATCTATTGT TCACTTTAAATTGAAATTGATATCCTTTAAGGTTAAAAT TAATACCTCTAAAATTAAAATTATTAAAGGCCCAGAAAA TAAAAAAAAAAGAAGACAGGCTATTAGTAAAATTATTAA GTATGTAAGGTTGATACACGCGCGAATTGAGCCGGCCCA CTTTTAGTTTCAATTTGAAACAGTCTCAATCAAGACCAA TTATTTATTTTATTATTTTATTGTTTAAGCTCAAT GGGTTGGACTTTGACAATAATATTTGAGGAGACGGGCT ATTAGTAAAATTAATAGTTGGAATCTTTTTGATATACT ATAAAAGAGGTATCTGGTGGAGCCTTAAATCTGCGCAA TTGAAGTCCTCAATACACATCTCGCTCTTCTTATTCTCT TTCATCTATTTCCTCCTTTGATCAAACTACGCCATGTCT CTCTTAAATGATCTCGTTAACCTTAATCTCTCTGAAACT CCGATAAGATTATCGCTGAATACATATGGTAATACAACA ATCCTTCCTCTTTTTCATTT | 234 |
| GS5 | AAAAAACCGTCTTATTTGTAGAAAATAAAAAACTAAAAA GTAGTATCAACTTTTAGACTAGTCATAAGTGAGTGGCAT CAAACTTGTTCTATAAAAAGGGAAGAGTTCCTCAACTTG AGATTCATATTTTTTGTGATTTCTAAATAGAAGAACATA CTCATCTTCCACTTCTCTTATTCATCAAATTTTATTTGT | 235 |

TABLE 22-continued

| Gene Name | Sequence | SEQ ID NO. |
|---|---|---|
| | TCCCCAAAAAAACATGTCTCTTCTTACAGATCTCATCAA<br>TCTTAATCTTTCTGACTCCACTGAGAAGATCATTGCTGA<br>ATACATATGGTCAGTTTTCATCCCTTTTTTTTACCTTTA<br>ATCCCACTTTTTGTTTTTACCCACCATTTTTTTCATCTA<br>TTTTCTCTTAAAGATTTTAACTTTTTACTTTTTTGTGTA<br>TATAACATTCATTTTTTCAATTGGGTAGGTTAGAAAATT<br>TCTATAAATAAATAAATAAATNNNNNNNNNTACCTTAAT<br>CCCACTTTTTGTTTCTACCCACCATTTTTTTCATCAATT<br>TTTCTTAAAGATTTTAACTTTTTTAACTTTTTCTTGGT<br>TTTTGTGTATATACCAATCATTTATTTTCACTAGTGTAG<br>GTTAAAAAATATCTAAAAATAAATAAAATAGAATAAAAA<br>TGTAATCACTAGATTAACCCATGAATTATTTCCCTTGTT<br>TTTACTCAAACTTTTTACCCTTGTTAAAAAAATAATGAT<br>ATAAATAAATTTTTGAGGGTTTGTTAAACCCATATGTAA<br>TCTATATCGAAAAAATTAGATAGCGGGTTTTGTTGTGGA<br>CAAACTAAATAACAAATTTAGGAATAAACTTTTGAGGGT<br>TTATTGAAAAAATAACCCATATTTAATCTATATCGAAAA<br>AATGATAGCGAGCTTTGTATAGAT | |
| HPPD | CGTCGAAGTAGAAGACGCGGAAGCTGCTTTTAACATCAG<br>CGTTTCGCATGGGGCTATTCCCTGTGTTTCTCCTATTCA<br>ATTGGAAAACGGTGTCGTTTTATCTGAGGTTCATTTATA<br>TGGGGATGTTGTGCTTCGGTATGTAAGCTACGGAAATGA<br>ATGTGGGGATGTGTTTTTCTTCCTGGGTTTGAGGAAAT<br>GCCGGAGGAATCATCGTTTAGAGGACTTGATTTTGGCAT<br>TCGAAGGTTGGATCATGCTGTAGGGAATGTCCCTGAGTT<br>GGCTCCTGCAATTGCTTATTTGAAGAAGTTTACTGGGTT<br>TCATGAGTTTGCTGAGTTTACAGCTGAAGATGTTGGGAC<br>GAGTGAAAGTGGATTGAATTCAGCCGTATTGGCAAACAA<br>TGATGAAATGGTGTTGTTTCCGATGAATGAACCTGTGTA<br>TGGGACAAAAAGGAAGAGCCAAATTCAAACTTATTTGGA<br>GCATAATGAAGGGGCTGGTGTACAGCATTTGGCTTTGAT<br>GAGTGAAGACATATTTTGGACTTTAAGGGAGATGAGGAA<br>GAGAAGTGTTCTTGGTGGGTTTGAGTTTATGCCGTCGCC<br>GCCTCCGACTTATTACCGGAATTTGAGGAACAGAGCTGC<br>TGATGTATTGAGTGAGGAGCAGATGAAGGAGTGTGAAGA<br>GTTGGGGATTTTGGTGGATAAAGATGATCAGGGCACTTT<br>GCTTCAAATCTTCACCAAACCTATTGGAGACAGGTAAAT<br>TTTAATCTTGCTTTCAATTGCTTTTGCTTGATGGATTGA<br>CTAGCAAATTTGATCGCATTTTGTTGCTTATATGACTTG<br>ATGATACTTCCTCTGTTTCGAAATACTCGCTACATTCGC<br>TACATTTTGTTTTGTGCACTATTCATCGTTCAAGCTTAT<br>TTTACATATTGCGACTAATGTGTAACTAAAAATATAGTC<br>AAGTGGGATCTTGTTTGAATCGTCTAATGGCATACTTTC<br>ATCATATTAAATTTTTATAATTTTTAGATTAGTGTAGTT<br>TAAGATATTAATGCTCAAAATTGTGCATTGGATTGCGTA<br>AAAAAGTGAAATGTAGCAAGTATTATGAAA | 236 |
| PDS | AAAACCAAAGGAAATAAGTTATAGGTAGGAAAAATTGTT<br>ATTGAAGTTAATGTAGTAAACTAGTAACTTAAACTGTGA<br>TACCCCGGATTTAGCTTAAAAAGAGATTGATAGACTACT<br>CATATCAACAAGGTGCATCTTCTTTTCTAGGGAGCCCAT<br>TTGCTAAGAACTCTACAGTTAAGCGTGCTTGGTGGGAG<br>CAATCTTAGGATGGGTGACCTCCTGGGAAGTTTTCCTGG<br>GTGCGCACGGGTGAGGCCAAAGTGCGTTAAAAAGACTTG<br>TGTTGGTCTGTGGGGCTTGTCTACAGTCTCCATGAGTAG<br>TCACCGGCGGTACGAGAGGCCGGGGTGTTACATAAACAG<br>ACTCAAAGGCGCTAAGCCAAGTAGCCAATAGCAACATGT<br>GTGGCCTGCGGACAGTCACAAAAACACACAATTTCTTAT<br>TTTTACTCTCTTTTATCTCTTTTAGGCTTTAGCCATCAA<br>CAATAAAACAACATGATAAAGCAATTCATTTACTGCTAA<br>ATTCCAACAATTTGGTCCCTTTTTCCTGTTCTTTCAGTT<br>TCACATACCCTCTTATCAATCTATATCCAAAACTATTTC<br>ATTTTCCAAACTCTTTTAAACCCAAAAATCAAAACTTTT<br>GATTGAAGAACAAACTTTGGGGGTTTTGGAAAATGAGTC<br>ATTTTGGATATGCTTGTGCTACTCAATCCACATCAAGAT<br>ATGTTCTTTTAGGAAATTCAAATAACCCCACTTCAATTT<br>CATCTATTGGAAGTGATTTTTTGGGTCATTCTGTGAGAA<br>ATTTCAGT | 237 |
| PPOX | TGGTACCTACCCTGTTTACATTTTCAATTTCCCCCTTTT<br>TTCTCTACTACTCCTACTTTATTGATTCTTATCCATGTG<br>TGTTCTATGGGAATTGACATTAATTGTTCAGGTGTGTAT<br>GCTGGTGATCCTTCTAAGTTGAGTATGAAAGCTGCATTT<br>GGAAAGGTCTGGACCTTAGAGCAAAAGGGTGGTAGTATC<br>ATTGCCGGTACACTCAAAACTATTCAGGAAAGGAAGAAT | 238 |
| | AATCCTCCACCGCCTCGAGACCCGTCCGTAATCACCATT<br>ACTCATTGCTTTCCTTCACCTTGTATCTTACCTTAATAT<br>ACATGTATTTAATTGATAATGTCACATTGCCTCATTTGC<br>AGCCGCCTTCCTAAACCTAAGGGCCAGACTGTTGGATCC<br>TTTAGGAAAGGGCTCATTATGTTACCTACCGCCATTGCT<br>GCTAGGTATCTTTTGACTCTCAAATCTTAAATATTTCTC<br>ATCTTCTCCTTCTGCTAATACTAGTATGTTTACCATCTT<br>TTTATTTTTTAGGCTTGGCAGTAAAGTCAAACTATCGT<br>GGACACTTTCTAATATTGATAAGTCGCTCAATGGTGAAT<br>ACAATCTCACTTATCAAACACCCGATGGACCGGTTTCTG<br>TTAGGACCAAAGCGGTTGTCATGACTGTCCCTTCATACA<br>TTGCAAGTAGCCTGCTTCGTCCGCTCTCAGTGAGTATCA<br>TTCTTTCCTTCATTTCTTTTCGTTTATTGTTGTCCAATG<br>TCTTGTTAAACACCAGTTTGGCCTTGTGCTCGTGAATTA<br>TGGCTACAATGTTAACTGATTCAGGCACTGTGGGAGATG<br>CCTAAGTTTCTAAAACCTCTGCGCATAATGTTTGTTTGG<br>ATGTTAGGAATTGCATTGAAAAATTGCTTTTGTGATGTT<br>GATGTTAATACCAATTACAAGTGTGTTCTTCAACTTCTG<br>CAATACCTTGTTCGAGTGAGCTTGAGGGGGTTTAGATTA<br>GTGTCCAATGTGAAACTAGCAAATGAACTCCAAGCGCTG<br>GGATAGGTCCTTGGGATGGAGCCCCTGATACCCAAGACA<br>GAAACTGGGTGGTTGTATTCAAACCCTCTAAGTAGAGTG<br>AGAGATCAAGGAAACCTCAAATCGTAAAAAATGAATACA<br>GTGTCATGATTGCTAATCTTATCACAAATCGTAAAAAAT<br>GAATTATGGTCGATTTTGGCATATTTTTGGGTCATTTTG<br>AGTGAATCTCGAACTTAAAAAGCGAGTCTTCTAGCAGTT<br>CTTGTTACAGCGGGGCATACATAGGTAGGAATTTGGTTT<br>TTTACTATTTGAGCCTTTTGACTGTTGTGGCCGGTAATA<br>TGGAATAGTCTAGCACTTCTGCGTGTGTACAACTAGTAT<br>TTGTAATTATGTGATCGCACTTAACTCTCAGATAAAACC<br>TTATTAAGCACTAACATTTTGTTTTGGTTGAAGGAATCA<br>GGAGGAAAGAAAATTGAGGGATTTGTTGGTATATAGATT<br>CCTTTGTTTGGATAACAAAATTGGAGTGGAGAGATTTGG<br>AAGGAAGAATTTTATAGGGATTAGTTCCCATTACACTTA<br>TGTTGATTACAAAATTTCTCCAAAAGTGGAAAGATTTTG<br>AGTGAAAATGTTTTTTATTTCTCTTCCTCTCCCTTTCTT<br>TCCCTCTTAAACAAACAAGGAAAGTTAATCTTATCATTC<br>CGTACCTTCCCCTTCTGTTCTTTTTTTTCTCTCCAAAAT<br>TCTTATCCTAACGTAGTGTTATTGTCACTGTCTTATGAA<br>CGAGAATTCTTTTCTTCCTAATACTGCTTGTGTTGCACA<br>GTCAATGATTTAGCTAGATCATCTTTGGTTAGCTACTCA<br>AAATATTTACATAAAATACTTGTAGAAATAAATACCAAT<br>AGGTCTTGTCAAGAAGTAGTTTCAATGCTATAAGTTTTA<br>ACCAATCCTCAAAATTTACACCATGGAGATATCTGCGGA<br>TAAGAACTAGTAACTGTAGCAGCTGTAACTGTTGCAATC<br>AGTTTTATGGTTTGCCTTGCAAATCAAACTTTGGATGTT<br>GTTTGCCTTACAATTTGTTACTATTACGTGAAGTTTAGT<br>GTTCGCCCTTCACATTGTACTTTGGTTTTTGTTTTCCTT<br>GCAATTTGCTCTTTGAAGTATAAAGTGCTGAGTGCTGAG<br>TGCTGAGTGCTGACCTTTCCTGCTCAGGATGTTGCTGCA<br>GATTCTCTTTCTCAATTTTACTATCCACCAGTCGCAGCA<br>GTGTCCCTTTCTTATCCCAAAGAAGCAATTAGACCAGAA<br>TGCTTGATCGATGGAGAACTAAAAGGATTCGGGCAATTG<br>CATCCTCGCAGCCAGGGTGTGGAAACCTTGGGTATATGC<br>TCCCATTCAACTATATCTCAATTTTTATGAGTATTTTC<br>TTTCTCTGAATTATTCAATTTGGTGACGTTAAATTTTGA<br>TTGTACTCGACAGGAACAATTTATAGTTCATCTCTTTTC<br>CCTGGTCGAGCACCCACCTGGTAGGACCTTGATCTTGAGC<br>TACATTGGAGGTGCTACAAATGTTGGCATATTACAAAAG<br>GCAAGTCATTTATACAATTATATCTGTTGTATCCTCAAA<br>TAAGTGGGTATCAATCCTGACGACATGCTTGCTTGTATC<br>GATGCAGAGTGAAGATGA | |

Example 31

This example illustrates a polynucleotide sequence that regulates gene expression in more than one plant species. Two highly conserved regions in EPSPS sequences from different weed species were identified and shown as the "Region 1" and "Region 2" sequences in Table 23.

TABLE 23

| Species/gene or consensus sequence | Region 1 | SEQ ID NO: | Region 2 | SEQ ID NO: |
|---|---|---|---|---|
| Euphorbia_heterophylla_1Contig1 | AGTTTACAGGGAGATGTAAAGTT | 239 | TCGATGTGAACATGAACAAAATGCCAGATGTCGCTATGACATTGGCTGTGGTTG | 251 |
| Euphorbia_heterophylla_2Contig1 | AGTTTGCAGGGAGATGTGAAATT | 240 | TCGATGTGAATATGAACAAAATGCCAGATGTTGCTATGACATTAGCTGTGGTTGC | 252 |
| Ambrosia_trifida_1Contig1 | AGTTTACAGGGGGATGTAAAGTT | 241 | TCGATGTTAACATGAACAAAATGCCAGATGTTGCCATGACGCTTGCAGTCGTTGC | 253 |
| velvetleaf_1Contig1 | AGTTTGCAGGGTGATGTAAAATT | 242 | TTGATGTCAACATGAACAAAATGCCAGATGTTGCCATGACTCTCGCTGTTGTTGC | 254 |
| Xanthium_strumarium_2Contig1 | AGTTTGCAGGGTGATGTGAAATT | 243 | TTGATGTCAACATGAACAAAATGCCTGATGTCGCAATGACTCTTGCTGTGGTTGC | 255 |
| Ipomoea_hederacea_1Contig_1 | AGTTTACAGGGGGATGTTAAGTT | 244 | TTGATGTCAACATGAACAAAATGCCAGATGTTGCCATGACTCTTGCTGTAGTTGC | 256 |
| Chenopodium_album_1Contig1 | AGTTTACAGGGTGATGTAAAATT | 245 | TTGATGTCAACATGAACAAAATGCCAGATGTCGCAATGACTCTTGCTGTTGTTGC | 257 |
| Digitaria_sanguinalis_1Contig1 | AGTTTGCAGGGTGATGTGAAATT | 246 | TTGACGTCAACATGAACAAAATGCCTGATGTCGCAATGACTCTTGCTGTGGTTGC | 258 |
| Senna_obtusifolia_1Contig3 | AGTTTACAGGGAGATGTAAAATT | 247 | TTGATGTCAACATGAACAAGATGCCAGATGTTGCCATGACGCTTGCTGTAGTTGC | 259 |
| Waterhemp_EPSPS | AGTTTACAGGGTGATGTAAAATT | 248 | TCGACGTCAACATGAATAAAATGCCAGATGTTGCTATGACTCTTGCAGTTGTTGC | 260 |
| Palmer_EPSPS | AGTTTACAGGGTGATGTAAAATT | 249 | TCGACGTCAACATGAACAAAATGCCAGATGTTGCTATGACTCTTGCAGTTGTTGC | 261 |
| palmer_1Contig1 | AGTTTACAGGGTGATGTAAAATT | 250 | TCGACGTCAACATGAACAAAATGCCAGATGTTGCTATGACTCTTGCAGTTGTTGC | 262 |

Table 24 lists 21-, 22-, 24-, 35-, 45-, and 55-mer dsRNA polynucleotide sequences designed based on the EPSPS consensus sequence for region 2, TNGANGTcAAcATGAAcAAaATGCCaGATGTNGCNATGACNcTtGCNGTNGTTGC (SEQ ID NO:263).

TABLE 24

| Name | Sequence | SEQ ID NO: |
|---|---|---|
| Consensus_21mer dsRNA | Sense: AACAUGAACAAAAUGCCAGAU | 264 |
| | Anti-sense: AUCUGGCAUUUUGUUCAUGUU | 265 |
| Consensus_22mer dsRNA | Sense: AACAUGAACAAAAUGCCAGAUG | 266 |
| | Anti-sense: CAUCUGGCAUUUUGUUCAUGUU | 267 |
| Consensus_24mer dsRNA | Sense: CAACAUGAACAAAAUGCCAGAUGU | 268 |
| | Anti-sense: ACAUCUGGCAUUUUGUUCAUGUUG | 269 |
| Consensus_35mer dsRNA | Sense: UCGACGUCAACAUGAACAAAAUGCCAGAUGUUGCU | 270 |
| | Anti-sense: AGCAACAUCUGGCAUUUUGUUCAUGUUGACGUCGA | 271 |
| Consensus_45mer dsRNA | Sense: UCGACGUCAACAUGAACAAAAUGCCAGAUGUUGCUAUGACUCUUG | 272 |
| | Anti-sense: CAAGAGUCAUAGCAACAUCUGGCAUUUUGUUCAUGUUGACGUCGA | 273 |

TABLE 24-continued

| Name | Sequence | SEQ ID NO: |
|---|---|---|
| Consensus_55mer dsRNA | Sense:<br>UCGACGUCAACAUGAACAAAAUGCCAGA<br>UGUUGCUAUGACUCUUGCAGUUGUUGC | 274 |
| | Anti-sense:<br>GCAACAACUGCAAGAGUCAUAGCAACAU<br>CUGGCAUUUUGUUCAUGUUGACGUCGA | 275 |

The EPSPS consensus dsRNA polynucleotides were synthesized by in vitro transcription and topically applied as crude RNA preparations. Glyphosate-resistant weeds (16-copy Palmer amaranth and horseweed) were treated with the six individual (21-, 22-, 24-, 35-, 45-, 55-mer) consensus dsRNAs; non-glyphosate-resistant weeds (waterhemp, sicklepod, crabgrass, morning glory, lambsquarter, *Euphorbia*) were treated with the three individual shorter (21-, 22-, 24-mer) consensus dsRNAs. Following polynucleotide treatment glyphosate-resistant plants were treated with glyphosate (1682 g acid equivalent per hectare of Roundup® WeatherMAX® brand herbicide) and non-glyphosate-resistant plants were treated with glyphosate (105 g acid equivalent per hectare of Roundup® WeatherMAX® brand herbicide). At 7 days after treatment all six EPSPS region 2 consensus dsRNA polynucleotides were found to give 100% control (killed plants) of glyphosate-resistant Palmer amaranth; control Palmer amaranth plants treated with glyphosate alone were not killed. At 7 days after treatment, the three shorter (21-, 22-, 24-mer) EPSPS region 2 consensus dsRNA polynucleotides tested individually were found to give 95%, 80% and 65% control (combining killed and injured plants), respectively, of waterhemp; waterhemp plants treated with glyphosate alone gave about 40% control (combining killed and injured plants); and a mixture of all three shorter (21-, 22-, 24-mer) consensus dsRNA polynucleotides gave about the same control as glyphosate alone. The EPSPS region 2 consensus dsRNA polynucleotides did not cause an observable effect on the other weed species (horseweed, sicklepod, crabgrass, morning glory, lambsquarter, *euphorbia*) tested.

Example 32

This example illustrates use of a topical polynucleotide treatment for transiently silencing a gene in a plant to effect a desired phenotype. Silencing polyphenol oxidase in plant tissues inhibits browning of cut or damaged plant tissues, a valuable trait for fruits and vegetables where resistance to browning is a desirable trait.

Anti-sense DNA oligonucleotides with the sequences shown in Table 25 were designed to target three polyphenol oxidase genes (PPO1, PPO2, and PPO3) from lettuce; the underlined text indicates T7 sequence that was included in the anti-sense polynucleotides.

TABLE 25

| Anti-sense oligo-nucleotide | Sequence (5'-3') | SEQ ID NO. | Length |
|---|---|---|---|
| HH07 | <u>TAATACGACTCACTATAGGG</u>CTTTA TTGAATTTAGCTATGTAATC | 276 | 45 |
| HH09 | <u>TAATACGACTCACTATAGGG</u>TTTAT CAACCAAATGTGCAGC | 277 | 41 |

TABLE 25-continued

| Anti-sense oligo-nucleotide | Sequence (5'-3') | SEQ ID NO. | Length |
|---|---|---|---|
| HH11 | <u>TAATACGACTCACTATAGGG</u>TTGTC TGTACATAATTGTGAGATTTGTGG | 278 | 49 |

Three-week old lettuce plants (variety SVR3603 L4) were treated as follows. Two source leaves (leaves that are older and are ~60% of their mature size) on each plant were pre-treated with 0.1% (v/v) SILWET L-77® brand surfactant and allowed to dry (~15 minutes). To each leaf 20 microliters of a mixture of the polyphenol oxidase anti-sense polynucleotides in a solution of 0.01% (v/v) SILWET L-77® brand surfactant and 2% (w/v) ammonium sulfate in 5 millimolar sodium phosphate, pH 6.8, were applied as small droplets; each plant was treated with 6.7 nanomoles of each of the three polynucleotides HH07, HH09, and HH11 (for a total of 20 nanomoles per plant). Control plants were treated either with an unrelated polynucleotide HH02-05 (anti-sense to phytoene desaturase) or with buffer (0.01% (v/v) SILWET L-77® brand surfactant and 2% (w/v) ammonium sulfate in 5 millimolar sodium phosphate, pH 6.8) alone.

Approximately 3 weeks after the topical polynucleotide treatment, "untreated" lettuce leaves (i.e., not those treated with the topical polynucleotides) were cut from the lettuce head under water and incubated in a cup with 1.33 millimolar methyl jasmonate in 5% ethanol. Leaves were inspected for central rib browning and photographed every 24 hours. Samples were taken from the remaining plants and frozen for small RNA and mRNA analysis Plants treated with the polyphenol oxidase anti-sense polynucleotides HH07, HH09, and HH11 showed significant reduction in central rib browning after treatment with methyl jasmonate. Plants treated with HH02-05 (anti-sense to phytoene desaturase) as a control showed a small reduction in central rib browning compared to the buffer-treated control.

Example 33

This example illustrates an herbicidal composition adapted for topical coating onto the exterior surface of a growing plant comprising surfactant and at least one plant lethal agent, the improvement wherein the plant lethal agent includes polynucleotides having a sequence essentially identical or complementary to sequence of a plant gene or sequence of the plant gene's transcribed RNA, the polynucleotides effecting systemic suppression of the plant gene. More specifically this example illustrates an herbicidal composition adapted for topical coating onto the exterior surface of a growing plant comprising surfactant and at least one plant lethal agent, the improvement wherein the plant lethal agent includes polynucleotides effecting suppression of the endogenous phytoene desaturase (PDS), 5-enolpyruvylshikimate-3-phosphate synthase (EPSPS), or ribulose-1,5-bisphosphate carboxylase oxygenase (RuBisCO) genes from *Nicotiana benthamiana*. This example also illustrates the use of topically applied polynucleotides to suppress a very highly expressed gene (ribulose-1,5-bisphosphate carboxylase oxygenase) in a plant.

An anti-sense polynucleotide with the sequence CATCTCCTTTAATTGTACTGC (SEQ ID NO:34) was designed for the endogenous *Nicotiana benthamiana* phytoene desaturase (PDS) gene, which has the cDNA sequence fragments ATGC- CCCAAATCGGACTTGTATCTGCTGT-
TAATTTGAGAGTCCAAGGTAATTCAGCTTATCTTTGGAGC TCGAGGTCTTCGT-
TGGGAACTGAAAGTCAAGATGTTTGCTTGCAAAGGAATTTGTTATGTTTTGGT
AGTAGCGACTCCATGGGGCATAAGT-
TAAGGATTCGTACTCCAAGTGCCACGACCCGAAGATTGACAAAGG ACTT-
TAATCCTTTAAAGGTAGTCTGCATTGAT-
TATCCAAGACCAGAGCTAGACAATACAGTTAACTATT
TGGAGGCGGCGTTATTATCAT-
CATCGTTTCGTACTTCCTCACGCCCAACTAAACCATTGGAGATTGTTA TTGCTG-
GTGCAGGTTTGGGTGGTTTGTCTACAG-
CAAAATATCTGGCAGATGCTGGTCACAAACCGATA
TTGCTGGAGGCAAGAGATGTCCTAG-
GTGGGAAGGTAGCTGCATGGAAAGATGATGATGGAGATTGGT
ACGAGACTGGGTTGCACATAT-
TCTTTGGGGCTTACCCAAATATGCAGAACCTGTTTGGAGAACTAGGG ATTGAT-
GATCGGTTGCAGTGGAAGGAACAT-
TCAATGATATTTGCGATGCCTAACAAGCCAGGGGAGTT
CAGCCGCTTTGATTTTCCTGAAGCTCT-
TCCTGCGCCATTAAATGGAATTTTGGCCATACTAAAGAACAA CGAAATGCT-
TACGTGGCCCGAGAAAGTCAAATTTGC-
TATTGGACTCTTGCCAGCAATGCTTGGAGGGC
AATCTTATGTTGAAGCTCAAGACGGTT-
TAAGTGTTAAGGACTGGATGAGAAAGCAAGGTGTGCCTGAT AGGGTGACA-
GATGAGGTGTTCATTGCCATGTCAAAG-
GCACTTAACTTCATAAACCCTGACGAGCTTTC
GATGCAGTGCATTTTGATTGCTTTGAA-
CAGATTTCTTCAGGAGAAACATGGTTCAAAAATGGCCTTTTT AGATGGTAAC-
CCTCCTGAGAGACTTTGCATGCCGAT-
TGTGGAACATATTGAGTCAAAAGGTGGCCAAG
TCAGACTAAAACTCACGAATAAAAAA-
GATCGAGCTGAATGAGGATGGAAGTGTCAAATGTTTTATACTG AATAATG-
GCAGTACAATTAAAGGAGATGCTTTTGT-
GTTTGCCACTCCAGTGGATATCTTGAAGCTTCTT
TTGCCTGAAGACTGGAAAGAGATC-
CCATATTTCCAAAAGTTGGAGAAGCTAGTGGGAGTTCCTGTGAT AAATGTC-
CATATATGGTTTGACAGAAAACTGAA-
GAACACATCTGATAATCTGCTCTTCAGCAGAAGCC
CGTTGCTCAGTGTGTACGCTGACAT-
GTCTGTTACATGTAAGGAATATTACAACCCCAATCAGTCTATGT TGGAATTGG-
TATTTGCACCCGCAGAAGAGTG-
GATAAATCGTAGTGACTCAGAAATTATTGATGCTACA
ATGAAGGAACTAGCGAAGCTTTTCCCT-
GATGAAATTTCGGCAGATCAGAGCAAAGCAAAAATATTGA AGTATCATGTTGT-
CAAAACCCCAAGGTCTGTTTATAAAACT-
GTGCCAGGTTGTGAAACCTGTCGGCCCT
TGCAAAGATCCCCTATAGAGGGTTTT-
TATTTAGCTGGTGACTACACGAAACAGAAGTACTTGGCTTCA ATGGAAGGT-
GCTGTCTTATCAGGAAAGCTTTGTGCA-
CAAGCTATTGTACAGGATTACGAGTTACTTCTT
GGCCGGAGCCAGAAGATGTTGGCAGAAG-
CAAGCGTAGTTAGCATAGTGAACTAA (SEQ ID NO:38). Anti-sense polynucleotides with the sequences CTGTGATCATCATATGTATCA (SEQ ID NO:279), CCTTAACTCTCCAGCTAGCAA (SEQ ID NO:280), CAGCCCGCAAATGTTTCATTC (SEQ ID NO:281), GCCGTCAATGGCCGCATTGCT (SEQ ID NO:282), TCCTTCCCTCAGAAAGGGCAG (SEQ ID NO:283), and TTGCCTCATGCTGCTAATCTG (SEQ ID NO:284) were designed for the endogenous *Nicotiana benthamiana* 5-enolpyruvylshikimate-3-phosphate synthase (EPSPS) gene, based on the *Nicotiana benthamiana* EPSPS cDNA sequence CTTATATGTGCTTAAGCCTAACGTGCACCCGGCCCCTTAACCCCAGCAGTTTTCAATCTACCTACCGTC TCTACCATTTTCTTCTAGTTGGT-
GAAAATTTCTAACTTTGAGAAAACAAGCCAAAGTTTTTGTTTCTAA
GAACGCAAAATGAGTGAAATTTTTTG-
CAGCAATGGCACAGATTAGCAGCATGAGGCAAGGGATACAG ACCCCTAATCT-
TAATTCCTATTTTCCTAAAACCCAAAAG-
GTTCCTCTTTTTTCGCATTCTATCTTCTTTG
GATCAAAGAAAATAACCCAAAATTCAG-
CAAAATCTTTGTGGGTGTGTAAGAAAGATTCAGTTTTGAGG GTGGCAAAGT-
CACCTTTTAGGATTTGTGCATCAGTGGC-
CACTGCACGAAAGCCCAACGAGATTGTGCT
GCAACCCATCAAAGATATATCAGGCACT-
GTTAAATTGCCTGGTTCTAAATCCCTTTCCAACCGTATTCT CCTTCTTGCTGC-
CCTTTCTGAGGGAAGGACTGTTGTTGA-
CAATTTACTGAGTAGTGATGACATTCATTA
CATGCTTGGTGCGTTGAAAACACTTG-
GACTTCATGTAGAAGATGACAATGAAAACCAACGAGCAATTG TGGAAGGT-
TGTGGTGGGCAGTTTCCTGTCGGC-
GAGAAGTCTGAGGAAGAAATCCAACTATTCCTTGGA
AATGCAGGAACAGCAATGCGGCCAT-
TGACGGCAGCAGTTACTGTAGCTGGAGGACATTCAAGATATG TACTTGATG-
GAGTTCCTAGGATGAGAGAGAGACCGAT (SEQ ID NO:285), CACTGACGTTGGATTAGAGGTAGGCTCCTTATATGTGCTTAAGCCTAACGTGCAGCC
GGCCCCCAACC CCAGCAGTTTTCAATCTACCTAC-
CGTCTCTACCATTTTCTTATAGTAGTTGAAAATTTCTAACTTTGAGA AAACAAGCCAAAGTTTTGTTTCTAAGAACA-
CAAAGGGAGTGAAATTTTTTGCAGCAATGGCACAGATT
AGCAGCATGAGGCAAGGGATACAGAC-
CCCTAATCTTAATTCCTATTTTCCTAAAACCCAAAAGGTTCC TCTTTTTTCGCAT-
TCTATCTTCATTGGATCAAA-
GAAAATAACCCAAAATTCAGCCAAAATCTTTGTGGGT
GTGTAAGAAAGATTCAGTTTTGAGGGTG-
GCAAAGTCACCTTTTAGGATTTGTGCATCAGTGGCCACTG CACAGAAGC-
CTAACGAGATTGTGCTGCAACCTAT-
CAAAGATATATCAGGCACTGTTAAATTACCTGGT
TCTAAATCCCTTTCCAATCGTATTCTC-
CTTCTTGCTGCCCTTTCTGAGGGAAGGACTGTTGTTGACAATT TACTGAGTAGT-
GATGACATTCATTACATGCTTGGTGCAT-
TGAAAACACTTGGACTTCATGTAGAAGAT
GACAATGAAAACCAACGAGCAATCGTA-
GAAGGTTGTGGTGGGCAGTTTCCTGTCGGCAAGAAGTCTG AGGAAGAAATC-
CAACTATTCCTTGGAAATGCAGGAACAG-
CAATGCGGCCATTGACGGCAGCAGTTAC
TGTAGCTGGTGGACATTCTAGATATGTACTTGATGGAGTTCCTAGGAT (SEQ ID NO:286), and AAATTCTTGGTTCGAGGAGGTCAGAAG-
TACAAGTCTCCTGGAAAAGCATATGTTGAAGGAGATGCCTC AAGTGCTAGC-
TACTTTTTGGCGGGTGCAGCTGTCACAG-
GTGGAACTGTCACTGTTGAAGGTTGTGGAA
CAAGCAGTTTACAGGGGGATGT-
TAAGTTTGCTGAGGTCCTCGAAAAGATGGGGGCAGAAGTTACATG GACAGAGAACAGTGTCACGGTTAAAGGACCTC-
CAAGGAACTCTTCTGGAATGAAACATTTGCGGGCTG
TTGACGTTAACATGAACAAAATGCCA-
GATGTTGCCATGACTCTTGCTGTAGTTGCACTTTTTGCTGATA GTCCTACTGC-
CATAAGAGATGTTGCTAGCTGGAGAGT-
TAAGGAAACTGAGCGGATGATTGCCATATGC
ACAGAACTTAGGAAGTTGGGTGCAA-
CAGTTGTAGAAGGGCCAGACTACTGCATAATCACTCCACCTGA AAAGTTAAAAGTAGCGGAAATTGATACATAT-
GATGATCACAGAATGGCCATGGCTTTCTCTCTTGCGG
CTTGTGCTGATGTTCCAGTCACCAT-
TAAGGACCCCGGTTGTACTCGCAAAACCTTCCCCAACTACTTTG ACGTTCTC-
CAGCAGTATTCCAAGCATTAAAC-
CACTTTCCATTAAGAATTTTGAAAAAGAGAGACTTTG
ACAACAATGGTGTCATACCGGAA-
GAGAAAAGCTTTGATCCAAGCTTTCAACTCCTTTTCATTTGTCATG TGATGAT-
CATTGTATTTGTTGAAGTTGAGCT-
GCTTTTCTTTTGTCCAGAAGACATGTATGGATACTATTA
CTATATAGTTAAGGTGAACTCAGCA (SEQ ID NO:287). Anti-sense polynucleotides with the sequences CCACATGGTTCCAGTATCTGCC (AK195, RBCS__1-2-3-4, SEQ ID NO:288), CAAGCAAGGAAC-
CCATCCATT (AK196, RBCS__1-2-3-4, SEQ ID NO:289), GGC-
CACACCTGCATGCATTGC (AK197, RBCS__1-2-3-4, SEQ ID NO:290), GTGTTCACGGTAGACAAATCC (AK198, RBCS__1-2, SEQ ID NO:291), TGCACTGCACTTGACGCACGT (AK199, RBCS_1-2, SEQ ID NO:292), AACTGATGCATTGCACTTGAC (AK200, RBCS_3-4, SEQ ID NO:293), CAAATCAGGAAGGTATGAGAG (AK201, RBCS_3-4, SEQ ID NO:294), and TGTCAAGGTTTTGTTTCCTGG (AK202, RBCS_3-4, SEQ ID NO:295) were designed for the endogenous *Nicotiana benthamiana* ribulose-1,5-bisphosphate carboxylase oxygenase (RuBisCO) gene, based on the *Nicotiana benthamiana* chloroplastic RuBisCO small chain 2A cDNA sequence fragments GCAATGGCTTCCTCAGTTCTTTCCTCAG-CAGCAGTTGCCACCCGCAGCAATGTTGCTCAAGCTAACATG GTTGCAC-CTTTCACAGGTCTTAAGTCTGCTGCCT-CATTCCCTGTTTCAAGAAAGCAAAACCTTGACATC ACTTCCATTGCCAGCAACGGCGGAA-GAGTGCAATGCATGCAGGTGTGGCCACCAATTAACATGAAGA AGTAT-GAGACTCTCTCATACCTTC-CCGATTTGAGCCAGGAGCAATTGCTCTCCGAAATTGAGTACCTTT TGAAGAATGGATGGGTTCCTTGCTTG-GAATTCGAGACTGAGAAAGGATTTGTCTACCGTGAACACCAC AAGTCAC-CAGGATACTATGATGGCAGATACTGGAC-CATGTGGAAGCTACCTATGTTCGGATGCACTGA TGCCACCCAAGTGTTGGCTGAGGTGG-GAGAGGCGAAGAAGGAATACCCACAGGCCTGGGTCCGTATC ATTG-GATTTGACAACGTGCGTCAAGTGCAGTG-CATCAGTTTCATTGCCTCCAAGCCTGACGGCTAC (SEQ ID NO:296), ACAATGGCTTCCTCAGTTCTTTCCTCAG-CAGCAGTTGCCACCCGCAGCAATGTTGCTCAAGCTAACATG GTTGCAC-CTTTCACTGGTCTTAAGTCAGCTGC-CTTTTTCCCTGTTTCAAGGAAGCAAAACCTTGACATC ACTTCCATTGCCAGCAACGGCGGAA-GAGTGCAATGCATGCAGGTGTGGCCACCAATTAACAAGAAGA AGTAC-GAGACTCTCTCATACCTTCCTGATCT-GAGCGTGGAGCAATTGCTTAGCGAAATTGAGTACCTCT TGAAAAATGGATGGGTTCCTTGCTTG-GAATTCGAGACTGAGCGCGGATTTGTCTACCGTGAACACCAC AAGTCAC-CGGGATACTATGACGGCAGATACTGGAC-CATGTGGAAGTTGCCTATGTTCGGATGCACTGA TGCCACCCAAGTGTTGGCCGAGGTGGAA-GAGGCGAAGAAGGCATACCCACAGGCCTGGATCCGTATT ATTGGATTCGA-CAACGTGCGTCAAGTGCAGTGCAT-CAGTTTCATTGCCTACAAGCCAGAAGGCTAC (SEQ ID NO:297), CAAGCCAACATGGTTGCACCCTTCACTG-GCCTCAAGTCCGCCTCCTCCTTCCCTGTTACCAGGAAACAA AACCTTGA-CATTACCTCCATTGCTAGCAATGGTG-GAAGAGTTCAATGCATGCAGGTGTGGCCACCAAT TAACATGAAGAAGTACGAGACACTCT-CATACCTTCCTGATTTGAGCCAGGAGCAATTGCTTAGTGAAG TTGAGTAC-CTTTTGAAAAATGGATGGGTTCCTTGCT-TGGAATTCGAGACTGAGCGTGGATTCGTCTACC GTGAACACCACAACTCACCAGGATAC-TACGATGGCAGATACTGGACCATGTGGAAGTTGCCCATGTTC GGGTGCACT-GATGCCACTCAGGTGTTGGCTGAGGTC-GAGGAGGCAAAGAAGGCTTACCCACAAGCCT GGGTTAGAATCATTGGATTCGA-CAACGTCCGTCAAGTGCAATGCATCAGTTTTATCGCCTCCAAGCCA GAAG-GCTAC (SEQ ID NO:298), and GGCTCAGTTATGTCCTCAGCTGCCGCT-GTTTCCACCGGCGCCAATGCTGTTCAAGCCAGCATGGTCGCA CCCT-TCACTGGCCTCAAGGCCGCCTCCTCCT-TCCCGGTTTCCAGGAAACAAAACCTTGACATTACTTCC ATTGCTAGAAATGGTGGAAGAGTCCAAT-GCATGCAGGTGTGGCCGCCAATTAACAAGAAGAAGTACG AGACACTCT-CATACCTTCCTGATTTGAGCGTGGAG-CAATTGCTTAGCGAAATTGAGTACCTTTTGAAAA ATGGATGGGTTCCTTGCTTGGAATTC-GAGACTGAGCATGGATTCGTCTACCGTGAACACCACCACTCA CCAGGATAC-TACGATGGCAGATACTGGACGATGTG- GAAGTTGCCCATGTTCGGGTGCACCGATGCCAC TCAGGTCTTGGCTGAGGTAGAGGAGGC-CAAGAAGGCTTACCCACAAGCCTGGGTCAGAATCATTGGAT TCGA-CAACGTCCGTCAAGTGCAATGCAT-CAGTTTCATCGCCTACAAGCCCGAAGGCTAT (SEQ ID NO:299).

Figure 36:
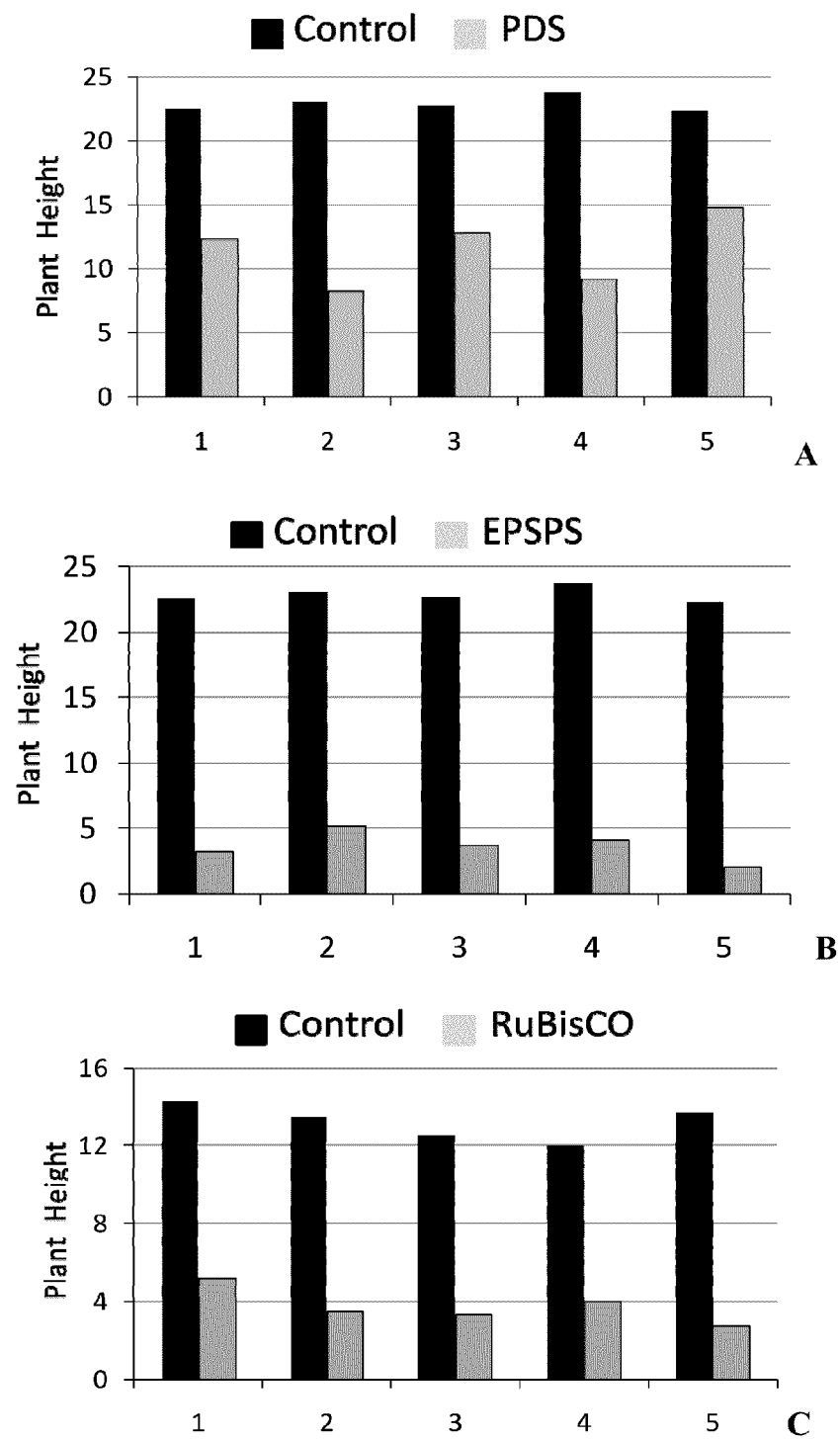
FIG. 36 illustrates the effect on plant height in *Nicotiana benthamiana* in plants treated with a PDS anti-sense polynucleotide (FIG. 36A), EPSPS anti-sense polynucleotides (FIG. 36B), or RuBisCO anti-sense polynucleotides (FIG. 36C), as described in Example 33.

*Nicotiana benthamiana* plants were treated using a procedure similar to that described in Example 12. Polynucleotide solution (or mixed polynucleotides in the case of EPSPS and RuBisCO) were prepared in 0.01% (v/v) SILWET L-77® brand surfactant and 2% (w/v) ammonium sulfate in 5 millimolar sodium phosphate, pH 6.8. Two fully expanded leaves per plant were dipped into 0.1% SILWET L-77® brand surfactant solution freshly made with ddH2O for a few seconds, and allowed to dry. About 30 minutes later, 20 microliters of polynucleotide solution, was applied to each of the two pretreated leaves. For PDS, each of 5 plants received 25 nanomoles of the PDS anti-sense polynucleotide (SEQ ID NO:34); for EPSPS, each of 5 plants received 50 nanomoles of each EPSPS anti-sense polynucleotide (SEQ ID NOS:279-284); and for RuBisCO, each of 5 plants received 50 nanomoles of each RuBisCO anti-sense polynucleotide (SEQ ID NOS:288-295). Paired control plants were treated with buffer (0.01% (v/v) SILWET L-77® brand surfactant and 2% (w/v) ammonium sulfate in 5 millimolar sodium phosphate, pH 6.8). The results measured as plant height at 12 days (PDS and EPSPS) or 10 days (RuBisCO) after treatment, are shown in FIGS. 36A-36B. Plants treated with the PDS anti-sense polynucleotide displayed severe stunting (FIG. 36A) and bleaching. Plants treated with the EPSPS anti-sense polynucleotides displayed severe stunting (FIG. 36B) and severe damage to the meristem and stem tissues. Plants treated with the RuBisCO anti-sense polynucleotides displayed severe stunting (FIG. 36C) and malformed apical tissues.

A second set of experiments was designed to investigate the effects of silencing a component of the endogenous RNAi silencing pathway in a plant. Argonaute (AGO) proteins are components of the RNA-induced silencing complex (RISC) which binds small RNAs in the RNAi silencing process. Suppression of Argonaute would be expected to reduce the observed phenotypic effect caused by an RNAi silencing process. AGO1 anti-sense polynucleotides with the sequences GGAGGCAAAATACGAGCCTCA (HL510, SEQ ID NO:300), CACTAATCTTAATACCAAACT (HL511, SEQ ID NO:301), TATGGGTCATTAGCATAGGCATTAT (HL512, SEQ ID NO:302), TCT-CAAGAATATCACGCTCCC (HL513, SEQ ID NO:303), CCCTTGGG-GACGCTGGCAGGTCAC (HL514, SEQ ID NO:304), TAATACGACTCAC-TATAGGGGAGAGAGCTAGATCTTTTG (HL515, SEQ ID NO:305), TAATACGACTCACTATAGGCACAGTATTTCTTCCTCCAACC (HL516, SEQ ID NO:306), TTGCTCATCTTAAATACATGT (HL517, SEQ ID NO:307), TCATCTTAAATACATGTTTTGTCA (HL518, SEQ ID NO:308), TTATCTTCAGGGATACATTAGC (HL519, SEQ ID NO:309), AATACTGCTTGCTCATCTTAAATA (HL520, SEQ ID NO:310), GACAATTCCAAGTTCAGTTTC (HL521, SEQ ID NO:311), CCGTTTTAGATCACCATAAAGAGA (HL522, SEQ ID NO:312), TTGTCTGGTAATATCACAATC (HL523, SEQ ID NO:313) were designed for the endogenous *Nicotiana benthamiana* Argonaute-1 (AGO1) gene, based on two *Nicotiana benthamiana* AGO1-2 partial cDNA sequences, ATGGTGAGGAAGAGGAGAACTGAGTTAC-CTGGTTCTGGTGAGAGCTCTGGGTCTCAAGAAACTGGCG GACAGGGTCGTGGCCAGCATCCACAG-CAGCTGCACCAAGCTACCTCCCAGACTCCATATCAAACTGCA ATGACTACT-CAGCCAATACCTTATGCAAGACCAACT-GAAACATCCTCCGAAGCTGGTTCCTCATCTCA GCCACCTGAGCAGGCAGCTCTACAAGT-GACACAACAGTTCCAGCAACTTGCTTTGCAACAAGAAGCGG CTACAACG-CAAGCAGTTCCACCTGCATCAAGCAAAT- TACTAAGGTTTCCCCTGCGTCCAGGGAAGGGGAGCAATGGTATGAGATGCATAGT-CAAAGCCAATCACTTCTTCGCAGAGCTGCCTGACAAAGACTTGCA CCAG-TATGATGTCACAATTTCTCCAGAGGTGT-CATCACGTGGCGTCAACCGTGCTGTCATGGCGCAACT GGTGAAGCTGTACCAAGAATCTCATCT-TGGGAAGAGACTTCCAGCATATGATGGAAGGAAAAGTCTAT ACACTG-CAGGGCCCCTTCCATTTGTTCAAAAA-GACTTCAAAATAACTCTTATTGATGATGAGGATGGG CCTGGTGGTGCTAGAAGGGAAAGG-GAATTTAAAGTTGTGATCAAATTGGCTGCCCGTGCTGATCTTCA TCACT-TGGGAATGTTTTTAGAAGGGAAACAG-GCTGATGCACCTCAAGAGGCGCTTCAAGTTCTGGATA TTGTTCTGCGTGAGTTGCCAACATCTAG-GTTTTGTCCTGTGGGTCGTTCTTTCTATTCCCGTGATTTAGG GCGAAAG-CAACCATTGGGTGAAGGTTTAGAAAGT-TGGCGTGGGTTCTATCAAAGCATTCGCCCCACAC AAATGGGCTTATCACTGAACATCGATAT-GTCTTCCACTGCATTCATTGAGCCACTGCCAGTCATTGATT TTGTGACA-CAGCTTCTGAACCGAGATGTGCCATCTA-GACCACTGTCTGATCTGGCCGTGTAAAGATA AAAAAAGCTCTGAGAGGTGTGAAGGTG-GAGGTTACTCATCGTGGAAATATGCGGAGGAAGTACCGCA TTTCGGGTT-TAACATCTCAAGCAACAAGAGAGTTGAC-CTTCCCTGTTGATGAAAATGGTACAGTGAAA TCTGTAATTGAGTATTTTCGAGAAA-CATATGGGTTTGTAATTCAGCATACTCAGTGGCCTTGTCTACAA GTTG-GAAATCAGCAGAGACCTAATTACTTGC-CAATGGAAGTCTGCAAGATTGTGGAGGGACAAAGGT ACTCAAAGCGCTTGAATGAGAGACAGAT-TACTGCACTTCTGAAAGTGACCTGCCAGCGTCCCCAAGGG AGGGAGCGT-GATATTCTTGAGACCGTACATCATAAT-GCCTATGCTAATGACCCATATGCCAAGGAGTT TGGTATTAAGATTAGTGACAAGTTGGCA-CAAGTTGAGGCTCGTATTTTGCCTCCACCTCGGCTTAAATA TCAT-GATAACGGTCGAGAAAAGGACTGCCTGC-CACAAGTTGGCCAATGGAATATGATGAATAAGAAA ATGGTAAATGGAGGGACGGTGAACAAT-TGGATCTGCATAAACTTCTCTCGCAATGTGCAAGATAGTGT TGCT-CATGGGTTTTGCTCTGAGCTTGCA-CAAATGTGCCAGATATCTGGCATGAATTTCAATCCAAATCC TGTTCTGCCACCTTCGAGTGCACGCCCT-GATCAGGTCGAAAGAGTATTGAAAACTCGATTTCATGATGC TATGAC-TAAGTTGCAGCTGCATGGGAGAGAGCT-TGATTTGCTAGTTGTCATCTTGCCAGACAATAATG GATCTCTTTATGGTGATCTGAAGCG-CATTTGTGAGACTGAACTAGGAGTCGTCTCACAGTGCTGTTTGA CAAAA-CATGTATTTAAGATGAGCAAACAG-TATCTAGCCAATGTAGCGCTGAAAATCAATGTGAAGGTG GGAGGGAGAAACACTGTGCTTGTTGATG-CAATATCGAGGCGAATTCCTCTTGTCAGCGACCGGCCTAC CATCATTTTTG-GTGCAGATGTCACCCACCCTCAC-CCTGGGGAGGACTCTAGCCCATCCATTGCCGCGGT GGTTGCTTCTCAAGATTGGCCTGAGAT-TACAAAGTATGCTGGTCTAGTTTCTGCTCAAGCCCATAGGCA AGAGCTTAT-TCAGGATCTGTACACGACTAGGCAA-GATCCTGTTAAGGGGACAGTTGCTGGTGGAATGA TTAAGGACTTACTTATATCCTTCCGAA-GAGCTACTGGACAAAAGCCCCAGAGAATAATTTTCTATAGG GATGGTGT-TAGTGAAGGACAATTTTATCAAGTGCT-TCTGTTCGAACTTGATGCGATCCGCAAAGCATGT
GCGTCTTTGGAGCCAAATTATCAGC-
CCCCAGTCACATTTGTTGTGGTTCAGAAACGACATCACACAAG
GCTTTTTGCCAATAACCACCGTGACA-
GAAATGCAGTTGACAGGAGCGGGAACATTATACCTGGTACTG TTGTAGAT-
TCAAAGATATGCCACCCGACA-
GAGTTTGATTTCTATCTTTGTAGCCATGCCGGCATACAGG
GTACGAGCCGTCCAGCTCACTACCATGT-
TCTATGGGACGAGAACAAATTCACAGCCGATGCGCTGCAG TCTTTGAC-
CAACAACCTCTGCTATACATATGCAAG-
GTGCACGCGTTCCGTCTCCATCGTTCCCCCTGCA
TATTATGCACATTTGGCAGCTTTCCGT-
GCTCGATTTTATATGGAGCCGGAGACATCTGACGGTGGTTCA GTAA-
CAAGTGGGGCTGCTGGTGGCA-
GAGGGGGTGGTGCAGGAGCTGCTGGAAGGAACACCCGAGCCC
CAAGTGCTGGTGCTGCTGTTAGACCTCT-
TCCTGCGCTCAAGGATAATGTGAAGAGGGTTATGTTCTACT GC (SEQ ID NO:314) and CACCTATCACTCTCTTTCTCTCTCTA-
CAAACATATCGTGCCGTTTCTCTCTCGGCCTCTCTTCGTGTTTTA GGGCAC-
CGTGGTGGTTGGTATCCAGGCGGCG-
GTTTTGAGTTATTACCATGGTGCGGAAGAAGAGGACT
GATGTTCCTGGTGGTGCT-
GAGAGTTTTGAGTCCCATGAAACTGGAGGGGCACGAGGTGGTGCCCAACG
CCCATCACAGCAGCAGCAACATCAGCAT-
CAGCAAGGCGGAGGAAGAGGCTGGGCACCTCAGCATGGA GGACATGGTG-
GCCGTGGTGGTGGGGGAGCTCCACGTG-
GTGGAATGGCCCCTCAACAATCCTATGGTGG
ACCTCCTGAATACTACCAA-
CAGGGCAGGGGAACTCAACAGTATCAACGAGGTGGAGGACAACCCCAG
CGCCGTGGTGGCATGGGGGGC-
CGTGGGGCACGGCCACCAGTACCCGAGCTGCACCAAGCAACCCAGA CTC-
CACATCAGCCTGTACCATATGGAAGAC-
CATCAGAAACATACTCAGAGGCTGGTTCCTCGTCTCAG
CCACCTGAACCAACGACACAGCAAGT-
GACTCAGCAATTCCAGCAACTTGTTGTGCAGCCAGAAGCAGC TGCAAC-
CCAAGCAATACAACCAGCATCGAG-
CAAGTCGATGAGGTTTCCACTCCGGCCAGGAAAGGGT
AGTACTGGTATTAGATGCATAGTTAAG-
GCCAATCACTTCTTTGCCGAGTTACCTGACAAAGATCTGCAC CAGTATGAT-
GTTTCAATTACTCCTGAGGTCGC-
CTCTCGGGGTGTCAACCGGGCCGTCATGGAGCAGCT
GGTGAAGCTTTATAGAGAATCCCATCT-
TGGGAAGAGGCTTCCAGCCTATGACGGAAGAAAAAGTCTAT ACACAG-
CAGGGCCCCTCCCTTTTGTTCAAAAG-
GATTTTAAAATCACTCTAATTGATGATGATGATGGAC
CTGGTGGTGCTAGGAGGGAAAGAGAGTT-
TAAAGTTGTGATCAAGCTGGCGGCTCGTGCTGATCTTCAT CACTTGGGGAT-
GTTCTTACAAGGGAGACAGGCTGATG-
CACCGCAAGAAGCACTTCAGGTGCTGGATAT
TGTGCTACGTGAGTTGCCAACATCTAGG-
TATTGTCCTGTGGGCCGCTCTTTCTATTCCCCTCATTTAGGA CGAAGA-
CAACCACTGGGTGAAGGTTTA-
GAGAGCTGGCGTGGCTTCTATCAAAGTATTCGTCCTACACA
GATGGGATTATCCCTGAATATTGATAT-
GTCTTCCACGGCTTTCATTGAGCCACTGCCGATTATTGACTT CGTGAGC-
CAGCTTCTGAATCGGGATATCTCTTCTA-
GACCACTGTCTGATGCTGACCGCGTTAAGATAAA
GAAGGCACTGAGAGGTGTAAAG-
GTGGGGGTCACTCATCGTGGAAATATGCGGAGGAAGTATCGCATT TCTG-
GCTTGACGTCTCAAGCAACAAGAGAGT-
TGACTTTTCCTGTCGATGAAAGGGGTACGATGAAAGC
TGTTGTGGAATATTTTCGGGAAAC-
CTATGGTTTTGTCATTCGGCATACCCAGTGGCCTTGTCTTCAAGT
TGGAAATACGCAGAGGCCAAATTACT-
TGCCAATGGAAGTATGTAAGATTGTAGAGGGACAGAGATAC TCAAAGCGCT-
TGAATGAGAGGCAGATAACAGCACT-
TCTAAAAGTGACCTGCCAACGTCCTCAAGAGA
GAGAACGTGATATTCTTCAGACTGT-
TCATCACAATGCTTATGCTGATGACCCATATGCGAAGGAGTTTG GTATTAA-
GATCAGTGAGGAGCTTGCTCAAGTTGAG-
GCTCGCGTTTTGCCTGCACCTTGGCTTAAATACC
ATGATACAGGTCGAGAGAAAGACTGTCT-
GCCACAAGTGGGCCAGTGGAATATGATGAATAAGAAAAT GGTTAATGGAG- GAACAGTGAACAACTGGATCTGTG-TAAACTTTTCTCGCAATGTGCAAGACACAGTTG CACGTGGATTTTGTTCCGAGCTTGCA-CAAATGTGCATGATATCCGGAATGAACTTCAATCCCAATCCTG TTCTAC-CACCAGTGAGTGCTCGCCCTGATCAAGT-TGAGAGAGTCTTGAAAACTCGATTTCACGATGCTA TGACAAAGTTGCAGCCAAATGG-GAGAGAGCTAGATCTTTTGATTGTGATATTACCAGACAATAACGGC TCTCTT-TATGGTGATCTAAAACGGATTTGT-GAAACTGAACTTGGAATTGTCTCACAATGCTGCTTGACA AAACATGTATTTAAGATGAGCAAGCAG-TATTTAGCTAATGTATCCCTGAAGATAAATGTGAAGGTTGG AGGAA-GAAATACTGTGCTGGTTGAT-GCGCTCTCTAGACGAATTCCCCTTGTCAGCGACCGCCCAACTA TCATTTTTGGTGCAGATGTCACCCATC-CCCACCCTGGGGAGGATTCTAGCCCGTCAATTGCTGCGGTGG TTGCTTCT-CAAGATTGGCCTGAAATTACAAAGTAT-GCTGGTTTGGTTTCTGCTCAAGCGCATAGGCAAG AGCTTATACAAGATCTGTACAAGACTTG-GCAAGATCCAGTTAGAGGACCTGTGACTGGTGGCATGATA AAGGAATTACT-TATTTCCTTCCGTCGAGCAACTGGACA-GAAGCCGCAGAGAATTATATTCTACAGAGA TGGTGTTAGTGAAGGACAATTTTAC-CAAGTTCTTCTTTTTGAACTTGATGCAATCCGCAAGGCATGTGC ATCTTTA-GAACCCAACTATCAGCCCCCGGT-TACGTTTGTTGTGGTCCAGAAACGGCATCATACTAGGTT GTTTGCCAATAACCACCACGACAGAAAT-GCAGTTGATCGGAGTGGGAACATTTTGCCTGGTACCGTTG TAGATTCAAA-GATATGCCACCCTACTGAATTTGATTTC-TATCTCTGTAGCCATGCCGGCATACAGGGTA CTAGCCGCCCAGCTCATTATCATGTTCT-
GTGGGATGAGAACAATTTTACTGCTGACGCCCTGCAGTCTT TGACTAA-
CAATCTTTGCTATACATATGCTAGGTG-
TACTCGTTCTGTCTCCATTGTTCCACCAGCATATTA
TGCACATTTGGCAGCTTTCCGTGCTCG-
GTTTTACATGGAGCCAGAGACATCTGATAATGGATCAGTCAC AAGCG-
CAGCTGCTTCAAACAGAGGAGGTTTAG-
GAGCTATGGGAAGGAGCACGCGAGCACCAGGTGCT
GGTGCTGCTGTAAGGCCCCTTCCT-
GCTCTCAAGGAGAATGTTAAGAGGGTTATGTTTTATTGT (SEQ ID NO:315).

*Nicotiana benthamiana* plants were treated using a procedure similar to that described in Example 12. Polynucleotide solution (or mixed polynucleotides in the case of AGO1) were prepared in 0.01% (v/v) SILWET L-77® brand surfactant and 2% (w/v) ammonium sulfate in 5 millimolar sodium phosphate, pH 6.8. Two fully expanded leaves per plant were dipped into 0.1% SILWET L-77® brand surfactant solution freshly made with ddH2O for a few seconds, and allowed to dry. About 30 minutes later, 20 microliters of polynucleotide solution was applied to each of the two pre-treated leaves. For PDS, each of 5 plants received 25 nanomoles of the PDS anti-sense polynucleotide (SEQ ID NO:34); for AGO1, each of 5 plants received 50 nanomoles of each of the 14 AGO1 anti-sense polynucleotides (SEQ ID NOS:300-313); for PDS and AGO combined treatments, each of 5 plants received 25 nanomoles of the PDS anti-sense polynucleotide (SEQ ID NO:34) and 50 nanomoles of each of the 14 AGO1 anti-sense polynucleotides (SEQ ID NOS:300-313) applied on separate leaves. Paired control plants were treated with buffer (0.01% (v/v) SILWET L-77® brand surfactant and 2% (w/v) ammonium sulfate in 5 millimolar sodium phosphate, pH 6.8). No difference was observed between plants treated with the AGO1 anti-sense polynucleotides and the plants treated with buffer alone. Plants treated with the PDS anti-sense polynucleotide displayed systemic bleaching. Plants treated with both the PDS anti-sense polynucleotide and the separately applied AGO1 anti-sense polynucleotides did not display systemic bleaching, indicating that suppression of AGO1 blocked the systemic spread of the silencing signal.

Example 34

This example illustrates a method for inducing systemic regulation of a target endogenous gene in a growing plant comprising topically coating onto leaves of said growing plant polynucleotides having sequence essentially identical to, or essentially complementary to, a sequence of 18 or more contiguous nucleotides in either said target endogenous gene or messenger RNA transcribed from said target endogenous gene, whereby said polynucleotides permeate the interior of said growing plant and induce systemic regulation of said target endogenous gene. More specifically this example illustrates use of a composition comprising surfactant and polynucleotides to at least transiently induce systemic regulation of the endogenous *Zea mays* 5-enolpyruvylshikimate-3-phosphate synthase (EPSPS) gene.

A genomic sequence of the endogenous *Zea mays* 5-enolpyruvylshikimate-3-phosphate synthase (EPSPS) gene was identified as ACCTACTTCCCCCTCGCCCCTCTCATG-
GTCTCTCTCGCGCCCAGATCTGCTACTAGACGGCACCGCTGC
AGCGCGTCGTGTCGCGGGGGTTGGTG-
GCAGGCAGCGAGAGCTTGCCGTTCCTCTCTCTCAGTTGTCAG GTCCTAG-
GCTCACCTCACCGGCTCCCAGCCCGCT-
TCTATTTCTTCCTCCCCGACCCCGTGCAGGTGGCA
GTCCAGTCCACGCCACCAACCGCGAGGC-
GAACCAAACCAACCCACTCTCCCCAACCCCGCGCGCCCAG GCCGCCCGC-
CCTACCAACCATCGGCGTCGGCAATG-
GCGGCCATGGCGACCAAGGCCGCCGCGGGCAC
CGTGTCGCTGGACCTCGCCGCGCCGCCG-
GCGGCGGCAGCGGCGGCGGCGGTGCAGGCGGGTGCCGAG GAGATCGT-
GCTGCAGCCCATCAAGGAGATCTCCG-
GCACCGTCAAGCTGCCGGGGTCCAAGTCGCTTTC
CAACCGGATCCTCCTGCTCGCCGCCCT-
GTCCGAGGTGAGCGATTTTGGTGCTTGCTGCGCTGCCCTGTC TCACTGC-
TACCTAAATGTTTTGCCTGTCGAATAC-
CATGGATTCTCGGTGTAATCCATCTCACGATCAGA
TGCACCGCATGTCGCATGC-
CTAGCTCTCTCTAATTTGTCTAGTAGTTTGTATACGGATTAATATTGATA
AATCGGTACCGCAAAAGCTAGGTG-
TAAATAAACACTAGAAAATTGGATGTTCCCCTATCGGCCTGTAC TCGGC-
TACTCGTTCTTGTGATGGCATGCT-
GTCTCTTCTTGGTGTTTGGTGAACAACCTTATGAAATTTGG
GCGCAAAGAACTCGCCCTCAAGGGT-
TGATCTTATGCCATCGTCATGATAAACAGTGGAGCACGGACGA TCCTT-
TACGTTGTTTTTAACAAACTTTGTCA-
GAAAACTAGCATCATTAACTTCTTAATGACGATTTCACA
ACAAAAAAAGGTAACCTCGCTACTAA-
CATAACAAAATACTTGTTGCTTATTAATTATATGTTTTTTAAT CTTTGAT-
CAGGGGACAACAGTGGTTGATAACCTGT-
TGAACAGTGAGGATGTCCACTACATGCTCGGGG
CCTTGAGGACTCTTGGTCTCTCTGTC-
GAAGCGGACAAAGCTGCCAAAAGAGCTGTAGTTGTTGGCTGT GGTG-
GAAAGTTCCCAGTTGAGGATTCTAAA-
GAGGAAGTGCAGCTCTTCTTGGGGAATGCTGGAACTGC
AATGCGGCCATTGACAGCAGCTGTTACT-
GCTGCTGGTGGAAATGCAACGTATGTTTCCTCTCTTTCTCT CTACAATACT-
TGCTGGAGTTAGTATGAAACCCATGGG-
TATGTCTAGTGGCTTATGGTGTATTGGTTTTT
GAACTTCAGTTACGTGCTTGATGGAG-
TACCAAGAATGAGGGAGAGACCCATTGGCGACTTGGTTGTCG GATTGAAG-
CAGCTTGGTGCAGATGTTGATTGTTTC-
CTTGGCACTGACTGCCCACCTGTTCGTGTCAATG GAATCGGAGGGCTACCTGGTGGCAAGGTTAGCTACTAAGGGCCACATGTTACATTCTTCTGTAAATGG TACAACTATTGTCGAGCTTTTGCATTTGTAAGGAAAGCATTGATTGATCTGAATTTGATGCTACACCAC AAAATATCCTACAAATGGTCATCCCTAACTAGCAAACAATGAAGTAATACTTGGCATGTGTTTATCAA ATTAATTTCCATCTTCTGGGGCATTGCCTGTTTTCTAGTCTAATAGCATTTGTTTTTAGCATTAATTAGC TCTTACAATTGTTATGTTCTACAGGTCAAGCTGTCTGGCTCCATCAGCAGTCAGTACTTGAGTGCCTTG CTGATGGCTGCTCCTTTGGCTCTTGGGGATGTGGAGATTGAAATCATTGATAAATTAATCTCCATTCCC TACGTCGAAATGACATTGAGATTGATGGAGCGTTTTGGTGTGAAAGCAGAGCATTCTGATAGCTGGGA CAGATTCTACATTAAGGGAGGTCAAAAATACAAGTAAGCTCTGTAATGTATTTCACTACTTTGATGCC AATGTTTCAGTTTTCAGTTTTCCAAACAGTCGCATCAATATTTGAATAGATGCACTGTAGAAAAAAAAT CATTGCAGGGAAAAACTAGTACTGAGTATTTTGACTGTAAATTATTTTACCAGTCGGAATATAGTCAGT CTATTGGAGTCAAGAGCGTGAACCGAAATAGCCAGTTAATTATCCCATTATACAGAGGACAACCATGT ATACTATTGAAACTTGGTTTATAAGAGAATCTAGGTAGCTGGACTCGTAGCTGCTTGGCATGGATACCT TCTTATCTTTAGGAAAAGACACTTGATTTTTTTTTTCTGTGGCCCTCTATGATGTGTGAACCTGCTTCTC TATTGCTTTAGAAGGATATATCTATGTCGTTATGCAACATGCTTCCCTTAGCCATTTGTACTGAAATCA GTTTCATAAGTTCGTTAGTGGTTCCCTAAACGAAACCTTGTTTTTCTTTGCAATCAACAGGTCCCCTAA AAATGCCTATGTTGAAGGTGATGCCTCAAGCGCAAGCTATTTCTTGGCTGGTGCTGCAATTACTGGAG GGACTGTGACTGTGGAAGGTTGTGGCACCACCAGTTTGCAGGTAAAGATTTCTTGGCTGGTGCTACAA TAACTGCTTTTGTCTTTTTGGTTTCAGCATTGTTCTCAGAGTCACTAAATAACATTATCATCTGCAAATG TCAAATAGACATACTTAGGTGAATTCATGTAACCGTTTCCTTACAAATTTGCTGAAACCTCAGGGTGAT GTGAAGTTTGCTGAGGTACTGGAGATGATGGGAGCGAAGGTTACATGGACCGAGACTAGCGTAACTG TTACTGGCCCACCGCGGGAGCCATTTGGGAGGAAACACCTCAAGGCGATTGATGTCAACATGAACAA GATGCCTGATGTCGCCATGACTCTTGCTGTGGTTGCCCTCTTTGCCGATGGCCCGACAGCCATCAGAGA CGGTAAAACATTCTCAGCCCTACAACCATGCCTCTTCTACATCACTACTTGACAAGACTAAAAACTATT GGCTCGTTGGCAGTGGCTTCCTGGAGAGTAAAGGAGACCGAGAGGATGGTTGCGATCCGGACGGAGC TAACCAAGGTAAGGCTACATACTTCACATGTCTCACGTCGTCTTTCCATAGCTCGCTGCCTCTTAGCGG CTTGCCTGCGGTCGCTCCATCCTCGGTTGCTGTCTGTGTTTTCCACAGCTGGGAGCATCTGTTGAGGAA GGGCCGGACTACTGCATCATCACGCCGCCGGAGAAGCTGAACGTGACGGCGATCGACACGTACGACG ACCACAGGATGGCCATGGCCTTCTCCCTTGCCGCCTGTGCCGAGGTCCCCGTGACCATCCGGGACCCT GGGTGCACCCGGAAGACCTTCCCCGACTACTTCGATGTGCTGAGCACTTTCGTCAAGAATTAATAAAG CGTGCGATACTACCACGCAGCTTGATTGAAGTGATAGGCTTGTGCTGAGGAAATACATTTCTTTTGTTC TGTTTTTTCTCTTTCACGGGATTAAGTTTTGAGTCTGTAACGTTAGTTGTTTGTAGCAAGTTTCTATTTC GGATCTTAAGTTTGTGCACTGTAAGCCAAATTTCATTTCAAGAGTGGTTCGTTGGAATAATAAGAATA ATAAATTACGTTTCAGTGGCTGTCAAGCCTGCTGCTACGTTTAGGAGATGGCATTAGACATTCATCAT CAACAACAATAAAACCTTTTAGCCTCAAACAATAATAGTGAAGTTATTTTTTAGTCCTAAACAAGTTGC ATTAGGATATAGTTAAAACACAAAAGAAGCTAAAGTTAGGGTTTAGACATGTGGATATTGTTTTCCAT (SEQ ID NO:316), with a 5' untranslated region located at nucleotide positions 1-306 and a 3' untranslated region located at nucleotide positions 3490-3907. A EPSPS cDNA sequence was identified as ACCTACTTCCCCCTCGCCCCTCTCATGGTCTCTCTCGCGCCCAGATCTGCTACTAGACGGCACCGCTGC AGCGCGTCGTGTCGCGGGGGTTGGTGGCAGGCAGCGAGAGCTTGCCGTTCCTCTCTCTCAGTTGTCAG GTCCTAGGCTCACCTCACCGGCTCCCAGCCCGCTTCTATTTCTTCCTCCCCGACCCCGTGCAGGTGGCA GTCCAGTCCACGCCACCAACCGCGAGGCGAACCAAACCAACCCACTCTCCCCAACCCCGCGCGCCCAG GCCGCCCGCCCTACCAACCATCGGCGTCGGCAATGGCGGCCATGGCGACCAAGGCCGCCGCGGGCAC CGTGTCGCTGGACCTCGCCGCGCCGCCGGCGGCGGCAGCGGCGGCGGCGGTGCAGGCGGGTGCCGAG GAGATCGTGCTGCAGCCCATCAAGGAGATCTCCGGCACCGTCAAGCTGCCGGGGTCCAAGTCGCTTTC CAACCGGATCCTCCTGCTCGCCGCCCTGTCCGAGGGGACAACAGTGGTTGATAACCTGTTGAACAGTG AGGATGTCCACTACATGCTCGGGGCCTTGAGGACTCTTGGTCTCTCTGTCGAAGCGGACAAAGCTGCC AAAAAGAGCTGTAGTTGTTGGCTGTGGTGGAAAGTTCCCAGTTGAGGATTCTAAAGAGGAAGTGCAGCT CTTCTTGGGGAATGCTGGAACTGCAATGCGGCCATTGACAGCAGCTGTTACTGCTGCTGGTGGAAATG CAACTTACGTGCTTGATGGAGTACCAAGAATGAGGGAGAGACCCATTGGCGACTTGGTTGTCGGATTG AAGCAGCTTGGTGCAGATGTTGATTGTTTCCTTGGCACTGACTGCCCACCTGTTCGTGTCAATGGAATC GGAGGGCTACCTGGTGGCAAGGTCAAGCTGTCTGGCTCCATCAGCAGTCAGTACTTGAGTGCCTTGCT GATGGCTGCTCCTTTGGCTCTTGGGGATGTGGAGATTGAAATCATTGATAAATTAATCTCCATTCCCTA CGTCGAAATGACATTGAGATTGATGGAGCGTTTTGGTGTGAAAGCAGAGCATTCTGATAGCTGGGACA GATTCTACATTAAGGGAGGTCAAAAATACAAGTCCCCTAAAAATGCCTATGTTGAAGGTGATGCCTCA AGCGCAAGCTATTTCTTGGCTGGTGCTGCAATTACTGGAGGGACTGTGACTGTGGAAGGTTGTGGCAC CACCAGTTTGCAGGGTGATGTGAAGTTTGCTGAGGTACTGGAGATGATGGGAGCGAAGGTTACATGGA CCGAGACTAGCGTAACTGTTACTGGCCCACCGCGGGAGCCATTTGGGAGGAAACACCTCAAGGCGATT GATGTCAACATGAACAAGATGCCTGATGTCGCCATGACTCTTGCTGTGGTTGCCCTCTTTGCCGATGGC CCGACAGCCATCAGAGACGTGGCTTCCTGGAGAGTAAAGGAGACCGAGAGGATGGTTGCGATCCGGA CGGAGCTAACCAAGCTGGGAGCATCTGTTGAGGAAGGGCCGGACTACTGCATCATCACGCCGCCGGA GAAGCTGAACGTGACGGCGATCGACACGTACGACGACCACAGGATGGCCATGGCCTTCTCCCTTGCCG CCTGTGCCGAGGTCCCCGTGACCATCCGGGACCCTGGGTGCACCCGGAAGACCTTCCCCGACTACTTC GATGTGCTGAGCACTTTCGTCAAGAATTAATAAAGCGTGCGATACTACCACGCAGCTTGATTGAAGTG ATAGGCTTGTGCTGAGGAAATACATTTCTTTTGTTCTGTTTTTTCTCTTTCACGGGATTAAGTTTTGAGT CTGTAACGTTAGTTGTTTGTAGCAAGTTTCTATTTCGGATCTTAAGTTTGTGCACTGTAAGCCAAATTTC ATTTCAAGAGTGGTTCGTTGGAATAATAAGAATAATAAATTACGTTTCAGTGGCTGTCAAGCCTGCTG CTACGTTTAGGAGATGGCATTAGACATTCATCATCAACAACAATAAAACCTTTTAGCCTCAAACAAT AATAGTGAAGT TATTTTTTAGTCCTAAACAAGTTGCATT-AGGATATAGTTAAAACACAAAAGAAGCTA AAGTTAGGGTTTAGACATGTGGATATTGTTTTCCAT (SEQ ID NO:317). A 240 base pair double-stranded RNA polynucleotide was designed with one strand corresponding to the DNA sequence TACTTGAGTGCCTTGCTGATGGCTGCTC-CTTTGGCTCTTGGGGATGTGGAGATTGAAATCATTGATAAA TTAATCTCCAT-TCCGTACGTCGAAATGACATTGAGAT-TGATGGAGCGTTTTGGTGTGAAAGCAGAGCA TTCTGATAGCTGGGACAGATTCTACAT-TAAGGGAGGTCAAAAATACAAGTCCCCTAAAAATGCCTATG TTGAAGGT-GATGCCTCAAGCGCAAGCTATTTCTTG (SEQ ID NO:318) which corresponds to a 240 nucleotide segment located at nucleotide positions 937-1176 of the EPSPS cDNA sequence.

Figure 37:
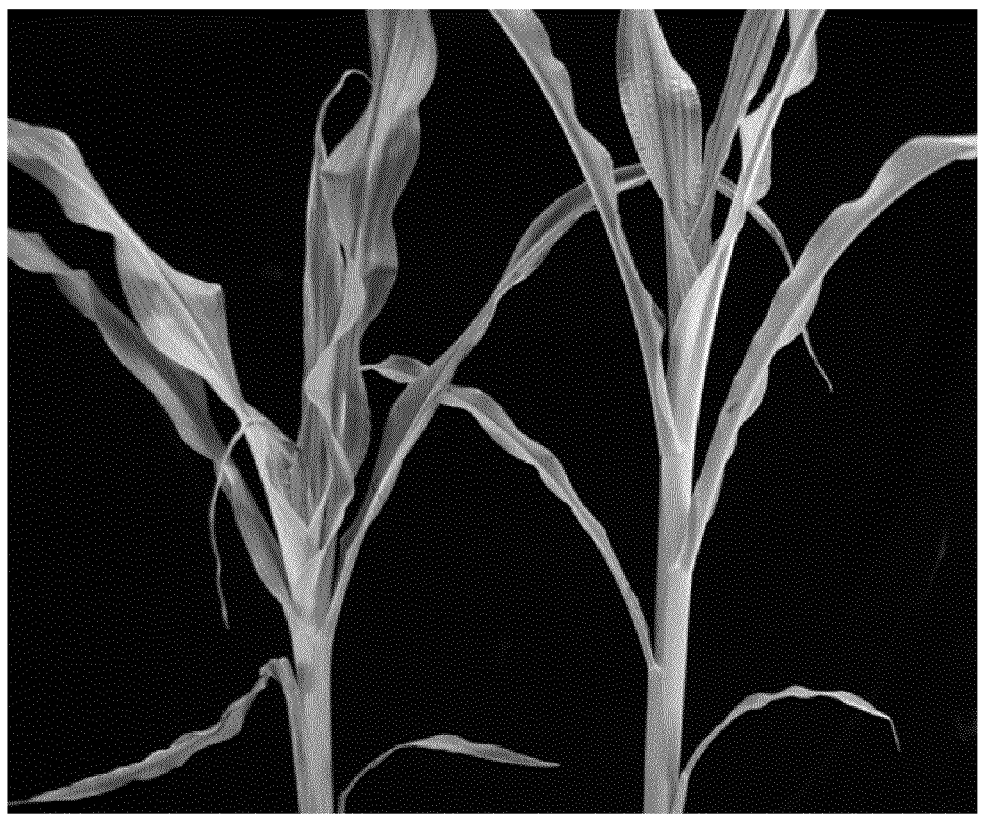
FIG. 37 illustrates the effect on *Zea mays* (Gaspe) monocot plants by topical treatment with dsRNA polynucleotides ("EPSPS DNA oligo") targeting the endogenous EPSPS gene, or with buffer alone as a control, as described in Example 34.

*Zea mays* (Gaspe) seeds were germinated on germination paper. Seedlings were transferred to 4 inch pots and plants were grown in a growth chamber. Three 17-day-old plants were topically treated with polynucleotides and three plants were used as controls. Two lower leaves of each plant were marked and then pre-treated by dipping in a solution of 0.1% SILWET L-77® brand surfactant. About 30 minutes after the surfactant pre-treatment, 20 microliters of treatment solution was applied to the upper side of each of the two pre-treated leaves. Treatment solution consisted of a mixture of 100 microliters of 2× buffer solution, 90 microliters water, 10 microliters of a 4.6 micrograms/microliter solution of the EPSPS dsRNA (with one strand corresponding to SEQ ID NO:318); the 2× buffer solution was a mixture of 200 microliters of 0.1% SILWET L-77® brand surfactant, 200 microliters 50 millimolar sodium phosphate, 146 microliters 34% ammonium phosphate, and 454 microliters water. At 8 days after treatment, two of the three polynucleotide-treated plants were stunted with damaged or dead apical leaves (similar to the phenotype observed in similarly EPSPS polynucleotide-treated *Nicotiana benthamiana* plants), whereas all three of the control plants had normal growth and morphology (FIG. 37).

Example 35

The efficacy of different substances (including salts, a chelating agent, a humectant, and polyamines) as polynucleotide transferring agents or as enhancers of a known polynucleotide transferring agent was investigated. Ammonium sulfate had previously been shown to enhance permeability of plants to polynucleotides (see, e. g., Example 13). Table 26 lists the effect on herbicidal activity (presented as percent of weed control/kill, and as plant height) of ammonium sulfate and EDTA as additives to 1% SILWET L-77® brand surfactant spray solutions of topically applied polynucleotides (RNA) on glyphosate-resistant Palmer amaranth plants. In this particular experiment, ethylenediaminetetraacetic acid (EDTA) at 0.004% was found to act similarly to 2% ammonium sulfate in the spray solution, enhancing the efficacy of the polynucleotides and potentiating the herbicidal activity of glyphosate.

TABLE 26

| Treatment | Palmer control (%) | Palmer height (cm) |
| --- | --- | --- |
| No addition | 0 | 7.5 |
| +2% ammonium sulfate | 43 | 1.8 |
| +0.004% EDTA | 45 | 1.0 |

Table 27 lists the effect on herbicidal activity (presented as percent of weed control/kill, and as plant height) of various salts including inorganic salts (sodium chloride, sodium sulfate, ammonium sulfate, ammonium chloride) and organic salts (tetramethylammonium chloride, tetraethylammonium chloride, tetrapropylammonium bromide, and tetrabutylphosphonium bromide) as additives to 1% SILWET L-77® brand surfactant spray solutions of topically applied polynucleotides (RNA) on glyphosate-resistant Palmer amaranth plants. In this particular experiment, ammonium chloride and tetrabutylphosphonium bromide were found to act similarly to ammonium sulfate in the spray solution, enhancing the efficacy of the polynucleotides and potentiating the herbicidal activity of glyphosate.

TABLE 27

| Treatment | Palmer control (%) | Palmer height (cm) |
| --- | --- | --- |
| No addition | 0 | 16.0 |
| +2% sodium chloride | 15 | 15.0 |
| +2% sodium sulfate | 7 | 17.0 |
| +2% ammonium sulfate | 54 | 9.3 |
| +2% ammonium chloride | 52 | 10.3 |
| +2% tetramethylammonium chloride | 19 | 15.0 |
| +2% tetraethylammonium chloride | 27 | 12.0 |
| +2% tetrapropylammonium bromide | 34 | 11.0 |
| +2% tetrabutylphosphonium bromide | 19 | 13.3 |
| +2% tetrabutylphosphonium bromide | 55 | 5.3 |

Table 28 lists the effect of the humectant glycerin on herbicidal activity (presented as percent of weed control/kill, and as plant height) of topically applied polynucleotides (RNA) on glyphosate-resistant Palmer amaranth plants. Glycerin was found to enhance the efficacy of the polynucleotides, potentiating the herbicidal activity of glyphosate.

TABLE 28

| Treatment | Palmer control (%) | Palmer height (cm) |
| --- | --- | --- |
| No addition | 0 | 16.0 |
| SILWET L-77 ® brand surfactant/AMS (no glycerin) | 54 | 9.3 |
| SILWET L-77 ® brand surfactant/AMS + 0.5% glycerin | 57 | 6.3 |

Figure 38:
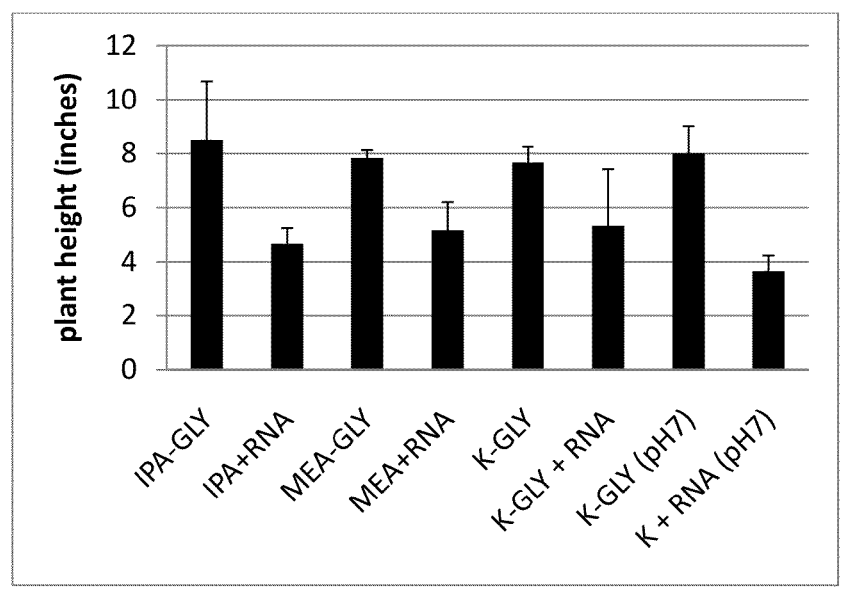
FIG. 38 illustrates the effect of varying glyphosate counter-ions on herbicidal activity on glyphosate-resistant Palmer amaranth plants, as described in Example 35.

FIG. 38 depicts the effect of varying glyphosate counterions on herbicidal activity (presented as percent of weed control/kill, and as plant height) of topically applied polynucleotides (RNA) on glyphosate-resistant Palmer amaranth plants. A mixture of EPSPS polynucleotides (IDT [1] (SEQ ID NO:83-84), IDT [2] (SEQ ID NO:85-86), IDT [3] (SEQ ID NO:87-88), and IDT [4] (SEQ ID NO:89-90)) in 0.5% SILWET L-77® brand surfactant, 2% ammonium sulfate in 10 millimolar sodium phosphate buffer, pH 6.8 with 0.2% Roundup® WeatherMax® carrier (MON56151 tallowamine surfactant blend of tallowamine (16-18C) and cocoamine (12-14C) in the ratio of 55:45) and 1682 g acid equivalent per hectare of one of the glyphosate salts; K+ glyphosate, isopropylammonium+ glyphosate or monoethanolammonium+ glyphosate at 215 liters/acre by Milli spray on 3 replicates of 4-6 inch glyphosate-resistant Palmer amaranth containing 16 copies of EPSPS. Plant height was scored at 21 days after glyphosate treatment. Results (presented as percent of weed control/kill, and as plant height) are given in Table 29. The isopropylammonium and monoethanolammonium salts of glyphosate provided better herbicidal activity compared to the potassium salt.

TABLE 29

| Treatment | Palmer control (%) | Palmer height (cm) |
|---|---|---|
| No addition | 0 | 16 |
| K + glyphosate | 23 | 12.3 |
| K + glyphosate + EPSPS polynucleotides | 32 | 10.8 |
| IPA + glyphosate | 9 | 14.5 |
| IPA + glyphosate + EPSPS polynucleotides | 66 | 5.5 |
| MEA + glyphosate | 9 | 14.5 |
| MEA + glyphosate + EPSPS polynucleotides | 66 | 5.5 |

Figure 39:
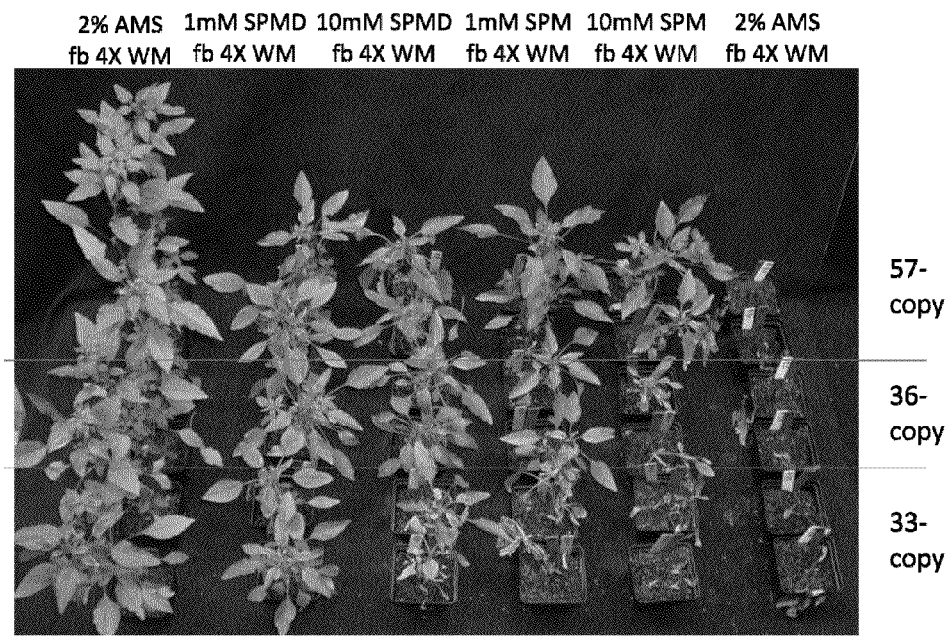
FIG. 39 illustrates the effect of the polyamines spermine ("SPM") and spermidine ("SPMD") or ammonium sulfate ("AMS") on glyphosate-resistant Palmer amaranth containing 33, 36, or 57 copies of EPSPS, as described in Example 35. "fb 4× WM" means "followed by treatment with glyphosate (3360 g acid equivalent per hectare of Roundup® WeatherMAX® brand herbicide)".

The effect of the polyamine cations spermine (N,N'-bis(3-aminopropyl)butane-1,4-diamine) and spermidine (N-(3-aminopropyl)butane-1,4-diamine) on herbicidal activity of topically applied polynucleotides (RNA) on glyphosate-resistant Palmer amaranth plants was investigated. Polynucleotide solutions were prepared using a mixture of equal amounts of the four oligonucleotide-size "short" dsRNA molecules described in Example 1, which have an anti-sense strand designed to hybridize to the mRNA transcribed from the Palmer amaranth EPSPS gene (SEQ ID NO:1) at positions 14-38 (short dsRNA-1), positions 153-177 (short dsRNA-2), 345-369 (short dsRNA-3), and 1105-1129 (short dsRNA-4), as indicated by underlined nucleotides in FIG. 1; the dsRNAs had a two nucleotide overhang at the 3' end of the anti-sense strand, and had two deoxynucleotides as the terminal nucleotides at the 3' end of the sense strand. The dsRNA polynucleotide solutions were prepared with either 1 or 10 millimolar spermine or spermidine or 2% ammonium sulfate, in a 10 millimolar sodium phosphate (pH 6.8) buffer. Control solutions (without polynucleotides) were prepared with either 1 or 10 millimolar spermine or spermidine or 2% ammonium sulfate, in a 10 millimolar sodium phosphate (pH 6.8) buffer. Glyphosate-resistant Palmer amaranth plants (33, 36, or 57 copies EPSPS) were pre-sprayed with 1% SILWET L-77® brand surfactant. The dsRNA polynucleotide solutions (11.6 grams/acre) or buffer solutions were applied as drops on four lower fully expanded leaves of glyphosate resistant Palmer amaranth by pipetting. Two days following polynucleotide treatment the plants were sprayed with glyphosate (3360 g acid equivalent per hectare of Roundup® WeatherMAX® brand herbicide). Plants were photographed at 14 days after glyphosate treatment; results are shown in FIG. 39. Treatment with dsRNA and 10 millimolar spermine followed by glyphosate treatment killed glyphosate-resistant Palmer amaranth with 33-copy EPSPS and severely injured and stunted glyphosate-resistant Palmer amaranth with 36-copy EPSPS. Treatment with 10 mM spermidine alone stunted 33-copy glyphosate-resistant Palmer amaranth. In this particular experiment, neither spermine nor spermidine at 1 or 10 millimolar performed as well as 2% ammonium sulfate.

Example 36

The efficacy of different surfactants as polynucleotide transferring agents was tested in polynucleotide spray solutions applied to glyphosate-resistant Palmer amaranth. BREAK-THRU® brand surfactants were obtained from Evonik Industries; SILWET® brand surfactants were obtained from Momentive. Spray solutions were prepared the same day as spraying. A mixture of EPSPS polynucleotides (IDT [1] (SEQ ID NO:83-84), IDT [3] (SEQ ID NO:87-88), and IDT [4] (SEQ ID NO:89-90)) was added to spray solutions 15 to 50 minutes before spraying and 1- to 2-milliliters applied using a custom low-dead-volume ("milli") sprayer to one-to-four inch glyphosate-resistant (R-22) Palmer amaranth plants grown from cuttings. Between 10 and 225 micrograms total polynucleotides were applied to each plant, depending on the experiment; typically 23 micrograms total polynucleotides were applied per plant. Treated plants were placed in a greenhouse set for either a 26.7/21.1 degrees Celsius or 29.4/21.1 degrees Celsius 14/10 hour temperature and supplemental light schedule. After 2 to 3 days, the plants were sprayed with glyphosate ("2× Wmax" or 1682 g acid equivalent per hectare of Roundup® WeatherMAX® brand herbicide) by regular sprayer (10 gallons/acre) and returned to the greenhouse. The amount of control (visual injury) relative to unsprayed treatments, plant height and pictures of Palmer amaranth were collected at different time intervals up to 21 days after glyphosate treatment. Fresh weight of above-soil plant material was collected at the last time point. An overall plant injury score between 0 and 3 was given each treatment based on the combined analysis of Control, Height, Fresh Weight and Visual Plant Phenotype, where "3" is strong herbicidal activity, "2" is moderate activity, "1" is mild activity and "0" is no activity observed after correction for any observed injury caused by treatment with glyphosate alone; results are shown in Table 30.

Physical properties of the different surfactants were also investigated and listed in Table 30. Seventy milliliters of surfactant solution (0.5% surfactant in aqueous solution containing 2% ammonium sulfate, buffer (20 millimolar potassium phosphate, pH 6.8), with or without an EPSPS polynucleotide (IDT [2] (SEQ ID NO:85-86), 0.09 milligrams/milliliter) added, were prepared on the same day as measurement. Dynamic surface tension was measured at ambient room temperature (22 to 23 degrees Celsius) on a Kruss BP100 tensiometer using the maximum bubble pressure method plotting surface tension versus surface age. The instrument was set to automatically detect the surface and immerse the capillary to a depth of 10 mm. Surface tension measurements for three surface ages (approximately 20, 500 and 1250 ms) were recorded. Surface tension in dynes per cm was reported at the 1250 ms interval as an approximation of static surface tension and the change between 20 and 500 ms was reported as an estimate of the dynamic surface tension. Hydrophile-lipophile balance (HLP) values for the surfactants were obtained from surfactant references and product information.

TABLE 30

| Surfactant name | CAS number | Chemistry | Surfactant Type | Surfactant Class | Palmer injury score | Surface tension literature | Surface tension 1250 ms | delta 20-500 ms | HLB |
|---|---|---|---|---|---|---|---|---|---|
| BREAK-THRU® S 321 | na | polyether-modified polysiloxane | organosilicone | nonionic | 3 | na | 22.7 | 27.1 | 40.0 |
| BREAK-THRU® S 200 | 67674-67-3 | polyether-modified polysiloxane | organosilicone | nonionic | 3 | 22 | 26.9 | 23.0 | |

TABLE 30-continued

| Surfactant name | CAS number | Chemistry | Surfactant Type | Surfactant Class | Palmer injury score | Surface tension literature | 1250 ms | delta 20- 500 ms | HLB |
|---|---|---|---|---|---|---|---|---|---|
| BREAK-THRU ® OE 441 | 68937-55-3 | polyether-modified polysiloxane | organosilicone | nonionic | 1 | na | 43.8 | 2.9 | 40.0 |
| BREAK-THRU ® S 278 | 27306-78-1 | polyether-modified polysiloxane | organosilicone | nonionic | 2 | 21 | 24.2 | 23.4 | |
| BREAK-THRU ® S 243 | na | polyether-modified polysiloxane | organosilicone | nonionic | 2 | 47 | 50.3 | 7.7 | 16.7 |
| SILWET L-77 ® | 27306-78-1 | trisiloxane; polyalkylene oxide-modified polymethylsiloxane | organosilicone | nonionic | 3 | 20.5 | 26.4 | 23.4 | 13.5 |
| SILWET ® HS 429 | na | hydrolytically stable silicone | organosilicone | nonionic | 3 | 32-40 | 40.1 | 12.1 | |
| SILWET ® HS 312 | na | silicone | organosilicone | nonionic | 3 | 26.7 | 29.5 | 11.3 | |
| BREAK-THRU ® S 233 | 134180-76-0 | trisiloxane | organosilicone | nonionic | 3 | 23 | 26.1 | 10.0 | |

What is claimed is:

1. A method for selectively controlling targeted herbicide-resistant weeds or volunteer plants comprising topically applying onto a surface of said weeds or volunteer plants one or more polynucleotides and a transfer agent in a manner that does not integrate said one or more polynucleotides into a chromosome of said weeds or volunteer plants;
   wherein said transfer agent is selected from the group consisting of an organosilicone surfactant and a cationic lipid;
   wherein said transfer agent enables said one or more polynucleotides to permeate from the surface of said weeds or volunteer plants into cells of said weeds or volunteer plants;
   wherein said one or more polynucleotides comprise a sequence essentially identical or essentially complementary to a coding or non-coding sequence of an endogenous gene of said weed or volunteer plant or a messenger RNA that is transcribed from an endogenous gene of said weed or volunteer plant; and
   wherein said endogenous gene: (i) is an essential gene for maintaining the growth or life of said weed or volunteer plant, (ii) encodes a protein that provides herbicide resistance to said weed or volunteer plant, or (iii) transcribes to an RNA regulatory agent.

2. The method of claim 1, further comprising applying one or more of a salt and a non-polynucleotide herbicide.

3. The method of claim 1, wherein said weed or volunteer plant is pigweed, waterhemp, other amaranth species, mare's tail (horseweed), giant ragweed, common ragweed, johnsongrass, goosegrass, ryegrass, hairy crabgrass, velvetleaf, prickly lettuce, dandelion, alfalfa, corn, soybean, canola, cotton, sugar beet, sugarcane, wheat, rice, or a vegetable.

4. The method of claim 1, wherein said endogenous gene encodes a protein that provides herbicide resistance to said weed or volunteer plant and said protein is selected from the group consisting of a 5-enolpyruvylshikimate-3-phosphate synthase (EPSPS), an acetohydroxyacid synthase, an acetolactate synthase (ALS), an acetyl-coenzyme A carboxylase (ACCase), a dihydropteroate synthase, a phytoene desaturase (PDS), a protoporphyrin IX oxygenase (PPO), a hydroxyphenylpyruvate dioxygenase (HPPD), a para-aminobenzoate synthase, a glutamine synthase (GS), a glufosinate-tolerant glutamine synthase, a 1-deoxy-D-xylulose 5-phosphate (DOXP) synthase, a dihydropteroate (DHP) synthase, a phenylalanine ammonia lyase (PAL), a glutathione S-transferase (GST), a D1 protein of photosystem II, a mono-oxygenase, a cytochrome P450, a cellulose synthase, a beta-tubulin, and a serine hydroxymethyltransferase.

5. The method of claim 4, further comprising applying onto said weed or volunteer plant a quantity of a herbicide for which said protein provides resistance.

6. The method of claim 1, wherein the targeted herbicide-resistant weeds or volunteer plants are growing in a field of herbicide-resistant crop plants.

7. The method of claim 6, wherein the crop plants are corn, soybean, cotton, canola, sugar beet, alfalfa, sugarcane, rice, wheat, fruit or vegetables.

8. The method of claim 1, wherein the targeted herbicide-resistant weeds or volunteer plants are resistant to one or more of glyphosate, dicamba and sulfonylurea.

9. The method of claim 1, wherein the endogenous gene is a native gene or a recombinant transgene.

10. The method of claim 1, wherein the polynucleotides are double-stranded RNA, single-stranded DNA, or double-stranded DNA/RNA hybrid polynucleotides.

11. The method of claim 1, wherein the organosilicone surfactant is BREAK-THRU® S 321, BREAK-THRU® S 200, BREAK-THRU® OE 441, BREAK-THRU® S 278, BREAK-THRU® S 243, SILWET L-77®, SILWET® HS 429, SILWET® HS 312, or BREAK-THRU® S 233.

12. The method of claim 1, wherein the cationic lipid is TransIT®.

13. The method of claim 1, comprising applying ammonium sulfate.

14. The method of claim 1, wherein one or more polynucleotides comprise a sequence essentially identical or essentially complementary to at least 18 or more contiguous nucleotides of SEQ ID NOs: 1, 41-52, 232, 233, 285-287, 316, or 317.

15. The method of claim 14, wherein one or more polynucleotides are medium-length polynucleotides having a length of 26-300 nucleotides.

16. The method of claim 15, wherein one or more polynucleotides have a length of 26-60 nucleotides.

17. The method of claim 1, wherein one or more polynucleotides comprise a sequence essentially identical or essentially complementary to nucleotides 14-38, 153-177, 345-369 or 1,105-1,129 of SEQ ID NO: 1.

18. The method of claim 1, wherein one or more polynucleotides comprise a sequence essentially identical or essentially complementary to nucleotides 16-170, 451-722 or 1,109-1328 of SEQ ID NO: 1.

19. The method of claim 1, wherein one or more polynucleotides comprise a sequence essentially identical or essentially complementary to nucleotides 564-588, 566-585, 743-764 or 743-767 of SEQ ID NO: 40.

20. The method of claim 1, wherein one or more polynucleotides comprise a sequence essentially identical or essentially complementary to SEQ ID NOs: 8-11, 63-70, 83-112, 239-275, 279-284 or 318.

21. The method of claim 1, wherein one or more polynucleotides comprise a sequence essentially identical or essentially complementary to at least 18 or more contiguous nucleotides of SEQ ID NO: 71.

22. The method of claim 1, wherein one or more polynucleotides comprise a sequence essentially identical or essentially complementary to SEQ ID NOs: 73 or 74.

23. The method of claim 1, wherein one or more polynucleotides comprise a sequence essentially identical or essentially complementary to SEQ ID NOs: 113 or 114.

24. The method of claim 1, wherein one or more polynucleotides comprise a sequence essentially identical or essentially complementary to at least 18 or more contiguous nucleotides of one or more of SEQ ID NOs: 225-229.

25. The method of claim 1, wherein one or more polynucleotides comprise a sequence essentially identical or essentially complementary to at least 18 or more contiguous nucleotides of SEQ ID NOs: 230 or 231.

26. The method of claim 1, wherein one or more polynucleotides comprise a sequence essentially identical or essentially complementary to at least 18 or more contiguous nucleotides of SEQ ID NO: 235.

27. The method of claim 1, wherein one or more polynucleotides comprise a sequence essentially identical or essentially complementary to at least 18 or more contiguous nucleotides of SEQ ID NO: 236.

28. The method of claim 1, wherein one or more polynucleotides comprise a sequence essentially identical or essentially complementary to at least 18 or more contiguous nucleotides of SEQ ID NO: 238.

29. The method of claim 1, wherein one or more polynucleotides comprise a sequence essentially identical or essentially complementary to at least 18 or more contiguous nucleotides of one or more of SEQ ID NOs: 296-299.

30. The method of claim 1, wherein one or more polynucleotides comprise a sequence essentially identical or essentially complementary to at least 18 or more contiguous nucleotides of SEQ ID NO: 2, 37, 53, 59 or 237.

* * * * *

UNITED STATES PATENT AND TRADEMARK OFFICE
CERTIFICATE OF CORRECTION

PATENT NO. : 9,121,022 B2
APPLICATION NO. : 13/042856
DATED : September 1, 2015
INVENTOR(S) : Robert D. Sammons et al.

Page 1 of 1

It is certified that error appears in the above-identified patent and that said Letters Patent is hereby corrected as shown below:

Title Page, Item (54) and in the Specification, at Column 1, lines 1 and 2, title should read "Method for Controlling Herbicide-Resistant Plants"

Signed and Sealed this
Fifth Day of July, 2016

Michelle K. Lee
*Director of the United States Patent and Trademark Office*

SEQUENCE LISTING

<160> NUMBER OF SEQ ID NOS: 320

<210> SEQ ID NO 1
<211> LENGTH: 1557
<212> TYPE: DNA
<213> ORGANISM: Amaranthus palmeri

<400> SEQUENCE: 1

```
atggctcaag ctactaccat caacaatggt gtccatactg gtcaattgca ccatacttta      60
cccaaaaccc agttacccaa atcttcaaaa actcttaatt ttggatcaaa cttgagaatt     120
tctccaaagt tcatgtcttt aaccaataaa agagttggtg ggcaatcatc aattgttccc     180
aagattcaag cttctgttgc tgctgcagct gagaaacctt catctgtccc agaaattgtg     240
ttacaaccca tcaaagagat ctctggtact gttcaattgc ctgggtcaaa gtctttatcc     300
aatcgaatcc ttcttttagc tgctttgtct gagggcacaa cagtggtcga caacttgctg     360
tatagtgatg atattcttta tatgttggac gctctcagaa ctcttggttt aaaagtggag     420
gatgatagta cagccaaaag ggcagtcgta gagggttgtg gtggtctgtt tcctgttggt     480
aaagatggaa aggaagagat tcaacttttc cttggtaatg caggaacagc gatgcgccca     540
ttgacagctg cggttgccgt tgctggagga aattcaagtt atgtgcttga tggagtacca     600
agaatgaggg agcgccccat tggggatctg gtagcaggtc taaagcaact tggttcagat     660
gtagattgtt ttcttggcac aaattgccct cctgttcggg tcaatgctaa aggaggcctt     720
ccagggggca aggtcaagct ctctggatcg gttagtagcc aatatttaac tgcacttctc     780
atggctactc ctttgggtct tggagacgtg gagattgaga tagttgataa attgatttct     840
gtaccgtatg ttgaaatgac aataaagttg atggaacgct ttggagtatc cgtagaacat     900
agtgatagtt gggacaggtt ctacattcga ggtggtcaga aatacaaatc tcctggaaag     960
gcatatgttg agggtgatgc ttcaagtgct agctacttcc tagccggagc cgccgtcact    1020
ggtgggactg tcactgtcaa gggttgtgga acaagcagtt tacagggtga tgtaaaattt    1080
gccgaagttc ttgagaagat gggttgcaag gtcacctgga cagagaatag tgtaactgtt    1140 actgaccac ccaggqattc atctggaaag aaacatctgc gtgctatcga cgtcaacatg    1200
```

```
aacaaaatgc cagatgttgc tatgactctt gcagttgttg ccttgtatgc agatgggccc    1260
accgccatca gagatgtggc tagctggaga gtgaaggaaa ccgaacggat gattgccatt    1320
tgcacagaac tgagaaagct tggggcaaca gttgaggaag atctgattta ctgtgtgatc    1380
actccgcctg aaaagctaaa ccccaccgcc attgaaactt atgacgatca ccgaatggcc    1440
atggcattct ctcttgctgc ctgtgcagat gttcccgtca ctatccttga tccgggatgc    1500
acccgtaaaa ccttcccgga ctactttgat gttttagaaa agttcgccaa gcattga      1557

<210> SEQ ID NO 2
<211> LENGTH: 1761
<212> TYPE: DNA
<213> ORGANISM: Nicotiana benthamiana

<400> SEQUENCE: 2
atgccccaaa tcggacttgt atctgctgtt aatttgagag tccaaggtaa ttcagcttat      60
ctttggagct cgaggtcttc gttgggaact gaaagtcaag atgtttgctt gcaaaggaat     120
ttgttatgtt ttggtagtag cgactccatg gggcataagt taaggattcg tactccaagt     180
gccacgaccc gaagattgac aaaggacttt aatcctttaa aggtagtctg cattgattat     240
ccaagaccag agctagacaa tacagttaac tatttggagg cggcgttatt atcatcatcg     300
tttcgtactt cctcacgccc aactaaacca ttggagattg ttattgctgg tgcaggtttg     360
ggtggtttgt ctacagcaaa atatctggca gatgctggtc acaaaccgat attgctggag     420
gcaagagatg tcctaggtgg aaggtagctg cat gggaaag atgatgatgg agattggtac     480
gagactgggt tgcacatatt cttgggggct acccaaata gcagaacct gtttggagaa       540 ctagggattg atgatcggtt gcagtggaag gaacattcaa tgatatttgc gatgcctaac    600
aagccagggg agttcagccg cttt gatttt cctgaagctc ttcctgcgcc attaaatgga     660
attttggcca tactaaagaa caacgaaatg cttacgtggc ccgagaaagt caaatttgct     720
attggactct gccagcaat gcttggaggg caatcttatg ttgaagctca agacggttta      780
agtgttaagg actggatgag aaagcaaggt gtgcctgata gggtgacaga tgaggtgttc     840
attgccatgt caaaggcact taacttcata aaccctgacg agcttccgat gcagtgcatt     900
ttgattgctt tgaacagatt tcttcaggag aaacatggtt caaaaatggc cttttttagat    960 ggtaaccctc ctgagagact ttgcatgccg attgtggaac atattgagtc aaaaggtggc   1020
caagtcagac taaactcacg aataaaaaag atcgagctga atgaggatgg aagtgtcaaa   1080 tgtttttatac tgaataatgg cagtacaatt aaaggagatg cttttgtgtt tgccactcca    1140
gtggatatct tgaagcttct tttgcctgaa gactggaaag agatcccata tttccaaaag    1200
ttggagaagc tagtgggagt tcctgtgata aatgtccata tatggtttga cagaaaactg    1260
aagaacacat ctgataatct gctcttcagc agaagcccgt tgctcagtgt gtacgctgac    1320
atgtctgtta catgtaagga atattacaac cccaatcagt ctatgttgga attggtatt     1380 gcacccgcag aagagtggat aaatcgtagt gactcagaaa ttattgatgc tacaatgaag   1440
gaactagcga agcttttccc tgatgaaatt tcggcagatc agagcaaagc aaaaatattg    1500
aagtatcatg ttgtcaaaac cccaaggtct gtttataaaa ctgtgccagg ttgtgaaccc    1560
tgtcggccct tgcaaagatc ccctatagag ggttttttatt tagctggtga ctacacgaaa   1620
cagaagtact tggcttcaat ggaaggtgct gtcttatcag gaaagctttg tgcacaagct   1680
attgtacagg attacgagtt acttcttggc cggagccaga gatgttggc agaagcaagc    1740 gtagttagca tagtgaacta a                                              1761
```

<210> SEQ ID NO 3
<211> LENGTH: 559
<212> TYPE: DNA
<213> ORGANISM: artificial sequence
<220> FEATURE:
<223> OTHER INFORMATION: Synthetic Construct

<400> SEQUENCE: 3

```
ggcccatagg cctttttcta aaataggccc atttaagcta ttaacaatct tcaaaagtac      60
cacatcgctt aggtaaagaa agcagctgag tttatatatg gttagagacg aagtagtgat     120
tgcgacgagc gacgtctcgc cctcatcgca atccacgcca ttgagcttga ggccattggc     180
gacggccgag aggcggtcgc ttaagattag catgtccttg acgcggagtt cttccagacc     240
gttcatcacg gtcgcccctt ccgcgaaggc ggcggcgaca gcgagaatcg gatattcgtc     300
gatcatcgaa ggcgcgcggt cttccggcac cgtgacgcat aaacacggtg ccggaagacc     360
gcgcgccttc gatgatcgac gaatatccga ttctcgctgt cgccgccgcc ttcgcggaag     420
gggcgaccgt gatgaacggt ctggaagaac tccgcgtcaa ggaaagcgac cgcctctcgg     480
ccgtcgccaa tggcctcaag ctcaatggcg tggattgcga tgagggcgag acgtcgctcg     540
tcgttttttt tggcaaaaa                                                  559
```

<210> SEQ ID NO 4
<211> LENGTH: 10
<212> TYPE: DNA
<213> ORGANISM: artificial sequence
<220> FEATURE:
<223> OTHER INFORMATION: Synthetic Construct

<400> SEQUENCE: 4

```
tcccacatcg                                                             10
```

<210> SEQ ID NO 5
<211> LENGTH: 13
<212> TYPE: DNA
<213> ORGANISM: artificial sequence
<220> FEATURE:
<223> OTHER INFORMATION: Synthetic Construct

<400> SEQUENCE: 5

```
aagattagca cgg                                                         13
```

<210> SEQ ID NO 6
<211> LENGTH: 11
<212> TYPE: DNA
<213> ORGANISM: artificial sequence
<220> FEATURE:
<223> OTHER INFORMATION: Synthetic Construct

<400> SEQUENCE: 6

```
acgcataaaa t                                                           11
```

<210> SEQ ID NO 7
<211> LENGTH: 6
<212> TYPE: DNA
<213> ORGANISM: artificial sequence
<220> FEATURE:
<223> OTHER INFORMATION: Synthetic Construct

<400> SEQUENCE: 7

```
tttttt                                                                  6
```

```
<210> SEQ ID NO 8
<211> LENGTH: 20
<212> TYPE: DNA
<213> ORGANISM: Amaranthus palmeri

<400> SEQUENCE: 8
accctccacg actgcccttt                                               20

<210> SEQ ID NO 9
<211> LENGTH: 19
<212> TYPE: DNA
<213> ORGANISM: Amaranthus palmeri

<400> SEQUENCE: 9
gtttccttca ctctccagc                                                19

<210> SEQ ID NO 10
<211> LENGTH: 20
<212> TYPE: DNA
<213> ORGANISM: Amaranthus palmeri

<400> SEQUENCE: 10
gtagcttgag ccattattgt                                               20

<210> SEQ ID NO 11
<211> LENGTH: 20
<212> TYPE: DNA
<213> ORGANISM: Amaranthus palmeri

<400> SEQUENCE: 11
gttgatggta gtagcttgag                                               20

<210> SEQ ID NO 12
<211> LENGTH: 20
<212> TYPE: DNA
<213> ORGANISM: Amaranthus palmeri

<400> SEQUENCE: 12
accctccacg actgcccttt                                               20

<210> SEQ ID NO 13
<211> LENGTH: 19
<212> TYPE: DNA
<213> ORGANISM: Amaranthus palmeri

<400> SEQUENCE: 13
gtttccttca ctctccagc                                                19

<210> SEQ ID NO 14
<211> LENGTH: 18
<212> TYPE: DNA
<213> ORGANISM: Hordeum vulgare

<400> SEQUENCE: 14
aagcggttga gcactgaa                                                 18

<210> SEQ ID NO 15
<211> LENGTH: 20
<212> TYPE: DNA
<213> ORGANISM: Amaranthus palmeri

<400> SEQUENCE: 15
accctccacg actgcccttt                                               20
```

<210> SEQ ID NO 16
<211> LENGTH: 40
<212> TYPE: DNA
<213> ORGANISM: artificial sequence
<220> FEATURE:
<223> OTHER INFORMATION: Synthetic Construct

<400> SEQUENCE: 16
taatacgact cactataggg caagagatgt cctaggtggg                          40

<210> SEQ ID NO 17
<211> LENGTH: 44
<212> TYPE: DNA
<213> ORGANISM: artificial sequence
<220> FEATURE:
<223> OTHER INFORMATION: Synthetic Construct

<400> SEQUENCE: 17
taatacgact cactatagga cagatttctt caggagaaac atgg                     44

<210> SEQ ID NO 18
<211> LENGTH: 21
<212> TYPE: DNA
<213> ORGANISM: artificial sequence
<220> FEATURE:
<223> OTHER INFORMATION: Synthetic Construct

<400> SEQUENCE: 18
gcaagagatg tcctaggtgg g                                              21

<210> SEQ ID NO 19
<211> LENGTH: 25
<212> TYPE: DNA
<213> ORGANISM: artificial sequence
<220> FEATURE:
<223> OTHER INFORMATION: Synthetic Construct

<400> SEQUENCE: 19
acagatttct tcaggagaaa catgg                                          25

<210> SEQ ID NO 20
<211> LENGTH: 41
<212> TYPE: DNA
<213> ORGANISM: artificial sequence
<220> FEATURE:
<223> OTHER INFORMATION: Synthetic Construct

<400> SEQUENCE: 20
taatacgact cactataggc atctccttta attgtactgc c                        41

<210> SEQ ID NO 21
<211> LENGTH: 41
<212> TYPE: DNA
<213> ORGANISM: artificial sequence
<220> FEATURE:
<223> OTHER INFORMATION: Synthetic Construct

<400> SEQUENCE: 21
taatacgact cactataggt ttaattgtac tgccattatt c                        41

<210> SEQ ID NO 22
<211> LENGTH: 22
<212> TYPE: DNA
<213> ORGANISM: artificial sequence
<220> FEATURE:

```
<223> OTHER INFORMATION: Synthetic Construct

<400> SEQUENCE: 22
catctccttt aattgtactg cc                                              22

<210> SEQ ID NO 23
<211> LENGTH: 22
<212> TYPE: DNA
<213> ORGANISM: artificial sequence
<220> FEATURE:
<223> OTHER INFORMATION: Synthetic Construct

<400> SEQUENCE: 23
tttaattgta ctgccattat tc                                              22

<210> SEQ ID NO 24
<211> LENGTH: 25
<212> TYPE: DNA
<213> ORGANISM: artificial sequence
<220> FEATURE:
<223> OTHER INFORMATION: Synthetic Construct

<400> SEQUENCE: 24
cacttccatc ctcattcagc tcgat                                           25

<210> SEQ ID NO 25
<211> LENGTH: 24
<212> TYPE: DNA
<213> ORGANISM: artificial sequence
<220> FEATURE:
<223> OTHER INFORMATION: Synthetic Construct

<400> SEQUENCE: 25
acacctcatc tgtcacccta tcag                                            24

<210> SEQ ID NO 26
<211> LENGTH: 24
<212> TYPE: DNA
<213> ORGANISM: artificial sequence
<220> FEATURE:
<223> OTHER INFORMATION: Synthetic Construct

<400> SEQUENCE: 26
cagtctcgta ccaatctcca tcat                                            24

<210> SEQ ID NO 27
<211> LENGTH: 41
<212> TYPE: DNA
<213> ORGANISM: artificial sequence
<220> FEATURE:
<223> OTHER INFORMATION: Synthetic Construct

<400> SEQUENCE: 27
taatacgact cactataggg atccatgata tcgtgaacat c                         41

<210> SEQ ID NO 28
<211> LENGTH: 38
<212> TYPE: DNA
<213> ORGANISM: artificial sequence
<220> FEATURE:
<223> OTHER INFORMATION: Synthetic Construct

<400> SEQUENCE: 28
taatacgact cactataggg gcaaagaaaa atgcgtcg                             38
```

```
<210> SEQ ID NO 29
<211> LENGTH: 21
<212> TYPE: DNA
<213> ORGANISM: artificial sequence
<220> FEATURE:
<223> OTHER INFORMATION: Synthetic Construct

<400> SEQUENCE: 29
atccatgata tcgtgaacat c                                              21

<210> SEQ ID NO 30
<211> LENGTH: 18
<212> TYPE: DNA
<213> ORGANISM: artificial sequence
<220> FEATURE:
<223> OTHER INFORMATION: Synthetic Construct

<400> SEQUENCE: 30
gcaaagaaaa atgcgtcg                                                  18

<210> SEQ ID NO 31
<211> LENGTH: 40
<212> TYPE: DNA
<213> ORGANISM: artificial sequence
<220> FEATURE:
<223> OTHER INFORMATION: Synthetic Construct

<400> SEQUENCE: 31
tgttttatac tgaataatgg cagtacaatt aaaggagatg                          40

<210> SEQ ID NO 32
<211> LENGTH: 15
<212> TYPE: DNA
<213> ORGANISM: artificial sequence
<220> FEATURE:
<223> OTHER INFORMATION: Synthetic Construct

<400> SEQUENCE: 32
catctccttt aattg                                                     15

<210> SEQ ID NO 33
<211> LENGTH: 18
<212> TYPE: DNA
<213> ORGANISM: artificial sequence
<220> FEATURE:
<223> OTHER INFORMATION: Synthetic Construct

<400> SEQUENCE: 33
catctccttt aattgtac                                                  18

<210> SEQ ID NO 34
<211> LENGTH: 21
<212> TYPE: DNA
<213> ORGANISM: artificial sequence
<220> FEATURE:
<223> OTHER INFORMATION: Synthetic Construct

<400> SEQUENCE: 34
catctccttt aattgtactg c                                              21

<210> SEQ ID NO 35
<211> LENGTH: 33
<212> TYPE: DNA
<213> ORGANISM: artificial sequence
<220> FEATURE:
<223> OTHER INFORMATION: Synthetic Construct
```

```
<400> SEQUENCE: 35
catctccttt aattgtactg ccattattca gta                                      33

<210> SEQ ID NO 36
<211> LENGTH: 21
<212> TYPE: DNA
<213> ORGANISM: artificial sequence
<220> FEATURE:
<223> OTHER INFORMATION: Synthetic Construct

<400> SEQUENCE: 36
gcagtacaat taaaggagat g                                                   21

<210> SEQ ID NO 37
<211> LENGTH: 1614
<212> TYPE: DNA
<213> ORGANISM: Amaranthus palmeri

<400> SEQUENCE: 37
tcaatttcat ctattggaag tgattttttg ggtcattctg tgagaaattt cagtgttagt         60
aaagtttatg gagcaaagca agaaatggg cactgcccctt taaaggttgt ttgtatagat        120
tatcctaggc cagagcttga agtacatcc aatttcttgg aagccgccta cttatcttct         180
acttttcgga attcgcctcg tcctcagaag ccattagaag ttgtaattgc tggagcaggt        240
ttggctggtc tatccacggc aaagtattta gctgatgcag gtcacaaacc catattgttg        300
gaagcacgag atgttttagg aggaaaggtt gcagcgtgga aggatgagga tggtgactgg        360
tatgagactg gctacatat attctttggg gcatatccaa atgtccaaaa tctatttgga         420
gaacttggta taaatgaccg actgcaatgg aaggagcact ctatgatttt tgcaatgccc        480
agcaagcccg gtgaattcag tcgctttgat tttcccgaaa tcctgcctgc accattaaat        540
ggcatatggg caatcctaag aaataatgaa atgctaacct ggccagaaaa aatcaagttt        600
gccattggct gttgcctgc tatggcaggc ggacagtcat atgttgaagc acaagatggt         660
ttgagtgtcc aagagtggat gagaaaacaa ggagtacccg atcgtgtaac tgatgatgtg        720
tttattgcca tgtcaaaggc actgaacttc ataaatcccg atgaactttc aatgcagtgc        780
atcttgattg ctctgaaccg attcctgcag gagaaacatg gttctaagat ggccttccta        840
gacggaaacc ctccagagag gctgtgcatg cctattgtta aacacatcga gtcactaggt        900
ggtgaagtta aacttaactc tcgtatacaa aagattcagt ggaccagag tggaagcgtg         960 aagagttttt tgctaaataa cgggagggaa atacgaggag atgcctatgt ttttgccacc       1020
ccagttgaca tcttgaagct gttactacct gatacttgga aggaaatctc atacttcaaa       1080
aaacttgaga aattagtggg cgttcctgtg attaatgttc acatatggtt tgacagaaaa       1140
ttaaagaata catatgacca tctactcttc agcaggagtc ctcttttgag tgtctatgct       1200
gatatgtcgg agacatgcaa ggaatataag gatccaaata gatccatgct ggaattggtt       1260
tttgcacccg cggaggaatg gatttcacga agcgacactg atattataga ggcaacaatg       1320
aaagagcttg ccaagctttt cccggatgaa atcgctgccg atggaagcaa ggccaagatc       1380
ctcaaatatc atgtcgtcaa aactccaagg tcggtttata agactgtacc ggattgtgaa       1440
ccttgtcggc cgctgcaaag atcaccaata gagggttttct atttagctgg tgattacaca       1500
aaacaaaaat atttggcttc tatggaaggt gctgtcttat ctgggaagct tgtgcacag        1560 gctatcgtac aggattatga tctgctgagt tctcgagcac aaagagaatt ggcg             1614
```

```
<210> SEQ ID NO 38
<211> LENGTH: 1761
<212> TYPE: DNA
<213> ORGANISM: Nicotiana benthamiana

<400> SEQUENCE: 38
atgccccaaa tcggacttgt atctgctgtt aatttgagag tccaaggtaa ttcagcttat      60
ctttggagct cgaggtcttc gttgggaact gaaagtcaag atgtttgctt gcaaaggaat     120
ttgttatgtt ttggtagtag cgactccatg gggcataagt taaggattcg tactccaagt     180
gccacgaccc gaagattgac aaaggacttt aatcctttaa aggtagtctg cattgattat     240
ccaagaccag agctagacaa tacagttaac tatttggagg cggcgttatt atcatcatcg     300
tttcgtactt cctcacgccc aactaaacca ttggagattg ttattgctgg tgcaggtttg     360
ggtggtttgt ctacagcaaa atatctggca gatgctggtc acaaaccgat attgctggag     420
gcaagagatg tcctaggtgg aaggtagct gcatggaaag atgatgatgg agattggtac      480
gagactgggt tgcacatatt cttttggggct acccaaata tgcagaacct gtttggagaa     540
ctagggattg atgatcggtt gcagtggaag gaacattcaa tgatatttgc gatgcctaac     600
aagccagggg agttcagccg cttttgatttt cctgaagctc ttcctgcgcc attaaatgga     660
attttggcca tactaaagaa caacgaaatg cttacgtggc ccgagaaagt caaatttgct     720
attggactct gccagcaat gcttggaggg caatcttatg ttgaagctca agacggttta     780
agtgttaagg actggatgag aaagcaaggt gtgcctgata gggtgacaga tgaggtgttc     840
attgccatgt caaaggcact taacttcata aaccctgacg agctttcgat gcagtgcatt     900
ttgattgctt tgaacagatt tcttcaggag aaacatggtt caaaaatggc cttttagat      960
ggtaaccctc ctgagagact ttgcatgccg attgtggaac atattgagtc aaaaggtggc    1020
caagtcagac taaactcacg aataaaaaag atcgagctga atgaggatgg aagtgtcaaa    1080
tgttttatac tgaataatgg cagtacaatt aaaggagatg cttttgtgtt tgccactcca    1140
gtggatatct tgaagcttct tttgcctgaa gactggaaag agatcccata tttccaaaag    1200
ttggagaagc tagtgggagt tcctgtgata aatgtccata tatggtttga cagaaaactg    1260
aagaacacat ctgataatct gctcttcagc agaagcccgt tgctcagtgt gtacgctgac    1320
atgtctgtta catgtaagga atattacaac cccaatcagt ctatgttgga attggtatt     1380
gcacccgcag aagagtggat aaatcgtagt gactcagaaa ttattgatgc tacaatgaag    1440
gaactagcga agcttttccc tgatgaaatt tcggcagatc agagcaaagc aaaaatattg    1500
aagtatcatg ttgtcaaaac cccaaggtct gtttataaaa ctgtgccagg ttgtgaaccc    1560
tgtcggccct tgcaaagatc ccctatagag ggttttatatt tagctggtga ctacacgaaa    1620
cagaagtact tggcttcaat ggaaggtgct gtcttatcag aaaagctttg tgcacaagct    1680
attgtacagg attacgagtt acttcttggc cggagccaga agatgttggc agaagcaagc    1740
gtagttagca tagtgaacta a                                              1761

<210> SEQ ID NO 39
<211> LENGTH: 22
<212> TYPE: DNA
<213> ORGANISM: Nicotiana benthamiana

<400> SEQUENCE: 39
ggcagtacaa ttaaaggaga tg                                              22

<210> SEQ ID NO 40
```

```
<211> LENGTH: 1557
<212> TYPE: DNA
<213> ORGANISM: Amaranthus palmeri

<400> SEQUENCE: 40
atggctcaag ctactaccat caacaatggt gtccatactg gtcaattgca ccatacttta      60
cccaaaaccc agttacccaa atcttcaaaa actcttaatt ttggatcaaa cttgagaatt     120
tctccaaagt tcatgtcttt aaccaataaa agagttggtg ggcaatcatc aattgttccc     180
aagattcaag cttctgttgc tgctgcagct gagaaacctt catctgtccc agaaattgtg     240
ttacaaccca tcaaagagat ctctggtact gttcaattgc ctgggtcaaa gtctttatcc     300
aatcgaatcc ttcttttagc tgctttgtct gagggcacaa cagtggtcga caacttgctg     360
tatagtgatg atattcttta tatgttggac gctctcagaa ctcttggttt aaaagtggag     420
gatgatagta cagccaaaag ggcagtcgta gagggttgtg gtggtctgtt tcctgttggt     480
aaagatggaa aggaagagat tcaacttttc cttggtaatg caggaacagc gatgcgccca     540
ttgacagctg cggttgccgt tgctggagga aattcaagtt atgtgcttga tggagtacca     600
agaatgaggg agcgccccat tggggatctg gtagcaggtc taaagcaact tggttcagat     660
gtagattgtt ttcttggcac aaattgccct cctgttcggg tcaatgctaa aggaggcctt     720
ccagggggca aggtcaagct ctctggatcg gttagtagcc aatatttaac tgcacttctc     780
atggctactc ctttgggtct tggagacgtg agattgaga tagttgataa attgatttct     840
gtaccgtatg ttgaaatgac aataaagttg atggaacgct tggagtatc cgtagaacat     900 agtgatagtt gggacaggtt ctacattcga ggtggtcaga aatacaaatc tcctggaaag     960
gcatatgttg agggtgatgc ttcaagtgct agctacttcc tagccggagc cgccgtcact    1020
ggtgggactg tcactgtcaa gggttgtgga acaagcagtt tacagggtga tgtaaaattt    1080
gccgaagttc ttgagaagat gggttgcaag gtcacctgga cagagaatag tgtaactgtt    1140 actgaccac ccagggattc atctggaaag aaacatctgc gtgctatcga cgtcaacatg    1200
aacaaaatgc cagatgttgc tatgactctt gcagttgttg ccttgtatgc agatgggccc    1260
accgccatca gagatgtggc tagctggaga gtgaaggaaa ccgaacggat gattgccatt    1320
tgcacagaac tgagaaagct tggggcaaca gttgaggaag gatctgatta ctgtgtgatc    1380
actccgcctg aaaagctaaa ccccaccgcc attgaaactt atgacgatca ccgaatggcc    1440
atggcattct ctcttgctgc ctgtgcagat gttcccgtca ctatccttga tccgggatgc    1500
acccgtaaaa ccttcccgga ctactttgat gttttagaaa agttcgccaa gcattga      1557

<210> SEQ ID NO 41
<211> LENGTH: 250
<212> TYPE: DNA
<213> ORGANISM: Amaranthus palmeri
<220> FEATURE:
<221> NAME/KEY: misc_feature
<222> LOCATION: (27)..(27)
<223> OTHER INFORMATION: n is a, c, g, or t

<400> SEQUENCE: 41
cgccagggct gcagacgcgt tacgtantcg gatccagaat tcgtgattaa cgtcacagca     60
tgtcatgtaa aacacgcgaa tcagaccggt ccactcttgt tttaatttga gacaattttg    120
atgttgagtc atcccacacc aaccccaaaa aattcaacaa caaactctta taatgattcc    180
ctctactcta ctagagtcta caccaaccca ctttctcttt gcccaccaaa actttggttt    240
ggtaagaact                                                           250
```

<210> SEQ ID NO 42
<211> LENGTH: 244
<212> TYPE: DNA
<213> ORGANISM: Amaranthus palmeri

<400> SEQUENCE: 42

```
caccaaccca ctttctcttt gcccaccaaa actttggttt ggtaagaact aagccctctt      60
ctttcccttc tctctcttaa aagcctaaaa tccacctaac tttttcagcc aacaaacaac     120
gccaaattca gaggaagaat aatgatggct caagctacta ccatcaacaa tggtgtccat     180
actggtcaat tgcaccatac tttacccaaa acccagttac ccaaatcttc aaaaactctt     240
aatt                                                                  244
```

<210> SEQ ID NO 43
<211> LENGTH: 250
<212> TYPE: DNA
<213> ORGANISM: Amaranthus palmeri

<400> SEQUENCE: 43

```
ccatacttta cccaaaaccc agttacccaa atcttcaaaa actcttaatt ttggatcaaa      60
cttgagaatt tctccaaagt tcatgtcttt aaccaataaa agagttggtg ggcaatcatc     120
aattgttccc aagattcaag cttctgttgc tgctgcagct gagaaacctt catctgtccc     180
agaaattgtg ttacaaccca tcaaagagat ctctggtact gttcaattgc ctgggtcaaa     240
gtctttatcc                                                            250
```

<210> SEQ ID NO 44
<211> LENGTH: 250
<212> TYPE: DNA
<213> ORGANISM: Amaranthus palmeri

<400> SEQUENCE: 44

```
tcaaagagat ctctggtact gttcaattgc ctgggtcaaa gtctttatcc aatcgaatcc      60
ttcttttagc tgctttgtct gagggcacaa cagtggtcga caacttgctg tatagtgatg     120
atattcttta tatgttggac gctctcagaa ctcttggttt aaaagtggag gatgatagta     180
cagccaaaag ggcagtcgta gagggttgtg gtggtctgtt tcctgttggt aaagatggaa     240
aggaagagat                                                            250
```

<210> SEQ ID NO 45
<211> LENGTH: 250
<212> TYPE: DNA
<213> ORGANISM: Amaranthus palmeri

<400> SEQUENCE: 45

```
gagggttgtg gtggtctgtt tcctgttggt aaagatggaa aggaagagat tcaacttttc      60
cttggtaatg caggaacagc gatgcgccca ttgacagctg cggttgccgt tgctggagga     120
aattcaagtt atgtgcttga tggagtacca agaatgaggg agcgccccat tggggatctg     180
gtagcaggtc taaagcaact tggttcagat gtagattgtt ttcttggcac aaattgccct     240
cctgttcggg                                                            250
```

<210> SEQ ID NO 46
<211> LENGTH: 250
<212> TYPE: DNA
<213> ORGANISM: Amaranthus palmeri

<400> SEQUENCE: 46

```
tggttcagat gtagattgtt ttcttggcac aaattgccct cctgttcggg tcaatgctaa    60
aggaggcctt ccaggggca aggtcaagct ctctggatcg gttagtagcc aatatttaac    120
tgcacttctc atggctactc ctttgggtct tggagacgtg gagattgaga tagttgataa    180
attgatttct gtaccgtatg ttgaaatgac aataaagttg atggaacgct ttggagtatc    240
cgtagaacat                                                          250
```

<210> SEQ ID NO 47
<211> LENGTH: 250
<212> TYPE: DNA
<213> ORGANISM: Amaranthus palmeri

<400> SEQUENCE: 47

```
ttgaaatgac aataaagttg atggaacgct ttggagtatc cgtagaacat agtgatagtt    60
gggacaggtt ctacattcga ggtggtcaga aatacaaatc tcctggaaag gcatatgttg    120
agggtgatgc ttcaagtgct agctacttcc tagccggagc cgccgtcact ggtgggactg    180
tcactgtcaa gggttgtgga acaagcagtt tacagggtga tgtaaaattt gccgaagttc    240
ttgagaagat                                                          250
```

<210> SEQ ID NO 48
<211> LENGTH: 250
<212> TYPE: DNA
<213> ORGANISM: Amaranthus palmeri

<400> SEQUENCE: 48

```
acaagcagtt tacagggtga tgtaaaattt gccgaagttc ttgagaagat gggttgcaag    60
gtcacctgga cagagaatag tgtaactgtt actggaccac ccagggattc atctggaaag    120
aaacatctgc gtgctatcga cgtcaacatg aacaaaatgc cagatgttgc tatgactctt    180
gcagttgttg ccttgtatgc agatgggccc accgccatca gagatgtggc tagctggaga    240
gtgaaggaaa                                                          250
```

<210> SEQ ID NO 49
<211> LENGTH: 250
<212> TYPE: DNA
<213> ORGANISM: Amaranthus palmeri

<400> SEQUENCE: 49

```
agatgggccc accgccatca gagatgtggc tagctggaga gtgaaggaaa ccgaacggat    60
gattgccatt tgcacagaac tgagaaagct tggggcaaca gttgaggaag atctgattac    120
ctgtgtgatc actccgcctg aaaagctaaa ccccaccgcc attgaaactt atgacgatca    180
ccgaatggcc atggcattct ctcttgctgc ctgtgcagat gttcccgtca ctatccttga    240
tccgggatgc                                                          250
```

<210> SEQ ID NO 50
<211> LENGTH: 257
<212> TYPE: DNA
<213> ORGANISM: Amaranthus palmeri

<400> SEQUENCE: 50

```
ctcttgctgc ctgtgcagat gttcccgtca ctatccttga tccgggatgc acccgtaaaa    60
ccttcccgga ctactttgat gttttagaaa agttcgccaa gcattgatga gtagctatat    120
acgagatcct taaattgtac gccgaaggtt ttgatttgag tctaatagta gataaaaggc    180
```

```
tataaataaa ctggctttct gcttgagtaa ttatgaaatt ctttgtatta tgtttgtgag      240
atttgaagta gcttata                                                    257

<210> SEQ ID NO 51
<211> LENGTH: 273
<212> TYPE: DNA
<213> ORGANISM: Amaranthus palmeri

<400> SEQUENCE: 51
taattatgaa attctttgta ttatgtttgt gagatttgaa gtagcttata aattacaatg      60
tactaaagtc tagaaataag ttatgtatct tttaaatcaa tgagaaatgc atacttgaaa     120
ggcttgacct tgtatttgtg acctaaagag tactaacttt ggagtttcca actcatttgt     180
ttatctcatt ttttttaat ttttgattta aattgtttat ttttatgagt aatcatgtat      240
ctttcttatt ctaaccaaat gtaatactcc ttc                                  273

<210> SEQ ID NO 52
<211> LENGTH: 301
<212> TYPE: DNA
<213> ORGANISM: Amaranthus palmeri

<400> SEQUENCE: 52
tatgagtaat catgtatctt tcttattcta accaaatgta atactccttc caactctctt      60
taaacgtcca cactctgggc acagagtgta atagtgtggt ggttggagtc ttttaagtga     120
ttataataat tgtaaatgtg gtagttagaa tattttaagt aatgtaggtg gggtattatg     180
gtcttgttga acataggata tttaggtaaa aaatctatgc aaaaaaagga aagtaagcaa     240
ataaagcgaa ttgacctgaa agaaaagtg gacatgtata gtgagttgga ggaagtatt     300 t                                                                    301

<210> SEQ ID NO 53
<211> LENGTH: 1710
<212> TYPE: DNA
<213> ORGANISM: Lactuca sativa

<400> SEQUENCE: 53
atgtctctgt ttggaaatgt ttctgccatt aactcaagtg gaaagtgtat agtaatgaat      60
ctttcaagca cacaaatcac ttcaagagat tgtttcaaga ttacctcagg gcaaaaagat     120
gttttgtcat ttggatgctg tgatgctatg ggtaacagat tgcaattccc aagtgctcgt     180
tcttttacac caagatcaaa gaagaatgtc tcccctctaa aggtagtttg tgttgattat     240
ccaagaccag atcttgataa cacatctaat ttcttggaag ctgctcactt gtcttcaacc     300
ttcagaactt ccccacgccc atcaagcca ttgaagattg taattgctgg tgcaggttta     360
gctggtttat caactgctaa gtatttagct gatgcaggtc acaagccaat tttactagaa     420
gcaagagatg ttcttggtgg aaaggtggca gcttggaaag atgatgatgg agattggtat     480
gagacaggtt tacacatatt ctttggagct tacccaaatg tacaaaattt atttggagag     540
ctaggaatta atgatagatt acagtggaag gagcattcta tgatatttgc aatgccaaat     600
aagcctggag aatttagtag gtttgacttc ccagatgttt tacctgcacc attgaatgga     660
attttgctta tattgaggaa caatgaaatg ctgacgtggc ctgagaaagt gaagtttgca     720
attgggctgt tgcctgcaat gttaggtgga caggcttatg ttgaggccca agatgggctt     780
agtgttcagg actggatgag aaagcaaggt atacctgatc gagttactac tgaagtgttt     840
```

| | |
|---|---|
| attgcaatgt caaaagcatt aaactttata aatccagatg aactttcaat gcaatgtatt | 900 |
| ctcattgctc taaaccgttt tcttcaggaa aagcatggtt ccaagatggc attttagat | 960 |
| gggagcccac cagaaagact ttgcaagcca attgttgacc acatcgagtc actcggtggc | 1020 |
| caagtcagag tcaactcacg aatacaaaaa attgagttaa acaaagacgg aactgtccgg | 1080 |
| aactttctat tgagtgatgg gaatgttcta gaagctgatg cttatgtttt cgctaccccct | 1140 |
| gttgacattc tcaagcttct tttacccgaa gaatggaaac caattccata tttcaaaaaa | 1200 |
| ttagagaagt tagtcggtgt tcctgttata aacgttcata tatggtttga cagaaagctg | 1260 |
| aaaaacacat atgatcactt acttttcagt aggtcacctc tgctgagtgt gtatgctgac | 1320 |
| atgtcagtga catgtaagga atattatgat ccgaataagt caatgttgga gttggttctt | 1380 |
| gctccagctg aggaatggat ttcaagaagt gacactgata ttattgatgc aacaatgagt | 1440 |
| gaactttcaa ggcttttcc tgatgaaatt gcagctgatc aaagtaaagc aaaaatcttg | 1500 |
| aaatataaag ttgttaaaac accaaggtct gtttataaaa ctgttccaga ttgtgaacca | 1560 |
| tgtcgacccc tacaaagatc tccaattcaa ggattttatt tatctggtga ttatactaaa | 1620 |
| caaaagtatt tggcttcaat gggggtgct gttttatctg gaaaatttg tgcacaagct | 1680 |
| attttacaag attatgagat gcttgctaca | 1710 |

<210> SEQ ID NO 54
<211> LENGTH: 42
<212> TYPE: DNA
<213> ORGANISM: artificial sequence
<220> FEATURE:
<223> OTHER INFORMATION: Synthetic Construct

<400> SEQUENCE: 54

| | |
|---|---|
| taatacgact cactataggg tttggagctt acccaaatgt ac | 42 |

<210> SEQ ID NO 55
<211> LENGTH: 45
<212> TYPE: DNA
<213> ORGANISM: artificial sequence
<220> FEATURE:
<223> OTHER INFORMATION: Synthetic Construct

<400> SEQUENCE: 55

| | |
|---|---|
| taatacgact cactataggg aggccacgtc agcatttcat tgttc | 45 |

<210> SEQ ID NO 56
<211> LENGTH: 23
<212> TYPE: DNA
<213> ORGANISM: artificial sequence
<220> FEATURE:
<223> OTHER INFORMATION: Synthetic Construct

<400> SEQUENCE: 56

| | |
|---|---|
| ccattcaatg gtgcaggtaa aac | 23 |

<210> SEQ ID NO 57
<211> LENGTH: 21
<212> TYPE: DNA
<213> ORGANISM: artificial sequence
<220> FEATURE:
<223> OTHER INFORMATION: Synthetic Construct

<400> SEQUENCE: 57

| | |
|---|---|
| catagaatgc tccttccact g | 21 |

```
<210> SEQ ID NO 58
<211> LENGTH: 33
<212> TYPE: DNA
<213> ORGANISM: artificial sequence
<220> FEATURE:
<223> OTHER INFORMATION: Synthetic Construct

<400> SEQUENCE: 58
caaataaatt ttgtacattt gggtaagctc caa                                    33

<210> SEQ ID NO 59
<211> LENGTH: 2349
<212> TYPE: DNA
<213> ORGANISM: Solanum lycopersicum

<400> SEQUENCE: 59
gggtttatct cgcaagtgtg gctatggtgg gacgtgtcaa attttggatt gtagccaaac        60
atgagatttg atttaaaggg aattggccaa atcaccgaaa gcaggcatct tcatcataaa       120
ttagtttgtt tatttataca gaattatacg cttttactag ttatagcatt cggtatcttt       180
ttctgggtaa ctgccaaacc accacaaatt tcaagtttcc atttaactct tcaacttcaa       240
cccaaccaaa tttatttgct taattgtgca gaaccactcc ctatatcttc taggtgcttt       300
cattcgttcc gagtaaaatg cctcaaattg gacttgtttc tgctgttaac ttgagagtcc       360
aaggtagttc agcttatctt tggagctcga ggtcgtcttc tttgggaact gaaagtcgag       420
atggttgctt gcaaaggaat tcgttatgtt ttgctggtag cgaatcaatg ggtcataagt       480
taaagattcg tactccccat gccacgacca aagattggt taaggacttg gggccttta         540
aggtcgtatg cattgattat ccaagaccag agctggacaa tacagttaac tatttggagg       600
ctgcattttt atcatcaacg ttccgtgctt ctccgcgccc aactaaacca ttggagattg       660
ttattgctgg tgcaggtttg ggtggtttgt ctacagcaaa atatttggca gatgctggtc       720
acaaaccgat actgctggag gcaagggatg ttctaggtgg aaaggtagct gcatggaaag       780
atgatgatgg agattggtac gagactggtt tgcatatatt ctttggggct tacccaaata       840
ttcagaacct gtttggagaa ttagggatta acgatcgatt gcaatggaag gaacattcaa       900
tgatatttgc aatgccaagc aagccaggag aattcagccg ctttgatttc tccgaagctt       960
tacccgctcc tttaaatgga attttagcca tcttaaagaa taacgaaatg cttacatggc      1020
cagagaaagt caaatttgca attggactct tgccagcaat gcttggaggg caatcttatg      1080
ttgaagctca agatgggata agtgttaagg actggatgag aaagcaaggt gtgccggaca      1140
gggtgacaga tgaggtgttc attgctatgt caaaggcact caactttata aaccctgacg      1200
aactttcaat gcagtgcatt ttgatcgcat tgaacaggtt tcttcaggag aaacatggtt      1260
caaaaatggc ctttttagat ggtaatcctc ctgagagact ttgcatgccg attgttgaac      1320
acattgagtc aaaaggtggc caagtcagac tgaactcacg aataaaaaag attgagctga      1380
atgaggatgg aagtgtcaag agtttttatac tgagtgacgg tagtgcaatc gagggagatg      1440
cttttgtgtt tgccgctcca gtggatattt tcaagcttct attgcctgaa gactggaaag      1500
agattccata tttccaaaag ttggagaagt tagtcggagt acctgtgata aatgtacata      1560
tatggtttga cagaaaactg aagaacacat atgatcattt gctcttcagc agaagctcac      1620
tgctcagtgt gtatgctgac atgtctgtta catgtaagga atattacaac cccaatcagt      1680
ctatgttgga attggttttt gcacctgcag aagagtggat atctcgcagc gactcagaaa      1740
ttattgatgc aacgatgaag gaactagcaa cgcttttttcc tgatgaaatt tcagcagatc      1800
```

```
aaagcaaagc aaaaatattg aagtaccatg ttgtcaaaac tccgaggtct gtttataaaa   1860
ctgtgccagg ttgtgaaccc tgtcggcctt tacaaagatc cccaatagag gggtttttatt   1920 tagccggtga ctacacgaaa cagaaatact tggcttcaat ggaaggcgct gtcttatcag   1980
gaaagctttg tgctcaagct attgtacagg attatgagtt acttgttgga cgtagccaaa   2040
agaagttgtc ggaagcaagc gtagtttagc tttgtggtta ttatttagct tctgtacact   2100
aaatttatga tgcaagaagc gttgtacaca acatatagaa gaagagtgcg aggtgaagca   2160
agtaggagaa atgttaggaa agctcctata caaaaggatg gcatgttgaa gattagcatc   2220
tttttaatcc caagtttaaa tataaagcat attttatgta ccactttctt tatctggggt   2280
ttgtaatccc tttatatctt tatgcaatct ttacgttagt taaaaaaaaa aaaaaaaaaa   2340
aaaactcga                                                          2349

<210> SEQ ID NO 60
<211> LENGTH: 200
<212> TYPE: DNA
<213> ORGANISM: artificial sequence
<220> FEATURE:
<223> OTHER INFORMATION: Synthetic Construct

<400> SEQUENCE: 60
tcgcagcgac tcagaaatta ttgatgcaac gatgaaggaa ctagcaacgc ttttcctga     60 tgaaatttca gcagatcaaa gcaaagcaaa aatattgaag taccatgttg tcaaaactcc   120
gaggtctgtt tataaaactg tgccaggttg tgaaccctgt cggcctttac aaagatcccc   180
aatagagggg ttttatttag                                              200

<210> SEQ ID NO 61
<211> LENGTH: 43
<212> TYPE: DNA
<213> ORGANISM: artificial sequence
<220> FEATURE:
<223> OTHER INFORMATION: Synthetic Construct

<400> SEQUENCE: 61
taatacgact cactataggg tcgcagcgac tcagaaatta ttg                      43

<210> SEQ ID NO 62
<211> LENGTH: 45
<212> TYPE: DNA
<213> ORGANISM: artificial sequence
<220> FEATURE:
<223> OTHER INFORMATION: Synthetic Construct

<400> SEQUENCE: 62
taatacgact cactataggg gtaaaggccg acagggttca caacc                    45

<210> SEQ ID NO 63
<211> LENGTH: 21
<212> TYPE: RNA
<213> ORGANISM: artificial sequence
<220> FEATURE:
<223> OTHER INFORMATION: Synthetic Construct

<400> SEQUENCE: 63
cuaccaucaa caauggugkc c                                              21

<210> SEQ ID NO 64
<211> LENGTH: 21
<212> TYPE: RNA
<213> ORGANISM: artificial sequence
```

```
<220> FEATURE:
<223> OTHER INFORMATION: Synthetic Construct

<400> SEQUENCE: 64
ggacaccauu guugauggua g                                              21

<210> SEQ ID NO 65
<211> LENGTH: 21
<212> TYPE: RNA
<213> ORGANISM: artificial sequence
<220> FEATURE:
<223> OTHER INFORMATION: Synthetic Construct

<400> SEQUENCE: 65
gucgacaacu ugcuguauag u                                              21

<210> SEQ ID NO 66
<211> LENGTH: 21
<212> TYPE: RNA
<213> ORGANISM: artificial sequence
<220> FEATURE:
<223> OTHER INFORMATION: Synthetic Construct

<400> SEQUENCE: 66
acuauacagc aaguugucga c                                              21

<210> SEQ ID NO 67
<211> LENGTH: 21
<212> TYPE: RNA
<213> ORGANISM: artificial sequence
<220> FEATURE:
<223> OTHER INFORMATION: Synthetic Construct

<400> SEQUENCE: 67
ggucaccugg acagagaaua g                                              21

<210> SEQ ID NO 68
<211> LENGTH: 21
<212> TYPE: RNA
<213> ORGANISM: artificial sequence
<220> FEATURE:
<223> OTHER INFORMATION: Synthetic Construct

<400> SEQUENCE: 68
cuauucucug uccaggugac c                                              21

<210> SEQ ID NO 69
<211> LENGTH: 21
<212> TYPE: RNA
<213> ORGANISM: artificial sequence
<220> FEATURE:
<223> OTHER INFORMATION: Synthetic Construct

<400> SEQUENCE: 69
aaugccagau guugcuauga c                                              21

<210> SEQ ID NO 70
<211> LENGTH: 21
<212> TYPE: RNA
<213> ORGANISM: artificial sequence
<220> FEATURE:
<223> OTHER INFORMATION: Synthetic Construct

<400> SEQUENCE: 70
gucauagcaa caucuggcau u                                              21
```

<210> SEQ ID NO 71
<211> LENGTH: 2827
<212> TYPE: DNA
<213> ORGANISM: Amaranthus palmeri

<400> SEQUENCE: 71

| | | | | | |
|---|---|---|---|---|---|
| atggcaacaa | tggcttccct | agtgagtttg | ggaagctctg | gagcaacttg | ctcagggcaa | 60 |
| ttggaggttt | cctttcatt | ggttaagaaa | attacattgc | ctagaagaaa | ttgtagttgc | 120 |
| aattttaggc | aattaggagg | ggggaggaga | tggcgttacg | tttcggtgtg | tagactttct | 180 |
| gtcactactg | attatgtttc | tgagcaagga | aatgctgttt | ctcttgaaaa | tgcatatagt | 240 |
| gagagtaaag | aagagggtct | catcttgaag | ccttctccta | agccggtttt | gaaatccggg | 300 |
| tctgatggaa | atcggaaatt | ggggagagt | tcggtggcgt | tttcgagtaa | tgggaaattg | 360 |
| gataatgtag | aggagaggaa | gaaggttatt | gattcattgg | atgaggtatt | agaaaaggcc | 420 |
| gagagattag | aaacggcgaa | cttacaagca | gataatagaa | aggatagcac | aaatgtaaat | 480 |
| aaaccgtctc | cgagtgtaag | tagttcaacc | aatggtaaac | ctgtaaataa | tttgaacaaa | 540 |
| gggaagccta | agctgcgaa | gagcgtttgg | agaaagggaa | atccagtttc | tactgtgcaa | 600 |
| aaagtagtgc | aagaatctcc | gaagattgaa | aaggttgaga | gagtggaagc | tcgaacgacc | 660 |
| agccaatcgt | ctgaaacgat | aagaccccca | gtgccactac | agaggcctga | gattaagttg | 720 |
| caggcaaagc | cttctactgc | tcctccaccc | atgcctaaga | agccggtttt | gaaggatgtg | 780 |
| gggatgtcct | ccagagctga | tgggaaggac | cagtctgtga | atctaaaga | gaggaagcct | 840 |
| attctagtgg | acaaatttgc | caccaagaag | gcatcagttg | atccgtcgat | tgctcaagca | 900 |
| gtaattgccc | caccaaaacc | tgctaaattt | ccttctggaa | agtttaaaga | tgattatcgg | 960 |
| aagaagggtc | ttgcagctgg | tgggccgaag | aggcgtatgg | tcaatgatga | tgatattgaa | 1020 |
| atgcatgaag | acacttcaga | gctcggtctt | tctattcctg | gtgctgctac | ggctcggaaa | 1080 |
| ggcaggaaat | ggagtaaggc | aagtcgcaag | gctgccagac | gccaagcagc | tagagatgcc | 1140 |
| gctcctgtta | aagtggaaat | cttagaggtt | gaagaaaagg | gcatgtcgac | cgaagaatta | 1200 |
| gcatacaact | tggctattag | cgaaggtgaa | attcttgggt | acctgtattc | taaggggata | 1260 |
| aaaccagatg | gtgtgcaaac | tcttgacaag | gcaatggtaa | agatgatatg | tgaaagatat | 1320 |
| gacgtggagg | ttttggacgc | actttctgaa | caaatggaag | aaatggctcg | aaagaaggaa | 1380 |
| atttcgacg | aagatgacct | tgacaagctt | gaagataggc | ctcctgtgct | tactataatg | 1440 |
| ggtcatgtag | atcatggcaa | gacgacccct | ctggattata | tacggaagag | caaggttgct | 1500 |
| gcttctgaag | ctggtgggat | tacacaaggt | attggtgctt | ataaagtgga | agtaccggtt | 1560 |
| gatggcaagt | tgctgccttg | tgtctttctt | gacactccg | gacacgaggc | gttcggggca | 1620 |
| atgagggctc | gtgagcaag | agtgacagat | attgctatta | gttgtagc | tgctgacgat | 1680 |
| gggatccgtc | ctcaaacaaa | tgaagccata | gcacatgcaa | aagcagctgg | tgtacctatt | 1740 |
| gtggttgcaa | ttaataagat | tgacaaggat | ggggctaatc | cggaccgtgt | gatgcaagag | 1800 |
| ctttcatcaa | ttggtctaat | gccagaggat | tggggtggtg | ataccccaat | ggtcaagata | 1860 |
| agtgctctaa | aagtgaaaaa | tgtggacgag | ttactcgaga | cagccatgct | tgtcgccgag | 1920 |
| ttgcaagagt | taaggctaa | tcctcagagg | aacgctaagg | gcactgtaat | tgaggctggt | 1980 |
| cttcataaat | caaaggacc | cattgccact | tttattgtgc | agaatggtac | cctcaaacaa | 2040 |
| ggggatactg | tagtttgtgg | ggaagcattt | gggaaggttc | gtgccctatt | tgatcacgga | 2100 |
| gggaatcgcg | ttgatgaagc | tggtccatct | attcccgtgc | aggttattgg | attgaataat | 2160 |

```
gttcctttg ccggtgatga gttcgaggta gtgagttccc ttgatatagc tcgtgaaaag    2220
gcagaggtcc gtgcagagtc tttacgaaat gagcgtatag ctgctaaggc cggagacgga    2280
aaggttacgc tgtcatcctt ggcatcggct gtttcttcag ggaagatggc tggtttggat    2340
ttgcaccagt taaatatcat tttgaaggtt gatgttcagg gatcaatcga ggcattgagg    2400
caagctctag aagttcttcc tcaagataac gtcactttga agtttctctt acaagcgacc    2460
ggagatgtta ctacaagtga tgttgatctt gcagttgcta gtaaagctat tatcttgggg    2520
ttcaatgtga aggcaccagg ttctgtcgaa aaattagcag ataacaaagg tgttgaaatt    2580
cggctttata aagtcattta tgatctaatt gacgacatgc ggagtgcaat ggaaggaatg    2640
ctagatcccg ttgaggaaca agttgcaatt ggttcagccg aagtgcgggc tacattcagt    2700
agtggtagtg gccgtgtcgc tggatgcatg gtgaccgagg gaaagattac caaaggctgt    2760
gggattcgag tgatacggaa gggaaaaact gtccacgttg gagttcttga ttcgttgcgt    2820
cgagtaa                                                             2827

<210> SEQ ID NO 72
<211> LENGTH: 200
<212> TYPE: DNA
<213> ORGANISM: artificial sequence
<220> FEATURE:
<223> OTHER INFORMATION: Synthetic Construct

<400> SEQUENCE: 72
tttcgagtaa tgggaaattg gataatgtag aggagaggaa gaaggttatt gattcattgg      60
atgaggtatt agaaaaggcc gagagattag aaacggcgaa cttacaagca gataatagaa     120
aggatagcac aaatgtaaat aaaccgtctc cgagtgtaag tagttcaacc aatggtaaac     180
ctgtaaataa tttgaacaaa                                                200

<210> SEQ ID NO 73
<211> LENGTH: 160
<212> TYPE: RNA
<213> ORGANISM: artificial sequence
<220> FEATURE:
<223> OTHER INFORMATION: Synthetic Construct

<400> SEQUENCE: 73
uucgaguaau gggaaauugg auaauguaga ggagaggaag aagguuauug auucauugga      60
ugagguauua gaaaaggccg agagauuaga aacggcgaac uuacaagcag auaauagaaa     120
ggauagcaca aauguaaaua aaccgucucc gaguguaagu                          160

<210> SEQ ID NO 74
<211> LENGTH: 160
<212> TYPE: RNA
<213> ORGANISM: artificial sequence
<220> FEATURE:
<223> OTHER INFORMATION: Synthetic Construct

<400> SEQUENCE: 74
acuuacacuc ggagacgguu uauuuacauu ugugcuaucc uuucuauuau cugcuuguaa      60
guucgccguu ucuaaucucu cggccuuuuc uaauaccuca uccaaugaau caauaaccuu     120
cuuccucucc ucuacauuau ccaauuuccc auuacucgaa                          160

<210> SEQ ID NO 75
<211> LENGTH: 22
<212> TYPE: DNA
```

```
<213> ORGANISM: artificial sequence
<220> FEATURE:
<223> OTHER INFORMATION: Synthetic Construct

<400> SEQUENCE: 75
atttctccaa acgctcttcg ca                                              22

<210> SEQ ID NO 76
<211> LENGTH: 22
<212> TYPE: DNA
<213> ORGANISM: artificial sequence
<220> FEATURE:
<223> OTHER INFORMATION: Synthetic Construct

<400> SEQUENCE: 76
atccaatttc ccattactcg aa                                              22

<210> SEQ ID NO 77
<211> LENGTH: 22
<212> TYPE: DNA
<213> ORGANISM: artificial sequence
<220> FEATURE:
<223> OTHER INFORMATION: Synthetic Construct

<400> SEQUENCE: 77
gtttctaatc tctcggcctt tt                                              22

<210> SEQ ID NO 78
<211> LENGTH: 21
<212> TYPE: DNA
<213> ORGANISM: artificial sequence
<220> FEATURE:
<223> OTHER INFORMATION: Synthetic Construct

<400> SEQUENCE: 78
ttgaactact tacactcgga g                                               21

<210> SEQ ID NO 79
<211> LENGTH: 21
<212> TYPE: DNA
<213> ORGANISM: artificial sequence
<220> FEATURE:
<223> OTHER INFORMATION: Synthetic Construct

<400> SEQUENCE: 79
taaccttctt cctctcctct a                                               21

<210> SEQ ID NO 80
<211> LENGTH: 21
<212> TYPE: DNA
<213> ORGANISM: artificial sequence
<220> FEATURE:
<223> OTHER INFORMATION: Synthetic Construct

<400> SEQUENCE: 80
gtccttccca tcagctctgg a                                               21

<210> SEQ ID NO 81
<211> LENGTH: 20
<212> TYPE: DNA
<213> ORGANISM: artificial sequence
<220> FEATURE:
<223> OTHER INFORMATION: Synthetic Construct

<400> SEQUENCE: 81
cgtagcagca ccaggaatag                                                 20
```

<210> SEQ ID NO 82
<211> LENGTH: 21
<212> TYPE: DNA
<213> ORGANISM: artificial sequence
<220> FEATURE:
<223> OTHER INFORMATION: Synthetic Construct

<400> SEQUENCE: 82
cagcagctac aactataata g                                    21

<210> SEQ ID NO 83
<211> LENGTH: 25
<212> TYPE: RNA
<213> ORGANISM: artificial sequence
<220> FEATURE:
<223> OTHER INFORMATION: Synthetic Construct

<400> SEQUENCE: 83
cuaccaucaa caauguguc cauac                                 25

<210> SEQ ID NO 84
<211> LENGTH: 27
<212> TYPE: RNA
<213> ORGANISM: artificial sequence
<220> FEATURE:
<223> OTHER INFORMATION: Synthetic Construct

<400> SEQUENCE: 84
guauggacac cauuguugau gguagua                              27

<210> SEQ ID NO 85
<211> LENGTH: 23
<212> TYPE: RNA
<213> ORGANISM: artificial sequence
<220> FEATURE:
<223> OTHER INFORMATION: Synthetic Construct

<400> SEQUENCE: 85 aguuggugg caaucaucaa uug                                   23

<210> SEQ ID NO 86
<211> LENGTH: 27
<212> TYPE: RNA
<213> ORGANISM: artificial sequence
<220> FEATURE:
<223> OTHER INFORMATION: Synthetic Construct

<400> SEQUENCE: 86
aacaauugau gauugcccac caacucu                              27

<210> SEQ ID NO 87
<211> LENGTH: 24
<212> TYPE: RNA
<213> ORGANISM: artificial sequence
<220> FEATURE:
<223> OTHER INFORMATION: Synthetic Construct

<400> SEQUENCE: 87
ggucgacaac uugcuguaua guga                                 24

<210> SEQ ID NO 88
<211> LENGTH: 27
<212> TYPE: RNA
<213> ORGANISM: artificial sequence
<220> FEATURE:

<223> OTHER INFORMATION: Synthetic Construct

<400> SEQUENCE: 88
aucacuauac agcaaguugu cgaccuc                                              27

<210> SEQ ID NO 89
<211> LENGTH: 24
<212> TYPE: RNA
<213> ORGANISM: artificial sequence
<220> FEATURE:
<223> OTHER INFORMATION: Synthetic Construct

<400> SEQUENCE: 89
ugcaagguca ccuggacaga gaaa                                                 24

<210> SEQ ID NO 90
<211> LENGTH: 27
<212> TYPE: RNA
<213> ORGANISM: artificial sequence
<220> FEATURE:
<223> OTHER INFORMATION: Synthetic Construct

<400> SEQUENCE: 90
uauucucugu ccaggugacc uugcaac                                              27

<210> SEQ ID NO 91
<211> LENGTH: 21
<212> TYPE: RNA
<213> ORGANISM: artificial sequence
<220> FEATURE:
<223> OTHER INFORMATION: Synthetic Construct

<400> SEQUENCE: 91
aacaugaaca aaaugccaga u                                                    21

<210> SEQ ID NO 92
<211> LENGTH: 21
<212> TYPE: RNA
<213> ORGANISM: artificial sequence
<220> FEATURE:
<223> OTHER INFORMATION: Synthetic Construct

<400> SEQUENCE: 92
aucuggcauu uuguucaugu u                                                    21

<210> SEQ ID NO 93
<211> LENGTH: 27
<212> TYPE: RNA
<213> ORGANISM: artificial sequence
<220> FEATURE:
<223> OTHER INFORMATION: Synthetic Construct

<400> SEQUENCE: 93
guauggacac cauuguugau gguagua                                              27

<210> SEQ ID NO 94
<211> LENGTH: 27
<212> TYPE: RNA
<213> ORGANISM: artificial sequence
<220> FEATURE:
<223> OTHER INFORMATION: Synthetic Construct

<400> SEQUENCE: 94
uacuaccauc aacaauggug uccauac                                              27

```
<210> SEQ ID NO 95
<211> LENGTH: 27
<212> TYPE: RNA
<213> ORGANISM: artificial sequence
<220> FEATURE:
<223> OTHER INFORMATION: Synthetic Construct

<400> SEQUENCE: 95
aauaauugau gauugcccac caacucu                                           27

<210> SEQ ID NO 96
<211> LENGTH: 27
<212> TYPE: RNA
<213> ORGANISM: artificial sequence
<220> FEATURE:
<223> OTHER INFORMATION: Synthetic Construct

<400> SEQUENCE: 96 agaguggug ggcaaucauc aauuauu                                            27

<210> SEQ ID NO 97
<211> LENGTH: 27
<212> TYPE: RNA
<213> ORGANISM: artificial sequence
<220> FEATURE:
<223> OTHER INFORMATION: Synthetic Construct

<400> SEQUENCE: 97
aucacuauac agcaaguugu cgaccac                                           27

<210> SEQ ID NO 98
<211> LENGTH: 27
<212> TYPE: RNA
<213> ORGANISM: artificial sequence
<220> FEATURE:
<223> OTHER INFORMATION: Synthetic Construct

<400> SEQUENCE: 98
guggucgaca acuugcugua uagugau                                           27

<210> SEQ ID NO 99
<211> LENGTH: 27
<212> TYPE: RNA
<213> ORGANISM: artificial sequence
<220> FEATURE:
<223> OTHER INFORMATION: Synthetic Construct

<400> SEQUENCE: 99
uauucucugu ccaggugacc uugcaac                                           27

<210> SEQ ID NO 100
<211> LENGTH: 27
<212> TYPE: RNA
<213> ORGANISM: artificial sequence
<220> FEATURE:
<223> OTHER INFORMATION: Synthetic Construct

<400> SEQUENCE: 100
guugcaaggu caccuggaca gagaaua                                           27

<210> SEQ ID NO 101
<211> LENGTH: 29
<212> TYPE: RNA
<213> ORGANISM: artificial sequence
<220> FEATURE:
<223> OTHER INFORMATION: Synthetic Construct
```

```
<400> SEQUENCE: 101
gguauggaca ccauuguuga ugguaguac                                29

<210> SEQ ID NO 102
<211> LENGTH: 29
<212> TYPE: RNA
<213> ORGANISM: artificial sequence
<220> FEATURE:
<223> OTHER INFORMATION: Synthetic Construct

<400> SEQUENCE: 102
gcuaccauca acaauggugu ccauaccac                                29

<210> SEQ ID NO 103
<211> LENGTH: 29
<212> TYPE: RNA
<213> ORGANISM: artificial sequence
<220> FEATURE:
<223> OTHER INFORMATION: Synthetic Construct

<400> SEQUENCE: 103
gaagaauuga ugauugccca ccaacucac                                29

<210> SEQ ID NO 104
<211> LENGTH: 29
<212> TYPE: RNA
<213> ORGANISM: artificial sequence
<220> FEATURE:
<223> OTHER INFORMATION: Synthetic Construct

<400> SEQUENCE: 104
gaguuggugg gcaaucauca auuauucac                                29

<210> SEQ ID NO 105
<211> LENGTH: 27
<212> TYPE: RNA
<213> ORGANISM: artificial sequence
<220> FEATURE:
<223> OTHER INFORMATION: Synthetic Construct

<400> SEQUENCE: 105
gaucacuaua cagcaaguug ucgacac                                  27

<210> SEQ ID NO 106
<211> LENGTH: 27
<212> TYPE: RNA
<213> ORGANISM: artificial sequence
<220> FEATURE:
<223> OTHER INFORMATION: Synthetic Construct

<400> SEQUENCE: 106
gucgacaacu ugcuguauag ugaucac                                  27

<210> SEQ ID NO 107
<211> LENGTH: 29
<212> TYPE: RNA
<213> ORGANISM: artificial sequence
<220> FEATURE:
<223> OTHER INFORMATION: Synthetic Construct

<400> SEQUENCE: 107
guauucucug uccaggugac cuugcacac                                29

<210> SEQ ID NO 108
<211> LENGTH: 29
```

```
<212> TYPE: RNA
<213> ORGANISM: artificial sequence
<220> FEATURE:
<223> OTHER INFORMATION: Synthetic Construct

<400> SEQUENCE: 108
gugcaagguc accuggacag agaauacac                                       29

<210> SEQ ID NO 109
<211> LENGTH: 58
<212> TYPE: RNA
<213> ORGANISM: artificial sequence
<220> FEATURE:
<223> OTHER INFORMATION: Synthetic Construct

<400> SEQUENCE: 109
guauggacac cauuguugau gguaguagaa auacuaccau caacaauggu guccauac       58

<210> SEQ ID NO 110
<211> LENGTH: 58
<212> TYPE: RNA
<213> ORGANISM: artificial sequence
<220> FEATURE:
<223> OTHER INFORMATION: Synthetic Construct

<400> SEQUENCE: 110
aauaauugau gauugcccac caacucugaa aagaguuggu gggcaaucau caauuauu       58

<210> SEQ ID NO 111
<211> LENGTH: 58
<212> TYPE: RNA
<213> ORGANISM: artificial sequence
<220> FEATURE:
<223> OTHER INFORMATION: Synthetic Construct

<400> SEQUENCE: 111
aucacuauac agcaaguugu cgaccacgaa aguggucgac aacuugcugu auagugau       58

<210> SEQ ID NO 112
<211> LENGTH: 58
<212> TYPE: RNA
<213> ORGANISM: artificial sequence
<220> FEATURE:
<223> OTHER INFORMATION: Synthetic Construct

<400> SEQUENCE: 112
uauucucugu ccaggugacc uugcaacgaa aguugcaagg ucaccuggac agagaaua       58

<210> SEQ ID NO 113
<211> LENGTH: 168
<212> TYPE: RNA
<213> ORGANISM: artificial sequence
<220> FEATURE:
<223> OTHER INFORMATION: Synthetic Construct

<400> SEQUENCE: 113
gaucacaaau uugccgguuu augaucaaau acggaacaua agacagauac acuugaacac       60
caugauucgc auggggggug ugguuacucg ucguucugga guauucccuc aguugaugca      120
ggugaaguau gacugcaaua aauguggggc uauccugggu cccuuuuu                  168

<210> SEQ ID NO 114
<211> LENGTH: 168
<212> TYPE: RNA
<213> ORGANISM: artificial sequence
<220> FEATURE:
```

<223> OTHER INFORMATION: Synthetic Construct

<400> SEQUENCE: 114
aaaaagggac ccaggauagc cccacauuua uugcagucau acuucaccug caucaacuga    60
gggaauacuc cagaacgacg aguaaccaca cccccaaugc gaaucauggu guucaagugu   120 aucugcuua uguuccguau uugaucauaa accggcaaau uugugauc                 168

<210> SEQ ID NO 115
<211> LENGTH: 25
<212> TYPE: RNA
<213> ORGANISM: artificial sequence
<220> FEATURE:
<223> OTHER INFORMATION: Synthetic Construct

<400> SEQUENCE: 115
uuuucuaaua ccucauccaa ugaau                                          25

<210> SEQ ID NO 116
<211> LENGTH: 25
<212> TYPE: RNA
<213> ORGANISM: artificial sequence
<220> FEATURE:
<223> OTHER INFORMATION: Synthetic Construct

<400> SEQUENCE: 116
auucauugga ugagguauua gaaaa                                          25

<210> SEQ ID NO 117
<211> LENGTH: 25
<212> TYPE: RNA
<213> ORGANISM: artificial sequence
<220> FEATURE:
<223> OTHER INFORMATION: Synthetic Construct

<400> SEQUENCE: 117
uaucugcuug uaaguucgcc guuuc                                          25

<210> SEQ ID NO 118
<211> LENGTH: 25
<212> TYPE: RNA
<213> ORGANISM: artificial sequence
<220> FEATURE:
<223> OTHER INFORMATION: Synthetic Construct

<400> SEQUENCE: 118
gaaacggcga acuuacaagc agaua                                          25

<210> SEQ ID NO 119
<211> LENGTH: 25
<212> TYPE: RNA
<213> ORGANISM: artificial sequence
<220> FEATURE:
<223> OTHER INFORMATION: Synthetic Construct

<400> SEQUENCE: 119
ggagacgguu uauuuacauu ugugc                                          25

<210> SEQ ID NO 120
<211> LENGTH: 25
<212> TYPE: RNA
<213> ORGANISM: artificial sequence
<220> FEATURE:
<223> OTHER INFORMATION: Synthetic Construct

<400> SEQUENCE: 120

```
gcacaaaugu aaauaaaccg ucucc                                          25

<210> SEQ ID NO 121
<211> LENGTH: 25
<212> TYPE: RNA
<213> ORGANISM: artificial sequence
<220> FEATURE:
<223> OTHER INFORMATION: Synthetic Construct

<400> SEQUENCE: 121
uauuuacagg uuuaccaug guuga                                           25

<210> SEQ ID NO 122
<211> LENGTH: 25
<212> TYPE: RNA
<213> ORGANISM: artificial sequence
<220> FEATURE:
<223> OTHER INFORMATION: Synthetic Construct

<400> SEQUENCE: 122
ucaaccaaug guaaaccugu aaaua                                          25

<210> SEQ ID NO 123
<211> LENGTH: 185
<212> TYPE: RNA
<213> ORGANISM: artificial sequence
<220> FEATURE:
<223> OTHER INFORMATION: Synthetic Construct

<400> SEQUENCE: 123
gacggaaacc cuccagagag gcugugcaug ccuauuguua aacacaucga gucacuaggu    60
ggugaaguua aacuuaacuc ucguauacaa aagauucagu uggaccagag uggaagcgug   120
aagaguuuuu ugcuaaauaa cgggagggaa auacgaggag augccuaugu uuugccacc   180 ccagu                                                              185

<210> SEQ ID NO 124
<211> LENGTH: 185
<212> TYPE: RNA
<213> ORGANISM: artificial sequence
<220> FEATURE:
<223> OTHER INFORMATION: Synthetic Construct

<400> SEQUENCE: 124
acuggggugg caaaaacaua ggcaucuccu cguauuuccc uccguuauu uagcaaaaaa    60 cucuucacgc uuccacucug guccaacuga aucuuugua uacgagaguu aaguuuaacu   120
ucaccaccua gugacucgau guguuuaaca auaggcaugc acagccucuc uggagggguu   180
ccguc                                                              185

<210> SEQ ID NO 125
<211> LENGTH: 22
<212> TYPE: DNA
<213> ORGANISM: artificial sequence
<220> FEATURE:
<223> OTHER INFORMATION: Synthetic Construct

<400> SEQUENCE: 125
gtgatattac ctccaacacg at                                             22

<210> SEQ ID NO 126
<211> LENGTH: 21
<212> TYPE: DNA
```

<213> ORGANISM: artificial sequence
<220> FEATURE:
<223> OTHER INFORMATION: Synthetic Construct

<400> SEQUENCE: 126
atagtaagca caggatcgga g                                    21

<210> SEQ ID NO 127
<211> LENGTH: 21
<212> TYPE: DNA
<213> ORGANISM: artificial sequence
<220> FEATURE:
<223> OTHER INFORMATION: Synthetic Construct

<400> SEQUENCE: 127
ctttcaatcc actgtcaacc g                                    21

<210> SEQ ID NO 128
<211> LENGTH: 22
<212> TYPE: DNA
<213> ORGANISM: artificial sequence
<220> FEATURE:
<223> OTHER INFORMATION: Synthetic Construct

<400> SEQUENCE: 128
atcaagcgtt cgaagacctc at                                   22

<210> SEQ ID NO 129
<211> LENGTH: 21
<212> TYPE: DNA
<213> ORGANISM: artificial sequence
<220> FEATURE:
<223> OTHER INFORMATION: Synthetic Construct

<400> SEQUENCE: 129
cagcaatggc ggtaggtaac a                                    21

<210> SEQ ID NO 130
<211> LENGTH: 21
<212> TYPE: DNA
<213> ORGANISM: artificial sequence
<220> FEATURE:
<223> OTHER INFORMATION: Synthetic Construct

<400> SEQUENCE: 130
gcaattgccc gaatcctttt a                                    21

<210> SEQ ID NO 131
<211> LENGTH: 21
<212> TYPE: DNA
<213> ORGANISM: artificial sequence
<220> FEATURE:
<223> OTHER INFORMATION: Synthetic Construct

<400> SEQUENCE: 131
tagctcaata tcaaggtcct a                                    21

<210> SEQ ID NO 132
<211> LENGTH: 21
<212> TYPE: DNA
<213> ORGANISM: artificial sequence
<220> FEATURE:
<223> OTHER INFORMATION: Synthetic Construct

<400> SEQUENCE: 132
tcataagcac cctctataca c                                    21

<210> SEQ ID NO 133
<211> LENGTH: 20
<212> TYPE: DNA
<213> ORGANISM: artificial sequence
<220> FEATURE:
<223> OTHER INFORMATION: Synthetic Construct

<400> SEQUENCE: 133
ttcttaacct cgtcgagatg                                                  20

<210> SEQ ID NO 134
<211> LENGTH: 21
<212> TYPE: DNA
<213> ORGANISM: artificial sequence
<220> FEATURE:
<223> OTHER INFORMATION: Synthetic Construct

<400> SEQUENCE: 134
atacccgagt atccttgcaa a                                                21

<210> SEQ ID NO 135
<211> LENGTH: 21
<212> TYPE: DNA
<213> ORGANISM: artificial sequence
<220> FEATURE:
<223> OTHER INFORMATION: Synthetic Construct

<400> SEQUENCE: 135
tagggcccac ggccttggag t                                                21

<210> SEQ ID NO 136
<211> LENGTH: 21
<212> TYPE: DNA
<213> ORGANISM: artificial sequence
<220> FEATURE:
<223> OTHER INFORMATION: Synthetic Construct

<400> SEQUENCE: 136
agcggatata acctcagcta g                                                21

<210> SEQ ID NO 137
<211> LENGTH: 21
<212> TYPE: DNA
<213> ORGANISM: artificial sequence
<220> FEATURE:
<223> OTHER INFORMATION: Synthetic Construct

<400> SEQUENCE: 137
cttcgtggcc caacgaatga c                                                21

<210> SEQ ID NO 138
<211> LENGTH: 21
<212> TYPE: DNA
<213> ORGANISM: artificial sequence
<220> FEATURE:
<223> OTHER INFORMATION: Synthetic Construct

<400> SEQUENCE: 138
caagctcggg tccctgcttg c                                                21

<210> SEQ ID NO 139
<211> LENGTH: 21
<212> TYPE: DNA
<213> ORGANISM: artificial sequence
<220> FEATURE:

<223> OTHER INFORMATION: Synthetic Construct

<400> SEQUENCE: 139
ggaaggtaga tgacatgagt t    21

<210> SEQ ID NO 140
<211> LENGTH: 21
<212> TYPE: DNA
<213> ORGANISM: artificial sequence
<220> FEATURE:
<223> OTHER INFORMATION: Synthetic Construct

<400> SEQUENCE: 140
gatggcatag ttaccactgt c    21

<210> SEQ ID NO 141
<211> LENGTH: 21
<212> TYPE: DNA
<213> ORGANISM: artificial sequence
<220> FEATURE:
<223> OTHER INFORMATION: Synthetic Construct

<400> SEQUENCE: 141
tccgtagctt acataccgaa g    21

<210> SEQ ID NO 142
<211> LENGTH: 21
<212> TYPE: DNA
<213> ORGANISM: artificial sequence
<220> FEATURE:
<223> OTHER INFORMATION: Synthetic Construct

<400> SEQUENCE: 142
tccaagtgaa taggagaaac a    21

<210> SEQ ID NO 143
<211> LENGTH: 21
<212> TYPE: DNA
<213> ORGANISM: artificial sequence
<220> FEATURE:
<223> OTHER INFORMATION: Synthetic Construct

<400> SEQUENCE: 143
agcagcttct gcgtcttcta c    21

<210> SEQ ID NO 144
<211> LENGTH: 21
<212> TYPE: DNA
<213> ORGANISM: artificial sequence
<220> FEATURE:
<223> OTHER INFORMATION: Synthetic Construct

<400> SEQUENCE: 144
acagcacgca cgccaagacc g    21

<210> SEQ ID NO 145
<211> LENGTH: 21
<212> TYPE: DNA
<213> ORGANISM: artificial sequence
<220> FEATURE:
<223> OTHER INFORMATION: Synthetic Construct

<400> SEQUENCE: 145
cgatgtaagg aatttggtaa a    21

```
<210> SEQ ID NO 146
<211> LENGTH: 21
<212> TYPE: DNA
<213> ORGANISM: artificial sequence
<220> FEATURE:
<223> OTHER INFORMATION: Synthetic Construct

<400> SEQUENCE: 146 cgagggatt gcagcagaag a                                      21

<210> SEQ ID NO 147
<211> LENGTH: 21
<212> TYPE: DNA
<213> ORGANISM: artificial sequence
<220> FEATURE:
<223> OTHER INFORMATION: Synthetic Construct

<400> SEQUENCE: 147
gtaggagaat acggtgaagt a                                     21

<210> SEQ ID NO 148
<211> LENGTH: 21
<212> TYPE: DNA
<213> ORGANISM: artificial sequence
<220> FEATURE:
<223> OTHER INFORMATION: Synthetic Construct

<400> SEQUENCE: 148
gaccccaaga aaatcgtctg c                                     21

<210> SEQ ID NO 149
<211> LENGTH: 19
<212> TYPE: DNA
<213> ORGANISM: artificial sequence
<220> FEATURE:
<223> OTHER INFORMATION: Synthetic Construct

<400> SEQUENCE: 149
gtcttacaag ggttctcaa                                        19

<210> SEQ ID NO 150
<211> LENGTH: 21
<212> TYPE: DNA
<213> ORGANISM: artificial sequence
<220> FEATURE:
<223> OTHER INFORMATION: Synthetic Construct

<400> SEQUENCE: 150
atctatgttc acctccctgt g                                     21

<210> SEQ ID NO 151
<211> LENGTH: 21
<212> TYPE: DNA
<213> ORGANISM: artificial sequence
<220> FEATURE:
<223> OTHER INFORMATION: Synthetic Construct

<400> SEQUENCE: 151
ataaaccatt agctttcccg g                                     21

<210> SEQ ID NO 152
<211> LENGTH: 21
<212> TYPE: DNA
<213> ORGANISM: artificial sequence
<220> FEATURE:
<223> OTHER INFORMATION: Synthetic Construct
```

```
<400> SEQUENCE: 152
tttattggaa caagcggagt t                                           21

<210> SEQ ID NO 153
<211> LENGTH: 21
<212> TYPE: DNA
<213> ORGANISM: artificial sequence
<220> FEATURE:
<223> OTHER INFORMATION: Synthetic Construct

<400> SEQUENCE: 153
tatagcacca cttcccgata g                                           21

<210> SEQ ID NO 154
<211> LENGTH: 21
<212> TYPE: DNA
<213> ORGANISM: artificial sequence
<220> FEATURE:
<223> OTHER INFORMATION: Synthetic Construct

<400> SEQUENCE: 154
gcaccacgag gatcacaaga a                                           21

<210> SEQ ID NO 155
<211> LENGTH: 21
<212> TYPE: DNA
<213> ORGANISM: artificial sequence
<220> FEATURE:
<223> OTHER INFORMATION: Synthetic Construct

<400> SEQUENCE: 155
ccacccgaga aacctctcca a                                           21

<210> SEQ ID NO 156
<211> LENGTH: 21
<212> TYPE: DNA
<213> ORGANISM: artificial sequence
<220> FEATURE:
<223> OTHER INFORMATION: Synthetic Construct

<400> SEQUENCE: 156
cagtcttgac gagtgattcc t                                           21

<210> SEQ ID NO 157
<211> LENGTH: 22
<212> TYPE: DNA
<213> ORGANISM: artificial sequence
<220> FEATURE:
<223> OTHER INFORMATION: Synthetic Construct

<400> SEQUENCE: 157
gttcttcagg gctaaatcgg ga                                          22

<210> SEQ ID NO 158
<211> LENGTH: 22
<212> TYPE: DNA
<213> ORGANISM: artificial sequence
<220> FEATURE:
<223> OTHER INFORMATION: Synthetic Construct

<400> SEQUENCE: 158
gttcaagagc ttcaacgaga ac                                          22

<210> SEQ ID NO 159
<211> LENGTH: 22
```

```
<212> TYPE: DNA
<213> ORGANISM: artificial sequence
<220> FEATURE:
<223> OTHER INFORMATION: Synthetic Construct

<400> SEQUENCE: 159
atacaaactc caacgcgtcc ag                                              22

<210> SEQ ID NO 160
<211> LENGTH: 22
<212> TYPE: DNA
<213> ORGANISM: artificial sequence
<220> FEATURE:
<223> OTHER INFORMATION: Synthetic Construct

<400> SEQUENCE: 160
ctcttggaaa gcatcagtac ca                                              22

<210> SEQ ID NO 161
<211> LENGTH: 22
<212> TYPE: DNA
<213> ORGANISM: artificial sequence
<220> FEATURE:
<223> OTHER INFORMATION: Synthetic Construct

<400> SEQUENCE: 161
ctagaaagat acccacccaa tt                                              22

<210> SEQ ID NO 162
<211> LENGTH: 22
<212> TYPE: DNA
<213> ORGANISM: artificial sequence
<220> FEATURE:
<223> OTHER INFORMATION: Synthetic Construct

<400> SEQUENCE: 162
actagaattc aaacacccac cc                                              22

<210> SEQ ID NO 163
<211> LENGTH: 22
<212> TYPE: DNA
<213> ORGANISM: artificial sequence
<220> FEATURE:
<223> OTHER INFORMATION: Synthetic Construct

<400> SEQUENCE: 163
tttctgctca ttcaactcct cc                                              22

<210> SEQ ID NO 164
<211> LENGTH: 22
<212> TYPE: DNA
<213> ORGANISM: artificial sequence
<220> FEATURE:
<223> OTHER INFORMATION: Synthetic Construct

<400> SEQUENCE: 164
tatgtatgtg cccggttagc tt                                              22

<210> SEQ ID NO 165
<211> LENGTH: 21
<212> TYPE: DNA
<213> ORGANISM: artificial sequence
<220> FEATURE:
<223> OTHER INFORMATION: Synthetic Construct

<400> SEQUENCE: 165
```
tcatatccaa gccagatcct c                    21

<210> SEQ ID NO 166
<211> LENGTH: 21
<212> TYPE: DNA
<213> ORGANISM: artificial sequence
<220> FEATURE:
<223> OTHER INFORMATION: Synthetic Construct

<400> SEQUENCE: 166
tgcatcacac atcaccaaga t                    21

<210> SEQ ID NO 167
<211> LENGTH: 21
<212> TYPE: DNA
<213> ORGANISM: artificial sequence
<220> FEATURE:
<223> OTHER INFORMATION: Synthetic Construct

<400> SEQUENCE: 167
gtactcctgt tcaatgccat a                    21

<210> SEQ ID NO 168
<211> LENGTH: 21
<212> TYPE: DNA
<213> ORGANISM: artificial sequence
<220> FEATURE:
<223> OTHER INFORMATION: Synthetic Construct

<400> SEQUENCE: 168
attgatacca gcatagagac a                    21

<210> SEQ ID NO 169
<211> LENGTH: 21
<212> TYPE: DNA
<213> ORGANISM: artificial sequence
<220> FEATURE:
<223> OTHER INFORMATION: Synthetic Construct

<400> SEQUENCE: 169
agcaattctc tctagaatgt a                    21

<210> SEQ ID NO 170
<211> LENGTH: 21
<212> TYPE: DNA
<213> ORGANISM: artificial sequence
<220> FEATURE:
<223> OTHER INFORMATION: Synthetic Construct

<400> SEQUENCE: 170
catcattcct catcgactta g                    21

<210> SEQ ID NO 171
<211> LENGTH: 21
<212> TYPE: DNA
<213> ORGANISM: artificial sequence
<220> FEATURE:
<223> OTHER INFORMATION: Synthetic Construct

<400> SEQUENCE: 171
ctctcgttgc cctctccata a                    21

<210> SEQ ID NO 172
<211> LENGTH: 21
<212> TYPE: DNA
<213> ORGANISM: artificial sequence

```
<220> FEATURE:
<223> OTHER INFORMATION: Synthetic Construct

<400> SEQUENCE: 172
caacgcccca ggagaaagtt c                                              21

<210> SEQ ID NO 173
<211> LENGTH: 195
<212> TYPE: RNA
<213> ORGANISM: artificial sequence
<220> FEATURE:
<223> OTHER INFORMATION: Synthetic Construct

<400> SEQUENCE: 173
cugaagcugg ugaaggugaa gauggacgaa ugaaaucugc gauuggaauu gggacccuuc     60
uucaggaugg cuugggagau acgaucaggg ugucucuaac agaaccacca gaagaggaga    120
uagacccuug cagaagguug gcaaaucuug gaacaaaagc agcugaaauu cagcaaggag    180
uggcaccauu ugaag                                                    195

<210> SEQ ID NO 174
<211> LENGTH: 195
<212> TYPE: RNA
<213> ORGANISM: artificial sequence
<220> FEATURE:
<223> OTHER INFORMATION: Synthetic Construct

<400> SEQUENCE: 174
cuucaaaugg ugccacuccu ugcugaauuu cagcugcuuu uguuccaaga uuugccaacc     60
uucugcaagg gucuaucucc ucuucuggug guucuguuag agacacccug aucguaucuc    120
ccaagccauc cugaagaagg gucccaauuc caaucgcaga uuucauucgu ccaucuucac    180
cuucaccagc uucag                                                    195

<210> SEQ ID NO 175
<211> LENGTH: 183
<212> TYPE: RNA
<213> ORGANISM: artificial sequence
<220> FEATURE:
<223> OTHER INFORMATION: Synthetic Construct

<400> SEQUENCE: 175
ucccaucaaa guucccuaca aaauaugugc aguuccuau cuuccuugcc gccauucaua      60
caaacuaugu ugauuguaca aggugggcuug gugauuuugu ucuuucaaag aguguugaca   120
augagauugu acuggggag ccaauuauga aggagcaauc uccggagag gguucaguug      180 aca                                                                 183

<210> SEQ ID NO 176
<211> LENGTH: 183
<212> TYPE: RNA
<213> ORGANISM: artificial sequence
<220> FEATURE:
<223> OTHER INFORMATION: Synthetic Construct

<400> SEQUENCE: 176
ugucaacuga acccucucca ggagauugcu ccuucauaau uggcucccac aguacaaucu     60
cauugucaac acucuuagaa agaacaaaau caccaagcca ccuuguacaa ucaacauagu    120
uuguaugaau ggcggcaagg aagauaggaa acugcacaua uuuuguaggg aacuuugaug    180
gga                                                                 183
```

```
<210> SEQ ID NO 177
<211> LENGTH: 143
<212> TYPE: RNA
<213> ORGANISM: artificial sequence
<220> FEATURE:
<223> OTHER INFORMATION: Synthetic Construct

<400> SEQUENCE: 177
uugugcuuaa aacaucgacc agacagacaa uauuucuucc uguuguugga cuaguugauc    60
cugauacgcu gaaaccuggu gauuuaguug gugucaacaa agauaguuau cuuauccugg   120
acacucugcc gucggaauau gau                                          143

<210> SEQ ID NO 178
<211> LENGTH: 143
<212> TYPE: RNA
<213> ORGANISM: artificial sequence
<220> FEATURE:
<223> OTHER INFORMATION: Synthetic Construct

<400> SEQUENCE: 178
aucauauucc gacggcagag uguccaggau aagauaacua ucuuuguuga caccaacuaa    60
aucaccaggu uucagcguau caggaucaac uaguccaaca acaggaagaa auauugucug   120
ucuggucgau guuuuaagca caa                                          143

<210> SEQ ID NO 179
<211> LENGTH: 159
<212> TYPE: RNA
<213> ORGANISM: artificial sequence
<220> FEATURE:
<223> OTHER INFORMATION: Synthetic Construct

<400> SEQUENCE: 179
cgcugcaguu ggugaaguag aucccggcaa ggggauuuca cuccgguuuc cacgucuggu    60
ucguauccga gaggauaaau uccagagga cgccacauca ucugagcagg uggcggauau    120
guacagaucu caagcaaaca auccacaccg caaaaagag                          159

<210> SEQ ID NO 180
<211> LENGTH: 159
<212> TYPE: RNA
<213> ORGANISM: artificial sequence
<220> FEATURE:
<223> OTHER INFORMATION: Synthetic Construct

<400> SEQUENCE: 180
cucuuuuugc ggguguggauu guuugcuuga gaucuguaca uauccgccac cugcucagau    60
gauguggcgu ccucuggaga uuuauccucu cggauacgaa ccagacgugg aaaccggagu   120
gaaauccccu ugccgggauc uacuucacca acugcagcg                         159

<210> SEQ ID NO 181
<211> LENGTH: 159
<212> TYPE: RNA
<213> ORGANISM: artificial sequence
<220> FEATURE:
<223> OTHER INFORMATION: Synthetic Construct

<400> SEQUENCE: 181
uaaagauggc ggaaaaaucg acuaugauaa auugauugac aaauucggcu gucagcgacu    60
ugauuuaucg cucauucaga gaauugagcg caucacugcu cguccugcuc auguauuucu   120
ucgccgcaac guuuucuucg cucaccguga uuugaauga                         159
```

<210> SEQ ID NO 182
<211> LENGTH: 159
<212> TYPE: RNA
<213> ORGANISM: artificial sequence
<220> FEATURE:
<223> OTHER INFORMATION: Synthetic Construct

<400> SEQUENCE: 182
ucauucaaau cacggugagc gaagaaaacg uugcggcgaa gaaauacaug agcaggacga      60
gcagugaugc gcucaauucu cugaaugagc gauaaaucaa gucgcugaca gccgaauuug     120
ucaaucaauu uaucauaguc gauuuuccg ccaucuuua                             159

<210> SEQ ID NO 183
<211> LENGTH: 150
<212> TYPE: RNA
<213> ORGANISM: artificial sequence
<220> FEATURE:
<223> OTHER INFORMATION: Synthetic Construct

<400> SEQUENCE: 183
ugaagcugau gcugaaggaa aggauauuga ugcuagugaa guaguucgcc caagggugcc      60
auuagaagcu ugccuagcua gcuacucagc uccggaggag gugauggacu ucuacagcac     120
ugcauugaag gcaaaggcaa cugcuacaaa                                      150

<210> SEQ ID NO 184
<211> LENGTH: 150
<212> TYPE: RNA
<213> ORGANISM: artificial sequence
<220> FEATURE:
<223> OTHER INFORMATION: Synthetic Construct

<400> SEQUENCE: 184
uuuguagcag uugccuuugc cuucaaugca gugcuguaga aguccaucac cuccuccgga      60
gcugaguagc uagcuaggca agcuucuaau ggcacccuug ggcgaacuac uucacuagca     120
ucaauauccu uuccuucagc aucagcuuca                                      150

<210> SEQ ID NO 185
<211> LENGTH: 155
<212> TYPE: RNA
<213> ORGANISM: artificial sequence
<220> FEATURE:
<223> OTHER INFORMATION: Synthetic Construct

<400> SEQUENCE: 185
acaccugccc uaacaucucg gguuuucuc gaagaagauu uuguuaaagu ggccgaguau       60
uuugaugcug cuguuaagcu ggcucuaaaa aucaaggcug acacaaaagg aacaaaguug     120
aaggacuucg uugccaccuu gcagucuggu guuuu                                155

<210> SEQ ID NO 186
<211> LENGTH: 155
<212> TYPE: RNA
<213> ORGANISM: artificial sequence
<220> FEATURE:
<223> OTHER INFORMATION: Synthetic Construct

<400> SEQUENCE: 186
aaaacaccag acugcaaggu ggcaacgaag uccuucaacu uuguuccuuu ugugucagcc      60
uugauuuuua gagccagcuu aacagcagca ucaaauacu cggccacuuu aacaaaaucu     120

```
ucuucgagaa aaccccgaga uguuagggca ggugu                                   155

<210> SEQ ID NO 187
<211> LENGTH: 159
<212> TYPE: RNA
<213> ORGANISM: artificial sequence
<220> FEATURE:
<223> OTHER INFORMATION: Synthetic Construct

<400> SEQUENCE: 187
ugaacuacga agcaggcaaa uucuccaaaa guaaaggcau uggaguuuuu gggaaugacg         60
ccaagaauuc uaauauaccu guagaagugu ggagauacua ucugcuaaca aacaggccug        120
agguaucaga cacauuguuc acuugggcgg aucuucaag                              159

<210> SEQ ID NO 188
<211> LENGTH: 159
<212> TYPE: RNA
<213> ORGANISM: artificial sequence
<220> FEATURE:
<223> OTHER INFORMATION: Synthetic Construct

<400> SEQUENCE: 188
cuugaagauc cgcccaagug aacaaugugu cugauaccuc aggccuguuu guuagcagau         60
aguaucucca cacuucuaca gguauauuag aauucuuggc gucauuccca aaaacuccaa        120
ugccuuuacu uuuggagaau uugccugcuu cguaguuca                              159

<210> SEQ ID NO 189
<211> LENGTH: 24
<212> TYPE: DNA
<213> ORGANISM: artificial sequence
<220> FEATURE:
<223> OTHER INFORMATION: Synthetic Construct

<400> SEQUENCE: 189
tcccatctcc cacatgggtt actg                                               24

<210> SEQ ID NO 190
<211> LENGTH: 24
<212> TYPE: DNA
<213> ORGANISM: artificial sequence
<220> FEATURE:
<223> OTHER INFORMATION: Synthetic Construct

<400> SEQUENCE: 190
cagtaaccca tgtgggagat ggga                                               24

<210> SEQ ID NO 191
<211> LENGTH: 22
<212> TYPE: DNA
<213> ORGANISM: artificial sequence
<220> FEATURE:
<223> OTHER INFORMATION: Synthetic Construct

<400> SEQUENCE: 191
ggctgatgaa attcaagtgc ta                                                 22

<210> SEQ ID NO 192
<211> LENGTH: 21
<212> TYPE: DNA
<213> ORGANISM: artificial sequence
<220> FEATURE:
<223> OTHER INFORMATION: Synthetic Construct

<400> SEQUENCE: 192
```
aaactgagct tggaaataat c                                             21

<210> SEQ ID NO 193
<211> LENGTH: 22
<212> TYPE: DNA
<213> ORGANISM: artificial sequence
<220> FEATURE:
<223> OTHER INFORMATION: Synthetic Construct

<400> SEQUENCE: 193
gaacccaaaa ttgtcactttt tt                                           22

<210> SEQ ID NO 194
<211> LENGTH: 24
<212> TYPE: DNA
<213> ORGANISM: artificial sequence
<220> FEATURE:
<223> OTHER INFORMATION: Synthetic Construct

<400> SEQUENCE: 194
atgcacttgt ttatactctt gtca                                          24

<210> SEQ ID NO 195
<211> LENGTH: 21
<212> TYPE: DNA
<213> ORGANISM: artificial sequence
<220> FEATURE:
<223> OTHER INFORMATION: Synthetic Construct

<400> SEQUENCE: 195
atttattagt gttctaaaga a                                             21

<210> SEQ ID NO 196
<211> LENGTH: 24
<212> TYPE: DNA
<213> ORGANISM: artificial sequence
<220> FEATURE:
<223> OTHER INFORMATION: Synthetic Construct

<400> SEQUENCE: 196
tgtagtagct tataagatta gctt                                          24

<210> SEQ ID NO 197
<211> LENGTH: 22
<212> TYPE: DNA
<213> ORGANISM: artificial sequence
<220> FEATURE:
<223> OTHER INFORMATION: Synthetic Construct

<400> SEQUENCE: 197
gttgtccctt ttatgggtct tt                                            22

<210> SEQ ID NO 198
<211> LENGTH: 21
<212> TYPE: DNA
<213> ORGANISM: artificial sequence
<220> FEATURE:
<223> OTHER INFORMATION: Synthetic Construct

<400> SEQUENCE: 198
cccgtgcaat ttctgggaag c                                             21

<210> SEQ ID NO 199
<211> LENGTH: 24
<212> TYPE: DNA

```
<213> ORGANISM: artificial sequence
<220> FEATURE:
<223> OTHER INFORMATION: Synthetic Construct

<400> SEQUENCE: 199
attagttttt tatacacgaa agat                                              24

<210> SEQ ID NO 200
<211> LENGTH: 24
<212> TYPE: DNA
<213> ORGANISM: artificial sequence
<220> FEATURE:
<223> OTHER INFORMATION: Synthetic Construct

<400> SEQUENCE: 200
atctttcgtg tataaaaaac taat                                              24

<210> SEQ ID NO 201
<211> LENGTH: 22
<212> TYPE: DNA
<213> ORGANISM: artificial sequence
<220> FEATURE:
<223> OTHER INFORMATION: Synthetic Construct

<400> SEQUENCE: 201
ttggtggttt ggccacttcc gt                                                22

<210> SEQ ID NO 202
<211> LENGTH: 21
<212> TYPE: DNA
<213> ORGANISM: artificial sequence
<220> FEATURE:
<223> OTHER INFORMATION: Synthetic Construct

<400> SEQUENCE: 202
tttgtttgct atttagctgg a                                                 21

<210> SEQ ID NO 203
<211> LENGTH: 24
<212> TYPE: DNA
<213> ORGANISM: artificial sequence
<220> FEATURE:
<223> OTHER INFORMATION: Synthetic Construct

<400> SEQUENCE: 203
caatttgcag caactcgcac tgga                                              24

<210> SEQ ID NO 204
<211> LENGTH: 22
<212> TYPE: DNA
<213> ORGANISM: artificial sequence
<220> FEATURE:
<223> OTHER INFORMATION: Synthetic Construct

<400> SEQUENCE: 204
tcccaccatt ggctattccg ac                                                22

<210> SEQ ID NO 205
<211> LENGTH: 21
<212> TYPE: DNA
<213> ORGANISM: artificial sequence
<220> FEATURE:
<223> OTHER INFORMATION: Synthetic Construct

<400> SEQUENCE: 205
ctgtctctct ttttaatttc t                                                 21
```

<210> SEQ ID NO 206
<211> LENGTH: 24
<212> TYPE: DNA
<213> ORGANISM: artificial sequence
<220> FEATURE:
<223> OTHER INFORMATION: Synthetic Construct

<400> SEQUENCE: 206
ccactttgca cacatctccc actt					24

<210> SEQ ID NO 207
<211> LENGTH: 22
<212> TYPE: DNA
<213> ORGANISM: artificial sequence
<220> FEATURE:
<223> OTHER INFORMATION: Synthetic Construct

<400> SEQUENCE: 207
gaggatccac gtatagtagt ag					22

<210> SEQ ID NO 208
<211> LENGTH: 21
<212> TYPE: DNA
<213> ORGANISM: artificial sequence
<220> FEATURE:
<223> OTHER INFORMATION: Synthetic Construct

<400> SEQUENCE: 208
tttaaataaa gaaattattt a						21

<210> SEQ ID NO 209
<211> LENGTH: 40
<212> TYPE: DNA
<213> ORGANISM: artificial sequence
<220> FEATURE:
<223> OTHER INFORMATION: Synthetic Construct

<400> SEQUENCE: 209
taatacgact cactataggg cttgagttta taacgaagct			40

<210> SEQ ID NO 210
<211> LENGTH: 39
<212> TYPE: DNA
<213> ORGANISM: artificial sequence
<220> FEATURE:
<223> OTHER INFORMATION: Synthetic Construct

<400> SEQUENCE: 210
taatacgact cactataggg cttctaattt tcaaggacg			39

<210> SEQ ID NO 211
<211> LENGTH: 24
<212> TYPE: DNA
<213> ORGANISM: artificial sequence
<220> FEATURE:
<223> OTHER INFORMATION: Synthetic Construct

<400> SEQUENCE: 211
agcttctaat tttcaaggac gata					24

<210> SEQ ID NO 212
<211> LENGTH: 25
<212> TYPE: DNA
<213> ORGANISM: artificial sequence
<220> FEATURE:

<223> OTHER INFORMATION: Synthetic Construct

<400> SEQUENCE: 212
gtcatgtgac tccactttga ttttg                                    25

<210> SEQ ID NO 213
<211> LENGTH: 25
<212> TYPE: DNA
<213> ORGANISM: artificial sequence
<220> FEATURE:
<223> OTHER INFORMATION: Synthetic Construct

<400> SEQUENCE: 213
ctcaattccg ataaatttaa gaaat                                    25

<210> SEQ ID NO 214
<211> LENGTH: 26
<212> TYPE: DNA
<213> ORGANISM: artificial sequence
<220> FEATURE:
<223> OTHER INFORMATION: Synthetic Construct

<400> SEQUENCE: 214
cgaagctatt ggaccgacct aatttc                                   26

<210> SEQ ID NO 215
<211> LENGTH: 26
<212> TYPE: DNA
<213> ORGANISM: artificial sequence
<220> FEATURE:
<223> OTHER INFORMATION: Synthetic Construct

<400> SEQUENCE: 215
ggaattgagg gcttcccaga aattgc                                   26

<210> SEQ ID NO 216
<211> LENGTH: 25
<212> TYPE: DNA
<213> ORGANISM: artificial sequence
<220> FEATURE:
<223> OTHER INFORMATION: Synthetic Construct

<400> SEQUENCE: 216 atgactttt gattggtgaa actaa                                     25

<210> SEQ ID NO 217
<211> LENGTH: 45
<212> TYPE: DNA
<213> ORGANISM: artificial sequence
<220> FEATURE:
<223> OTHER INFORMATION: Synthetic Construct

<400> SEQUENCE: 217
taatacgact cactataggt ggaactccaa cacacaaaaa atttc              45

<210> SEQ ID NO 218
<211> LENGTH: 41
<212> TYPE: DNA
<213> ORGANISM: artificial sequence
<220> FEATURE:
<223> OTHER INFORMATION: Synthetic Construct

<400> SEQUENCE: 218
taatacgact cactataggt tgaaaaataa tcataatttt a                  41

```
<210> SEQ ID NO 219
<211> LENGTH: 22
<212> TYPE: DNA
<213> ORGANISM: artificial sequence
<220> FEATURE:
<223> OTHER INFORMATION: Synthetic Construct

<400> SEQUENCE: 219
gcataatata ttgatccggt at                                              22

<210> SEQ ID NO 220
<211> LENGTH: 24
<212> TYPE: DNA
<213> ORGANISM: artificial sequence
<220> FEATURE:
<223> OTHER INFORMATION: Synthetic Construct

<400> SEQUENCE: 220
ctgaaagttc atacataggt actc                                            24

<210> SEQ ID NO 221
<211> LENGTH: 22
<212> TYPE: DNA
<213> ORGANISM: artificial sequence
<220> FEATURE:
<223> OTHER INFORMATION: Synthetic Construct

<400> SEQUENCE: 221
ggtactccaa ttttcagtat at                                              22

<210> SEQ ID NO 222
<211> LENGTH: 24
<212> TYPE: DNA
<213> ORGANISM: artificial sequence
<220> FEATURE:
<223> OTHER INFORMATION: Synthetic Construct

<400> SEQUENCE: 222
ctgaaaattg gagtacctat gtat                                            24

<210> SEQ ID NO 223
<211> LENGTH: 27
<212> TYPE: DNA
<213> ORGANISM: artificial sequence
<220> FEATURE:
<223> OTHER INFORMATION: Synthetic Construct

<400> SEQUENCE: 223
atgtatgaac tttcagaata ttatacc                                         27

<210> SEQ ID NO 224
<211> LENGTH: 22
<212> TYPE: DNA
<213> ORGANISM: artificial sequence
<220> FEATURE:
<223> OTHER INFORMATION: Synthetic Construct

<400> SEQUENCE: 224
taccggatca atatattatg ct                                              22

<210> SEQ ID NO 225
<211> LENGTH: 647
<212> TYPE: DNA
<213> ORGANISM: Amaranthus palmeri

<400> SEQUENCE: 225
```

```
ttcaaaatga atttaaaatt atataaaaat caatatggac acaagaccgg atatcaatcc      60
gacccgaaat agttgacttg aaatcaacct gatgacccga atgaacacct ctagttatca     120
ctaacaaggg tcagattgcg tacatcaaac ccctcaaatc ctgcttaggt gggagcttgt     180
caatggctta ggggtaacgg gaatgtgtgt gctatgtaca ttgtgcatct attcttatgc     240
ttatttatgt tgagttagtt ttttttttgg atcaaatata aagagcttaa cttttgtatt     300
ttcttgatgt ggtgtagtgg tgatgaagat caggctgaga gaatctaaat tggccaaaat     360
tctgagagaa caagaagtga gttcagccct tcgtgctgct ggtgttggtg tgattagttg     420
catcatacag agagatgaag gcgaactcc gatgaggcat tcattctatt ggtcagcaga      480
aaaacaatat tatagtgagg agcctttact acgtcatttg gaaccccctc tatctatgta     540
tctcgagctg gtactagtct ctgaaccgat tgcctttctt ctgctttgtt attttgtgtg     600
atatttcgac ttaagtctaa tttacatcgt tttgtacatt tgttatc                   647
```

<210> SEQ ID NO 226
<211> LENGTH: 738
<212> TYPE: DNA
<213> ORGANISM: Amaranthus palmeri

<400> SEQUENCE: 226

```
ttttgctttt ttactattat ttccttcttt tcaaggattt gagttgttta ttgctgactg      60
cttcctatgt attacccata tgtctctgta taggcattac gggagctgta cctacatcta     120
actcctatac aacgtgtgaa tattgcccgg catcctaatc gccccacttt tcttgaccac     180
gtattcagca tcacagaaaa ggtttctgat ttattataat ttttgtcatt tgtattcact     240
cttcaataaa gtacatccat tatcaatctt tacggaggtt gttcacacaa cttcttgttt     300
cattttgcat aattagtttg tggaactaca tggagatcgt gctggttatg atgaccctgc     360
tatagttact ggccttggta cgatagatgg taggcgttat atgttcattg gtcatcaaaa     420
gggaagaaat acgaaggaaa atattgcacg gaatttcggg atgcctactc ctcatgggta     480
aatgctttac tataatgttt tactttaatt taattaccta tgttatttag gatgaaaatg     540
aatacttttc ttattactat tacttaggtt cctaatgcac aaaaaccgta attattaatg     600
taccctaatg gaattaacac atggtaatta agctctccgc tttgtgtaat taatccaatt     660
ttttagagag tcaaatagtt caggttaaac tagagctttt catacccaaa taataaaacc     720
aagggtaaat ttccaaaa                                                    738
```

<210> SEQ ID NO 227
<211> LENGTH: 880
<212> TYPE: DNA
<213> ORGANISM: Amaranthus palmeri

<400> SEQUENCE: 227

```
atgtgatcaa ttaaagaaaa agtctaatta tatgagcccg tctcacagtg acggagctat      60
catagagccc atggggtcac gtgcccttcg gggtttttag aaaaaattca agtatactt      120 ttctattaat aagagtaaaa atgtaaaatt aatattaaac tcttttgata ataaatactc     180
tctcacttta gtaattttgt cttatttatt tattttatct catgtgttta ataaggtcag     240
ttgacttatt ttgttccatt ttcttttatg gtatgccgta tttaaaattt tagcaagtaa     300
agataaaata gttgttaatc ttacaaataa aactctatcg aaattcatc cattagttaa      360 tgtccccaaa aagtccgaac tacaaatcga ccactgtcat cacatggtga gatagtctca     420
tataaaacga gttcagttat taaggaaaaa taggaaacac gaaacagtta atttaggcgg     480
```

```
ggcctatgta ttatccaaat gtgatactcc agtccacatt actcagtcct tccaattgaa      540
cagttggctt aatctaccaa gcgcgtggcc ataaatgcct ctaacacttt tcaatctctc      600
agataactct cacaccactt atcatcacaa ttcacaatta ctctaattct ttttattcct      660
ttccatgtcg ctaattttct actgattcag gtttttattct cagcttttat caattttatt    720
tcatgctttt tatgtcaatt tcttgtttcg cattttgtct tccacttgct gtctgtttta     780
ttaatcaatt ttgtatgatt gttggaataa ttgtatgtat ttttcatgat tttcctctta     840
tggaggttca taatgtattg ctagatttgt ttactttcac                           880
```

```
<210> SEQ ID NO 228
<211> LENGTH: 453
<212> TYPE: DNA
<213> ORGANISM: Amaranthus palmeri

<400> SEQUENCE: 228
aatttgagcg ggaaaatttt aatatcatta aatagtcttt gctttagtat atagaatagt      60
taaaattaat agtcaaactt attgtaatag catgcactaa tctataataa tcttatcctg     120
aaagctataa taaaattata aaaaaatata tgtgaaaaac taatttgagc gggaaaattt     180
taaccaaggg ctaacacgta tcattaaata gtctttactt tagtatatag aatgataatt     240
aacgatcata aaacaaaatt gtcactttca gtagcaaact tacaaaatga gcagagtacc    300
tcatatcata aaattgcttc tttctcattt gttgtgttgc tctcatttta ggagttcatc     360
gtttatatcg tcgtcttacc actcaatcac ttttagattt attagtagca cttcctcaat    420
ctacagcagc aatttctaca gttcaacaac ctc                                  453
```

```
<210> SEQ ID NO 229
<211> LENGTH: 3953
<212> TYPE: DNA
<213> ORGANISM: Amaranthus palmeri

<400> SEQUENCE: 229
ggaaaattta cctagaataa tccaatttat tcgtgatttt tctacaaatt ccaacttcaa      60
ggggtatttg cctaaagtaa ttaaacttgg atacccgat  gacctgctat agtagataat     120
ttaccagaaa attaaaaatg aaaattaatt taaaattaga gaaaaatttt gaaatttcat     180
ataaaaaatt ttaataata  aaaaaaatat aaatttttt  gaacatttta ttttaatcta     240
tcttttttga aaaataaaa  cttagttata gcaagtgatc tggtcaccgg gtttactcta     300
ggaaaatatc cctcaaagtt gagattattc atggttaata aataggtgag attattatag    360
aaaaattacg aataaattgg attattgttg gtaatttttt tttcaaaact atccctagga    420
aggaccttat tagtgattct ccctctactt tggaggagta tattgtggac ttcccatctt    480
ccttaattgt attgtaactt ttaactattg attctttaaa aaaagaact  tataaaattg    540 tagggttaat aaaatctaag attttatcta atttcacttt gattattccg attttgtatt   600
cacattattt taaatgacat tcgtcaaata aaaaaaaata gtttcattgc attccaattt   660
tgttgactag ggggattaaa gaagaatag  tatcaataat cgtaatgtag caagtagtac    720
aaaagaagta tatttcaata tgtcaaactt tgatctcgtt gtaacttgta atttgtacga    780
tgcggtgtga atgacatact tcaccttttt cattatttta tactggtagt gacatgggat   840
tattattgcg atatttgcag taatgaaaat ttttttggtt gttgctttta caaacaaaaa    900
ttctaccgaa ttttttatta atttaattca acacgttggt gttacccatg atttataggt   960
```

```
ctgggtccgc cactgctagc taacattaaa caatttaaca aactcaatac accaacctaa    1020
aaataaaatt ttttggcca taattttag aattttagtt tttaaacatt atatttggga      1080
attttttttc cttttatata tataaaataa aaaaaaatcc aaaaaagggg acacacatta    1140
atacacactt gaaagcatcg atgatatcga agaaaaacca gatggggtgc ccaattatct    1200
tcgtctcctt cgatattatc gaattcatta acaacattat atcaaaaacc aaccaaatta   1260
ccaactttcg aaaccaatat tcgccgtatt tttctctatt caacaatccc tacaatggcg    1320
gcattgccag cttcttcttc tcctgcaatt tcggaatcac ccacttgcaa ttttcttcct    1380
attcaaaaaa tcactaccac tcgctttcta aggtttcatt cggttttact cccaagccta    1440
aatttggcct tttctccaag gtttattttc tatctctttt ttaattggtt aatcaattgg    1500
attgttgaat ttttcagggt ttaacggtat aatatttgtg ggttttttcg agtacattct    1560
gggtttgtag tattggattt ggcattgctt ttaattttg agattgggtt ttttgggttt     1620
tatttggttc ttgtgattca aggttattga tttgctgcat taaactgtat ttatggaatg    1680
atgtcaatta actgttacat tacattgctt tatggttttc atcatgctga ttagtgatta    1740
ctgtgtttga atctcttgct tctctatgta ctatttaatc tgatacaaca agtacaacct    1800
agaaaacagg ttaagggaa atctataagc ttagtaaatt aacacttgaa agaagctaat     1860
gacggagaga ggggtctttt tggagaaggc agttttcata ttattgctca gttctctagt    1920
gcagctttac ttcacttaga cactcttaag tagaggtcat aggtgttcag aatagatcca    1980
aagacccgat atttaccgga ctttgtaaac aacttaaccc gacttcaaaa tgaatttaca    2040
atcatataaa agcaatatgg acttaaaccg attttgaacc gaccttgacc ggttgatccg    2100
aatgaatgcc tctactctta agcatgtcaa ctgtaatatg aaatagaatt ataatataaa    2160
ctaagttcat gttttcttca actacaaatg aaatttatg acccaaataa tgtgtgaata     2220
cccccagcaa taggttgaat ggcatttagt tcagttgatt ttagcagacc acatctgccc    2280
tcatattcca ttgttcagtt tagttgttag tagctgtaca taatagacta attaagttgt    2340
cattttgatc catgttatgg ttgtctggga taaacggatt ggaattgtat aataaaagtt    2400
tgggttagtt tattttgctc taggaggggt tatgtcatat gtgcactctg ttggcaaccc    2460
gacaatgcaa aacattttca tacttggtac gttgttgcgt gttttgtgcc cttcgtatt     2520 tgtaactgtt gatgaatgtg taaaaatata ctacatgatc atatgctagt aggtcttctt    2580
cacctagtaa agaaattttt ctaacacgag aagttcaaaa catattccca ttaccattat    2640
ccaacatcag tacccgagtc caagtaacat agggtgtccc tttatgatag tataagaatt    2700
ggtgcatgaa aaacgcgtga ttgtagcgag gatagtaggc gggagaggta caggatttga    2760 aaatttgaa ttgctaaaac gctatcagga tcttgttttt cttactttga tgttgctttt     2820
ttgaaatttg atccaaattg ttaaattatt gagactaatt cctgttgatc ctgtcgtgaa    2880
ctttgtagaa tctttcaggc cgcattctca cagtgaaggc tcaattaaac aaggtgagtc    2940
tttttttgtc ttaactctta tgcagttcat tatctcttct actgatgaga aaaccactat    3000
ttggcctaat tctaatttcc ttctaggttg ctttggatgg ttcaaatcat gctccatcac    3060
cttcgcacga aaaatctggg ctaccagccc aagaaaagaa gaacgatgag ccgtctagtg    3120
aatcttctcc tgcagcatca gtgtctgaag aacgagtctc cgaattcttg agccaagttg    3180
ccggtcttgt caagtatgta acattcttta ttttcattct tccacacact cgcaatttgg    3240
ataacgagat gtctttagag acgtctgggg aacaagggga aaatgagtct agaggttgct    3300
agagagaacg agataaatac taatatatat gaatatttca taatccacat taaaaaaata   3360
```

```
caattgaatt tgcattatgg tgaactacca agaatcgaa tatttttta tactccatgt    3420 tttgtggtct agacttgtgg attctagaga cattgtagag ttgcaattaa aacaactgga    3480
ctgtgagata ttgatccgca agcaggaagc tattcctcaa ccacaaattc ctaatcctac    3540
acatgtcgtt gcaatgcaac caccaccacc tgctgtagcg tctgcccag ctcccgtctc    3600 ttcaccagcc actcctcgtc ctgcgttacc tgccccagcg cctgctgcca cgtcagctaa    3660
gccatcactt ccacctctca agagcccat gtcaggcaca ttctaccgta gtccagctcc    3720
tggcgagccg cctttcgtga aggtaagtgt atacccctt tttagtgttg tatttctgtg    3780
ttatatcaat ttttgcattt tgtgaagctg aaaataaatc tttcatttc cataggttgg    3840 agataaagtt aagaaaggac aagtcatatg cattatcgag gctatgaagt tgatgaatga    3900
aatcgaggta cgtatgttat tgctttaaac ttcatgcctt aggccgtgaa gtt           3953
```

<210> SEQ ID NO 230
<211> LENGTH: 595
<212> TYPE: DNA
<213> ORGANISM: Amaranthus palmeri

<400> SEQUENCE: 230

```
acaaaaagca caaattcaat aatatactct ttaagtttgt ttatcttcta attagttcgg     60
ttaaaacggt tccccacttt cttctccgac tctcacaatt atcttcccct attcattttt    120
cttccaccct ctctaatggc ggctgtttcc ttcaatatca atggtggaaa gattggaact    180
ttatgttcaa gacacgaatt cgtttgtggg tttgtaagaa aatttcattt tagaactcat    240
acttctatat ttgaaaaaca tatgccaaaa acttcaaggt ttaaagcaat ggaagtttct    300
gcaaatgcaa cagtaaatat agttcctgtt tcagctcatt ctaggtaatt ttatttctcg    360
aaaatttccg atttacaatt aaattaatct tgttttgtag gtaatgaatt gcagaagaaa    420
tagatggatt cttatttgtt tattggtatt tgttttataaa ttttgttta tattagtttc    480 tgaattgtga ttattctgat tgtatgtcaa ggtttaggtt gttattaata aatgtaaatt    540
ggattgattg aagttgcaat aaggtgatgg cgtgatgctg attgttgtaa atttt          595
```

<210> SEQ ID NO 231
<211> LENGTH: 667
<212> TYPE: DNA
<213> ORGANISM: Amaranthus palmeri

<400> SEQUENCE: 231

```
caacaatgag aatttagaat ccatatcaat cttgatattc aagggtattt aagtaattaa     60
agaacaacca ttgttaagcg cctccactat cttcttcctt ctcattctcc attctcgctt    120
agctttcctc tcgcactaat tacctccatt tgcaacctt caagctttca acaatggcgt    180
ccacttcttc aaacccacca ttttcctctt ttactaaacc taacaaatc cctaatctgc    240 aatcatccat ttacgctatc cctttgtcca attctcttaa acccacttct tcttcttcaa    300
tcctccgccg cccccttcaa atctcatcat cttcttctca atcacctaaa cctaaacctc    360
cttccgctac tataactcaa tcaccttcat ctctcaccga tgataaaccc tcttcttttg    420
tttcccgatt tagccctgaa gaacccagaa aaggttgcga tgttctcgtt gaagctcttg    480
aacgtgaagg tgttaccgat gttttttgctt accctggtgg agcatccatg gaaatccatc    540
aagctcttac tcgttctaat atcattagaa atgttcttcc tcgacatgaa caaggtgggg    600
ttttcgctgc tgaaggctac gctcgtgcta ctggacgcgt tggagtttgt attgccactt    660
```

| | |
|---|---:|
| ctggtcc | 667 |

<210> SEQ ID NO 232
<211> LENGTH: 2415
<212> TYPE: DNA
<213> ORGANISM: Amaranthus palmeri

<400> SEQUENCE: 232

| | |
|---|---:|
| atttggataa cttttccctt tgattcgaat cggattatt ttaatacagt attatgaact | 60 |
| gatttaatga aagtggagga agtttcaatt tttaaagttg taggtgtaat gttttctcat | 120 |
| tttggatatg aaagtggagg aagtttcaat ttcgaatcat gtttgccagt tgattcaatg | 180 |
| aatgctcttg gaaatgacca agagttcaag gcttcttgtt ataaaacatt tcaattttga | 240 |
| tctaagaatg aactatttag aacttaaagt aattaaatta ttagttataa cttataaaaa | 300 |
| aattcaattt taaccttaaa tttataaatt atgaccttaa aagatcaag tattgaacgc | 360 |
| atatttagaa aaattataat tcggcttatc agtctcatat tgagacggtc tcgtccaaga | 420 |
| caagttgtat catttatata atcaaatata attatgagtg tattcatgta ggtttcaact | 480 |
| ttaaagccta ggtgaaagat atgttgtagc atctttgtga aagtcagcct ataacttggt | 540 |
| tctaaaattt tgaagcataa ccatatagtc cctcgaattc attcaagttg tccaatttac | 600 |
| ttttttatac ttgccgagac aacatttaaa cccttaatat ttctaattaa tcttaattaa | 660 |
| aaattatgaa aatttgatat taataatctt tgtattgaaa cgaatttaac aagatctcac | 720 |
| atgactatgt tttaacttat agattaaaaa aaaatacaaa ttaagagtga taagtgaata | 780 |
| gtgccccaaa acaaatggga caacttagat gaattggagg taatattagg tagcaagtga | 840 |
| tcactttaac atcaaaattg atcacttata ggttcaaatt gaaactttta ctttaattga | 900 |
| tatgtttaaa tactacttta aattgaaatt gatatttta aggtcaaaat tgaaaccttt | 960 |
| aagattataa ttgaaaattg gcagaagaaa acaaagaga aagaatataa gacacgcaaa | 1020 |
| ttgtaccgat ctactcttat ttcaatttga gacggtctcg cccaagacta gatgttcggt | 1080 |
| catcctacac caaccccaaa aaattcaaca acaaagtctt ataatgattc cctctaatct | 1140 |
| actacagtct acaccaaccc actttctctt tgcccaccaa aactttggtt tggtaagaac | 1200 |
| taagccctct tcttccctt ctctctctct taaaagcctg aaaatccac ctaacttttt | 1260 |
| tttaagccaa caaacaacgc caaattcaga gaaagaataa tggctcaagc tactaccatc | 1320 |
| aacaatggtg tccaaactgg tcaattgcac catactttac ccaaatccca gttacccaaa | 1380 |
| tcttcaaaaa ctcttaattt tggatcaaac ttgagaattt ctccaaagtt catgtcttta | 1440 |
| accaataaaa aagagttggt gggcaatcat tcaattgttc ccaagattca agcttctgtt | 1500 |
| gctgctgcag ctgagaaacc ttcatctgtc ccagaaattg tgttacaacc catcaaagag | 1560 |
| atctctggta ctgttcaatt gcctgggtca aagtctttat ccaatcgaat ccttctttta | 1620 |
| gctgctttgt ctgaggtatt tatttctcaa ctgcgaaaac aatctctatt tgatattgga | 1680 |
| atttatatta catactccat cttgttgtaa ttgcattagt agatacttat gttttgacct | 1740 |
| ttgttcatt gtttgttgaa ttggtagtgt tgagaatttg aatgtaatta tttgtttttc | 1800 |
| catgtgaatt taatctgatt aaatccactt cttatttatg ttaagttgca atgatgtttg | 1860 |
| ccaaatggtt atcattgaag gataagtttg cctactttg accctcccaa cttcgcggtg | 1920 |
| gtagagccat tttatgttat tgggggaaat tagaaagatt tatttgtttt gcctttcgaa | 1980 |
| atagtagcgt tcgtgattct gatttgggtg tctttataga tatgatatat ggttattca | 2040 |
| tgtaatgtgt aggtttatgc attatgttgg atgcatgtct ggtgttattg ctgtaaatgg | 2100 |

```
atgaatgttg ttatttggag acattttttc attcattttt tcccttttta attggaactg   2160
gaagagggaa agttattggg agtaattaaa aggttgtgag ttcgatacac tgcatcaaag   2220
acgaagaact tgacatagat gttgaaggct aatccttatc actgcttgaa ttcaatatgt   2280
atctgaaaat tttacccctc tatatgcatc tgttttttgct aataaagtgt ttttggacta   2340
tcatgttttg tgatgcttaa gagggtgata ttactgagat aaatggaaat atcaaaataa   2400
catctattgt gaagt                                                    2415
```

```
<210> SEQ ID NO 233
<211> LENGTH: 3049
<212> TYPE: DNA
<213> ORGANISM: Amaranthus palmeri

<400> SEQUENCE: 233
```

```
caagcttcaa ttatcgtttt caaaataagt atttcaaagt ctataaagat attgtataag     60
ttttagttca aatttaataa gttttttttt tttttttttt tttttttttg aaaatccaaa    120
ttgaataagt taatarttaa attatgacat ataattatga catataattt gaccatgata    180
ttttacaatc taacttaatt ttgaacttat tatttctaat attcaattat cgttctaaaa    240
ataagtattt aaattgtata gatatattgt ataacattta gttcaaattt aattattgat    300
agttttattg actatttatt tggkgtttga aattcatcca tagaatgata gaataacacc    360
attttttata taacttcgtt ctaaaatttt gaagcataac catatactcc ctccaattca    420
tccaagttgt ccaatttact ttttcatact tgccgaggca acatttaaac ccttaatatt    480
tctaattaat gttaattaaa aattatgaaa atttgatatt aataatcctt gtattgaaac    540
aaatctaaca agatcccaca tgactatgtt ttaacttata gattaagaat aaaatacaaa    600
ttaagagtaa taagtgaata gtgtcccaaa acaaatagga caacttggat gaattggagg    660
tagtattagg tagcaagtga tcactttaac atcaaaattg atcagttaca ggttcaaatt    720 gaaacttta ctttaattga tatgtttaaa tactacttta aattgaaatt gatattctta    780
aggtcaaaat tgaaaacttt aagattataa ttgaaaaatg cccagaagat gaaaaaacag    840
agagaaagca tgtaagacac gcaaattgaa ccagtctact cttgtttcaa tttgagacgg    900
tctcgcccaa gaccagatgt tcagtcatcc tacaccaacc ccaaaaaatt caacaacaaa    960
ctcttataat gattccctct aatctactag agtctacacc aacccacttt ctctttgccc   1020
accaaaactt tggtttggtg agaactaagc cctcttcttt cccttctctc tcttaaaagc   1080
ctaaaaccca ccaacttttt cagccaagaa acaacgcgaa attcagagga agaataatgg   1140
ctcaagctac taccatcaac aatggtgtcc atactggtca attgcaccat actttaccca   1200
aaacccagtt acccaaatct tcaaaaactc ttaattttgg atcaaacttg agaatttctc   1260
caaagttcat gtctttaacc aataaaagag ttggtgggca atcatcaatt gttcccaaga   1320
ttcaagcttc tgttgctgct gcagctgaga aaccttcatc tgtcccagaa attgtgttac   1380
aacccatcaa agagatctct ggtactgttc aattgcctgg gtcaaagtct ttatccaatc   1440
gaatccttct tttagctgct ttgtctgagg gcacaacagt ggtcgacaac ttgctgtata   1500
gtgatgatat tctttatatg ttggacgctc tcagaactct tggttaaaaa gtggaggatg   1560
atagtacagc caaagggca gtcgtagagg gttgtggtgg tctgtttcct gttggtaaag   1620
atggaaagga agagattcaa cttttccttg gtaatgcagg aacagcgatg cgcccattga   1680
cagctgcggt tgccgttgct ggaggaaatt caagttatgt gcttgatgga gtaccaagaa   1740
```

```
tgagggagcg ccccattggg gatctggtag caggtctaaa gcaacttggt tcagatgtag     1800
attgttttct tggcacaaat tgccctcctg ttcgggtcaa tgctaaagga ggccttccag     1860
ggggcaaggt caagctctct ggatcggtta gtagccaata tttaactgca cttctcatgg     1920
ctactccttt gggtcttgga gacgtggaga ttgagatagt tgataaattg atttctgtac     1980
cgtatgttga aatgacaata aagttgatgg aacgctttgg agtatccgta gaacatagtg     2040
atagttggga caggttctac attcgaggtg gtcagaaata caaatctcct ggaaaggcat     2100
atgttgaggg tgatgcttca agtgctagct acttcctagc cggagccgcc gtcactggtg     2160
ggactgtcac tgtcaagggt tgtggaacaa gcagtttaca ggtataatgt taacccttac     2220
ccttcacatt gttctgctaa attctagagg acccttccaa ttctgggtgg ataagcacg     2280 gcaatttgac cgcaaaaaaa ttgcaaaatt attctgctga tagaacatct cgagatgaga     2340
tcatattgag ttttggcgtc aacataaacc taatcaaata atgaaaaata caaacatcat     2400
atggtttctt ttgtctttat gactagacac tctctattat tccttgattg ggatcttatt     2460
tgaaattgct gtgtagccta cacctcatgt tcagattttg ttcgtatacc agacttttct     2520
tgattgggat cttatttgtc ccctggattt tgcatagggt gatgtaaaat ttgccgaagt     2580
tcttgagaag atgggttgca aggtcacctg gacagagaat agtgtaactg ttactggacc     2640
acccagggat tcatctggaa agaaacatct gcgtgctatc gacgtcaaca tgaacaaaat     2700
gccagatgtt gctatgactc ttgcagttgt tgccttgtat gcagatgggc ccaccgccat     2760
cagagatgtg gctagctgga gagtgaagga aaccgaacgg atgattgcca tttgcacaga     2820
actgagaaag cttggggcaa cagttgagga aggatctgat tactgtgtga tcactccgcc     2880
tgaaaagcta accccaccg ccattgaaac ttatgacgat caccgaatgg ccatggcatt     2940
ctctcttgct gcctgtgcag atgttcccgt cactatcctt gatccgggat gcacccgtaa     3000
aaccttcccg gactactttg atgttttaga aaagttcgcc aagcattga              3049

<210> SEQ ID NO 234
<211> LENGTH: 1113
<212> TYPE: DNA
<213> ORGANISM: Amaranthus palmeri

<400> SEQUENCE: 234
tcttaatttg tatttattta ttaatctata agttaaaaca tagtcaagtg agatcttgtt       60
tgattcgtct ctatgcaagg attttcatat caacttttca taattttga ttatacacaa      120 ttacaaatat taacgaacga ataagtgcat taaaaagagt gcaaaagca aatgggacac      180 ttgtgttgaa taggagggag tatacattaa gatgaatcta acgagatctc acatggatat      240
aatttgtctt ctatatatgt ctaaaaaatc ttgatcaaat ttctctttcc aaaatagaat      300
attctaaatg ggaagaacat taagaaacgg agggagtact tataagttaa gatagttggg      360
ggtatttagg taaaaaaatc tatgccaaaa gtagaaagtg gacaattaga gtgactttac      420
taaataagga aagtggacat ttaaaatgaa tcggagggag catattaact ttattttcaa      480
agtgtgaaac ataatcatat ttaggtaaaa aaattatcaa tttaacgtca aaattgatca      540
caaataggtt aaaattgaaa tttttatgt taattgatct attgttcact ttaaattgaa      600
attgatatcc tttaaggtta aaattaatac ctctaaaatt aaaattatta aaggcccaga      660
aaataaaaaa aaagaagac aggctattag taaaattatt aagtatgtaa ggttgataca      720
cgcgcgaatt gagccggccc acttttagtt tcaatttgaa acagtctcaa tcaagaccaa      780
ttatttatta ttttattatt ttattgtttt aagctcaatg ggttggactt gataaattat      840
```

```
attttgagga gacgggctat tagtaaaatt aatagttgga atctttttg atatactata      900 aaaagaggta tctggtggag ccttaaatct gcgcaattga agtcctcaat acacatctcg      960
ctcttcttat tctctttcat ctatttcctc ctttgatcaa actacgccat gtctctctta     1020
aatgatctcg ttaaccttaa tctctctgaa actaccgata agattatcgc tgaatacata     1080
tggtaataca acaatccttc ctcttttca ttt                                   1113
```

<210> SEQ ID NO 235
<211> LENGTH: 882
<212> TYPE: DNA
<213> ORGANISM: Amaranthus palmeri
<220> FEATURE:
<221> NAME/KEY: misc_feature
<222> LOCATION: (451)..(459)
<223> OTHER INFORMATION: n is a, c, g, or t

<400> SEQUENCE: 235

```
aaaaaaccgt cttatttgta gaaaataaaa aactaaaaag tagtatcaac ttttagacta       60
gtcataagtg agtggcatca aacttgttct ataaaaggg aagagttcct caacttgaga      120
ttcatatttt ttgtgatttc taaatagaag aacatactca tcttccactt ctcttattca      180
tcaaatttta tttgttcccc aaaaaaacat gtctcttctt acagatctca tcaatcttaa      240
tctttctgac tccactgaga agatcattgc tgaatacata tggtcagttt tcatccctt      300 tttttacctt taatcccact ttttgttttt acccaccatt tttttcatct attttctctt      360
aaagatttta acttttact tttttgtgta tataacattc attttttcaa ttgggtaggt      420
tagaaaattt ctataaataa ataaataaat nnnnnnnnnt accttaatcc cacttttgt      480 ttctacccac catttttttc atcaattttt cttaaagatt ttaactttt ttaactttt      540 cttggttttt gtgtatatac caatcattta ttttcactag tgtaggttaa aaaatatcta      600
aaaataaata aaatagaata aaatgtaat cactagatta acccatgaat tatttccctt      660 gttttactc aaactttta cccttgttaa aaaaataatg atataaataa attttgagg      720 gtttgttaaa cccatatgta atctatatcg aaaaaattag atagcgggtt ttgttgtgga      780
caaactaaat aacaaattta ggaataaact tttgagggtt tattgaaaaa ataacccata      840
tttaatctat atcgaaaaaa tgatagcgag ctttgtatag at                        882
```

<210> SEQ ID NO 236
<211> LENGTH: 1083
<212> TYPE: DNA
<213> ORGANISM: Amaranthus palmeri

<400> SEQUENCE: 236

```
cgtcgaagta gaagacgcgg aagctgcttt taacatcagc gtttcgcatg gggctattcc       60
ctgtgtttct cctattcaat tggaaaacgg tgtcgtttta tctgaggttc atttatatgg      120
ggatgttgtg cttcggtatg taagctacgg aaatgaatgt ggggatgtgt ttttcttcc      180 tgggtttgag gaaatgccgg aggaatcatc gtttagagga cttgattttg gcattcgaag      240
gttggatcat gctgtaggga atgtccctga gttggctcct gcaattgctt atttgaagaa      300
gtttactggg tttcatgagt ttgctgagtt tacagctgaa gatgttggga cgagtgaaag      360
tggattgaat tcagccgtat tggcaaacaa tgatgaaatg gtgttgtttc cgatgaatga      420
acctgtgtat gggacaaaaa ggaagagcca aattcaaact tatttggagc ataatgaagg      480
ggctggtgta cagcatttgg ctttgatgag tgaagacata ttttggactt aagggagat      540
```

```
gaggaagaga agtgttcttg gtgggtttga gtttatgccg tcgccgcctc cgacttatta      600
ccggaatttg aggaacagag ctgctgatgt attgagtgag gagcagatga aggagtgtga      660
agagttgggg attttggtgg ataaagatga tcagggcact ttgcttcaaa tcttcaccaa      720
acctattgga gacaggtaaa ttttaatctt gctttcaatt gcttttgctt gatggattga      780
ctagcaaatt tgatcgcatt tgttgctta tatgacttga tgatacttcc tctgtttcga       840
aatactcgct acattcgcta cattttgttt tgtgcactat tcatcgttca agcttatttt      900
acatattgcg actaatgtgt aactaaaaat atagtcaagt gggatcttgt ttgaatcgtc      960
taatggcata ctttcatcat attaaatttt tataatttt agattagtgt agtttaagat       1020
attaatgctc aaaattgtgc attggattgc gtaaaaaagt gaaatgtagc aagtattatg      1080
aaa                                                                    1083

<210> SEQ ID NO 237
<211> LENGTH: 788
<212> TYPE: DNA
<213> ORGANISM: Amaranthus palmeri

<400> SEQUENCE: 237
aaaaccaaag gaaataagtt ataggtagga aaaattgtta ttgaagttaa tgtagtaaac       60
tagtaactta aactgtgata ccccggattt agcttaaaaa gagattgata gactactcat      120
atcaacaagg tgcatcttct tttctaggga gcccatttgc taagaactct acagttaagc      180
gtgcttggtg gggagcaatc ttaggatggg tgacctcctg ggaagttttc ctgggtgcgc      240
acgggtgagc ccaaagtgcg ttaaaaagac ttgtgttggt ctgtggggct tgtctacagt      300
ctccatgagt agtcaccggc ggtacgagag gccggggtgt tacataaaca gactcaaagg      360
cgctaagcca agtagccaat agcaacatgt gtggcctgcg gacagtcaca aaaacacaca      420
atttcttatt tttactctct tttatctctt ttaggcttta gccatcaaca ataaaacaac      480
atgataaagc aattcattta ctgctaaatt ccaacaattt ggtcccttt tcctgttctt      540 tcagtttcac ataccctctt atcaatctat atccaaaact atttcatttt ccaaactctt     600
ttaaacccaa aaatcaaaac ttttgattga agaacaaact ttgggggttt tggaaaatga     660
gtcattttgg atatgcttgt gctactcaat ccacatcaag atatgttctt ttaggaaatt     720
caaataaccc cacttcaatt tcatctatt gaagtgattt ttggtcat tctgtgagaa        780 atttcagt                                                              788

<210> SEQ ID NO 238
<211> LENGTH: 2631
<212> TYPE: DNA
<213> ORGANISM: Amaranthus palmeri

<400> SEQUENCE: 238
tggtacctac cctgtttaca ttttcaattt ccccctttt tctctactac tcctacttta        60
ttgattctta tccatgtgtg ttctatggga attgacatta attgttcagg tgtgtatgct      120
ggtgatcctt ctaagttgag tatgaaagct gcatttggaa aggtctggac cttagagcaa      180
aagggtggta gtatcattgc cggtacactc aaaactattc aggaaaggaa gaataatcct      240
ccaccgcctc gagacccgtc cgtaatcacc attactcatt gctttccttc accttgtatc      300
ttaccttaat atacatgtat ttaattgata atgtcacatt gcctcatttg cagccgcctt      360
cctaaaccta agggcagac tgttggatcc tttaggaaag gctcattat gttacctacc       420 gccattgctg ctaggtatct tttgactctc aaatcttaaa tatttctcat cttctccttc      480
```

```
tgctaatact agtatgttta ccatctttt atttttttag gcttggcagt aaagtcaaac      540
tatcgtggac actttctaat attgataagt cgctcaatgg tgaatacaat ctcacttatc     600
aaacacccga tggaccggtt tctgttagga ccaaagcggt tgtcatgact gtcccttcat     660
acattgcaag tagcctgctt cgtccgctct cagtgagtat cattctttcc ttcatttctt     720
ttcgtttatt gttgtccaat gtcttgttaa acaccagttt ggccttgtgc tcgtgaatta     780
tggctacaat gttaactgat tcaggcactg tgggagatgc ctaagtttct aaaacctctg     840
cgcataatgt ttgtttggat gttaggaatt gcattgaaaa attgcttttg tgatgttgat     900
gttaatacca attacaagtg tgttcttcaa cttctgcaat accttgttcg agtgagcttg     960
agggggttta gattagtgtc caatgtgaaa ctagcaaatg aactccaagc gctgggatag    1020
gtccttggga tggagcccct gatacccaag acagtattca aaccctctaa gtagagtgag    1080
agatcaagga aagaaactgg gtggttcctc aaatcgtaaa aaatgaatac agtgtcatga    1140
ttgctaatct tatcacaaat cgtaaaaaat gaattatggt cgattttgga ctattttgg     1200
gtcattttga gtgaatctcg aacttaaaaa gcgagtcttc tagcagttct tgttacagcg    1260
gggcatacat aggtaggaat ttggtttttt actatttgag cctttgact gttgtggccg     1320
gtaatatgga atagtctagc acttctgcgt gtgtacaact agtatttatt gtaattatgt    1380
gatcgcactt aactctcaga taaaaccta agcactaaca ttttgttttg gttgaaggaa     1440
tcaggaggaa agaaaattga gggatttgtt ggtatataga ttccttttgtt tggataacaa   1500
aattggagtg gagagatttg gaaggaagaa tttataggg attagttccc attacactta     1560
tgttgattac aaaatttctc caaagtggaa agatttga gtgaaaatgt tttttatttc      1620
tcttcctctc ccttctttc cctcttaaac aaacaaggaa agttaatctt atcattccgt     1680
accttcccct tctgttcttt tttttctctc caaaattctt atcctaacgt agtgttattg    1740
tcactgtctt atgaacgaga attcttttct tcctaatact gcttgtgttg cacagtcaat    1800
gatttagcta gatcatcttt ggttagctac tcaaaatatt tacataaaat acttgtagaa    1860
ataaatacca ataggtcttg tcaagaagta gtttcaatgc tataagtttt aaccaatcct    1920
caaaatttac accatggaga tatctgcgga taagaactag taactgtagc agctgtaact    1980
gttgcaatca gttttatggt ttgccttgca atcaaactt tggatgttgt ttgccttaca    2040
atttgttact attacgtgaa gtttagtgtt cgcccttcac attgtacttt ggttttgtt    2100
ttccttgcaa tttgctcttt gaagtataaa gtgctgagtg ctgagtgctg agtgctgacc    2160
tttcctgctc aggatgttgc tgcagattct ctttctcaat tttactatcc accagtcgca    2220
gcagtgtccc tttcttatcc caaagaagca attagaccag aatgcttgat cgatggagaa    2280
ctaaaaggat tcgggcaatt gcatcctcgc agccagggtg tggaaccttt gggtatatgc    2340
tcccattcaa ctatatctca attttatga gtattttct ttctctgaat tattcaattt     2400
ggtgacgtta aattttgatt gtactcgaca ggaacaattt atagttcatc tcttttccct    2460
ggtcgagcac cacctggtag gaccttgatc ttgagctaca ttggaggtgc tacaaatgtt    2520
ggcatattac aaaaggcaag tcatttatac aattatatct gttgtatcct caaataagtg    2580
ggtatcaatc ctgacgacat gcttgcttgt atcgatgcag agtgaagatg a             2631
```

<210> SEQ ID NO 239
<211> LENGTH: 23
<212> TYPE: DNA
<213> ORGANISM: Euphorbia heterophylla

```
<400> SEQUENCE: 239
agtttacagg gagatgtaaa gtt                                              23

<210> SEQ ID NO 240
<211> LENGTH: 23
<212> TYPE: DNA
<213> ORGANISM: Euphorbia heterophylla

<400> SEQUENCE: 240
agtttgcagg gagatgtgaa att                                              23

<210> SEQ ID NO 241
<211> LENGTH: 23
<212> TYPE: DNA
<213> ORGANISM: Ambrosia trifida

<400> SEQUENCE: 241
agtttacagg gggatgtaaa gtt                                              23

<210> SEQ ID NO 242
<211> LENGTH: 23
<212> TYPE: DNA
<213> ORGANISM: Abutilon theophrasti

<400> SEQUENCE: 242
agtttgcagg gtgatgtaaa att                                              23

<210> SEQ ID NO 243
<211> LENGTH: 23
<212> TYPE: DNA
<213> ORGANISM: Xanthium strumarium

<400> SEQUENCE: 243
agtttgcagg gtgatgtgaa att                                              23

<210> SEQ ID NO 244
<211> LENGTH: 23
<212> TYPE: DNA
<213> ORGANISM: Ipomoea hederacea

<400> SEQUENCE: 244
agtttacagg gggatgttaa gtt                                              23

<210> SEQ ID NO 245
<211> LENGTH: 23
<212> TYPE: DNA
<213> ORGANISM: Chenopodium album

<400> SEQUENCE: 245
agtttacagg gtgatgtaaa att                                              23

<210> SEQ ID NO 246
<211> LENGTH: 23
<212> TYPE: DNA
<213> ORGANISM: Digitaria sanguinalis

<400> SEQUENCE: 246
agtttgcagg gtgatgtgaa att                                              23

<210> SEQ ID NO 247
<211> LENGTH: 23
<212> TYPE: DNA
<213> ORGANISM: Senna obtusifolia
```

```
<400> SEQUENCE: 247
agtttacagg gagatgtaaa att                                              23

<210> SEQ ID NO 248
<211> LENGTH: 23
<212> TYPE: DNA
<213> ORGANISM: Amaranthus rudis/tuberculatus

<400> SEQUENCE: 248
agtttacagg gtgatgtaaa att                                              23

<210> SEQ ID NO 249
<211> LENGTH: 23
<212> TYPE: DNA
<213> ORGANISM: Amaranthus palmeri

<400> SEQUENCE: 249
agtttacagg gtgatgtaaa att                                              23

<210> SEQ ID NO 250
<211> LENGTH: 23
<212> TYPE: DNA
<213> ORGANISM: Amaranthus palmeri

<400> SEQUENCE: 250
agtttacagg gtgatgtaaa att                                              23

<210> SEQ ID NO 251
<211> LENGTH: 54
<212> TYPE: DNA
<213> ORGANISM: Euphorbia heterophylla

<400> SEQUENCE: 251
tcgatgtgaa catgaacaaa atgccagatg tcgctatgac attggctgtg gttg            54

<210> SEQ ID NO 252
<211> LENGTH: 55
<212> TYPE: DNA
<213> ORGANISM: Euphorbia heterophylla

<400> SEQUENCE: 252
tcgatgtgaa tatgaacaaa atgccagatg ttgctatgac attagctgtg gttgc           55

<210> SEQ ID NO 253
<211> LENGTH: 55
<212> TYPE: DNA
<213> ORGANISM: Ambrosia trifida

<400> SEQUENCE: 253
tcgatgttaa catgaacaaa atgccagatg ttgccatgac gcttgcagtc gttgc           55

<210> SEQ ID NO 254
<211> LENGTH: 55
<212> TYPE: DNA
<213> ORGANISM: Abutilon theophrasti

<400> SEQUENCE: 254
ttgatgtcaa catgaacaaa atgccagatg ttgccatgac tctcgctgtt gttgc           55

<210> SEQ ID NO 255
<211> LENGTH: 55
<212> TYPE: DNA
```

```
<213> ORGANISM: Xanthium strumarium

<400> SEQUENCE: 255
ttgatgtcaa catgaacaaa atgcctgatg tcgcaatgac tcttgctgtg gttgc        55

<210> SEQ ID NO 256
<211> LENGTH: 55
<212> TYPE: DNA
<213> ORGANISM: Ipomoea hederacea

<400> SEQUENCE: 256
ttgatgtcaa catgaacaaa atgccagatg ttgccatgac tcttgctgta gttgc        55

<210> SEQ ID NO 257
<211> LENGTH: 55
<212> TYPE: DNA
<213> ORGANISM: Chenopodium album

<400> SEQUENCE: 257
ttgatgtcaa catgaacaaa atgccagatg tcgcaatgac tcttgctgtt gttgc        55

<210> SEQ ID NO 258
<211> LENGTH: 55
<212> TYPE: DNA
<213> ORGANISM: Digitaria sanguinalis

<400> SEQUENCE: 258
ttgacgtcaa catgaacaaa atgcctgatg tcgcaatgac tcttgctgtg gttgc        55

<210> SEQ ID NO 259
<211> LENGTH: 55
<212> TYPE: DNA
<213> ORGANISM: Senna obtusifolia

<400> SEQUENCE: 259
ttgatgtcaa catgaacaag atgccagatg ttgccatgac gcttgctgta gttgc        55

<210> SEQ ID NO 260
<211> LENGTH: 55
<212> TYPE: DNA
<213> ORGANISM: Amaranthus rudis/tuberculatus

<400> SEQUENCE: 260
tcgacgtcaa catgaataaa atgccagatg ttgctatgac tcttgcagtt gttgc        55

<210> SEQ ID NO 261
<211> LENGTH: 55
<212> TYPE: DNA
<213> ORGANISM: Amaranthus palmeri

<400> SEQUENCE: 261
tcgacgtcaa catgaacaaa atgccagatg ttgctatgac tcttgcagtt gttgc        55

<210> SEQ ID NO 262
<211> LENGTH: 55
<212> TYPE: DNA
<213> ORGANISM: Amaranthus palmeri

<400> SEQUENCE: 262
tcgacgtcaa catgaacaaa atgccagatg ttgctatgac tcttgcagtt gttgc        55

<210> SEQ ID NO 263
<211> LENGTH: 55
```

```
<212> TYPE: DNA
<213> ORGANISM: artificial sequence
<220> FEATURE:
<223> OTHER INFORMATION: Synthetic Construct
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (50)..(50)
<223> OTHER INFORMATION: n is a, c, g, or t

<400> SEQUENCE: 263
tngangtcaa catgaacaaa atgccagatg tngcnatgac ncttgcngtn gttgc         55

<210> SEQ ID NO 264
<211> LENGTH: 21
<212> TYPE: RNA
<213> ORGANISM: artificial sequence
<220> FEATURE:
<223> OTHER INFORMATION: Synthetic Construct

<400> SEQUENCE: 264
aacaugaaca aaaugccaga u                                              21

<210> SEQ ID NO 265
<211> LENGTH: 21
<212> TYPE: RNA
<213> ORGANISM: artificial sequence
<220> FEATURE:
<223> OTHER INFORMATION: Synthetic Construct

<400> SEQUENCE: 265
aucuggcauu uuguucaugu u                                              21

<210> SEQ ID NO 266
<211> LENGTH: 22
<212> TYPE: RNA
<213> ORGANISM: artificial sequence
<220> FEATURE:
<223> OTHER INFORMATION: Synthetic Construct

<400> SEQUENCE: 266
aacaugaaca aaaugccaga ug                                             22

<210> SEQ ID NO 267
<211> LENGTH: 22
<212> TYPE: RNA
<213> ORGANISM: artificial sequence
<220> FEATURE:
```

```
<223> OTHER INFORMATION: Synthetic Construct

<400> SEQUENCE: 267
caucuggcau uuuguucaug uu                                          22

<210> SEQ ID NO 268
<211> LENGTH: 24
<212> TYPE: RNA
<213> ORGANISM: artificial sequence
<220> FEATURE:
<223> OTHER INFORMATION: Synthetic Construct

<400> SEQUENCE: 268
caacaugaac aaaaugccag augu                                        24

<210> SEQ ID NO 269
<211> LENGTH: 24
<212> TYPE: RNA
<213> ORGANISM: artificial sequence
<220> FEATURE:
<223> OTHER INFORMATION: Synthetic Construct

<400> SEQUENCE: 269
acaucuggca uuuuguucau guug                                        24

<210> SEQ ID NO 270
<211> LENGTH: 35
<212> TYPE: RNA
<213> ORGANISM: artificial sequence
<220> FEATURE:
<223> OTHER INFORMATION: Synthetic Construct

<400> SEQUENCE: 270
ucgacgucaa caugaacaaa augccagaug uugcu                            35

<210> SEQ ID NO 271
<211> LENGTH: 35
<212> TYPE: RNA
<213> ORGANISM: artificial sequence
<220> FEATURE:
<223> OTHER INFORMATION: Synthetic Construct

<400> SEQUENCE: 271
agcaacaucu ggcauuuugu ucauguugac gucga                            35

<210> SEQ ID NO 272
<211> LENGTH: 45
<212> TYPE: RNA
<213> ORGANISM: artificial sequence
<220> FEATURE:
<223> OTHER INFORMATION: Synthetic Construct

<400> SEQUENCE: 272
ucgacgucaa caugaacaaa augccagaug uugcuaugac ucuug                 45

<210> SEQ ID NO 273
<211> LENGTH: 45
<212> TYPE: RNA
<213> ORGANISM: artificial sequence
<220> FEATURE:
<223> OTHER INFORMATION: Synthetic Construct

<400> SEQUENCE: 273
caagagucau agcaacaucu ggcauuuugu ucauguugac gucga                 45
```

```
<210> SEQ ID NO 274
<211> LENGTH: 55
<212> TYPE: RNA
<213> ORGANISM: artificial sequence
<220> FEATURE:
<223> OTHER INFORMATION: Synthetic Construct

<400> SEQUENCE: 274
ucgacgucaa caugaacaaa augccagaug uugcuaugac ucuugcaguu guugc          55

<210> SEQ ID NO 275
<211> LENGTH: 55
<212> TYPE: RNA
<213> ORGANISM: artificial sequence
<220> FEATURE:
<223> OTHER INFORMATION: Synthetic Construct

<400> SEQUENCE: 275
gcaacaacug caagagucau agcaacaucu ggcauuuugu ucauguugac gucga          55

<210> SEQ ID NO 276
<211> LENGTH: 45
<212> TYPE: DNA
<213> ORGANISM: artificial sequence
<220> FEATURE:
<223> OTHER INFORMATION: Synthetic Construct

<400> SEQUENCE: 276
taatacgact cactataggg ctttattgaa tttagctatg taatc                    45

<210> SEQ ID NO 277
<211> LENGTH: 41
<212> TYPE: DNA
<213> ORGANISM: artificial sequence
<220> FEATURE:
<223> OTHER INFORMATION: Synthetic Construct

<400> SEQUENCE: 277
taatacgact cactataggg tttatcaacc aaatgtgcag c                        41

<210> SEQ ID NO 278
<211> LENGTH: 49
<212> TYPE: DNA
<213> ORGANISM: artificial sequence
<220> FEATURE:
<223> OTHER INFORMATION: Synthetic Construct

<400> SEQUENCE: 278
taatacgact cactataggg ttgtctgtac ataattgtga gatttgtgg                49

<210> SEQ ID NO 279
<211> LENGTH: 21
<212> TYPE: DNA
<213> ORGANISM: artificial sequence
<220> FEATURE:
<223> OTHER INFORMATION: Synthetic Construct

<400> SEQUENCE: 279
ctgtgatcat catatgtatc a                                              21

<210> SEQ ID NO 280
<211> LENGTH: 21
<212> TYPE: DNA
<213> ORGANISM: artificial sequence
<220> FEATURE:
<223> OTHER INFORMATION: Synthetic Construct
```

<400> SEQUENCE: 280
ccttaactct ccagctagca a                                          21

<210> SEQ ID NO 281
<211> LENGTH: 21
<212> TYPE: DNA
<213> ORGANISM: artificial sequence
<220> FEATURE:
<223> OTHER INFORMATION: Synthetic Construct

<400> SEQUENCE: 281
cagcccgcaa atgtttcatt c                                          21

<210> SEQ ID NO 282
<211> LENGTH: 21
<212> TYPE: DNA
<213> ORGANISM: artificial sequence
<220> FEATURE:
<223> OTHER INFORMATION: Synthetic Construct

<400> SEQUENCE: 282
gccgtcaatg gccgcattgc t                                          21

<210> SEQ ID NO 283
<211> LENGTH: 21
<212> TYPE: DNA
<213> ORGANISM: artificial sequence
<220> FEATURE:
<223> OTHER INFORMATION: Synthetic Construct

<400> SEQUENCE: 283
tccttccctc agaaagggca g                                          21

<210> SEQ ID NO 284
<211> LENGTH: 21
<212> TYPE: DNA
<213> ORGANISM: artificial sequence
<220> FEATURE:
<223> OTHER INFORMATION: Synthetic Construct

<400> SEQUENCE: 284
ttgcctcatg ctgctaatct g                                          21

<210> SEQ ID NO 285
<211> LENGTH: 789
<212> TYPE: DNA
<213> ORGANISM: Nicotiana benthamiana

<400> SEQUENCE: 285
cttatatgtg cttaagccta acgtgcaccc ggcccttaa ccccagcagt tttcaatcta      60
cctaccgtct ctaccatttt cttctagttg gtgaaaattt ctaactttga gaaaacaagc   120
caaagttttt gtttctaaga acgcaaaatg agtgaaattt tttgcagcaa tggcacagat   180
tagcagcatg aggcaaggga tacagacccc taatcttaat tcctattttc ctaaaaccca   240
aaaggttcct ctttttttcgc attctatctt ctttggatca agaaaataa cccaaaattc    300
agcaaaatct ttgtgggtgt gtaagaaaga ttcagttttg agggtggcaa agtcacctttt  360
taggatttgt gcatcagtgg ccactgcaca gaagcccaac gagattgtgc tgcaacccat   420
caaagatata tcaggcactg ttaaattgcc tggttctaaa tccctttcca accgtattct   480
ccttcttgct gcccttttctg agggaaggac tgttgttgac aatttactga gtagtgatga   540
cattcattac atgcttggtg cgttgaaaac acttggactt catgtagaag atgacaatga   600

```
aaaccaacga gcaattgtgg aaggttgtgg tgggcagttt cctgtcggcg agaagtctga    660
ggaagaaatc caactattcc ttggaaatgc aggaacagca atgcggccat tgacggcagc    720
agttactgta gctggaggac attcaagata tgtacttgat ggagttccta ggatgagaga    780
gagaccgat                                                            789
```

<210> SEQ ID NO 286
<211> LENGTH: 799
<212> TYPE: DNA
<213> ORGANISM: Nicotiana benthamiana

<400> SEQUENCE: 286

```
cactgacgtt ggattagagg taggctcctt atatgtgctt aagcctaacg tgcagccggc     60
ccccaacccc agcagttttc aatctaccta ccgtctctac catttttctta tagtagttga   120 aaatttctaa ctttgagaaa acaagccaaa gttttgtttc taagaacaca aagggagtga   180 aatttttttgc agcaatggca cagattagca gcatgaggca agggatacag accctaatc    240 ttaattccta ttttcctaaa acccaaaagg ttcctctttt ttcgcattct atcttcattg    300
gatcaaagaa ataacccaa aattcagcaa atctttgtg ggtgtgtaag aaagattcag      360
ttttgagggt ggcaaagtca ccttttagga tttgtgcatc agtggccact gcacagaagc    420
ctaacgagat tgtgctgcaa cctatcaaag atatatcagg cactgttaaa ttacctggtt    480
ctaaatccct ttccaatcgt attctccttc ttgctgccct ttctgaggga aggactgttg    540
ttgacaattt actgagtagt gatgacattc attacatgct tggtgcattg aaaacacttg    600
gacttcatgt agaagatgac aatgaaaacc aacgagcaat cgtagaaggt tgtggtgggc    660
agtttcctgt cggcaagaag tctgaggaag aaatccaact attccttgga aatgcaggaa    720
cagcaatgcg gccattgacg gcagcagtta ctgtagctgg tggacattct agatatgtac    780
ttgatggagt tcctaggat                                                 799
```

<210> SEQ ID NO 287
<211> LENGTH: 845
<212> TYPE: DNA
<213> ORGANISM: Nicotiana benthamiana

<400> SEQUENCE: 287

```
aaattcttgg ttcgaggagg tcagaagtac aagtctcctg gaaaagcata tgttgaagga     60
gatgcctcaa gtgctagcta cttttttggcg ggtgcagctg tcacaggtgg aactgtcact    120
gttgaaggtt gtggaacaag cagtttacag ggggatgtta agtttgctga ggtcctcgaa    180
aagatggggg cagaagttac atggacagag aacagtgtca cggttaaagg acctccaagg    240
aactcttctg gaatgaaaca tttgcgggct gttgacgtta acatgaacaa atgccagat     300 gttgccatga ctcttgctgt agttgcactt tttgctgata gtcctactgc cataagagat    360
gttgctagct ggagagttaa ggaaactgag cggatgattg ccatatgcac agaacttagg    420
aagttgggtg caacagttgt agaagggcca gactactgca taatcactcc acctgaaaag    480
ttaaaagtag cggaaattga tacatatgat gatcacagaa tggccatggc ttttctctctt   540 gcggcttgtg ctgatgttcc agtcaccatt aaggaccccg ttgtactcg caaaaccttc     600 cccaactact tgacgttct ccagcagtat tccaagcatt aaaccacttt ccattaagaa     660
ttttgaaaaa gagagacttt gacaacaatg gtgtcatacc ggaagagaaa agctttgatc    720
caagctttca actcctttctc atttgtcatg tgatgatcat tgtatttgtt gaagttgagc    780
```

```
tgcttttctt ttgtccagaa gacatgtatg gatactatta ctatatagtt aaggtgaact    840
cagca                                                                845
```

<210> SEQ ID NO 288
<211> LENGTH: 21
<212> TYPE: DNA
<213> ORGANISM: artificial sequence
<220> FEATURE:
<223> OTHER INFORMATION: Synthetic Construct

<400> SEQUENCE: 288

```
ccacatggtc cagtatctgc c                                               21
```

<210> SEQ ID NO 289
<211> LENGTH: 21
<212> TYPE: DNA
<213> ORGANISM: artificial sequence
<220> FEATURE:
<223> OTHER INFORMATION: Synthetic Construct

<400> SEQUENCE: 289

```
caagcaagga acccatccat t                                               21
```

<210> SEQ ID NO 290
<211> LENGTH: 21
<212> TYPE: DNA
<213> ORGANISM: artificial sequence
<220> FEATURE:
<223> OTHER INFORMATION: Synthetic Construct

<400> SEQUENCE: 290

```
ggccacacct gcatgcattg c                                               21
```

<210> SEQ ID NO 291
<211> LENGTH: 21
<212> TYPE: DNA
<213> ORGANISM: artificial sequence
<220> FEATURE:
<223> OTHER INFORMATION: Synthetic Construct

<400> SEQUENCE: 291

```
gtgttcacgg tagacaaatc c                                               21
```

<210> SEQ ID NO 292
<211> LENGTH: 21
<212> TYPE: DNA
<213> ORGANISM: artificial sequence
<220> FEATURE:
<223> OTHER INFORMATION: Synthetic Construct

<400> SEQUENCE: 292

```
tgcactgcac ttgacgcacg t                                               21
```

<210> SEQ ID NO 293
<211> LENGTH: 21
<212> TYPE: DNA
<213> ORGANISM: artificial sequence
<220> FEATURE:
<223> OTHER INFORMATION: Synthetic Construct

<400> SEQUENCE: 293

```
aactgatgca ttgcacttga c                                               21
```

<210> SEQ ID NO 294
<211> LENGTH: 21

```
<212> TYPE: DNA
<213> ORGANISM: artificial sequence
<220> FEATURE:
<223> OTHER INFORMATION: Synthetic Construct

<400> SEQUENCE: 294
caaatcagga aggtatgaga g                                              21

<210> SEQ ID NO 295
<211> LENGTH: 21
<212> TYPE: DNA
<213> ORGANISM: artificial sequence
<220> FEATURE:
<223> OTHER INFORMATION: Synthetic Construct

<400> SEQUENCE: 295
tgtcaaggtt ttgtttcctg g                                              21

<210> SEQ ID NO 296
<211> LENGTH: 543
<212> TYPE: DNA
<213> ORGANISM: Nicotiana benthamiana

<400> SEQUENCE: 296
gcaatggctt cctcagttct ttcctcagca gcagttgcca cccgcagcaa tgttgctcaa    60
gctaacatgg ttgcaccttt cacaggtctt aagtctgctg cctcattccc tgtttcaaga   120
aagcaaaacc ttgacatcac ttccattgcc agcaacggcg gaagagtgca atgcatgcag   180
gtgtggccac caattaacat gaagaagtat gagactctct catacctttcc cgatttgagc   240 caggagcaat tgctctccga aattgagtac cttttgaaga atggatgggt tccttgcttg   300
gaattcgaga ctgagaaagg atttgtctac cgtgaacacc acaagtcacc aggatactat   360
gatggcagat actggaccat gtggaagcta cctatgttcg gatgcactga tgccacccaa   420
gtgttggctg aggtgggaga ggcgaagaag gaatacccac aggcctgggt ccgtatcatt   480
ggatttgaca acgtgcgtca agtgcagtgc atcagtttca ttgcctccaa gcctgacggc   540
tac                                                                 543

<210> SEQ ID NO 297
<211> LENGTH: 543
<212> TYPE: DNA
<213> ORGANISM: Nicotiana benthamiana

<400> SEQUENCE: 297
acaatggctt cctcagttct ttcctcagca gcagttgcca cccgcagcaa tgttgctcaa    60
gctaacatgg ttgcaccttt cactggtctt aagtcagctg cctttttccc tgtttcaagg   120
aagcaaaacc ttgacatcac ttccattgcc agcaacggcg gaagagtgca atgcatgcag   180
gtgtggccac caattaacaa gaagaagtac gagactctct catacctttcc tgatctgagc   240 gtggagcaat tgcttagcga aattgagtac ctcttgaaaa atggatgggt tccttgcttg   300
gaattcgaga ctgagcgcgg atttgtctac cgtgaacacc acaagtcacc gggatactat   360
gacggcagat actggaccat gtggaagttg cctatgttcg gatgcactga tgccacccaa   420
gtgttggccg aggtggaaga ggcgaagaag gcatacccac aggcctggat ccgtattatt   480
ggattcgaca acgtgcgtca agtgcagtgc atcagtttca ttgcctacaa gccagaaggc   540
tac                                                                 543

<210> SEQ ID NO 298
```

```
<211> LENGTH: 486
<212> TYPE: DNA
<213> ORGANISM: Nicotiana benthamiana

<400> SEQUENCE: 298
caagccaaca tggttgcacc cttcactggc ctcaagtccg cctcctcctt ccctgttacc      60
aggaaacaaa accttgacat tacctccatt gctagcaatg gtggaagagt tcaatgcatg     120
caggtgtggc caccaattaa catgaagaag tacgagacac tctcataccT tcctgatttg     180
agccaggagc aattgcttag tgaagttgag tacctttTga aaaatggatg ggttccttgc     240
ttggaattcg agactgagcg tggattcgtc taccgtgaac accacaactc accaggatac     300
tacgatggca gatactggac catgtggaag ttgcccatgt tcgggtgcac tgatgccact     360
caggtgttgg ctgaggtcga ggaggcaaag aaggcttacc cacaagcctg gttagaatc     420
attggattcg acaacgtccg tcaagtgcaa tgcatcagtt ttatcgcctc caagccagaa    480
ggctac                                                                486

<210> SEQ ID NO 299
<211> LENGTH: 537
<212> TYPE: DNA
<213> ORGANISM: Nicotiana benthamiana

<400> SEQUENCE: 299
ggctcagtta tgtcctcagc tgccgctgtt ccaccggcg ccaatgctgt tcaagccagc       60
atggtcgcac ccttcactgg cctcaaggcc gcctcctcct tcccggtttc caggaaacaa    120
aaccttgaca ttacttccat tgctagaaat ggtggaagag tccaatgcat gcaggtgtgg    180
ccgccaatta caagaagaa gtacgagaca ctctcatacc ttcctgattt gagcgtggag     240
caattgctta gcgaaattga gtaccttttg aaaaatggat gggttccttg cttggaattc    300
gagactgagc atggattcgt ctaccgtgaa caccaccact caccaggata ctacgatggc    360
agatactgga cgatgtggaa gttgcccatg ttcgggtgca ccgatgccac tcaggtcttg    420
gctgaggtag aggaggccaa gaaggcttac ccacaagcct gggtcagaat cattggattc    480
gacaacgtcc gtcaagtgca atgcatcagt ttcatcgcct acaagcccga aggctat       537

<210> SEQ ID NO 300
<211> LENGTH: 21
<212> TYPE: DNA
<213> ORGANISM: artificial sequence
<220> FEATURE:
<223> OTHER INFORMATION: Synthetic Construct

<400> SEQUENCE: 300
ggaggcaaaa tacgagcctc a                                                21

<210> SEQ ID NO 301
<211> LENGTH: 21
<212> TYPE: DNA
<213> ORGANISM: artificial sequence
<220> FEATURE:
<223> OTHER INFORMATION: Synthetic Construct

<400> SEQUENCE: 301
cactaatctt aataccaaac t                                                21

<210> SEQ ID NO 302
<211> LENGTH: 25
<212> TYPE: DNA
<213> ORGANISM: artificial sequence
```

```
<220> FEATURE:
<223> OTHER INFORMATION: Synthetic Construct

<400> SEQUENCE: 302
tatgggtcat tagcataggc attat                                          25

<210> SEQ ID NO 303
<211> LENGTH: 21
<212> TYPE: DNA
<213> ORGANISM: artificial sequence
<220> FEATURE:
<223> OTHER INFORMATION: Synthetic Construct

<400> SEQUENCE: 303
tctcaagaat atcacgctcc c                                              21

<210> SEQ ID NO 304
<211> LENGTH: 24
<212> TYPE: DNA
<213> ORGANISM: artificial sequence
<220> FEATURE:
<223> OTHER INFORMATION: Synthetic Construct

<400> SEQUENCE: 304
cccttgggga cgctggcagg tcac                                           24

<210> SEQ ID NO 305
<211> LENGTH: 40
<212> TYPE: DNA
<213> ORGANISM: artificial sequence
<220> FEATURE:
<223> OTHER INFORMATION: Synthetic Construct

<400> SEQUENCE: 305
taatacgact cactataggg ggagagagct agatcttttg                          40

<210> SEQ ID NO 306
<211> LENGTH: 41
<212> TYPE: DNA
<213> ORGANISM: artificial sequence
<220> FEATURE:
<223> OTHER INFORMATION: Synthetic Construct

<400> SEQUENCE: 306
taatacgact cactataggc acagtatttc ttcctccaac c                        41

<210> SEQ ID NO 307
<211> LENGTH: 21
<212> TYPE: DNA
<213> ORGANISM: artificial sequence
<220> FEATURE:
<223> OTHER INFORMATION: Synthetic Construct

<400> SEQUENCE: 307
ttgctcatct taaatacatg t                                              21

<210> SEQ ID NO 308
<211> LENGTH: 24
<212> TYPE: DNA
<213> ORGANISM: artificial sequence
<220> FEATURE:
<223> OTHER INFORMATION: Synthetic Construct

<400> SEQUENCE: 308
tcatcttaaa tacatgtttt gtca                                           24
```

<210> SEQ ID NO 309
<211> LENGTH: 22
<212> TYPE: DNA
<213> ORGANISM: artificial sequence
<220> FEATURE:
<223> OTHER INFORMATION: Synthetic Construct

<400> SEQUENCE: 309
ttatcttcag ggatacatta gc                                              22

<210> SEQ ID NO 310
<211> LENGTH: 24
<212> TYPE: DNA
<213> ORGANISM: artificial sequence
<220> FEATURE:
<223> OTHER INFORMATION: Synthetic Construct

<400> SEQUENCE: 310
aatactgctt gctcatctta aata                                            24

<210> SEQ ID NO 311
<211> LENGTH: 21
<212> TYPE: DNA
<213> ORGANISM: artificial sequence
<220> FEATURE:
<223> OTHER INFORMATION: Synthetic Construct

<400> SEQUENCE: 311
gacaattcca agttcagttt c                                               21

<210> SEQ ID NO 312
<211> LENGTH: 24
<212> TYPE: DNA
<213> ORGANISM: artificial sequence
<220> FEATURE:
<223> OTHER INFORMATION: Synthetic Construct

<400> SEQUENCE: 312
ccgttttaga tcaccataaa gaga                                            24

<210> SEQ ID NO 313
<211> LENGTH: 21
<212> TYPE: DNA
<213> ORGANISM: artificial sequence
<220> FEATURE:
<223> OTHER INFORMATION: Synthetic Construct

<400> SEQUENCE: 313
ttgtctggta atatcacaat c                                               21

<210> SEQ ID NO 314
<211> LENGTH: 2937
<212> TYPE: DNA
<213> ORGANISM: Nicotiana benthamiana

<400> SEQUENCE: 314
atggtgagga agaggagaac tgagttacct ggttctggtg agagctctgg gtctcaagaa      60
actggcggac agggtcgtgg ccagcatcca cagcagctgc accaagctac ctcccagact     120
ccatatcaaa ctgcaatgac tactcagcca ataccttatg caagaccaac tgaaacatcc     180
tccgaagctg gttcctcatc tcagccacct gagcaggcag ctctacaagt gacacaacag     240
ttccagcaac ttgctttgca acaagaagcg gctacaacgc aagcagttcc acctgcatca     300 agcaaaattac taaggtttcc cctgcgtcca gggaagggga gcaatggtat gagatgcata     360

```
gtcaaagcca atcacttctt cgcagagctg cctgacaaag acttgcacca gtatgatgtc      420
acaatttctc cagaggtgtc atcacgtggc gtcaaccgtg ctgtcatggc gcaactggtg      480
aagctgtacc aagaatctca tcttgggaag agacttccag catatgatgg aaggaaaagt      540
ctatacactg cagggcccct tccatttgtt caaaaagact tcaaaataac tcttattgat      600
gatgaggatg ggcctggtgg tgctagaagg gaaagggaat ttaaagttgt gatcaaattg      660
gctgcccgtg ctgatcttca tcacttggga atgtttttag aagggaaaca ggctgatgca      720
cctcaagagg cgcttcaagt tctggatatt gttctgcgtg agttgccaac atctaggttt      780
tgtcctgtgg gtcgttcttt ctattcccgt gatttagggc gaaagcaacc attgggtgaa      840
ggtttagaaa gttggcgtgg gttctatcaa agcattcgcc ccacacaaat gggcttatca      900
ctgaacatcg atatgtcttc cactgcattc attgagccac tgccagtcat tgattttgtg      960
acacagcttc tgaaccgaga tgtgccatct agaccactgt ctgatgctgg ccgtgtaaag     1020
ataaaaaaag ctctgagagg tgtgaaggtg gaggttactc atcgtggaaa tatgcggagg     1080
aagtaccgca tttcgggttt aacatctcaa gcaacaagag agttgacctt ccctgttgat     1140
gaaaatggta cagtgaaatc tgtaattgag tattttcgag aaacatatgg gtttgtaatt     1200
cagcatactc agtggccttg tctacaagtt ggaaatcagc agagacctaa ttacttgcca     1260
atggaagtct gcaagattgt ggagggacaa aggtactcaa agcgcttgaa tgagagacag     1320
attactgcac ttctgaaagt gacctgccag cgtccccaag ggagggagcg tgatattctt     1380
gagaccgtac atcataatgc ctatgctaat gacccatatg ccaaggagtt tggtattaag     1440
attagtgaca agttggcaca agttgaggct cgtatttttgc ctccacctcg gcttaaatat     1500
catgataacg gtcgagaaaa ggactgcctg ccacaagttg gccaatggaa tatgatgaat     1560
aagaaaatgg taaatggagg gacggtgaac aattggatct gcataaactt ctctcgcaat     1620
gtgcaagata tgtgttgctca tgggttttgc tctgagcttg cacaaatgtg ccagatatct     1680
ggcatgaatt tcaatccaaa tcctgttctg ccaccttcga gtgcacgccc tgatcaggtc     1740
gaaagagtat tgaaaactcg atttcatgat gctatgacta agttgcagct gcatgggaga     1800
gagcttgatt tgctagttgt catcttgcca gacaataatg gatctcttta tggtgatctg     1860
aagcgcattt gtgagactga actaggagtc gtctcacagt gctgtttgac aaaacatgta     1920
tttaagatga gcaaacagta tctagccaat gtagcgctga aaatcaatgt gaaggtggga     1980
gggagaaaca ctgtgcttgt tgatgcaata tcgaggcgaa ttcctcttgt cagcgaccgg     2040
cctaccatca tttttggtgc agatgtcacc caccctcacc ctggggagga ctctagccca     2100
tccattgccg cggtggttgc ttctcaagat tggcctgaga ttacaaagta tgctggtcta     2160
gtttctgctc aagcccatag gcaagagctt attcaggatc tgtacacgac taggcaagat     2220
cctgttaagg ggacagttgc tggtggaatg attaaggact tacttatatc cttccgaaga     2280
gctactggac aaaagcccca gagataatt ttctataggg atggtgttag tgaaggacaa     2340
ttttatcaag tgcttctgtt cgaacttgat gcgatccgca agcatgtgc gtctttggag     2400 ccaaattatc agcccccagt cacatttgtt gtggttcaga acgacatca cacaaggctt     2460 tttgccaata accaccgtga cagaaatgca gttgacagga gcgggaacat tatacctggt     2520
actgttgtag attcaaagat atgccacccg acagagtttg atttctatct ttgtagccat     2580
gccggcatac agggtacgag ccgtccagct cactaccatg ttctatggga cgagaacaaa     2640
ttcacagccg atgcgctgca gtctttgacc aacaacctct gctatacata tgcaaggtgc     2700
```

-continued

| | |
|---|---|
| acgcgttccg tctccatcgt tccccctgca tattatgcac atttggcagc tttccgtgct | 2760 |
| cgattttata tggagccgga gacatctgac ggtggttcag taacaagtgg ggctgctggt | 2820 |
| ggcagagggg gtggtgcagg agctgctgga aggaacaccc gagccccaag tgctggtgct | 2880 |
| gctgttagac ctcttcctgc gctcaaggat aatgtgaaga gggttatgtt ctactgc | 2937 |

<210> SEQ ID NO 315
<211> LENGTH: 3274
<212> TYPE: DNA
<213> ORGANISM: Nicotiana benthamiana

<400> SEQUENCE: 315

| | |
|---|---|
| cacctatcac tctctttctc tctctacaaa catatcgtgc cgtttctctc tcggcctctc | 60 |
| ttcgtgtttt agggcaccgt ggtggttggt atccaggcgg cggttttgag ttattaccat | 120 |
| ggtgcggaag aagaggactg atgttcctgg tggtgctgag agttttgagt cccatgaaac | 180 |
| tggaggggca cgaggtggtg cccaacgccc atcacagcag cagcaacatc agcatcagca | 240 |
| aggcggagga agaggctggg cacctcagca tggaggacat ggtggccgtg gtggtggggg | 300 |
| agctccacgt ggtggaatgg cccctcaaca atcctatggt ggacctcctg aatactacca | 360 |
| acagggcagg gaactcaac agtatcaacg aggtggagga caaccccagc gccgtggtgg | 420 |
| catgggggggc cgtggggcac ggccaccagt acccgagctg caccaagcaa cccagactcc | 480 |
| acatcagcct gtaccatatg gaagaccatc agaaacatac tcagaggctg gttcctcgtc | 540 |
| tcagccacct gaaccaacga cacagcaagt gactcagcaa ttccagcaac ttgttgtgca | 600 |
| gccagaagca gctgcaaccc aagcaataca accagcatcg agcaagtcga tgaggtttcc | 660 |
| actccggcca ggaaagggta gtactggtat tagatgcata gttaaggcca atcacttctt | 720 |
| tgccgagtta cctgacaaag atctgcacca gtatgatgtt tcaattactc ctgaggtcgc | 780 |
| ctctcggggt gtcaaccggg ccgtcatgga gcagctggtg aagctttata gagaatccca | 840 |
| tcttgggaag aggcttccag cctatgacgg aagaaaaagt ctatacacag cagggccccct | 900 |
| cccttttgtt caaaaggatt ttaaaatcac tctaattgat gatgatgatg acctggtgg | 960 |
| tgctaggagg gaaagagagt ttaaagttgt gatcaagctg gcggctcgtg ctgatcttca | 1020 |
| tcacttgggg atgttcttac aagggagaca ggctgatgca ccgcaagaag cacttcaggt | 1080 |
| gctggatatt gtgctacgtg agttgccaac atctaggtat tgtcctgtgg gccgctcttt | 1140 |
| ctattcccct catttaggac gaagacaacc actgggtgaa ggtttagaga ctggcgtgg | 1200 |
| cttctatcaa agtattcgtc ctacacagat gggattatcc ctgaatattg atatgtcttc | 1260 |
| cacggctttc attgagccac tgccgattat tgacttcgtg agccagcttc tgaatcggga | 1320 |
| tatctcttct agaccactgt ctgatgctga ccgcgttaag ataaagaagg cactgagagg | 1380 |
| tgtaaaggtg ggggtcactc atcgtggaaa tatgcggagg aagtatcgca tttctggctt | 1440 |
| gacgtctcaa gcaacaagag agttgacttt tcctgtcgat gaaaggggta cgatgaaagc | 1500 |
| tgttgtggaa tattttcggg aaacctatgg ttttgtcatt cggcataccc agtggccttg | 1560 |
| tcttcaagtt ggaaatacgc agaggccaaa ttacttgcca atggaagtat gtaagattgt | 1620 |
| agagggacag agatactcaa agcgcttgaa tgagaggcag ataacagcac ttctaaaagt | 1680 |
| gacctgccaa cgtcctcaag agagagaacg tgatattctt cagactgttc atcacaatgc | 1740 |
| ttatgctgat gacccatatg cgaaggagtt tggtattaag atcagtgagg agcttgctca | 1800 |
| agttgaggct cgcgttttgc ctgcacccttg gcttaaatac catgatacag gtcgagagaa | 1860 |
| agactgtctg ccacaagtgg gccagtggaa tatgatgaat aagaaaatgg ttaatggagg | 1920 |

-continued

```
aacagtgaac aactggatct gtgtaaactt ttctcgcaat gtgcaagaca cagttgcacg    1980
tggattttgt tccgagcttg cacaaatgtg catgatatcc ggaatgaact tcaatcccaa    2040
tcctgttcta ccaccagtga gtgctcgccc tgatcaagtt gagagagtct tgaaaactcg    2100
atttcacgat gctatgacaa agttgcagcc aaatgggaga gagctagatc ttttgattgt    2160
gatattacca gacaataacg gctctctttta tggtgatcta aaacggattt gtgaaactga    2220
acttggaatt gtctcacaat gctgcttgac aaaacatgta tttaagatga gcaagcagta    2280
tttagctaat gtatccctga agataaatgt gaaggttgga ggaagaaata ctgtgctggt    2340
tgatgcgctc tctagacgaa ttccccttgt cagcgaccgc ccaactatca tttttggtgc    2400
agatgtcacc catccccacc ctggggagga ttctagcccg tcaattgctg cggtggttgc    2460
ttctcaagat tggcctgaaa ttacaaagta tgctggtttg gtttctgctc aagcgcatag    2520
gcaagagctt atacaagatc tgtacaagac ttggcaagat ccagttagag gacctgtgac    2580
tggtggcatg ataaaggaat tacttatttc cttccgtcga gcaactggac agaagccgca    2640
gagaattata ttctacagag atggtgttag tgaaggacaa ttttaccaag ttcttctttt    2700
tgaacttgat gcaatccgca aggcatgtgc atctttagaa cccaactatc agccccggt    2760 tacgtttgtt gtggtccaga aacggcatca tactaggttg tttgccaata accaccacga    2820
cagaaatgca gttgatcgga gtgggaacat tttgcctggt accgttgtag attcaaagat    2880
atgccaccct actgaatttg atttctatct ctgtagccat gccggcatac agggtactag    2940
ccgcccagct cattatcatg ttctgtggga tgagaacaat tttactgctg acgccctgca    3000
gtctttgact aacaatcttt gctatacata tgctaggtgt actcgttctg tctccattgt    3060
tccaccagca tattatgcac atttggcagc tttccgtgct cggttttaca tggagccaga    3120
gacatctgat aatggatcag tcacaagcgc agctgcttca aacagaggag gtttaggagc    3180
tatgggaagg agcacgcgag caccaggtgc tggtgctgct gtaaggcccc ttcctgctct    3240
caaggagaat gttaagaggg ttatgttttta ttgt                              3274
```

<210> SEQ ID NO 316
<211> LENGTH: 3907
<212> TYPE: DNA
<213> ORGANISM: Zea mays

<400> SEQUENCE: 316

```
acctacttcc ccctcgcccc tctcatggtc tctctcgcgc ccagatctgc tactagacgg     60
caccgctgca gcgcgtcgtg tcgcgggggt tggtggcagg cagcgagagc ttgccgttcc    120
tctctctcag ttgtcaggtc ctaggctcac ctcaccggct cccagcccgc ttctatttct    180
tcctccccga ccccgtgcag gtggcagtcc agtccacgcc accaaccgcg aggcgaacca    240
aaccaaccca ctctccccaa ccccgcgcgc ccaggccgcc cgccctacca accatcggcg    300
tcggcaatgg cggccatggc gaccaaggcc gccgcgggca ccgtgtcgct ggacctcgcc    360
gcgccgccgg cggcggcagc ggcggcggcg gtgcaggcgg gtgccgagga gatcgtgctg    420
cagcccatca aggagatctc cggcaccgtc aagctgccgg ggtccaagtc gctttccaac    480
cggatcctcc tgctcgccgc cctgtccgag gtgagcgatt ttggtgcttg ctgcgctgcc    540
ctgtctcact gctacctaaa tgttttgcct gtcgaatacc atggattctc ggtgtaatcc    600
atctcacgat cagatgcacc gcatgtcgca tgcctagctc tctctaattt gtctagtagt    660
ttgtatacgg attaatattg ataaatcggt accgcaaaag ctaggtgtaa ataaacacta    720
```

```
gaaaattgga tgttccccta tcggcctgta ctcggctact cgttcttgtg atggcatgct    780
gtctcttctt ggtgtttggt gaacaacctt atgaaatttg ggcgcaaaga actcgccctc    840
aagggttgat cttatgccat cgtcatgata aacagtggag cacggacgat cctttacgtt    900
gtttttaaca aactttgtca gaaaactagc atcattaact tcttaatgac gatttcacaa    960 caaaaaagg taacctcgct actaacataa caaaatactt gttgcttatt aattatatgt    1020
tttttaatct ttgatcaggg gacaacagtg gttgataacc tgttgaacag tgaggatgtc    1080
cactacatgc tcggggcctt gaggactctt ggtctctctg tcgaagcgga caaagctgcc    1140
aaaagagctg tagttgttgg ctgtggtgga aagttcccag ttgaggattc taaagaggaa    1200
gtgcagctct tcttggggaa tgctggaact gcaatgcggc cattgacagc agctgttact    1260
gctgctggtg gaaatgcaac gtatgttccc tctctttctc tctacaatac ttgctggagt    1320
tagtatgaaa cccatgggta tgtctagtgg cttatggtgt attggttttt gaacttcagt    1380
tacgtgcttg atggagtacc aagaatgagg gagagaccca ttggcgactt ggttgtcgga    1440
ttgaagcagc ttggtgcaga tgttgattgt ttccttggca ctgactgccc acctgttcgt    1500
gtcaatggaa tcgagggct acctggtggc aaggttagct actaagggcc acatgttaca    1560
ttcttctgta aatggtacaa ctattgtcga gcttttgcat ttgtaaggaa agcattgatt    1620
gatctgaatt tgatgctaca ccacaaaata tcctacaaat ggtcatccct aactagcaaa    1680
caatgaagta atacttggca tgtgtttatc aaattaattt ccatcttctg ggcattgcc    1740 tgttttctag tctaatagca tttgttttta gcattaatta gctcttacaa ttgttatgtt    1800
ctacaggtca agctgtctgg ctccatcagc agtcagtact tgagtgcctt gctgatggct    1860
gctcctttgg ctcttgggga tgtggagatt gaaatcattg ataaattaat ctccattccc    1920
tacgtcgaaa tgacattgag attgatggag cgttttggtg tgaaagcaga gcattctgat    1980
agctgggaca gattctacat taagggaggt caaaaataca agtaagctct gtaatgtatt    2040
tcactacttt tgatgccaatg tttcagtttt cagttttcca aacagtcgca tcaatatttg    2100
aatagatgca ctgtagaaaa aaaatcattg cagggaaaaa ctagtactga gtattttgac    2160
tgtaaattat tttaccagtc ggaatatagt cagtctattg gagtcaagag cgtgaaccga    2220
aatagccagt taattatccc attatacaga ggacaaccat gtatactatt gaaacttggt    2280
ttataagaga atctaggtag ctggactcgt agctgcttgg catggatacc ttcttatctt    2340
taggaaaaga cacttgattt ttttttttctg tggccctcta tgatgtgtga acctgcttct    2400
ctattgcttt agaaggatat atctatgtcg ttatgcaaca tgcttcccctt agccatttgt    2460 actgaaatca gtttcataag ttcgttagtg gttccctaaa cgaaaccttg tttttctttg    2520
caatcaacag gtcccctaaa aatgcctatg ttgaaggtga tgcctcaagc gcaagctatt    2580
tcttggctgg tgctgcaatt actggaggga ctgtgactgt ggaaggttgt ggcaccacca    2640
gtttgcaggt aaagatttct tggctggtgc tacaataact gcttttgtct ttttggtttc    2700
agcattgttc tcagagtcac taaataacat tatcatctgc aaatgtcaaa tagacatact    2760
taggtgaatt catgtaaccg tttccttaca aatttgctga aacctcaggg tgatgtgaag    2820
tttgctgagg tactggagat gatgggagcg aaggttacat ggaccgagac tagcgtaact    2880
gttactggcc caccgcggga gccatttggg aggaaacacc tcaaggcgat tgatgtcaac    2940
atgaacaaga tgcctgatgt cgccatgact cttgctgtgg ttgccctctt tgccgatggc    3000
ccgacagcca tcagagacgg taaaacattc tcagccctac aacctatgcct cttctacatc    3060 actacttgac aagactaaaa actattggct cgttggcagt ggcttcctgg agagtaaagg    3120
```

```
agaccgagag gatggttgcg atccggacgg agctaaccaa ggtaaggcta catacttcac    3180
atgtctcacg tcgtctttcc atagctcgct gcctcttagc ggcttgcctg cggtcgctcc    3240
atcctcggtt gctgtctgtg ttttccacag ctgggagcat ctgttgagga agggccggac    3300
tactgcatca tcacgccgcc ggagaagctg aacgtgacgg cgatcgacac gtacgacgac    3360
cacaggatgg ccatggcctt ctcccttgcc gcctgtgccg aggtcccccgt gaccatccgg   3420 gaccctgggt gcacccggaa gaccttcccc gactacttcg atgtgctgag cactttcgtc    3480
aagaattaat aaagcgtgcg atactaccac gcagcttgat tgaagtgata ggcttgtgct    3540
gaggaaatac atttcttttg ttctgttttt tctctttcac gggattaagt tttgagtctg    3600
taacgttagt tgtttgtagc aagtttctat ttcggatctt aagtttgtgc actgtaagcc    3660
aaatttcatt tcaagagtgg ttcgttggaa taataagaat aataaattac gtttcagtgg    3720
ctgtcaagcc tgctgctacg ttttaggaga tggcattaga cattcatcat caacaacaat    3780 aaaaccttt agcctcaaac aataatagtg aagttatttt ttagtcctaa acaagttgca     3840
ttaggatata gttaaaacac aaaagaagct aaagttaggg tttagacatg tggatattgt    3900
tttccat                                                              3907

<210> SEQ ID NO 317
<211> LENGTH: 2149
<212> TYPE: DNA
<213> ORGANISM: Zea mays

<400> SEQUENCE: 317
acctacttcc ccctcgcccc tctcatggtc tctctcgcgc ccagatctgc tactagacgg      60
caccgctgca gcgcgtcgtg tcgcgggggt tggtggcagg cagcgagagc ttgccgttcc     120
tctctctcag ttgtcaggtc ctaggctcac ctcaccggct cccagcccgc ttctatttct     180
tcctccccga ccccgtgcag gtggcagtcc agtccacgcc accaaccgcg aggcgaacca     240
aaccaaccca ctctccccaa ccccgcgcgc ccaggccgcc cgccctacca accatcggcg     300
tcggcaatgg cggccatggc gaccaaggcc gccgcgggca ccgtgtcgct ggacctcgcc     360
gcgccgccgg cggcggcagc ggcggcggcg gtgcaggcgg gtgccgagga gatcgtgctg     420
cagcccatca aggagatctc cggcaccgtc aagctgccgg ggtccaagtc gctttccaac     480
cggatcctcc tgctcgccgc cctgtccgag gggacaacag tggttgataa cctgttgaac     540
agtgaggatg tccactacat gctcggggcc ttgaggactc ttggtctctc tgtcgaagcg     600
gacaaagctg ccaaaagagc tgtagttgtt ggctgtggtg aaagttccc agttgaggat     660 tctaaagagg aagtgcagct cttcttgggg aatgctggaa ctgcaatgcg gccattgaca     720
gcagctgtta ctgctgctgg tggaaatgca acttacgtgc ttgatggagt accaagaatg     780
agggagagac ccattggcga cttggttgtc ggattgaagc agcttggtgc agatgttgat     840
tgtttccttg gcactgactg cccacctgtt cgtgtcaatg gaatcggagg ctacctggt     900 ggcaaggtca agctgtctgg ctccatcagc agtcagtact tgagtgcctt gctgatggct    960 gctccttgg ctcttgggga tgtggagatt gaaatcattg ataaattaat ctccattccc    1020
tacgtcgaaa tgacattgag attgatggag cgttttggtg tgaaagcaga gcattctgat   1080
agctgggaca gattctacat taagggaggt caaaaataca gtcccctaa aaatgcctat    1140 gttgaaggtg atgcctcaag cgcaagctat ttccttggctg gtgctgcaat tactggaggg   1200
actgtgactg tggaaggttg tggcaccacc agtttgcagg gtgatgtgaa gtttgctgag   1260
```

```
gtactggaga tgatgggagc gaaggttaca tggaccgaga ctagcgtaac tgttactggc    1320
ccaccgcggg agccatttgg gaggaaacac ctcaaggcga ttgatgtcaa catgaacaag    1380
atgcctgatg tcgccatgac tcttgctgtg gttgccctct tgccgatgg cccgacagcc     1440 atcagagacg tggcttcctg gagagtaaag gagaccgaga ggatggttgc gatccggacg    1500
gagctaacca agctgggagc atctgttgag gaagggccgg actactgcat catcacgccg    1560
ccggagaagc tgaacgtgac ggcgatcgac acgtacgacg accacaggat ggccatggcc    1620
ttctcccttg ccgcctgtgc cgaggtcccc gtgaccatcc gggaccctgg gtgcacccgg    1680
aagaccttcc ccgactactt cgatgtgctg agcactttcg tcaagaatta ataaagcgtg    1740
cgatactacc acgcagcttg attgaagtga taggcttgtg ctgaggaaat acatttcttt    1800
tgttctgttt tttctctttc acgggattaa gttttgagtc tgtaacgtta gttgtttgta    1860
gcaagtttct atttcggatc ttaagtttgt gcactgtaag ccaaatttca tttcaagagt    1920
ggttcgttgg aataataaga ataataaatt acgtttcagt ggctgtcaag cctgctgcta    1980
cgttttagga gatggcatta gacattcatc atcaacaaca ataaaacctt ttagcctcaa    2040
acaataatag tgaagttatt ttttagtcct aaacaagttg cattaggata tagttaaaac    2100
acaaaagaag ctaaagttag ggtttagaca tgtggatatt gttttccat              2149

<210> SEQ ID NO 318
<211> LENGTH: 240
<212> TYPE: DNA
<213> ORGANISM: Zea mays

<400> SEQUENCE: 318
tacttgagtg ccttgctgat ggctgctcct ttggctcttg gggatgtgga gattgaaatc      60
attgataaat taatctccat tccgtacgtc gaaatgacat tgagattgat ggagcgtttt    120
ggtgtgaaag cagagcattc tgatagctgg gacagattct acattaaggg aggtcaaaaa    180
tacaagtccc ctaaaaatgc ctatgttgaa ggtgatgcct caagcgcaag ctatttcttg    240

<210> SEQ ID NO 319
<211> LENGTH: 297
<212> TYPE: DNA
<213> ORGANISM: Nicotiana benthamiana

<400> SEQUENCE: 319
gctgtatcat atcttcttct ttagaacact aataaattaa acttcgagat aatgatttct      60
gacaagagta taaacaagtg catctatgaa gatttgaggt tgtccaaaaa agtgacaatt    120
ttgggttcct ataaactgta tttacattat tgttatttgc aactataaaa attttagatt    180
atttccaagc tcagtttctt caacttaaat gaaggtagca cttgaatttc atcagcctct    240
atgacccagt aacccatgtg ggagatggga gcaaagtggt caaactttag aaggaat      297

<210> SEQ ID NO 320
<211> LENGTH: 269
<212> TYPE: DNA
<213> ORGANISM: Nicotiana benthamiana

<400> SEQUENCE: 320
gtatgaactt tcagaatatt ataccggatc aatatattat gctgaaatat ttttcggact      60
ttaaataatt tctttatttta aatttatttt tatacaaaaa taactaaatt tcaattactt    120
ttaaaattat gattattttt caattaccac ttatacatcc tgctattttg aatttcaccc    180
```

```
gaaagaacta ctactatacg tggatcctca atgacccagt aacccaagtg ggagatgtgt    240
gcaaagtggt caaatcttag aaggaatga                                      269
```